(12) United States Patent
Luettgen et al.

(10) Patent No.: US 12,065,505 B2
(45) Date of Patent: Aug. 20, 2024

(54) ANTIBODIES AND ANTIGEN BINDING PEPTIDES FOR FACTOR XIA INHIBITORS AND USES THEREOF

(71) Applicants: Bristol-Myers Squibb Company, Princeton, NJ (US); Janssen Pharmaceuticals, Inc., Titusville, NJ (US)

(72) Inventors: Joseph M. Luettgen, Princeton, NJ (US); Lumelle Schneeweis, Princeton, NJ (US); Ginger Chao Rakestraw, Cambridge, MA (US); Christina Terragni, Cambridge, MA (US); Andrew Karl Dilger, Princeton, NJ (US); Jason Robert Pinckney, Cambridge, MA (US); Steven Sheriff, Princeton, NJ (US); Kevin Kish, Princeton, NJ (US); Yongmi An, Princeton, NJ (US); William R. Ewing, Princeton, NJ (US); Stanley Richard Krystek, Jr., Ringoes, NJ (US); Aaron Paul Yamniuk, Vancouver (CA)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 17/570,649

(22) Filed: Jan. 7, 2022

(65) Prior Publication Data
US 2022/0220220 A1 Jul. 14, 2022

Related U.S. Application Data

(60) Provisional application No. 63/153,045, filed on Feb. 24, 2021, provisional application No. 63/152,595, (Continued)

(51) Int. Cl.
 C07K 16/36 (2006.01)
 A61K 39/00 (2006.01)
 (Continued)

(52) U.S. Cl.
 CPC ............. *C07K 16/36* (2013.01); *A61P 7/04* (2018.01); *C07K 16/44* (2013.01); *G01N 33/86* (2013.01);
 (Continued)

(58) Field of Classification Search
 CPC .... C07K 16/36; C07K 16/44; C07K 2317/21; C07K 2317/55; C07K 2317/565;
 (Continued)

(56) References Cited

U.S. PATENT DOCUMENTS 7,288,251 B2 * 10/2007 Bedian ................ A61P 13/10
 424/153.1
2008/0160035 A1 7/2008 Stevens et al.
 (Continued)

FOREIGN PATENT DOCUMENTS

WO WO-2008068048 A2 * 6/2008 ............ A61P 31/10
WO 2016053455 A1 4/2016
WO 2020216379 A1 10/2020

OTHER PUBLICATIONS

Kussie, Paul H., "A Single Engineered Amino Acid Substitution Changes Antibody Fine Specificity", 1994, Journal of Immunology 152(1): pp. 146-152. (Year: 1994).*

(Continued)

*Primary Examiner* — Aurora M Fontainhas
*Assistant Examiner* — Selam Berhane
(74) *Attorney, Agent, or Firm* — Mintz Levin Cohn Ferris Glovsky and Popeo, P.C.

(57) ABSTRACT

The present invention provides novel antigen binding peptides, such as an antibody or antibody fragment, that spe- (Continued)

cifically bind to selective FXIa inhibitors and/or dual inhibitors of FXIa, and plasma kallikrein. The present invention further relates to methods of reducing the antithrombotic effect of FXIa inhibitors by administering to a subject a pharmaceutically effective dose of the antigen binding peptides provided herein. In addition, the present invention provides detection reagents and methods for detecting the level of the inhibitors of FXIa in a biological sample.

18 Claims, 41 Drawing Sheets

Specification includes a Sequence Listing.

Related U.S. Application Data filed on Feb. 23, 2021, provisional application No. 63/148,767, filed on Feb. 12, 2021, provisional application No. 63/135,016, filed on Jan. 8, 2021.

(51) Int. Cl.
  A61P 7/04      (2006.01)
  C07K 16/44     (2006.01)
  G01N 33/86     (2006.01)
  G01N 33/94     (2006.01)

(52) U.S. Cl.
  CPC ........ G01N 33/94 (2013.01); A61K 2039/505 (2013.01); C07K 2317/21 (2013.01); C07K 2317/55 (2013.01); C07K 2317/565 (2013.01); C07K 2317/92 (2013.01)

(58) Field of Classification Search
  CPC ....... C07K 2317/92; A61P 7/04; G01N 33/86; G01N 33/94; A61K 2039/505
  See application file for complete search history.

(56) References Cited

U.S. PATENT DOCUMENTS

2014/0186362 A1    7/2014  Ferlin et al.
2017/0355756 A1*  12/2017  Julien ..................... A61P 25/00
2018/0134787 A1    5/2018  Liu et al.

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*
Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Abhinandan et al. (Aug. 2008) "Analysis and Improvements to Kabat and Structurally Correct Numbering of Antibody Variable Domains", Molecular Immunology, 45(14):3832-3839.
Araya et al. (2011) "Deep Mutational Scanning: Assessing Protein Function on a Massive Scale", Trends in Biotechnology, 29(9):435-442.
Atschul et al. (Oct. 5, 1990) "Basic Local Alignment Search Tool", Journal of Molecular Biology, 215(3):403-410.
Brutlag et al. (1990) "Improved Sensitivity of Biological Sequence Database Searches", Computer Applications in the Biosciences, 6(3):237-245.
Carrillo et al. (Oct. 1988) "The Multiple Sequence Alignment Problem in Biology", SIAM Journal on Applied Mathematics, 48(5):1073-1082.
Devereux et al. (Jan. 11, 1984) "A Comprehensive Set of Sequence Analysis Programs for the VAX", Nucleic Acids Research, 12(1 Pt 1):387-395.
Emsley et al. (2010) "Features and Development of Coot", Acta Crystallographica Section D, 66(Pt 4):486-501.
Forsyth et al. (2013) "Deep Mutational Scanning of an Antibody Against Epidermal Growth Factor Receptor Using Mammalian Cell Display and Massively Parallel Pyrosequencing", MAbs, 5(4):523-532.
Kurz et al. (2000) "Psoralen Photo-crosslinked mRNA-puromycin Conjugates: a Novel Template for the Rapid and Facile Preparation of mRNA-protein Fusions", Nucleic Acids Research, 28(18):E83 (5 pages).
Lonberg et al. (Apr. 28, 1994) "Antigen-Specific Human Antibodies from Mice Comprising Four Distinct Genetic Modifications", Nature, 368(6474):856-859.
Lonberg, N (1994) "Transgenic Approaches to Human Monoclonal Antibodies", Handbook of Experimental Pharmacology, 113:49 (2 pages).
Magoc et al. (Nov. 1, 2011) "FLASH: Fast Length Adjustment of Short Reads to Improve Genome Assemblies", Bioinformatics, 27(21):2957-2963.
McCoy (Aug. 2007) "Phaser Crystallographic Software", Journal of Applied Crystallography, 40(Pt 4):658-674.
Mohammed et al. (2018) "An Update on Factor XI Structure and Function", Thrombosis Research, 161:94-105.
Roberts et al. (1997) "RNA-Peptide Fusions for the in Vitro Selection of Peptides and Proteins", Proceedings of the National Academy of Sciences of the United States of America, 94(23):12297-12302.
Smart et al. (Apr. 2012) "Exploiting Structure Similarity in Refinement: Automated NCS and Target-structure Restraints in BUSTER", Acta Crystallographica. Section D, Biological Crystallography, 68(4):368-380.
Smith et al. (Dec. 1981) "Comparison of Biosequences", Advances in Applied Mathematics, 2(4):482-489.
Swindells et al. (Feb. 3, 2017) "abYsis: Integrated Antibody Sequence and Structure-Management, Analysis, and Prediction", Journal of Molecular Biology, 429(3):356-364.
Tyle, Praveen (1986) "Iontophoretic Devices for Drug Delivery", Pharmaceutical Research, 3(6):318 (9 pages).
Verdino et al. (2008) "Closely Related Antibody Receptors Exploit Fundamentally Different Strategies for Steroid Recognition", Proceedings of the National Academy of Sciences of the United States of America, 105(33):11725-11730.
Vonrhein et al. (2011) "Data Processing and Analysis With the autoPROC Toolbox", Acta Crystallographica. Section D, Biological Crystallography, 67(Pt 4):293-302.
Wolfgang, Kabsch (2010) "Integration, Scaling, Space-Group Assignment and Post-refinement", Acta Crystallographica. Section D, Biological Crystallography, 66(Pt 2):133-144.
Wolfgang, Kabsch (2010) "XDS", Acta Crystallographica. Section D, Biological Crystallography, 66(Pt 2):125-132.
Wrenbec et al. (2017) "Deep Sequencing Methods for Protein Engineering and Design", Current Opinion in Structural Biology, 45:36-44.
Wyrzucki et al. (2014) "Alternative Recognition of the Conserved Stem Epitope in Influenza A Virus Hemagglutinin by a VH3-30-Encoded Heterosubtypic Antibody", Journal of Virology, 88(12):7083-7092.
Xu et al. (2002) "Directed Evolution of High-Affinity Antibody Mimics Using mRNA Display", Chemistry & Biology, 9(8):933-942.

* cited by examiner

FIG. 1A

Sequence alignment of IGHV3-53 / IGHJ4 germline with antibody 26D5 (heavy chain variable region). Residues are numbered according to Kabat numbering (positions 1–113, including insertions 82a, 82b, 82c). Dashes indicate identity with the germline sequence.

| Pos | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| IGHV3-53 | E | V | Q | L | V | E | S | G | G | G | L | I | Q | P | G | G | S | L | R | L | S | C | A |
| 26D5     | – | – | – | – | – | – | – | – | – | A | – | – | – | – | – | – | – | – | – | – | – | – | – |

| Pos | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|---|---|
| IGHV3-53 | A | S | G | F | T | V | S | S | N | Y | M | S | W | V | R | Q | A | P | G | K | G | L | E |
| 26D5     | – | – | – | – | – | – | – | – | – | – | – | – | – | – | – | – | – | – | – | – | – | – | – |

CDR1-AbM: 26–35; CDR1-Kabat: 31–35

| Pos | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|---|---|---|---|---|---|---|
| IGHV3-53 | W | V | S | V | I | Y | S | G | G | S | T | Y | Y | A | D | S | V | K | G | R | F | T | I |
| 26D5     | – | – | – | F | – | – | – | – | – | – | – | – | – | – | – | – | – | – | – | – | – | – | – |

CDR2: 50–65

| Pos | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 |
|---|---|---|---|---|---|---|---|---|---|---|---|---|---|---|---|---|---|---|---|---|---|---|---|
| IGHV3-53 | S | R | D | N | S | K | N | T | L | Y | L | Q | M | N | S | L | R | A | E | D | T | A | V |
| 26D5     | – | – | – | – | – | – | – | – | R | – | – | – | – | – | – | – | – | – | – | – | – | – | – |

| Pos | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|---|---|---|---|
| IGHV3-53 | Y | Y | C | A | R |   |   |   |   |   |     |     |     |     |     |     |     |     |     |     |     |     |     |
| IGHJ4    |   |   |   |   |   |   | G | G | F | G | G   |     | D   | Y   | W   | G   | Q   | G   | T   | L   | V   | T   | V   |
| 26D5     | – | – | – | – | – |   | – | – | – | – | –   |     | –   | –   | –   | –   | –   | –   | –   | –   | –   | –   | –   |

CDR3: 95–102

| Pos | 113 |
|---|---|
| IGHJ4 | S |
| 26D5  | – |

FIG. 1B

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| IGKV1-12 | D | I | Q | M | T | Q | S | P | S | S | V | S | A | S | V | G | D | R | V | T | I | T | C |
| 26D5 | - | - | - | - | - | - | - | - | - | - | - | - | - | - | - | - | - | - | - | - | - | - | - |

CDR1

| | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|---|---|
| IGKV1-12 | R | A | S | Q | G | I | S | S | W | L | A | W | Y | Q | Q | K | P | G | K | A | P | K | L |
| 26D5 | - | - | - | - | - | - | - | - | - | - | - | - | - | - | H | - | - | - | - | - | - | - | - |

CDR2

| | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|---|---|---|---|---|---|---|
| IGKV1-12 | L | I | Y | A | A | S | S | L | Q | S | G | V | P | S | R | F | S | G | S | G | S | G | T |
| 26D5 | - | - | - | - | - | - | - | - | - | - | - | - | - | - | - | - | - | - | - | - | - | - | - |

| | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|
| IGKV1-12 | D | F | T | L | T | I | S | S | L | Q | P | E | D | F | A | T | Y | Y | C | Q | Q | A | N |
| 26D5 | - | - | - | - | - | - | - | - | - | - | - | - | - | - | - | - | - | - | - | - | - | - | - |

CDR3

| | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|
| IGKV1-12 | S | | | | | | | | | | | | | | |
| IGHJ4 | | | | | | L | T | F | G | G | G | T | K | V | E | I | K |
| 26D5 | F | | P | L | T | F | G | G | G | T | K | V | E | I | K |

| LIGHT CHAIN | |
|---|---|
| LCDR1 | 24 25 26 27 28 29 30 31 32 33 34<br>R A S Q G I S S W L A |
| LCDR2 | NONE |
| LCDR3 | 89 90 91 92 93 94 95 96 97<br>Q Q A N S F P L T |
| HEAVY CHAIN | |
| HCDR1 | 26 27 28 29 30 31 32 33 34 35<br>G F T V S S N Y M S |
| HCDR2 | 50 51 52 53 54 55 56 57 58 59<br>F I Y S G G R T Y Y |
| HCDR3 | 95 96 97 98 99 100 101 102<br>G G F G G G D Y |

FIG. 2

| PARENTAL | Q | Q | A | N | S | F | P | L | T |
|---|---|---|---|---|---|---|---|---|---|
| COUNT OF NORM | 89 | 90 | 91 | 92 | 93 | 94 | 95 | 96 | 97 |
| * | 0.00 | 0.25 | 0.00 | 0.02 | 0.00 | 0.02 | 0.00 | 0.00 | 0.00 |
| P | 0.05 | 0.04 | 0.03 | 0.02 | 0.04 | 0.03 | 1.00 | 0.05 | 0.15 |
| G | 0.02 | 0.03 | 0.05 | 0.09 | 0.36 | 0.03 | 0.04 | 0.03 | 0.08 |
| A | 0.02 | 0.04 | 1.00 | 1.36 | 0.50 | 0.03 | 0.06 | 0.02 | 0.16 |
| C | 0.02 | 0.03 | 0.23 | 0.96 | 0.12 | 0.04 | 0.05 | 0.03 | 0.02 |
| S | 0.03 | 0.14 | 0.11 | 0.82 | 1.00 | 0.04 | 0.07 | 0.04 | 0.47 |
| T | 0.03 | 0.03 | 0.05 | 0.15 | 0.34 | 0.02 | 0.08 | 0.02 | 1.00 |
| V | 0.02 | 0.03 | 0.04 | 0.13 | 0.17 | 0.04 | 0.05 | 0.03 | 0.11 |
| L | 0.03 | 0.05 | 0.03 | 0.33 | 0.06 | 0.06 | 0.04 | 1.00 | 0.05 |
| I | 0.03 | 0.04 | 0.03 | 0.21 | 0.13 | 0.02 | 0.04 | 0.10 | 0.10 |
| M | 0.04 | 0.03 | 0.04 | 0.40 | 0.20 | 0.03 | 0.03 | 0.03 | 0.14 |
| K | 0.05 | 0.09 | 0.02 | 0.49 | 0.16 | 0.02 | 0.04 | 0.03 | 0.14 |
| R | 0.04 | 0.05 | 0.03 | 0.25 | 0.26 | 0.03 | 0.03 | 0.04 | 0.06 |
| H | 0.06 | 0.08 | 3.98 | 1.45 | 0.21 | 0.02 | 0.08 | 0.09 | 0.04 |
| F | 0.03 | 0.02 | 2.07 | 0.41 | 0.06 | 1.00 | 0.04 | 0.05 | 0.06 |
| Y | 0.03 | 0.02 | 6.54 | 0.50 | 0.08 | 0.03 | 0.05 | 0.03 | 0.04 |
| W | 0.03 | 0.03 | 0.02 | 0.74 | 0.05 | 0.07 | 0.03 | 0.03 | 0.04 |
| N | 0.03 | 0.31 | 0.03 | 1.00 | 0.68 | 0.03 | 0.03 | 0.03 | 0.12 |
| D | 0.04 | 0.00 | 0.11 | 1.46 | 0.34 | 0.04 | 0.03 | 0.02 | 0.02 |
| E | 0.03 | 0.03 | 0.02 | 0.56 | 0.70 | 0.02 | 0.04 | 0.06 | 0.04 |
| Q | 1.00 | 1.00 | 0.02 | 0.38 | 1.06 | 0.04 | 0.02 | 0.02 | 0.06 |

FIG. 3B

| PARENTAL | G | F | T | V | S | S | N | Y | M | S |
|---|---|---|---|---|---|---|---|---|---|---|
| COUNT OF NORM | | | | | | | | | | |
| | 26 | 27 | 28 | 29 | 30 | 31 | 32 | 33 | 34 | 34 |
| * | 0.00 | 0.00 | 0.00 | 0.00 | 0.00 | 0.00 | 0.00 | 0.11 | 0.00 | 0.00 |
| P | 0.04 | 0.05 | 3.88 | 0.04 | 0.02 | 0.08 | 0.02 | 3.48 | 0.02 | 0.03 |
| G | 1.01 | 0.04 | 0.93 | 0.05 | 0.15 | 1.62 | 0.17 | 2.38 | 0.03 | 0.04 |
| A | 0.14 | 0.05 | 3.71 | 0.04 | 1.49 | 0.10 | 1.89 | 5.97 | 0.05 | 0.36 |
| C | 0.11 | 0.08 | 2.77 | 0.05 | 0.36 | 0.21 | 0.07 | 1.89 | 0.05 | 0.04 |
| S | 0.34 | 0.05 | 4.38 | 0.04 | 1.01 | 1.01 | 3.13 | 5.76 | 0.05 | 1.01 |
| T | 0.73 | 0.08 | 1.01 | 0.04 | 0.86 | 3.14 | 0.46 | 0.92 | 0.12 | 0.77 |
| V | 0.16 | 0.20 | 1.33 | 1.01 | 2.24 | 0.28 | 0.37 | 0.61 | 0.09 | 0.06 |
| L | 0.09 | 2.73 | 3.58 | 1.46 | 0.34 | 1.61 | 0.07 | 2.74 | 0.07 | 0.05 |
| I | 0.14 | 3.50 | 2.09 | 2.97 | 2.48 | 0.49 | 0.07 | 0.61 | 0.14 | 0.04 |
| M | 0.04 | 2.88 | 4.03 | 1.10 | 1.45 | 1.12 | 0.07 | 4.93 | 1.01 | 0.03 |
| K | 0.07 | 0.03 | 4.10 | 0.00 | 0.74 | 4.29 | 0.04 | 0.32 | 0.09 | 0.02 |
| R | 0.12 | 0.04 | 4.08 | 0.03 | 0.33 | 2.91 | 0.04 | 0.42 | 0.05 | 0.04 |
| H | 0.23 | 0.02 | 4.25 | 0.05 | 0.38 | 3.03 | 1.74 | 4.99 | 0.00 | 0.03 |
| F | 0.09 | 1.01 | 2.91 | 0.07 | 0.98 | 0.12 | 0.40 | 0.84 | 0.43 | 0.04 |
| Y | 0.12 | 0.05 | 3.74 | 0.04 | 1.13 | 0.17 | 0.45 | 1.01 | 0.11 | 0.04 |
| W | 0.11 | 0.05 | 3.09 | 0.06 | 1.44 | 0.07 | 0.25 | 0.55 | 0.12 | 0.04 |
| N | 0.18 | 0.02 | 4.43 | 0.03 | 0.13 | 4.28 | 1.01 | 2.34 | 0.00 | 0.06 |
| D | 0.07 | 0.04 | 5.72 | 0.03 | 0.09 | 4.33 | 0.05 | 5.83 | 0.05 | 0.05 |
| E | 0.05 | 0.03 | 5.23 | 0.04 | 0.89 | 5.58 | 0.16 | 4.80 | 0.03 | 0.07 |
| Q | 0.12 | 0.02 | 6.00 | 0.00 | 1.34 | 4.19 | 0.11 | 4.05 | 0.03 | 0.07 |

FIG. 3C

| PARENTAL | F | I | Y | S | G | G | R | T | Y | Y |
|---|---|---|---|---|---|---|---|---|---|---|
| COUNT OF NORM | 50 | 51 | 52 | 53 | 54 | 55 | 56 | 57 | 58 | 59 |
| * | 0.00 | 0.00 | 0.00 | 0.00 | 0.00 | 0.00 | 0.00 | 0.00 | 0.00 | 0.06 |
| P | 0.01 | 0.03 | 0.05 | 4.51 | 0.86 | 1.05 | 0.16 | 0.22 | 0.11 | 0.08 |
| G | 0.03 | 0.03 | 0.07 | 0.51 | 1.01 | 1.01 | 0.39 | 0.21 | 0.05 | 0.45 |
| A | 0.03 | 0.09 | 0.04 | 1.34 | 1.41 | 0.48 | 2.01 | 1.03 | 0.06 | 0.60 |
| C | 0.04 | 0.02 | 0.15 | 0.42 | 0.83 | 0.18 | 0.23 | 0.21 | 0.20 | 0.24 |
| S | 0.04 | 0.13 | 0.05 | 1.01 | 2.40 | 0.44 | 1.48 | 0.88 | 0.08 | 0.66 |
| T | 0.02 | 0.71 | 0.07 | 2.36 | 1.09 | 0.35 | 2.22 | 1.01 | 0.13 | 0.92 |
| V | 0.04 | 0.90 | 0.05 | 1.54 | 0.99 | 0.22 | 0.97 | 1.28 | 0.31 | 0.75 |
| L | 0.07 | 0.21 | 0.08 | 0.44 | 1.25 | 0.43 | 1.27 | 0.76 | 0.16 | 0.69 |
| I | 0.07 | 1.01 | 0.04 | 1.93 | 1.11 | 0.16 | 1.04 | 0.78 | 0.16 | 0.39 |
| M | 0.11 | 0.20 | 0.49 | 1.01 | 1.42 | 0.27 | 2.36 | 1.39 | 0.14 | 0.52 |
| K | 0.00 | 0.00 | 0.00 | 0.88 | 0.99 | 0.22 | 1.36 | 1.66 | 0.08 | 0.77 |
| R | 0.05 | 0.04 | 0.01 | 0.49 | 0.83 | 0.23 | 1.01 | 1.17 | 0.05 | 0.47 |
| H | 0.03 | 0.00 | 0.12 | 0.52 | 0.89 | 0.30 | 1.97 | 0.48 | 0.59 | 0.85 |
| F | 1.01 | 0.13 | 0.45 | 0.25 | 0.50 | 0.21 | 1.30 | 0.54 | 2.83 | 0.98 |
| Y | 1.37 | 0.04 | 1.01 | 0.38 | 0.56 | 0.28 | 1.47 | 0.40 | 1.01 | 1.01 |
| W | 0.07 | 0.04 | 0.07 | 0.46 | 0.98 | 0.16 | 2.12 | 0.13 | 0.05 | 0.36 |
| N | 0.03 | 0.10 | 0.07 | 0.44 | 2.36 | 0.23 | 1.82 | 0.71 | 0.09 | 0.19 |
| D | 0.04 | 0.02 | 0.08 | 1.38 | 1.62 | 0.24 | 1.89 | 0.30 | 0.08 | 0.42 |
| E | 0.05 | 0.04 | 0.07 | 0.50 | 1.31 | 0.20 | 2.80 | 0.70 | 1.10 | 0.51 |
| Q | 0.02 | 0.06 | 0.04 | 0.92 | 1.40 | 0.35 | 3.30 | 1.06 | 0.25 | 0.58 |

FIG. 3D

| PARENTAL | G | G | F | G | G | G | D | Y |
|---|---|---|---|---|---|---|---|---|
| COUNT OF NORM | 95 | 96 | 97 | 98 | 99 | 100 | 101 | 102 |
| * | 0.00 | 0.00 | 0.00 | 0.02 | 0.00 | 0.00 | 0.03 | 0.03 |
| P | 0.02 | 0.02 | 0.02 | 0.02 | 0.04 | 1.82 | 0.02 | 0.03 |
| G | 1.00 | 1.00 |  | 1.00 | 1.00 | 1.00 | 0.05 | 0.03 |
| A | 4.24 | 0.03 | 0.04 | 0.04 | 0.16 | 0.21 | 0.04 | 0.41 |
| C | 0.07 | 0.10 | 0.03 | 0.05 | 0.27 | 0.04 | 0.03 | 0.38 |
| S | 0.04 | 0.03 | 0.03 | 0.05 | 0.21 | 0.04 | 0.03 | 0.70 |
| T | 0.02 | 0.02 | 0.03 | 0.04 | 0.11 | 0.05 | 0.02 | 1.93 |
| V | 0.03 | 0.03 | 0.02 | 0.05 | 0.10 | 0.09 | 0.03 | 1.44 |
| L | 0.02 | 0.03 | 0.04 | 0.03 | 0.19 | 0.01 | 0.02 | 0.37 |
| I | 0.02 | 0.03 | 0.02 | 0.04 | 0.07 | 0.03 | 0.04 | 1.62 |
| M | 0.01 | 0.08 | 0.00 | 0.04 | 0.23 | 0.04 | 0.05 | 0.15 |
| K | 0.03 | 0.01 | 0.03 | 0.03 | 0.15 | 0.33 | 0.05 | 0.04 |
| R | 0.06 | 0.03 | 0.02 | 0.03 | 0.29 | 0.25 | 0.04 | 0.03 |
| H | 0.02 | 0.03 | 0.03 | 0.04 | 0.32 | 0.00 | 0.04 | 1.40 |
| F | 0.04 | 0.02 | 1.00 | 0.04 | 0.13 | 0.03 | 0.04 | 0.40 |
| Y | 0.02 | 0.02 | 0.03 | 0.03 | 0.15 | 0.03 | 0.07 | 1.00 |
| W | 0.04 | 0.18 |  | 0.05 | 0.15 | 0.03 | 0.03 | 1.33 |
| N | 0.03 | 0.14 | 0.03 | 0.04 | 0.60 | 0.05 | 0.03 | 0.93 |
| D | 0.03 | 0.11 | 0.00 | 0.10 | 0.91 | 0.34 | 1.00 | 0.48 |
| E | 0.08 | 0.05 | 0.00 | 0.06 | 0.29 | 0.60 | 0.04 | 0.06 |
| Q | 0.03 | 0.03 | 0.04 | 0.04 | 0.50 | 0.09 | 0.05 | 0.07 |

| KABAT | | HCDR1 | HCDR2 |
|---|---|---|---|
| | 5....10....15....20....25....30....35....40....45....50....55....60 | | |
| | EVQLVESGGALIQPGGSLRLSCAASGFTVSSNYMSWVRQAPGKGLEWVSFIYSGGRTYYA | | |
| 26D5 | ------------------------------------------------------------ | | |
| 26D5-GV-Q | --------G--------------------------------------------------- | | |
| 26D5-295-A08 | --------G-------------------E----------------P-------------- | | |
| 26D5-295-B08 | --------G-------------------A----------------P-------------- | | |
| 26D5-295-C07 | --------G----------------Q--A----------------P-------------- | | |
| 26D5-295-C08 | --------G----------------Q--E------------------------------- | | |
| 26D5-295-D07 | --------G----------------Q--A------------------------------- | | |
| 26D5-295-E07 | --------G----------------Q-HE-A----------------------------- | | |
| 26D5-295-F07 | --------G----------------Q--A----------------P-------------- | | |
| 26D5-295-G07 | --------G----------------Q--A------------------------------- | | |
| 26D5-295-H07 | --------G----------------Q--A----------------P-------------- | | |
| 26D5-296-A07 | --------G-------------------A----------------P-------------- | | |
| 26D5-296-B07 | --------G----------------Q--A----------------P-------------- | | |
| 26D5-296-C07 | --------G----------------Q-------------------P-------------- | | |
| 26D5-296-C08 | --------G----------------Q-----------------------E-F-------- | | |
| 26D5-296-D03 | --------G--------------------------------------------------- | | |
| 26D5-296-D08 | --------G------------------------------------P----E-------- | | |
| 26D5-296-F03 | --------G----------------Q---------------------------------- | | |
| 26D5-296-F07 | --------G----------------Q--E------------------------------- | | |
| 26D5-296-F08 | --------G--------------------------------------------------- | | |
| 26D5-296-G03 | --------G----------------Q-------------------P----P-------- | | |
| 26D5-296-G07 | --------G--------------------------------------------------- | | |
| 26D5-296-G08 | --------G------------------------------------P-------------- | | |
| 26D5-296-H03 | --------G-------------------A---------------------P-------- | | |

FIG. 4A CONT.

| KABAT | 65 — 70 — 75 — 80 — 82a-b-c — 85 — 90 — 95 — 100 — 105 — 110 — 113 |
|---|---|
| | HCDR2                                                              HCDR3 |
| 26D5 | DSVKGRFTISRDNSKNTLYLQMNSLRAEDTAMYYCARGGFGGGDYWGQGTLVTVSS |
| 26D5-GV-Q | --------------------------------V---------------------- |
| 26D5-295-A08 | --------------------------------V----A----------------- |
| 26D5-295-B08 | --------------------------------V----A----------------- |
| 26D5-295-C07 | --------------------------------V---------------------- |
| 26D5-295-C08 | --------------------------------V---------------------- |
| 26D5-295-D07 | --------------------------------V---------------------- |
| 26D5-295-E07 | --------------------------------V---------------------- |
| 26D5-295-F07 | --------------------------------V---------------------- |
| 26D5-295-G07 | --------------------------------V----A----------------- |
| 26D5-295-H07 | --------------------------------V----A----------------- |
| 26D5-296-A07 | --------------------------------V----A----------------- |
| 26D5-296-B07 | --------------------------------V---------------------- |
| 26D5-296-C07 | --------------------------------V---------------------- |
| 26D5-296-C08 | --------------------------------V---------------------- |
| 26D5-296-D03 | --------------------------------V----A----------------- |
| 26D5-296-D08 | --------------------------------V----A----------------- |
| 26D5-296-F03 | --------------------------------V----A----------------- |
| 26D5-296-F07 | --------------------------------V---------------------- |
| 26D5-296-F08 | --------------------------------V----A----------------- |
| 26D5-296-G03 | --------------------------------V----A----------------- |
| 26D5-296-G07 | --------------------------------V----A----------------- |
| 26D5-296-G08 | --------------------------------V----A----------------- |
| 26D5-296-H03 | --------------------------------V----A----------------- |

| KABAT | | DIQMTQSPSSVSASVGDRVTITCRASQGISSWLAWYQHKPGKAPKLLIYAASSLQSGVPS |
|---|---|---|
| | | LCDR1 LCDR2 |
| 26D5 | | ------------------------------------------------------------ |
| 26D5-GV-Q | | -------------------------------Q---------------------------- |
| 26D5-295-A08 | | ----------------------------N--Q---------------------------- |
| 26D5-295-B08 | | ----------------------------N--Q---------------------------- |
| 26D5-295-C07 | | ----------------------------N--Q---------------------------- |
| 26D5-295-C08 | | ----------------------------N--Q---------------------------- |
| 26D5-295-D07 | | ----------------------------N--Q---------------------------- |
| 26D5-295-E07 | | ----------------------------N--Q---------------------------- |
| 26D5-295-F07 | | ----------------------------N--Q---------------------------- |
| 26D5-295-G07 | | ----------------------------N--Q---------------------------- |
| 26D5-295-H07 | | ----------------------------N--Q---------------------------- |
| 26D5-296-A07 | | -------------------------Y-E-N--Q---------------------------- |
| 26D5-296-B07 | | -------------------------Y-E-N--Q---------------------------- |
| 26D5-296-C07 | | ----------------------------N--Q---------------------------- |
| 26D5-296-C08 | | -------------------------Y-E-N--Q---------------------------- |
| 26D5-296-D03 | | ----------------------------N--Q---------------------------- |
| 26D5-296-D08 | | -------------------------Y-E-N--Q---------------------------- |
| 26D5-296-E03 | | ----------------------------N--Q---------------------------- |
| 26D5-296-F07 | | -------------------------Y-E-N--Q---------------------------- |
| 26D5-296-F08 | | ----------------------------N--Q---------------------------- |
| 26D5-296-G03 | | -------------------------Y-E-N--Q---------------------------- |
| 26D5-296-G07 | | ----------------------------N--Q---------------------------- |
| 26D5-296-G08 | | -------------------------Y-E-N--Q---------------------------- |
| 26D5-296-H03 | | ----------------------------N--Q---------------------------- |

FIG. 4B

| KABAT | 65 — 70 — 75 — 80 — 85 — 90 — 95 — 100 — 105-107 |
|---|---|
| |                                     LCDR3 |
| 26D5 | RESGSGSGTDFTLTISSLQPEDFATYYCQQANSFPLTFGGGTKVEIK |
| 26D5-GV-Q | ---------------------------------------------- |
| 26D5-295-A08 | ---------------------------------------------- |
| 26D5-295-B08 | ---------------------------------------------- |
| 26D5-295-C07 | ---------------------------------------------- |
| 26D5-295-C08 | ---------------------------------------------- |
| 26D5-295-D07 | ---------------------------------------------- |
| 26D5-295-E07 | ---------------------------------------------- |
| 26D5-295-F07 | ---------------------------------------------- |
| 26D5-295-G07 | ---------------------------------------------- |
| 26D5-295-H07 | ---------------------------------------------- |
| 26D5-296-A07 | ------------------------------H--------------- |
| 26D5-296-B07 | ------------------------------H--------------- |
| 26D5-296-C07 | ---------------------------------------------- |
| 26D5-296-C08 | ---------------------------------------------- |
| 26D5-296-D03 | ---------------------------------------------- |
| 26D5-296-D08 | ---------------------------------------------- |
| 26D5-296-F03 | ---------------------------------------------- |
| 26D5-296-F07 | ---------------------------------------------- |
| 26D5-296-F08 | ---------------------------------------------- |
| 26D5-296-G03 | ---------------------------------------------- |
| 26D5-296-G07 | ---------------------------------------------- |
| 26D5-296-G08 | ---------------------------------------------- |
| 26D5-296-H03 | ---------------------------------------------- |

*FIG. 4B CONT.*

| | | |
|---|---|---|
| LIGHT CHAIN | | |
| LCDR1 AND ADJACENT FRAMEWORK | 24 25 26 27 28 29 30 31 32 33 34 35 36<br>R A S Q G I S S N L A W Y | |
| LCDR2 AND ADJACENT FRAMEWORK | 46 47 48 49 50 51 52 53 54 55 56<br>L L I Y A A S S L Q S | |
| LCDR3 AND ADJACENT FRAMEWORK | 89 90 91 92 93 94 95 96 97 98<br>Q Q A N S F P L T F | |
| HEAVY CHAIN | | |
| HCDR1 AND ADJACENT FRAMEWORK | 26 27 28 29 30 31 32 33 34 35 36 37<br>G F T V S S N A M S W V | |
| HCDR2 AND ADJACENT FRAMEWORK | 47 48 49 50 51 52 53 54 55 56 57 58 59<br>W V S F I Y P G G R T Y Y | |
| HCDR3 AND ADJACENT FRAMEWORK | 93 94 95 96 97 98 99 100 101 102 103<br>A R A G F G G G D Y W | |

| PARENTAL | L | L | I | Y | A | A | S | S | L | Q | S |
|---|---|---|---|---|---|---|---|---|---|---|---|
| COUNT OF NORM | | | | | | | | | | | |
| | 46 | 47 | 48 | 49 | 50 | 51 | 52 | 53 | 54 | 55 | 56 |
| * | 0.04 | 0.00 | 0.00 | 0.48 | 0.07 | 0.00 | 0.00 | 0.00 | 0.19 | 0.00 | 0.09 |
| P | 0.05 | 0.10 | 0.03 | 0.05 | 0.14 | 0.07 | 0.05 | 0.20 | 0.38 | 0.41 | 0.80 |
| G | 0.11 | 0.15 | 0.18 | 0.08 | 0.84 | 0.88 | 0.56 | 0.44 | 0.32 | 0.39 | 0.95 |
| A | 0.16 | 0.34 | 0.51 | 0.21 | 1.00 | 1.00 | 0.75 | 0.86 | 0.44 | 0.52 | 0.99 |
| C | 0.32 | 0.65 | 0.15 | 0.18 | 0.40 | 0.43 | 0.98 | 1.39 | 0.38 | 0.31 | 1.53 |
| S | 0.33 | 0.27 | 0.31 | 0.25 | 0.86 | 0.96 | 1.00 | 1.00 | 0.42 | 0.43 | 1.00 |
| T | 0.46 | 0.31 | 0.28 | 0.20 | 0.41 | 0.49 | 1.11 | 3.48 | 0.42 | 0.35 | 1.11 |
| V | 0.33 | 0.46 | 1.02 | 0.15 | 0.24 | 0.30 | 0.85 | 2.60 | 0.74 | 0.30 | 0.74 |
| L | 1.00 | 1.00 | 0.94 | 0.13 | 0.49 | 0.18 | 0.56 | 1.51 | 1.00 | 0.46 | 0.88 |
| I | 0.35 | 0.44 | 1.00 | 0.23 | 0.26 | 0.21 | 0.57 | 2.29 | 1.03 | 0.36 | 0.89 |
| M | 0.29 | 0.46 | 0.77 | 0.18 | 0.57 | 0.42 | 0.90 | 1.19 | 0.58 | 0.32 | 1.36 |
| K | 0.00 | 0.29 | 0.19 | 0.27 | 0.26 | 0.40 | 1.12 | 1.39 | 0.45 | 0.21 | 1.02 |
| R | 0.03 | 0.38 | 0.09 | 0.16 | 0.73 | 0.29 | 0.84 | 1.50 | 0.67 | 0.33 | 1.27 |
| H | 0.41 | 0.41 | 0.21 | 0.30 | 2.52 | 0.16 | 0.78 | 0.75 | 0.43 | 0.37 | 1.08 |
| F | 0.04 | 0.46 | 0.31 | 0.67 | 3.90 | 0.14 | 0.53 | 0.82 | 0.41 | 0.32 | 1.23 |
| Y | 0.04 | 0.31 | 0.29 | 1.00 | 6.41 | 0.14 | 0.47 | 0.67 | 0.40 | 0.24 | 1.06 |
| W | 0.04 | 0.31 | 0.18 | 0.48 | 3.17 | 0.09 | 0.72 | 0.68 | 0.45 | 0.30 | 1.74 |
| N | 0.40 | 0.23 | 0.21 | 0.15 | 1.23 | 0.17 | 0.82 | 0.82 | 0.55 | 0.62 | 0.74 |
| D | 0.07 | 0.06 | 0.09 | 0.18 | 1.61 | 0.09 | 0.71 | 0.29 | 0.22 | 0.44 | 0.98 |
| E | 0.03 | 0.17 | 0.06 | 0.13 | 1.22 | 0.29 | 1.09 | 0.72 | 0.27 | 0.47 | 1.06 |
| Q | 0.13 | 0.40 | 0.27 | 0.13 | 0.53 | 0.19 | 0.95 | 0.95 | 0.43 | 1.00 | 1.02 |

*FIG. 6B*

| PARENTAL | Q | Q | A | N | S | F | P | L | T | F |
|---|---|---|---|---|---|---|---|---|---|---|
| COUNT OF NORM | | | | | | | | | | |
| | 89 | 90 | 91 | 92 | 93 | 94 | 95 | 96 | 97 | 98 |
| * | 0.00 | 0.22 | 0.04 | 0.06 | 0.00 | 0.00 | 0.00 | 0.00 | 0.00 | 0.05 |
| P | 0.02 | 0.08 | 0.02 | 0.02 | 0.03 | 0.01 | 1.00 | 0.13 | 0.28 | 0.05 |
| G | 0.20 | 0.24 | 0.40 | 0.33 | 0.96 | 0.02 | 0.23 | 0.02 | 0.51 | 0.01 |
| A | 0.02 | 0.39 | 1.00 | 0.29 | 0.55 | 0.01 | 0.47 | 0.03 | 0.53 | 0.03 |
| C | 0.02 | 0.18 | 0.28 | 0.35 | 0.67 | 0.04 | 0.13 | 0.03 | 0.34 | 0.16 |
| S | 0.09 | 0.98 | 0.84 | 0.34 | 1.00 | 0.00 | 0.32 | 0.03 | 0.65 | 0.02 |
| T | 0.00 | 0.20 | 0.26 | 0.27 | 0.58 | 0.00 | 0.14 | 0.04 | 1.00 | 0.05 |
| V | 0.02 | 0.04 | 0.15 | 0.19 | 0.38 | 0.01 | 0.11 | 0.06 | 0.50 | 0.18 |
| L | 0.02 | 0.09 | 0.04 | 0.27 | 0.40 | 0.10 | 0.08 | 1.00 | 0.36 | 0.39 |
| I | 0.03 | 0.04 | 0.09 | 0.30 | 0.51 | 0.12 | 0.07 | 0.10 | 0.52 | 0.34 |
| M | 0.04 | 0.20 | 0.19 | 0.41 | 0.49 | 0.15 | 0.17 | 0.11 | 0.65 | 0.26 |
| K | 0.08 | 0.31 | 0.07 | 0.41 | 0.42 | 0.04 | 0.13 | 0.00 | 0.42 | 0.03 |
| R | 0.03 | 0.13 | 0.01 | 0.23 | 0.36 | 0.03 | 0.11 | 0.78 | 0.38 | 0.02 |
| H | 0.13 | 0.25 | 0.49 | 1.06 | 1.55 | 0.04 | 0.06 | 0.14 | 0.33 | 0.11 |
| F | 0.03 | 0.02 | 0.21 | 0.21 | 0.36 | 1.00 | 0.04 | 0.08 | 0.25 | 1.00 |
| Y | 0.01 | 0.04 | 0.25 | 0.33 | 0.38 | 0.23 | 0.03 | 0.03 | 0.35 | 0.32 |
| W | 0.02 | 0.12 | 0.01 | 0.33 | 0.52 | 0.43 | 0.04 | 0.02 | 0.20 | 0.38 |
| N | 0.03 | 1.49 | 0.02 | 1.00 | 1.48 | 0.00 | 0.20 | 0.02 | 0.49 | 0.02 |
| D | 0.03 | 0.12 | 0.15 | 1.02 | 0.73 | 0.02 | 0.23 | 0.03 | 0.15 | 0.02 |
| E | 0.06 | 0.48 | 0.00 | 0.50 | 1.73 | 0.03 | 0.12 | 0.03 | 0.40 | 0.02 |
| Q | 1.00 | 1.00 | 0.05 | 0.32 | 1.73 | 0.04 | 0.18 | 0.00 | 0.43 | 0.03 |

FIG. 6C

| PARENTAL | G | F | T | V | S | S | N | A | M | S | W | V |
|---|---|---|---|---|---|---|---|---|---|---|---|---|
| COUNT OF NORM | 26 | 27 | 28 | 29 | 30 | 31 | 32 | 33 | 34 | 35 | 36 | 37 |
| * | 0.00 | 0.00 | 0.00 | 0.00 | 0.17 | 0.00 | 0.09 | 0.00 | 0.00 | 0.00 | 0.26 | 0.00 |
| P | 0.35 | 0.40 | 1.46 | 0.28 | 0.61 | 0.41 | 0.23 | 1.49 | 0.01 | 0.14 | 0.06 | 0.13 |
| G | 1.00 | 0.37 | 1.03 | 0.30 | 0.88 | 0.88 | 0.35 | 0.49 | 0.47 | 0.05 | 0.29 | 0.13 |
| A | 0.68 | 0.37 | 0.99 | 0.37 | 1.40 | 1.24 | 0.49 | 1.00 | 0.47 | 0.50 | 0.42 | 0.25 |
| C | 0.73 | 0.49 | 1.24 | 0.51 | 1.46 | 1.45 | 0.76 | 4.55 | 0.56 | 0.20 | 0.49 | 0.16 |
| S | 0.60 | 0.34 | 1.32 | 0.26 | 1.00 | 1.00 | 0.50 | 1.79 | 0.37 | 1.00 | 0.37 | 0.18 |
| T | 0.62 | 0.45 | 1.00 | 0.59 | 1.00 | 0.98 | 0.47 | 0.42 | 0.38 | 0.53 | 0.60 | 0.30 |
| V | 0.79 | 0.77 | 1.15 | 1.00 | 0.99 | 0.96 | 0.62 | 0.32 | 0.46 | 0.30 | 0.49 | 1.00 |
| L | 0.92 | 1.80 | 1.33 | 0.86 | 1.10 | 1.38 | 0.35 | 1.07 | 0.54 | 0.02 | 0.40 | 0.79 |
| I | 0.73 | 2.23 | 1.19 | 0.76 | 1.10 | 1.11 | 0.39 | 0.22 | 0.51 | 0.06 | 0.61 | 1.54 |
| M | 0.65 | 1.77 | 1.16 | 1.09 | 1.00 | 1.34 | 0.53 | 6.93 | 1.00 | 0.00 | 0.58 | 0.37 |
| K | 0.58 | 0.26 | 1.31 | 0.17 | 1.19 | 1.38 | 0.68 | 6.00 | 0.41 | 0.05 | 0.38 | 0.06 |
| R | 0.71 | 0.35 | 1.01 | 0.14 | 1.05 | 1.29 | 0.59 | 0.74 | 0.33 | 0.03 | 0.45 | 0.03 |
| H | 0.60 | 0.41 | 0.75 | 0.24 | 1.76 | 1.11 | 1.50 | 0.45 | 0.49 | 0.05 | 0.42 | 0.00 |
| F | 0.86 | 1.00 | 1.34 | 0.34 | 0.95 | 1.13 | 1.31 | 0.28 | 1.16 | 0.03 | 1.11 | 0.02 |
| Y | 0.66 | 0.30 | 0.78 | 0.31 | 0.95 | 0.74 | 1.74 | 0.33 | 0.35 | 0.02 | 1.20 | 0.03 |
| W | 0.73 | 0.39 | 1.48 | 0.48 | 0.82 | 1.20 | 1.07 | 0.64 | 0.98 | 0.00 | 1.00 | 0.00 |
| N | 0.67 | 0.40 | 1.11 | 0.24 | 0.74 | 1.11 | 1.00 | 0.35 | 0.16 | 0.00 | 0.35 | 0.00 |
| D | 0.61 | 0.61 | 1.36 | 0.17 | 1.00 | 1.11 | 0.49 | 0.87 | 0.03 | 0.08 | 0.05 | 0.00 |
| E | 0.74 | 0.39 | 1.64 | 0.13 | 0.88 | 1.71 | 0.88 | 1.11 | 0.36 | 0.06 | 0.46 | 0.00 |
| Q | 0.57 | 0.38 | 1.19 | 0.29 | 1.19 | 1.07 | 0.72 | 5.38 | 0.45 | 0.00 | 0.20 | 0.08 |

| PARENTAL | W | V | S | F | I | Y | P | G | G | R | T | Y | Y |
|---|---|---|---|---|---|---|---|---|---|---|---|---|---|
| COUNT OF NORM | 47 | 48 | 49 | 50 | 51 | 52 | 53 | 54 | 55 | 56 | 57 | 58 | 59 |
| * | 0.28 | 0.13 | 0.00 | 0.11 | 0.00 | 0.15 | 0.00 | 0.13 | 0.19 | 0.12 | 0.18 | 0.20 | 0.19 |
| P | 0.02 | 0.10 | 0.04 | 0.00 | 0.29 | 0.29 | 1.00 | 0.50 | 0.67 | 0.89 | 0.38 | 0.59 | 0.29 |
| G | 0.19 | 0.44 | 0.51 | 0.02 | 0.45 | 0.33 | 0.45 | 1.00 | 1.00 | 0.62 | 0.51 | 0.29 | 0.59 |
| A | 0.03 | 0.57 | 1.15 | 0.00 | 0.38 | 0.40 | 0.88 | 1.34 | 0.74 | 0.91 | 0.93 | 0.27 | 0.61 |
| C | 0.10 | 0.65 | 0.67 | 0.19 | 0.45 | 0.47 | 0.47 | 1.29 | 1.21 | 0.76 | 0.84 | 0.72 | 0.57 |
| S | 0.11 | 0.83 | 1.00 | 0.05 | 0.36 | 0.41 | 0.73 | 1.01 | 0.85 | 1.02 | 1.28 | 0.29 | 0.59 |
| T | 0.05 | 0.42 | 0.63 | 0.08 | 0.47 | 0.52 | 0.63 | 1.04 | 0.85 | 0.87 | 1.00 | 0.36 | 0.50 |
| V | 0.04 | 1.00 | 0.53 | 0.09 | 0.84 | 0.59 | 0.53 | 1.05 | 0.55 | 0.92 | 0.92 | 0.42 | 0.49 |
| L | 0.04 | 0.37 | 0.33 | 0.38 | 0.93 | 0.72 | 0.47 | 1.17 | 1.11 | 0.96 | 0.78 | 0.44 | 0.51 |
| I | 0.04 | 0.47 | 0.45 | 0.37 | 1.00 | 0.75 | 0.44 | 1.12 | 0.55 | 0.99 | 0.45 | 0.49 | 0.37 |
| M | 0.04 | 0.42 | 0.52 | 0.36 | 0.73 | 0.30 | 0.42 | 0.97 | 0.95 | 1.23 | 1.14 | 0.41 | 0.53 |
| K | 0.46 | 0.24 | 0.36 | 0.07 | 0.38 | 0.41 | 0.66 | 1.62 | 1.18 | 0.85 | 1.58 | 0.24 | 0.46 |
| R | 0.00 | 0.57 | 0.18 | 0.02 | 0.30 | 0.22 | 0.59 | 1.36 | 0.91 | 1.00 | 1.09 | 0.33 | 0.73 |
| H | 0.11 | 0.24 | 0.48 | 0.09 | 0.41 | 0.44 | 0.31 | 1.20 | 0.74 | 1.08 | 0.76 | 0.88 | 0.61 |
| F | 0.24 | 0.35 | 0.39 | 0.00 | 0.48 | 0.40 | 0.53 | 1.09 | 0.62 | 0.72 | 0.79 | 1.03 | 0.53 |
| Y | 0.56 | 0.34 | 0.63 | 0.37 | 0.46 | 1.00 | 0.64 | 1.16 | 0.90 | 0.83 | 0.80 | 1.00 | 1.00 |
| W | 0.09 | 0.29 | 0.43 | 0.04 | 0.49 | 0.30 | 0.51 | 0.75 | 0.93 | 0.75 | 0.70 | 0.37 | 0.39 |
| N | 1.00 | 1.12 | 0.53 | 0.00 | 0.48 | 0.26 | 0.53 | 1.07 | 1.12 | 1.03 | 0.64 | 0.25 | 0.39 |
| D | 0.11 | 0.51 | 0.35 | 0.00 | 0.49 | 0.43 | 0.39 | 1.07 | 0.82 | 1.02 | 1.02 | 0.36 | 0.62 |
| E | 0.00 | 0.38 | 0.37 | 0.00 | 0.46 | 0.40 | 0.89 | 1.46 | 0.81 | 1.39 | 1.00 | 0.59 | 0.51 |
| Q | 0.06 | 0.73 | 0.36 | 0.00 | 0.61 | 0.28 | 0.53 | 1.30 | 0.65 | 1.30 | 1.14 | 0.37 | 0.46 |

| PARENTAL | A | R | A | G | F | G | G | G | D | Y | W |
|---|---|---|---|---|---|---|---|---|---|---|---|
| COUNT OF NORM | 93 | 94 | 95 | 96 | 97 | 98 | 99 | 100 | 101 | 102 | 103 |
| * | 0.00 | 0.06 | 0.00 | 0.07 | 0.00 | 0.00 | 0.08 | 0.00 | 0.00 | 0.35 | 0.23 |
| P | 0.46 | 0.09 | 0.00 | 0.09 | 0.00 | 0.36 | 0.47 | 5.60 | 0.14 | 0.36 | 0.07 |
| G | 0.31 | 0.44 | 0.73 | 1.00 | 0.00 | 1.00 | 1.00 | 1.00 | 0.38 | 0.44 | 0.35 |
| A | 1.00 | 0.42 | 1.00 | 0.47 | 0.00 | 0.46 | 0.48 | 1.41 | 0.31 | 0.45 | 0.13 |
| C | 1.49 | 1.44 | 0.07 | 2.41 | 0.05 | 0.41 | 0.82 | 0.21 | 0.19 | 0.57 | 0.17 |
| S | 0.45 | 0.39 | 0.30 | 0.35 | 0.02 | 0.43 | 0.45 | 0.63 | 0.37 | 0.45 | 0.20 |
| T | 0.46 | 0.29 | 0.10 | 0.41 | 0.00 | 0.45 | 0.47 | 0.84 | 0.29 | 0.48 | 0.42 |
| V | 0.50 | 0.44 | 0.10 | 1.63 | 0.02 | 0.67 | 0.36 | 1.09 | 0.17 | 0.49 | 0.27 |
| L | 0.30 | 0.44 | 0.02 | 0.95 | 0.16 | 0.39 | 0.58 | 0.05 | 0.02 | 0.52 | 0.04 |
| I | 0.47 | 0.48 | 0.00 | 1.00 | 0.02 | 0.42 | 0.48 | 0.43 | 0.05 | 0.46 | 0.28 |
| M | 0.20 | 0.45 | 0.00 | 3.08 | 0.05 | 0.43 | 0.54 | 0.10 | 0.08 | 0.54 | 0.13 |
| K | 0.00 | 2.22 | 0.00 | 0.46 | 0.00 | 0.31 | 0.51 | 1.30 | 0.08 | 0.34 | 0.14 |
| R | 0.02 | 1.00 | 0.04 | 0.43 | 0.00 | 0.35 | 0.52 | 1.09 | 0.09 | 0.33 | 0.35 |
| H | 0.03 | 0.49 | 0.03 | 0.66 | 0.00 | 0.24 | 0.75 | 0.14 | 0.31 | 0.41 | 0.15 |
| F | 0.25 | 0.48 | 0.03 | 1.32 | 1.00 | 0.42 | 0.50 | 0.01 | 0.09 | 0.71 | 0.15 |
| Y | 0.17 | 0.43 | 0.03 | 0.67 | 0.25 | 0.36 | 0.16 | 0.29 | 0.21 | 1.00 | 0.03 |
| W | 0.09 | 0.55 | 0.04 | 2.33 | 0.41 | 0.39 | 0.32 | 0.15 | 0.00 | 0.66 | 1.00 |
| N | 0.17 | 0.47 | 0.05 | 0.42 | 0.00 | 0.36 | 2.27 | 0.49 | 0.47 | 0.29 | 0.00 |
| D | 0.03 | 0.06 | 0.08 | 0.50 | 0.00 | 0.36 | 0.66 | 1.41 | 1.00 | 0.36 | 0.00 |
| E | 0.10 | 0.38 | 0.16 | 2.03 | 0.00 | 0.57 | 0.45 | 1.28 | 0.50 | 0.32 | 0.00 |
| Q | 0.00 | 0.41 | 0.00 | 0.83 | 0.00 | 0.43 | 0.50 | 1.27 | 0.47 | 0.38 | 0.00 |

FIG. 6F

| LIGHT CHAIN | | |
|---|---|---|
| LCDR1 AND ADJACENT FRAMEWORK | 32 33 34 35 36<br>N L A W Y | (50% W AT 32) |
| LCDR2 AND ADJACENT FRAMEWORK | 46 50 55<br>L A Q | |
| LCDR3 | 91 92 93<br>A N S | (50% H AT 91) |
| HEAVY CHAIN | | |
| HCDR1 AND ADJACENT FRAMEWORK | 33 34 35 36 37<br>A M S W V | (50% Y AT 33) |
| HCDR2 AND ADJACENT FRAMEWORK | 47 48 49 50 51<br>W V S F I | (50% S AT 53) |
| HCDR3 AND ADJACENT FRAMEWORK | 93 94 95 96 97<br>A R A G F | (50% G AT 95) |

*FIG. 7A*

| HEAVY CHAIN | |
|---|---|
| HCDR3 AND ADJACENT FRAMEWORK | 93 94 95 96 97 98 99 100 101 102 103<br>A R A G F G G G D Y W |

*FIG. 7B*

| KABAT | | HCDR1 | HCDR2 |
|---|---|---|---|
| | 5   10   15   20   25   30   35   40   45   50   55   60 | | |
| 26D5 | EVQLVESGGALIQPGGSLRLSCAASGFTVSSNTMSWVRQAPGKGLEWVSFIYSGGRTYYA | | |
| 26D5-GV-Q | ----------G------------------------------------------------ | | |
| 26D5-295-B08 | ----------G--------------------A--------------------------P | | |
| 26D5-75202-343-A09 | ----------G--------------------A-----------------Y--------P | | |
| 26D5-75229-343-A10 | ----------G--------------------A-----------------Y--------P | | |
| 26D5-75203-343-B09 | ----------G--------------------A-----------------Y--------P | | |
| 26D5-75017-343-F04 | ----------G--------------------A-----------------Y--------P | | |
| 26D5-75214-343-F06 | ----------G--------------------A--------------------------P | | |
| 25D5-75592-348-A04 | ----------G-------------------ATA----------------AY-------P | | |
| 26D5-75768-348-A10 | ----------G-------------------AV-I---------------AY-------P | | |
| 26D5-75576-348-B03 | ----------G--------------------D-Y---------------AY-------P | | |
| 26D5-75746-348-C07 | ----------G--------------------AF----------------Y--------P | | |
| 26D5-75747-348-D07 | ----------G--------------------AF----------------Y--------P | | |
| 26D5-75602-348-F04 | ----------G--------------------QF----------------YF-------P | | |
| 26D5-75616-348-F10 | ----------G--------------------A-----------------Y--------P | | |

FIG. 8A

| KABAT | 65 70 75 80 80a-c 85 90 95 100 105 110 113 |
|---|---|
| | HCDR2 HCDR3 |
| 26D5 | DSVKGRFTISRDNSKNTLYLQMNSLRAEDTAMYYCARGGFGGGDYWGQGTLVTVSS |
| 26D5-GV-Q | ---------------------------------V-------------------- |
| 26D5-295-B08 | ------------------------------------A------------------ |
| 26D5-75202-343-A09 | ---------------------------------V--A------------------ |
| 26D5-75229-343-A10 | ---------------------------------V--A------------------ |
| 26D5-75203-343-B09 | ---------------------------------V--A---P-------------- |
| 26D5-75017-343-F04 | ---------------------------------V--A------------------ |
| 26D5-75214-343-F06 | ---------------------------------V--A---P-------------- |
| 25D5-75592-348-A04 | ---------------------------------V--VTA---------------- |
| 26D5-75768-348-A10 | ---------------------------------V--TI----------------- |
| 26D5-75576-348-B03 | ---------------------------------V--VTA---------------- |
| 26D5-75746-348-C07 | ---------------------------------V--AA----------------- |
| 26D5-75747-348-D07 | ---------------------------------V--AA----------------- |
| 26D5-75602-348-F04 | ---------------------------------V--KA----------------- |
| 26D5-75616-348-F10 | ---------------------------------V--AE---LE--I--------- |

FIG. 8A CONT.

| KABAT | 65 — 70 — 75 — 80 — 85 — 90 — 95 — 100 — 105—107 |
|---|---|
| | LCDR3 |
| 26D5 | RFSGSGSGTDFTLTISSLQPEDFATYYCQQANSFPLTFGGGTKVEIK |
| 26D5-GV-Q | ---------------------------------------------- |
| 26D5-295-B08 | ---------------------------------------------- |
| 26D5-75202-343-A09 | ---------------------------E------------------ |
| 26D5-75229-343-A10 | ---------------------------Q------------------ |
| 26D5-75203-343-B09 | ---------------------------E------------------ |
| 26D5-75017-343-F04 | ---------------------------E------------------ |
| 26D5-75214-343-F06 | --------------------------GE------------------ |
| 26D5-75592-348-A04 | ---------------------------E------------------ |
| 26D5-75768-348-A10 | --------------------------GE------------------ |
| 26D5-75576-348-B03 | ---------------------------------------------- |
| 26D5-75746-348-C07 | ----------------------------N----------------- |
| 26D5-75747-348-D07 | --------------------------GE------------------ |
| 26D5-75602-348-F04 | ---------------------------------------------- |
| 26D5-75616-348-F10 | ---------------------------------------------- |

*FIG. 8B CONT.*

ANTIBODIES AND ANTIGEN BINDING PEPTIDES FOR FACTOR XIA INHIBITORS AND USES THEREOF

CROSS-REFERENCE TO RELATED APPLICATIONS

This application claims benefit of priority to U.S. Provisional Application Ser. No. 63/135,016 filed Jan. 8, 2021, U.S. Provisional Application Ser. No. 63/148,767 filed Feb. 12, 2021, U.S. Provisional Application Ser. No. 63/152,595 filed Feb. 23, 2021 and U.S. Provisional Application Ser. No. 63/153,045 filed Feb. 24, 2021, each of which is herein incorporated by reference in its entirety.

REFERENCE TO SEQUENCE LISTING

This application contains a Sequence Listing file entitled 055920-553P01US_Sequence_Listing.txt, with a file size of about 316,130 bytes and created on 23 Dec. 2020, has been submitted electronically in ASCII format and is hereby incorporated by reference in its entirety.

BACKGROUND OF THE INVENTION

Thromboembolic diseases remain the leading cause of death in developed countries despite the availability of anticoagulants such as dabigatran, apixaban, rivaroxaban, warfarin (COUMADIN®), heparin, low molecular weight heparins (LMWH), and synthetic pentasaccharides and anti-platelet agents such as aspirin and clopidogrel (PLAVIX®). Discovering and developing safe and efficacious oral anticoagulants for the prevention and treatment of a wide range of thromboembolic disorders remains important. One approach is to reduce thrombin generation by targeting the inhibition of coagulation factor XIa (FXIa). FXIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. The resulting burst of thrombin converts fibrinogen to fibrin that polymerizes to form the structural framework of a blood clot, and activates platelets, which are a key cellular component of coagulation. Therefore, FXIa plays a key role in propagating this amplification loop and is thus an attractive target for anti-thrombotic therapy.

Plasma prekallikrein is a zymogen of a trypsin-like serine protease and is present in plasma at 35 to 50 µg/mL. The structure is similar to that of Factor XI (FXI). Overall, the amino acid sequence of plasma kallikrein has 58% homology to FXI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (RAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability.

The plasma kallikrein-kinin system is abnormally abundant in patients with advanced diabetic macular edema. It has been recently published that plasma kallikrein contributes to retinal vascular dysfunctions in diabetic rats. Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor. To date, no small molecule synthetic plasma kallikrein inhibitor has been approved for medical use. The large protein plasma kallikrein inhibitors present risks of anaphylactic reactions, as has been reported for Ecallantide.

Novel and effective selective FXIa inhibitors or dual inhibitors of FXIa and plasma kallikrein have been provided in WO2016053455A1, which is incorporated by reference in its entirety, for treating thromboembolic and/or inflammatory disorders. The development of these selective FXIa inhibitors or dual inhibitors of FXIa and plasma kallikrein, such as the compounds provided in the present invention, is based on the ability to achieve a high level of antithrombotic efficacy with little or no additional bleeding risk. However, bleeding can occur in rare clinical situations where such FXIa inhibitors have been administered to patients. In humans, FXI-deficiency bleeding can occur for example following trauma, especially in tissues with high fibrinolytic activity, e.g. oral pharynx and urinary tract.

Pro-hemostatic approaches exist, including coagulation factor concentrates and recombinant activated Factor VII. These agents are approved primarily for use in patients with hemophilia and may be considered for bleeding patients treated with thrombin or FXa inhibitors when a specific reversal agent is not available. However, these approaches have a pro-thrombotic risk. Thus, there is an urgent need to develop compounds that can immediately reverse the anti-thrombotic effect of these selective FXIa inhibitors or dual inhibitors of FXIa and plasma kallikrein, such as the compounds disclosed herein, in subjects with serious bleeding or who need urgent surgical intervention, without associated pro-thrombotic risk.

BRIEF SUMMARY OF THE INVENTION

The present invention provides novel antibodies or antigen binding peptides that specifically bind to selective FXIa inhibitors and/or dual inhibitors of FXIa and plasma kallikrein. The present invention further provides methods of reducing the antithrombotic effect of FXIa inhibitors by administering to a subject a pharmaceutically effective dose of the antibodies or antigen binding peptides provided herein. In addition, the present invention provides detection reagents and methods for detecting the level of the inhibitors of FXIa in a biological sample.

Specific embodiment 1: An isolated antigen binding peptide comprising at least one heavy chain variable region (VH) and at least one light chain variable region (VL), wherein the at least one VH comprises at least one of:

(a) a VH complementarity-determining region 1 (VH-CDR1) comprising an amino acid sequence selected from the group consisting of SEQ ID NOs: 1-12;
(b) a VH-CDR2 comprising an amino acid sequence selected from the group consisting of SEQ ID NOs: 13-22; or
(c) a VH-CDR3 comprising an amino acid sequence selected from the group consisting of SEQ ID NOs: 23-28; and wherein the at least one VL comprises at least one of:
(d) a VL-CDR1 comprising an amino acid sequence selected from the group consisting of SEQ ID NOs: 29-37;
(e) a VL-CDR2 comprising an amino acid sequence selected from the group consisting of SEQ ID NOs: 38-43; or
(f) a VL-CDR3 comprising an amino acid sequence selected from the group consisting of SEQ ID NOs: 44-51.

Specific embodiment 2: An isolated antigen binding peptide comprising:
(a) at least one heavy chain variable region comprising an amino acid sequence selected from the group consisting of SEQ ID NOs: 52-83; and
(b) at least one light chain variable region comprising an amino acid sequence selected from the group consisting of SEQ ID NOs: 84-99.

Specific embodiment 3: An isolated antigen binding peptide comprising at least one heavy chain variable region (VH) and at least one light chain variable region (VL), wherein the VH comprises three complementarity determining regions (CDRs): VH-CDR1, VH-CDR2, and VH-CDR3 and the VL comprises three CDRs: VL-CDR1, VL-CDR2, and VL-CDR3, wherein the amino acid sequences of the VH-CDR1, VH-CDR2, VH-CDR3, VL-CDR1, VL-CDR2, and VL-CDR3, respectively comprise the sequences selected from the group consisting of:
(a) SEQ ID NOs: 1, 13, 23, 29, 38, and 44, respectively;
(b) SEQ ID NOs: 1, 14, 23, 29, 38, and 45, respectively;
(c) SEQ ID NOs: 1, 13, 24, 30, 38, and 45, respectively;
(d) SEQ ID NOs: 1, 13, 24, 29, 39, and 45, respectively;
(e) SEQ ID NOs: 1, 14, 25, 29, 38, and 46, respectively;
(f) SEQ ID NOs: 2, 13, 26, 31, 40, and 47, respectively;
(g) SEQ ID NOs: 3, 15, 24, 32, 40, and 47, respectively;
(h) SEQ ID NOs: 4, 16, 24, 29, 38, and 46, respectively;
(i) SEQ ID NOs: 5, 15, 24, 29, 38, and 46, respectively;
(j) SEQ ID NOs: 1, 14, 24, 29, 38, and 46, respectively;
(k) SEQ ID NOs: 6, 13, 24, 31, 40, and 47, respectively;
(l) SEQ ID NOs: 3, 15, 24, 32, 41, and 48, respectively;
(m) SEQ ID NOs: 1, 14, 24, 33, 38, and 49, respectively;
(n) SEQ ID NOs: 1, 14, 26, 29, 38, and 46, respectively;
(o) SEQ ID NOs: 7, 17, 26, 29, 38, and 46, respectively;
(p) SEQ ID NOs: 8, 17, 24, 34, 38, and 46, respectively;
(q) SEQ ID NOs: 1, 17, 26, 29, 38, and 46, respectively;
(r) SEQ ID NOs: 1, 17, 26, 35, 38, and 46, respectively;
(s) SEQ ID NOs: 1, 17, 24, 33, 38, and 49, respectively;
(t) SEQ ID NOs: 9, 14, 26, 29, 38, and 46, respectively;
(u) SEQ ID NOs: 9, 14, 26, 35, 38, and 46, respectively;
(v) SEQ ID NOs: 9, 17, 24, 29, 38, and 46, respectively;
(w) SEQ ID NOs: 9, 17, 24, 35, 38, and 46, respectively;
(x) SEQ ID NOs: 9, 17, 24, 34, 38, and 46, respectively;
(y) SEQ ID NOs: 9, 14, 24, 29, 38, and 46, respectively;
(z) SEQ ID NOs: 9, 18, 26, 35, 38, and 46, respectively;
(aa) SEQ ID NOs: 8, 14, 24, 29, 38, and 46, respectively;
(bb) SEQ ID NOs: 8, 17, 26, 29, 38, and 46, respectively;
(cc) SEQ ID NOs: 9, 19, 26, 29, 38, and 46, respectively;
(dd) SEQ ID NOs: 9, 17, 26, 34, 38, and 46, respectively;
(ee) SEQ ID NOs: 10, 20, 27, 36, 42, and 50, respectively;
(ff) SEQ ID NOs: 11, 21, 28, 37, 43, and 51, respectively;
(gg) SEQ ID NOs: 12, 22, 26, 33, 38, and 46, respectively;
(hh) SEQ ID NOs: 12, 17, 26, 33, 38, and 46, respectively;
(ii) SEQ ID NOs: 9, 17, 26, 33, 38, and 46, respectively; and
(jj) variants of (a) to (ii) wherein any of the amino acid sequences have 1, 2, or 3 conservative amino acid substitutions therein.

Specific embodiment 4: The isolated antigen binding peptide of embodiment 3, wherein the at least one VH region and the at least one VL region, respectively, comprise amino acid sequences selected from the group consisting of:
(a) SEQ ID NO: 52 and SEQ ID NO: 84, respectively;
(b) SEQ ID NO: 53 and SEQ ID NO: 85, respectively;
(c) SEQ ID NO: 54 and SEQ ID NO: 86, respectively;
(d) SEQ ID NO: 54 and SEQ ID NO: 87, respectively;
(e) SEQ ID NO: 55 and SEQ ID NO: 88, respectively;
(f) SEQ ID NO: 56 and SEQ ID NO: 89, respectively;
(g) SEQ ID NO: 57 and SEQ ID NO: 90, respectively;
(h) SEQ ID NO: 58 and SEQ ID NO: 88, respectively;
(i) SEQ ID NO: 59 and SEQ ID NO: 88, respectively;
(j) SEQ ID NO: 60 and SEQ ID NO: 91, respectively;
(k) SEQ ID NO: 61 and SEQ ID NO: 89, respectively;
(l) SEQ ID NO: 57 and SEQ ID NO: 92, respectively;
(m) SEQ ID NO: 60 and SEQ ID NO: 93, respectively;
(n) SEQ ID NO: 60 and SEQ ID NO: 88, respectively;
(o) SEQ ID NO: 62 and SEQ ID NO: 88, respectively;
(p) SEQ ID NO: 63 and SEQ ID NO: 88, respectively;
(q) SEQ ID NO: 64 and SEQ ID NO: 88, respectively;
(r) SEQ ID NO: 65 and SEQ ID NO: 94, respectively;
(s) SEQ ID NO: 66 and SEQ ID NO: 88, respectively;
(t) SEQ ID NO: 66 and SEQ ID NO: 95, respectively;
(u) SEQ ID NO: 67 and SEQ ID NO: 88, respectively;
(v) SEQ ID NO: 68 and SEQ ID NO: 93, respectively;
(w) SEQ ID NO: 69 and SEQ ID NO: 88, respectively;
(x) SEQ ID NO: 69 and SEQ ID NO: 95, respectively;
(y) SEQ ID NO: 70 and SEQ ID NO: 88, respectively;
(z) SEQ ID NO: 70 and SEQ ID NO: 95, respectively;
(aa) SEQ ID NO: 71 and SEQ ID NO: 88, respectively;
(bb) SEQ ID NO: 71 and SEQ ID NO: 94, respectively;
(cc) SEQ ID NO: 72 and SEQ ID NO: 88, respectively;
(dd) SEQ ID NO: 73 and SEQ ID NO: 95, respectively;
(ee) SEQ ID NO: 74 and SEQ ID NO: 88, respectively;
(ff) SEQ ID NO: 75 and SEQ ID NO: 88, respectively;
(gg) SEQ ID NO: 76 and SEQ ID NO: 88, respectively;
(hh) SEQ ID NO: 77 and SEQ ID NO: 94, respectively;
(ii) SEQ ID NO: 78 and SEQ ID NO: 96, respectively;
(jj) SEQ ID NO: 79 and SEQ ID NO: 97 respectively;
(kk) SEQ ID NO: 80 and SEQ ID NO: 98, respectively;
(ll) SEQ ID NO: 81 and SEQ ID NO: 99, respectively;
(mm) SEQ ID NO: 81 and SEQ ID NO: 98, respectively;
(nn) SEQ ID NO: 82 and SEQ ID NO: 99, respectively;
(oo) SEQ ID NO: 83 and SEQ ID NO: 98, respectively; and
(pp) variants of (a) to (oo) comprising 1, 2, 3, or 4 conservative amino acid substitutions.

Specific embodiment 5: The isolated antigen binding peptide of any one of the preceding embodiments, comprising two heavy chain variable regions, each paired with one light chain variable region.

Specific embodiment 6: The isolated antigen binding peptide of embodiment 5, further comprising a polypeptide linker comprising a sequence selected from SEQ ID NO: 196-199.

Specific embodiment 7: The isolated antigen binding peptide of any one of the preceding embodiments, wherein the antigen binding peptide specifically binds to the compound set forth in Formula (I):

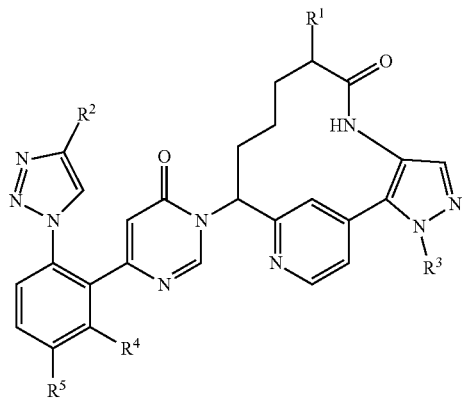

or a stereoisomer or a tautomer thereof, wherein:
$R^1$ is $C_{1-4}$ alkyl;
$R^2$ is independently selected from F, Cl, $CF_3$, $CHF_2$, $CH_2F$, $CH_3$;
$R^3$ is independently selected from $CF_3$, $CHF_2$, $CH_2F$, and $CH_3$;
$R^4$ is H; and
$R^5$ is independently selected from F and Cl.

Specific embodiment 8: The isolated antigen binding peptide of embodiment 7, wherein the compound has Formula (II):

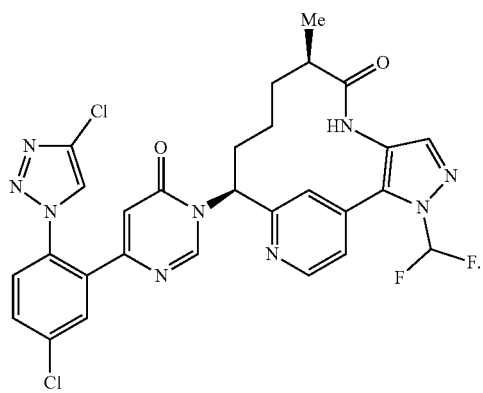

Specific embodiment 9: The isolated antigen binding peptide of any one of the preceding embodiments is an antibody.

Specific embodiment 10: The isolated antigen binding peptide of any one of the preceding embodiments, wherein said antigen binding peptide is a Fab, Fab', F(ab')2, Fd, single chain Fv or scFv, disulfide linked Fv, V-NAR domain, IgNar, intrabody, IgGACH2, minibody, F(ab')$_3$, tetrabody, triabody, diabody, single-domain antibody, DVD-Ig, Fcab, mAb$^2$, (scFv)$_2$, scFv-Fc, or a tandem Fab.

Specific embodiment 11: The isolated antigen binding peptide of any one of the preceding embodiments, comprising sequences selected from the group consisting of:
(a) SEQ ID NO: 100 and SEQ ID NO: 160, respectively;
(b) SEQ ID NO: 101 and SEQ ID NO: 160, respectively;
(c) SEQ ID NO: 102 and SEQ ID NO: 161, respectively;
(d) SEQ ID NO: 103 and SEQ ID NO: 161, respectively;
(e) SEQ ID NO: 104 and SEQ ID NO: 162, respectively;
(f) SEQ ID NO: 105 and SEQ ID NO: 162, respectively;
(g) SEQ ID NO: 104 and SEQ ID NO: 163, respectively;
(h) SEQ ID NO: 105 and SEQ ID NO: 163, respectively;
(i) SEQ ID NO: 106 and SEQ ID NO: 164, respectively;
(j) SEQ ID NO: 107 and SEQ ID NO: 164, respectively;
(k) SEQ ID NO: 108 and SEQ ID NO: 165, respectively;
(l) SEQ ID NO: 109 and SEQ ID NO: 165, respectively;
(m) SEQ ID NO: 110 and SEQ ID NO: 166, respectively;
(n) SEQ ID NO: 111 and SEQ ID NO: 166, respectively;
(o) SEQ ID NO: 112 and SEQ ID NO: 164, respectively;
(p) SEQ ID NO: 113 and SEQ ID NO: 164, respectively;
(q) SEQ ID NO: 114 and SEQ ID NO: 164, respectively;
(r) SEQ ID NO: 115 and SEQ ID NO: 164, respectively;
(s) SEQ ID NO: 116 and SEQ ID NO: 167, respectively;
(t) SEQ ID NO: 117 and SEQ ID NO: 167, respectively;
(u) SEQ ID NO: 118 and SEQ ID NO: 165, respectively;
(v) SEQ ID NO: 119 and SEQ ID NO: 165, respectively;
(w) SEQ ID NO: 110 and SEQ ID NO: 168, respectively;
(x) SEQ ID NO: 111 and SEQ ID NO: 168, respectively;
(y) SEQ ID NO: 116 and SEQ ID NO: 169, respectively;
(z) SEQ ID NO: 117 and SEQ ID NO: 169, respectively;
(aa) SEQ ID NO: 116 and SEQ ID NO: 164, respectively;
(bb) SEQ ID NO: 117 and SEQ ID NO: 164, respectively;
(cc) SEQ ID NO: 120 and SEQ ID NO: 164, respectively;
(dd) SEQ ID NO: 121 and SEQ ID NO: 164, respectively;
(ee) SEQ ID NO: 122 and SEQ ID NO: 164, respectively;
(ff) SEQ ID NO: 123 and SEQ ID NO: 164, respectively;
(gg) SEQ ID NO: 124 and SEQ ID NO: 164, respectively;
(hh) SEQ ID NO: 125 and SEQ ID NO: 164, respectively;
(ii) SEQ ID NO: 126 and SEQ ID NO: 170, respectively;
(jj) SEQ ID NO: 127 and SEQ ID NO: 170, respectively;
(kk) SEQ ID NO: 128 and SEQ ID NO: 164, respectively;
(ll) SEQ ID NO: 129 and SEQ ID NO: 164, respectively;
(mm) SEQ ID NO: 128 and SEQ ID NO: 171, respectively;
(nn) SEQ ID NO: 129 and SEQ ID NO: 171, respectively;
(oo) SEQ ID NO: 130 and SEQ ID NO: 164, respectively;
(pp) SEQ ID NO: 131 and SEQ ID NO: 164, respectively;
(qq) SEQ ID NO: 132 and SEQ ID NO: 169, respectively;
(rr) SEQ ID NO: 133 and SEQ ID NO: 169, respectively;
(ss) SEQ ID NO: 134 and SEQ ID NO: 164, respectively;
(tt) SEQ ID NO: 135 and SEQ ID NO: 164, respectively;
(uu) SEQ ID NO: 134 and SEQ ID NO: 171, respectively;
(vv) SEQ ID NO: 135 and SEQ ID NO: 171, respectively;
(ww) SEQ ID NO: 136 and SEQ ID NO: 164, respectively;
(xx) SEQ ID NO: 137 and SEQ ID NO: 164, respectively;
(yy) SEQ ID NO: 136 and SEQ ID NO: 171, respectively;
(zz) SEQ ID NO: 137 and SEQ ID NO: 171, respectively;
(aaa) SEQ ID NO: 138 and SEQ ID NO: 164, respectively;
(bbb) SEQ ID NO: 139 and SEQ ID NO: 164, respectively;
(ccc) SEQ ID NO: 138 and SEQ ID NO: 170, respectively;
(ddd) SEQ ID NO: 139 and SEQ ID NO: 170, respectively;
(eee) SEQ ID NO: 140 and SEQ ID NO: 164, respectively;
(fff) SEQ ID NO: 141 and SEQ ID NO: 164, respectively;
(ggg) SEQ ID NO: 142 and SEQ ID NO: 171, respectively;
(hhh) SEQ ID NO: 143 and SEQ ID NO: 171, respectively;
(iii) SEQ ID NO: 144 and SEQ ID NO: 164, respectively;

(jjj) SEQ ID NO: 145 and SEQ ID NO: 164, respectively;
(kkk) SEQ ID NO: 146 and SEQ ID NO: 164, respectively;
(lll) SEQ ID NO: 147 and SEQ ID NO: 164, respectively;
(mmm) SEQ ID NO: 148 and SEQ ID NO: 164, respectively;
(nnn) SEQ ID NO: 149 and SEQ ID NO: 164, respectively;
(ooo) SEQ ID NO: 150 and SEQ ID NO: 170, respectively;
(ppp) SEQ ID NO: 151 and SEQ ID NO: 170, respectively;
(qqq) SEQ ID NO: 152 and SEQ ID NO: 172, respectively;
(rrr) SEQ ID NO: 153 and SEQ ID NO: 172, respectively;
(sss) SEQ ID NO: 154 and SEQ ID NO: 173, respectively;
(tit) SEQ ID NO: 155 and SEQ ID NO: 173, respectively;
(uuu) SEQ ID NO: 156 and SEQ ID NO: 174, respectively;
(vvv) SEQ ID NO: 157 and SEQ ID NO: 174, respectively;
(www) SEQ ID NO: 158 and SEQ ID NO: 175, respectively;
(xxx) SEQ ID NO: 159 and SEQ ID NO: 175, respectively;
(yyy) SEQ ID NO: 158 and SEQ ID NO: 174, respectively; and
(zzz) SEQ ID NO: 159 and SEQ ID NO: 174, respectively;
wherein said isolated antigen binding peptide specifically binds to the compound of Formula (II):

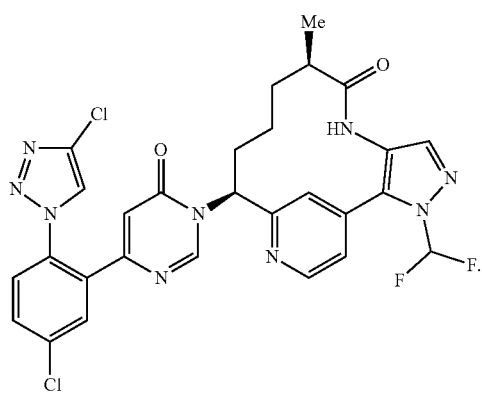

Specific embodiment 12: The isolated antigen binding peptide of any one of the preceding embodiments, comprising sequences selected from the group consisting of:
(a) SEQ ID NO: 176 and SEQ ID NO: 160, respectively;
(b) SEQ ID NO: 177 and SEQ ID NO: 160, respectively;
(c) SEQ ID NO: 178 and SEQ ID NO: 160, respectively;
(d) SEQ ID NO: 179 and SEQ ID NO: 160, respectively;
(e) SEQ ID NO: 180 and SEQ ID NO: 164, respectively;
(f) SEQ ID NO: 181 and SEQ ID NO: 164, respectively;
(g) SEQ ID NO: 182 and SEQ ID NO: 164, respectively;
(h) SEQ ID NO: 183 and SEQ ID NO: 164, respectively;
(i) SEQ ID NO: 184 and SEQ ID NO: 163, respectively;
(j) SEQ ID NO: 185 and SEQ ID NO: 163, respectively;
(k) SEQ ID NO: 186 and SEQ ID NO: 163, respectively;
(l) SEQ ID NO: 187 and SEQ ID NO: 163, respectively;
(m) SEQ ID NO: 184 and SEQ ID NO: 162, respectively;
(n) SEQ ID NO: 185 and SEQ ID NO: 162, respectively;
(o) SEQ ID NO: 186 and SEQ ID NO: 162, respectively;
(p) SEQ ID NO: 187 and SEQ ID NO: 162, respectively;
(q) SEQ ID NO: 188 and SEQ ID NO: 165, respectively;
(r) SEQ ID NO: 189 and SEQ ID NO: 165, respectively;
(s) SEQ ID NO: 190 and SEQ ID NO: 165, respectively;
(t) SEQ ID NO: 191 and SEQ ID NO: 165, respectively;
(u) SEQ ID NO: 192 and SEQ ID NO: 161, respectively;
(v) SEQ ID NO: 193 and SEQ ID NO: 161, respectively;
(w) SEQ ID NO: 194 and SEQ ID NO: 161, respectively; and
(x) SEQ ID NO: 195 and SEQ ID NO: 161, respectively;
wherein said isolated antigen binding peptide specifically binds to the compound of Formula (II):

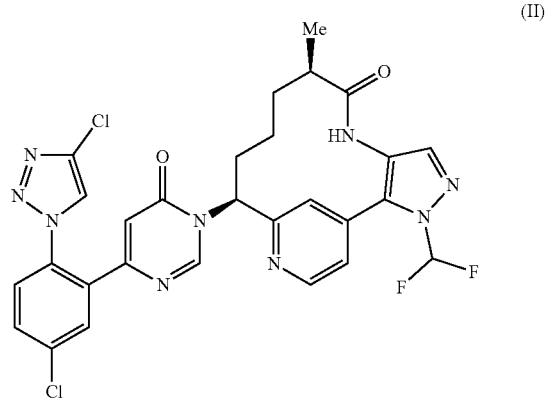 [SMILES: C[C@@H]1CCC[C@H](n2cnc(-c3cc(Cl)ccc3-n3cc(Cl)nn3)cc2=O)c2cc(ccn2)-c2c(cnn2C(F)F)NC1=O]

Specific embodiment 13: The isolated antigen binding peptide of embodiment 11, comprising sequences SEQ ID NO: 106 and SEQ ID NO: 164, respectively;
wherein said isolated antigen binding peptide specifically binds to the compound of Formula (II):

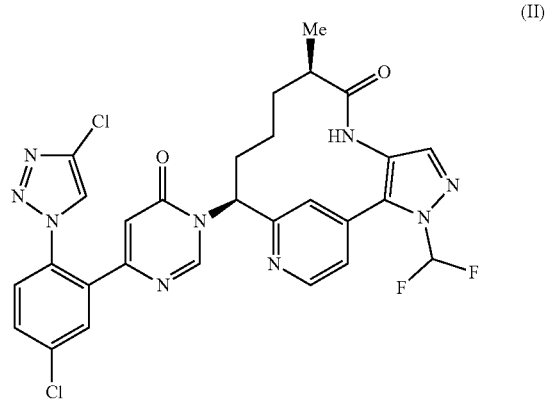 [SMILES: C[C@@H]1CCC[C@H](n2cnc(-c3cc(Cl)ccc3-n3cc(Cl)nn3)cc2=O)c2cc(ccn2)-c2c(cnn2C(F)F)NC1=O]

Specific embodiment 14: An isolated antibody Fab fragment comprising sequences SEQ ID NO: 106 and SEQ ID NO: 164;
wherein said isolated antibody Fab fragment specifically binds to the compound of Formula (II):

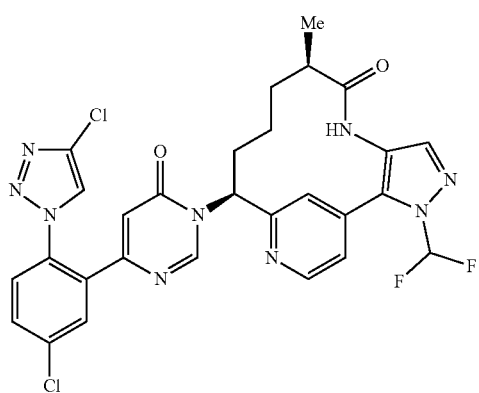

Specific embodiment 15: The isolated antigen binding peptide of embodiment 12, comprising sequences SEQ ID NO: 180 and SEQ ID NO: 164, respectively;
  wherein said isolated antigen binding peptide specifically binds to the compound of Formula (II):

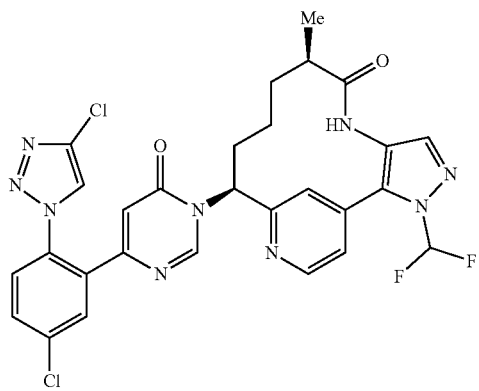

Specific embodiment 16: An isolated antibody tandem Fab fragment comprising sequences SEQ ID NO: 180 and SEQ ID NO: 164;
  wherein said isolated antibody tandem Fab fragment specifically binds to the compound of Formula (II):

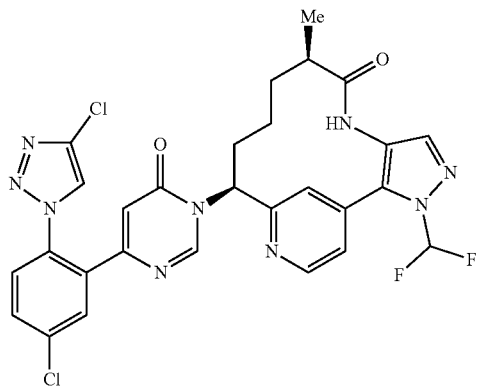

Specific embodiment 17: The isolated antigen binding peptide of embodiment 12, comprising sequences SEQ ID NO: 181 and SEQ ID NO: 164, respectively;
  wherein said isolated antigen binding peptide specifically binds to the compound of Formula (II):

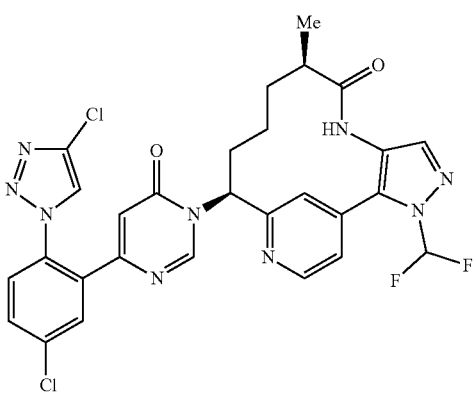

Specific embodiment 18: An isolated antibody tandem Fab fragment comprising sequences SEQ ID NO: 181 and SEQ ID NO: 164;
  wherein said isolated antibody tandem Fab fragment specifically binds to the compound of Formula (II):

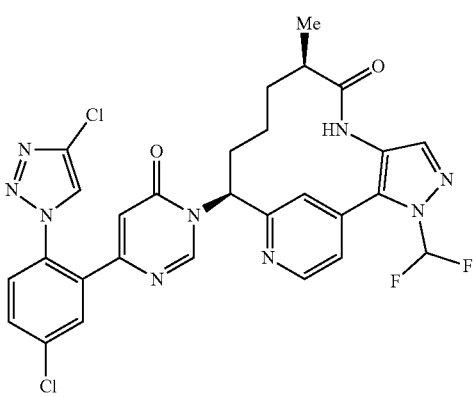

Specific embodiment 19: The isolated antigen binding peptide of embodiment 12, comprising sequences SEQ ID NO: 182 and SEQ ID NO: 164, respectively;
  wherein said isolated antigen binding peptide specifically binds to the compound of Formula (II):

(II)

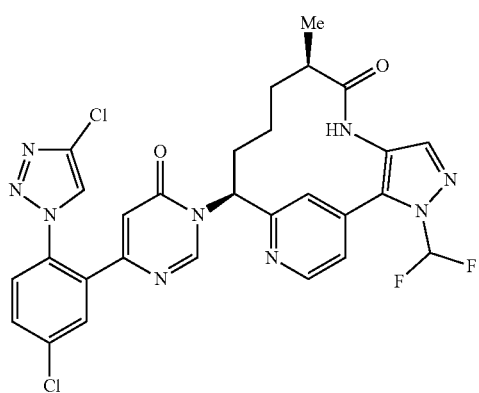

Specific embodiment 20: An isolated antibody tandem Fab fragment comprising sequences SEQ ID NO: 182 and SEQ ID NO: 164;
   wherein said isolated antibody tandem Fab fragment specifically binds to the compound of Formula (II):

(II)

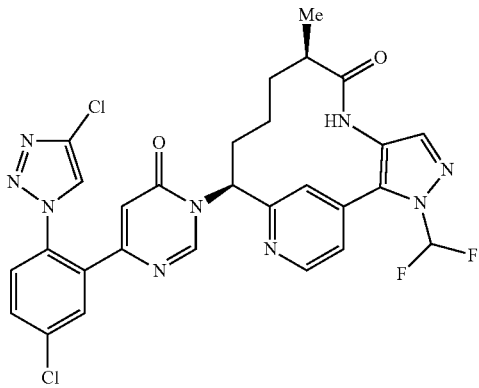

Specific embodiment 21: The isolated antigen binding peptide of embodiment 12, comprising sequences SEQ ID NO: 183 and SEQ ID NO: 164, respectively;
   wherein said isolated antigen binding peptide specifically binds to the compound of Formula (II):

(II)

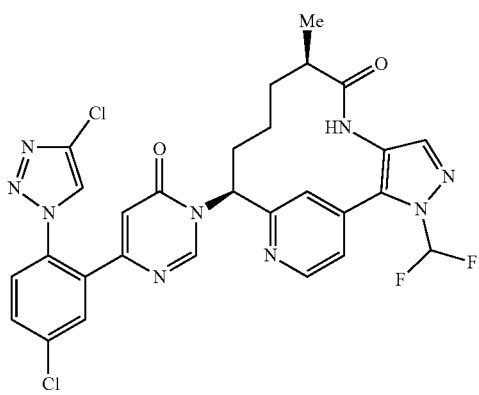

Specific embodiment 22: An isolated antibody tandem Fab fragment comprising sequences SEQ ID NO: 183 and SEQ ID NO: 164;
   wherein said isolated antibody tandem Fab fragment specifically binds to the compound of Formula (II):

(II)

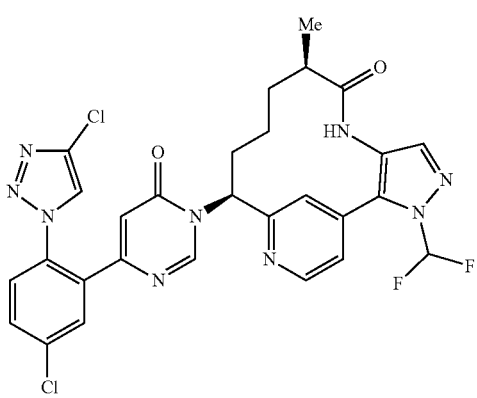

Specific embodiment 23: The isolated antigen binding peptide of embodiment 12, comprising sequences SEQ ID NO: 176 and SEQ ID NO: 160, respectively;
   wherein said isolated antigen binding peptide specifically binds to the compound of Formula (II):

(II)

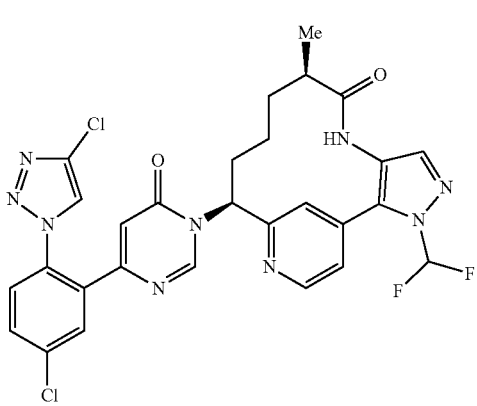

Specific embodiment 24: An isolated antibody tandem Fab fragment comprising sequences SEQ ID NO: 176 and SEQ ID NO: 160;
   wherein said isolated antibody tandem Fab fragment specifically binds to the compound of Formula (II):

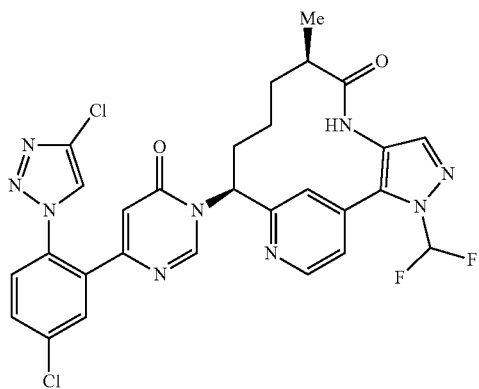
(II)

Specific embodiment 25: The isolated antigen binding peptide of embodiment 12, comprising sequences SEQ ID NO: 177 and SEQ ID NO: 160, respectively;
  wherein said isolated antigen binding peptide specifically binds to the compound of Formula (II):

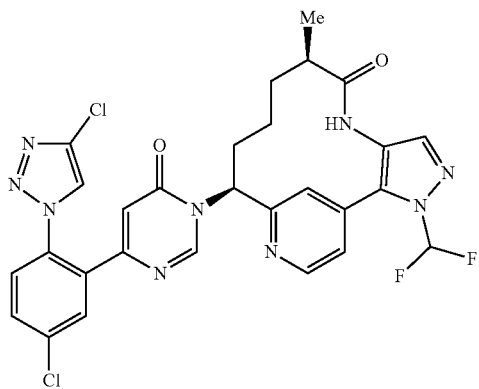
(II)

Specific embodiment 26: An isolated antibody tandem Fab fragment comprising sequences SEQ ID NO: 177 and SEQ ID NO: 160;
  wherein said isolated antibody tandem Fab fragment specifically binds to the compound of Formula (II):

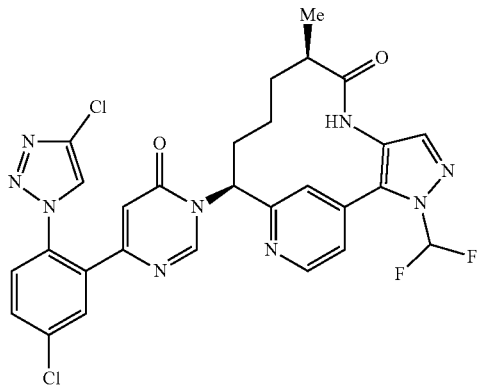
(II)

Specific embodiment 27: The isolated antigen binding peptide of embodiment 12, comprising sequences SEQ ID NO: 184 and SEQ ID NO: 162, respectively;
  wherein said isolated antigen binding peptide specifically binds to the compound of Formula (II):

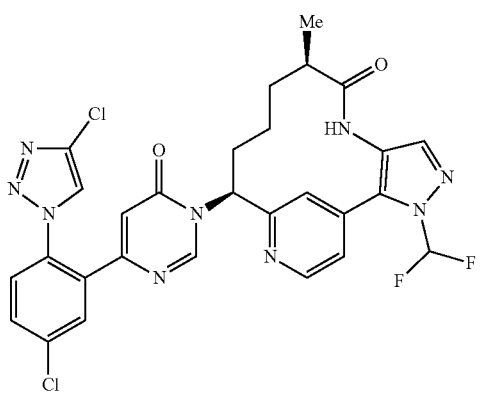
(II)

Specific embodiment 28: An isolated antibody tandem Fab fragment comprising sequences SEQ ID NO: 184 and SEQ ID NO: 162;
  wherein said isolated antibody tandem Fab fragment specifically binds to the compound of Formula (II):

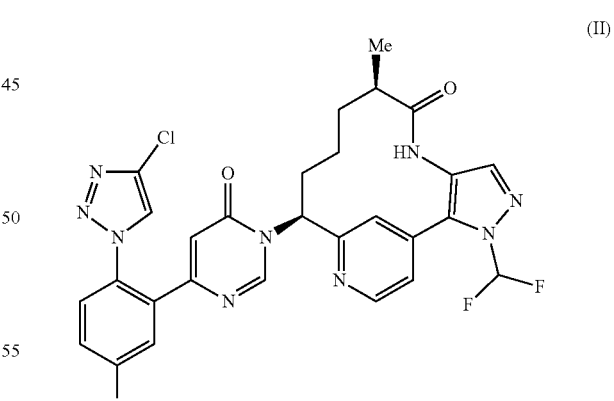
(II)

Specific embodiment 29: The isolated antigen binding peptide of embodiment 12, comprising sequences SEQ ID NO: 184 and SEQ ID NO: 163, respectively;
  wherein said isolated antigen binding peptide specifically binds to the compound of Formula (II):

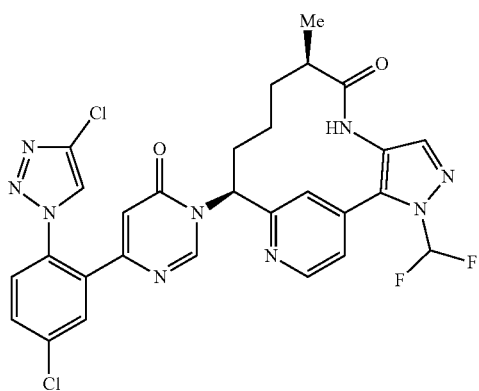
(II)

Specific embodiment 30: An isolated antibody tandem Fab fragment comprising sequences SEQ ID NO: 184 and SEQ ID NO: 163;
  wherein said isolated antibody tandem Fab fragment specifically binds to the compound of Formula (II):

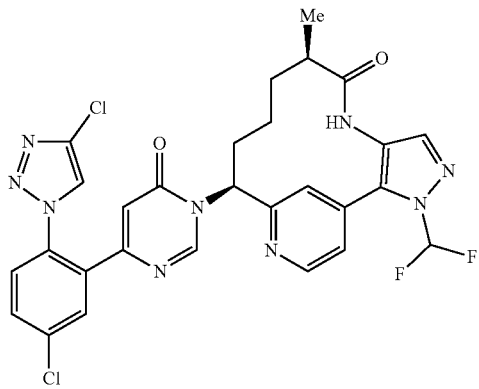
(II)

Specific embodiment 31: The isolated antigen binding peptide of embodiment 12, comprising sequences SEQ ID NO: 188 and SEQ ID NO: 165, respectively;
  wherein said isolated antigen binding peptide specifically binds to the compound of Formula (II):

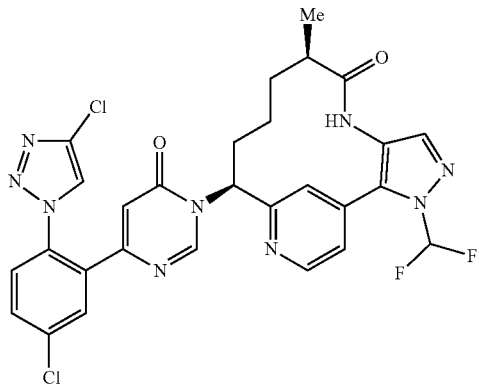
(II)

Specific embodiment 32: An isolated antibody tandem Fab fragment comprising sequences SEQ ID NO: 188 and SEQ ID NO: 165;
  wherein said isolated antibody tandem Fab fragment specifically binds to the compound of Formula (II):

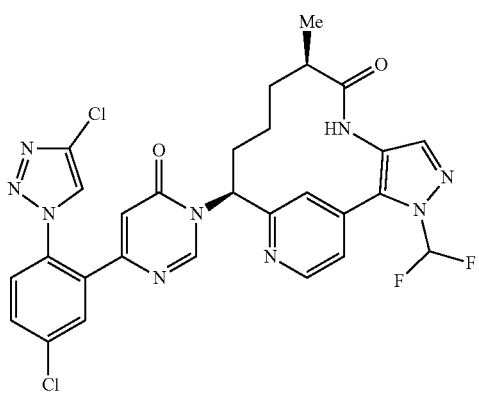
(II)

Specific embodiment 33: The isolated antigen binding peptide of embodiment 12, comprising sequences SEQ ID NO: 192 and SEQ ID NO: 161, respectively;
  wherein said isolated antigen binding peptide specifically binds to the compound of Formula (II):

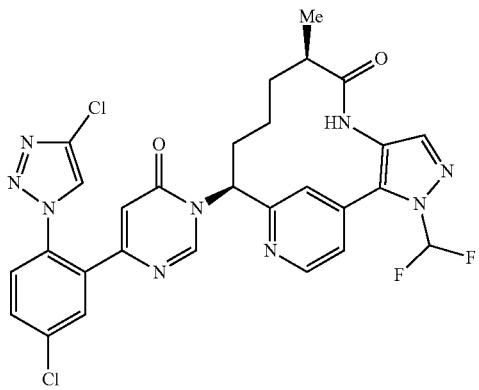
(II)

Specific embodiment 34: An isolated antibody tandem Fab fragment comprising sequences SEQ ID NO: 192 and SEQ ID NO: 161;
  wherein said isolated antibody tandem Fab fragment specifically binds to the compound of Formula (II):

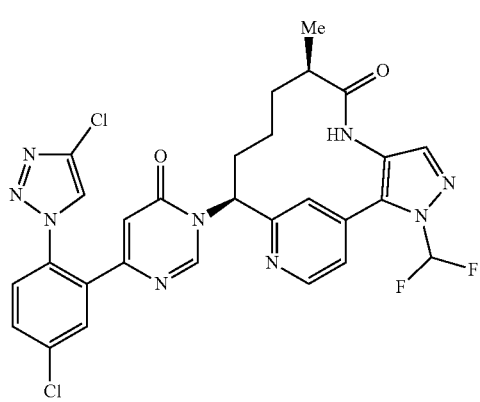

(II)

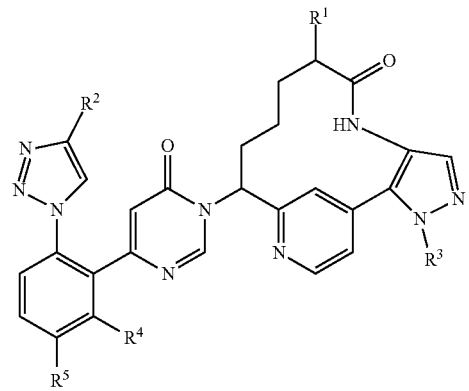

(I)

$R^1$ is $C_{1-4}$ alkyl;
$R^2$ is independently selected from F, Cl, $CF_3$, $CHF_2$, $CH_2F$, $CH_3$;
$R^3$ is independently selected from $CF_3$, $CHF_2$, $CH_2F$, and $CH_3$;
$R^4$ is H; and
$R^5$ is independently selected from F and Cl.

Specific embodiment 42: The method of embodiment 41, wherein the compound of Formula (I) has Formula (II):

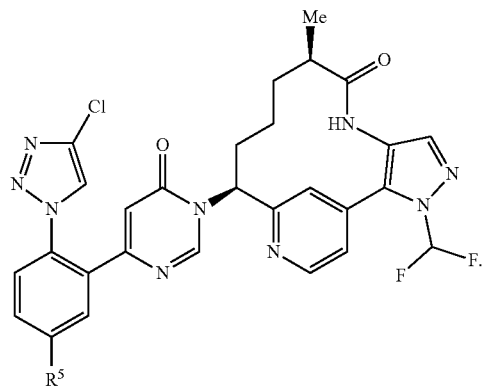

(II)

Specific embodiment 35: An isolated polynucleotide comprising a nucleic acid sequence encoding the antigen binding peptide or the antibody Fab fragment or the antibody tandem Fab fragment of any one of embodiments 1-34.

Specific embodiment 36: An isolated vector comprising the polynucleotide of embodiment 35.

Specific embodiment 37: An isolated host cell comprising the vector of embodiment 36.

Specific embodiment 38: A method of making an antigen binding peptide or an antibody Fab fragment or an antibody tandem Fab fragment comprising (a) culturing the host cell of embodiment 37 under culture conditions that promote protein production such that the host cell produces the antigen binding peptide or the antibody Fab fragment or the antibody tandem Fab fragment, and (b) isolating said antigen binding peptide or said antibody Fab fragment or said antibody tandem Fab fragment from said culture.

Specific embodiment 39: A detection reagent comprising the isolated antigen binding peptide or the isolated antibody Fab fragment or the isolated antibody tandem Fab fragment of any one of embodiments 1-34 and a detectable label.

Specific embodiment 40: The detection reagent of embodiment 39, wherein the isolated antigen binding peptide or the isolated antibody Fab fragment or the isolated antibody tandem Fab fragment is linked to the detectable label.

Specific embodiment 41: A method of reducing the antithrombotic effect of the compound of Formula (I) or a stereoisomer or a tautomer thereof, in a subject in need thereof, comprising administering to the subject a pharmaceutically effective dose of the isolated antigen binding peptide or the isolated antibody Fab fragment or the isolated antibody tandem Fab fragment of any one of embodiments 1-34, wherein:

Specific embodiment 43: The method of embodiment 41 or 42, wherein the pharmaceutically effective dose of the isolated antigen binding peptide or the isolated antibody Fab fragment or the isolated antibody tandem Fab fragment comprises the antigen binding peptide or the antibody Fab fragment or the antibody tandem Fab fragment at an at least about 1:1 molar ratio to the dose of the compound of Formula (I) or (II), or an at least about 1:1 molar ratio to the presence of the compound of Formula (I) or (II) in the subject.

Specific embodiment 44: The method of any one of embodiments 41-43, wherein the isolated antigen binding peptide or the isolated antibody Fab fragment or the isolated antibody tandem Fab fragment is administered concurrently with or after the administration of the compound of Formula (I) or (II).

Specific embodiment 45: The method of any one of embodiments 41-44, wherein the isolated antigen binding peptide or the isolated antibody Fab fragment or the isolated antibody tandem Fab fragment is administered intravenously, intramuscularly, or subcutaneously.

Specific embodiment 46: The method of any one of embodiments 41-45, wherein the subject is a human.

Specific embodiment 47: A method of detecting the level of a compound of Formula (I) or a stereoisomer, a tautomer, or a pharmaceutically acceptable salt thereof, in a biological sample, wherein:

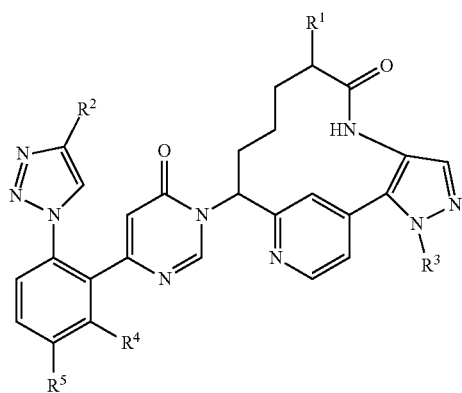

(I)

$R^1$ is $C_{1-4}$ alkyl;
$R^2$ is independently selected from F, Cl, $CF_3$, $CHF_2$, $CH_2F$, $CH_3$;
$R^3$ is independently selected from $CF_3$, $CHF_2$, $CH_2F$, and $CH_3$;
$R^4$ is H; and
$R^5$ is independently selected from F and Cl; the method comprising:
(a) contacting the biological sample with the isolated antigen binding peptide or the isolated antibody Fab fragment or the isolated antibody tandem Fab fragment of any one of embodiments 1-34, and
(b) detecting the level of a bound complex of the compound and the isolated antigen binding peptide or the isolated antibody Fab fragment or the isolated antibody tandem Fab fragment.

Specific embodiment 48: The method of embodiment 47, wherein the compound of Formula (I) has Formula (II):

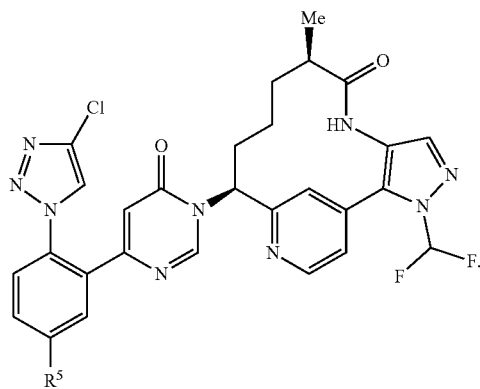

(II)

Specific embodiment 49: The method of embodiment 47 or 48, wherein the isolated antigen binding peptide or the isolated antibody Fab fragment or the isolated antibody tandem Fab fragment is labeled.

Specific embodiment 50: The method of any one of embodiments 47-49, wherein the detection is performed by an immunological assay.

Specific embodiment 51: The method of any one of embodiments 47-50, wherein the biological sample comprises urine, feces, saliva, whole blood, plasma, organ tissue, hair, skin, cells, or cell cultures.

Specific embodiment 52: A method of binding a compound of Formula (I) or a stereoisomer or a tautomer thereof, in a subject who is taking therapeutically effective amount of the compound of formula (I) or a stereoisomer or a tautomer thereof, comprising administering to the subject a pharmaceutically effective dose of the isolated antigen binding peptide or the isolated antibody Fab fragment or the isolated antibody tandem Fab fragment of any one of claims 1-34, wherein

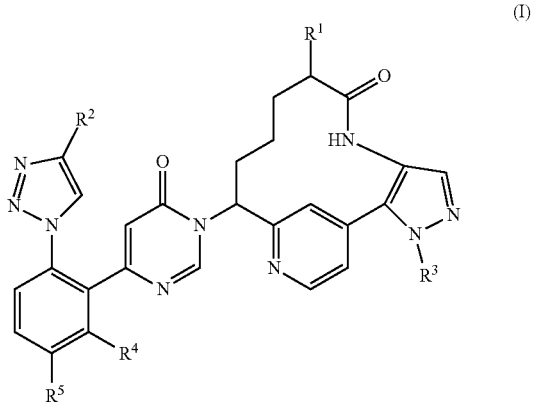

(I)

$R^1$ is C1-4 alkyl;
$R^2$ is independently selected from F, Cl, $CF_3$, $CHF_2$, $CH_2F$, $CH_3$;
$R^3$ is independently selected from $CF_3$, $CHF_2$, $CH_2F$, and $CH_3$;
$R^4$ is H; and
R5 is independently selected from F and Cl.

Specific embodiment 53: The method of embodiment 52, wherein the compound of Formula (I) has Formula (II):

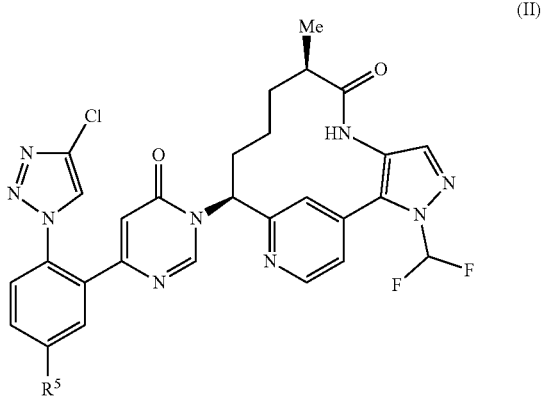

(II)

Specific embodiment 54: The method of any one of embodiments 52 or 53, wherein the pharmaceutically effective dose of the isolated antigen binding peptide or the isolated antibody Fab fragment or the isolated antibody tandem Fab fragment comprises the antigen binding peptide or the antibody Fab fragment or the antibody tandem Fab fragment at an at least about 1:1 molar ratio to the dose of the compound of Formula (I) or (II), or an at least about 1:1 molar ratio to the presence of the compound of Formula (I) or (II) in the subject.

Specific embodiment 55: The method of any one of embodiments 52-54, wherein the isolated antigen binding peptide or the isolated antibody Fab fragment or the isolated the antibody tandem Fab fragment is administered concurrently with or after the administration of the compound of Formula (I) or (II).

Specific embodiment 56: The method of any one of embodiments 52-55, wherein the isolated antigen binding peptide or the isolated antibody Fab fragment or the isolated the antibody tandem Fab fragment is administered intravenously, intramuscularly, or subcutaneously.

Specific embodiment 57: The method of any one of embodiments 52-56, wherein the subject is a human.

BRIEF DESCRIPTION OF THE DRAWINGS

FIGS. 1A and 1B depict a comparison of the sequence of the 26D5 mAb to the closest human germline V and J gene sequences. FIG. 1A: Shows VH sequence of 26D5 compared to IGHV3-53 and IGHJ4 germline sequences. Kabat numbering is shown. Kabat definitions of HCDR2 and HCDR3 are shown. Kabat and AbM definitions of HCDR1 are shown. FIG. 1A discloses SEQ ID NOS 205, 83 and 220, respectively, in order of appearance. FIG. 1B: Shows VK sequence of 26D5 compared to IGKV1-12 and IGKJ4 germline sequences. Kabat numbering is shown. Kabat definitions of CDRs are shown. FIG. 1B discloses SEQ ID NOS 206, 98 and 207, respectively, in order of appearance.

FIG. 2 depicts the positions of the 26D5-GV-Q mAb that were randomized for a mutational scan. Kabat numbering is shown for each position randomized in the mutational scan. Kabat definition is shown for LCDR1-3, HCDR2-3 (but last 6 amino acids missing from HCDR2 here); AbM definition is shown for HCDR1. FIG. 2 discloses SEQ ID NOS 33, 46, 208-209 and 26, respectively, in order of appearance.

FIGS. 3A-E depict heat map scans of the positions of the 26D5-GV-Q mAb indicating the effect of mutations at the indicated positions on antibody binding (favorable, neutral or unfavorable). FIG. 3A shows LCDR1 (SEQ ID NO: 33); FIG. 3B shows LCDR3 (SEQ ID NO: 46); FIG. 3C shows HCDR1 (SEQ ID NO: 208); FIG. 3D shows HCDR2 (SEQ ID NO: 209); FIG. 3E shows HCDR3 (SEQ ID NO: 26).

FIGS. 4A and 4B depict the alignment of amino acid sequences of progeny derived from affinity maturation of the 26D5-GV-Q antibody. Kabat definitions are used for CDRs and numbering. FIG. 4A shows alignment of the heavy chain variable region (SEQ ID NOS 83, 82, 74, 60, 67, 62, 75, 66, 64, 69, 71, 60, 68, 77, 66, 76, 69, 70, 71, 73, 72, 65, 70 and 63, respectively, in order of appearance). FIG. 4B shows alignment of the light chain variable region (SEQ ID NOS 98, 99, 88, 88, 88, 88, 88, 88, 88, 88, 88, 93, 93, 94, 95, 88, 95, 88, 94, 95, 88, 94, 95 and 88, respectively, in order of appearance).

FIG. 5 depicts the positions of the 26D5-295-B08 mAb that were randomized for a mutational scan. Kabat numbering is shown for each position randomized in the mutational scan. FIG. 5 discloses SEQ ID NOS 210-215, respectively, in order of appearance.

Figure 6A:
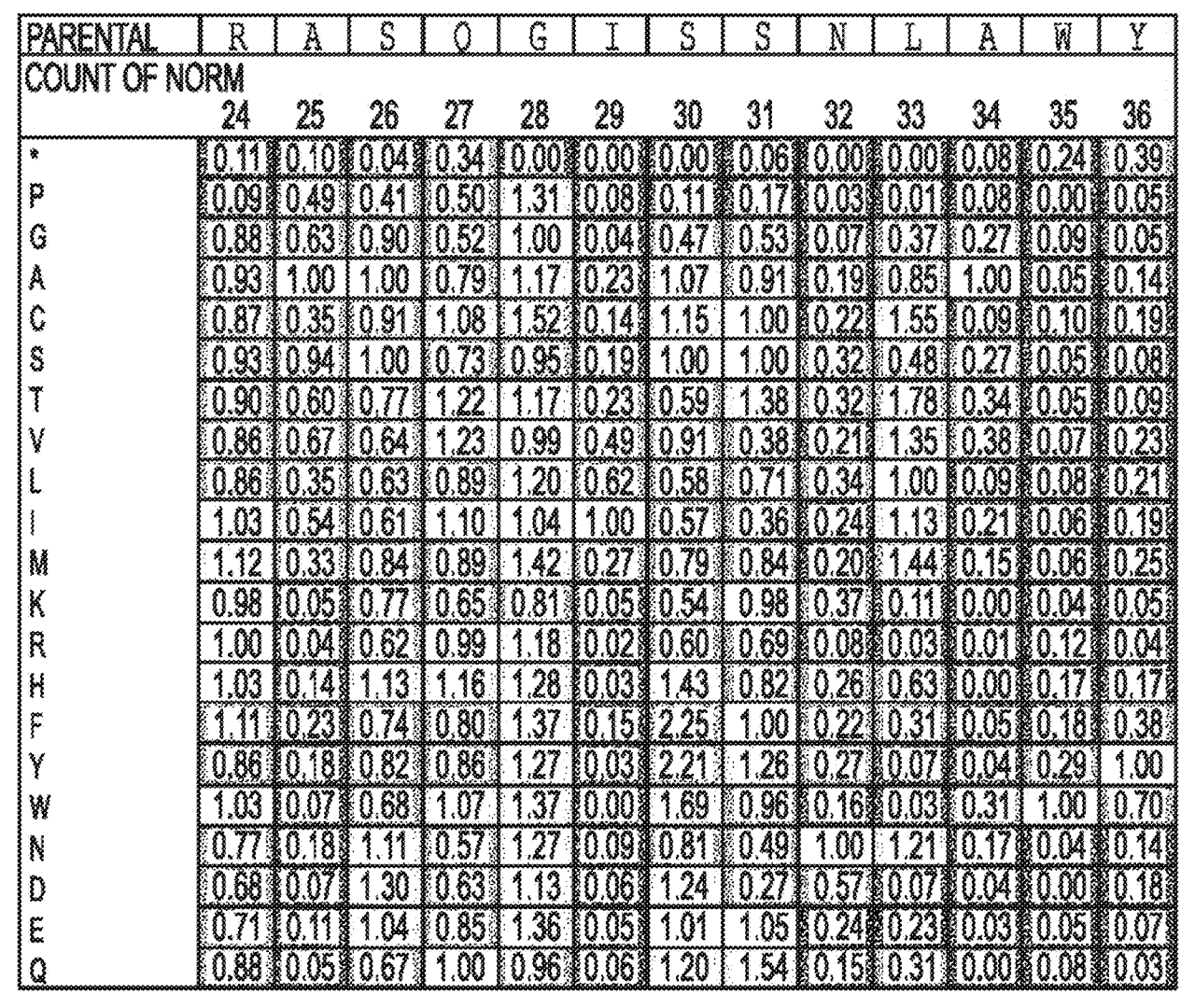

FIGS. 6A-F depict heat map scans of the CDRs and adjacent framework positions of the 26D5-295-B08 mAb indicating the effect of mutations at the indicated positions on antibody binding (see FIG. 3A for further explanation). FIG. 6A shows LCDR1 (SEQ ID NO: 210); FIG. 6B shows LCDR2 (SEQ ID NO: 211); FIG. 6C shows LCDR3 (SEQ ID NO: 212); FIG. 6D shows HCDR1 (SEQ ID NO: 213); FIG. 6E shows HCDR2 (SEQ ID NO: 214); FIG. 6F shows HCDR3 (SEQ ID NO: 215).

FIGS. 7A and 7B depict the amino acid positions of the 26D5-295-B08 mAb randomized to create complex libraries (FIG. 7A, Complex Chip Library (SEQ ID NOS 216-219, respectively, in order of appearance); FIG. 7B, Complex Doped Library (SEQ ID NO: 215)).

FIGS. 8A and 8B depict the alignment of amino acid sequences of progeny derived from affinity maturation of the 26D5-295-B08 mAb. Kabat definition is used for CDRs and numbering. FIG. 8A shows alignment of the heavy chain variable region (SEQ ID NOS 83, 82, 60, 54, 52, 54, 60, 53, 61, 56, 59, 57, 57, 58 and 55, respectively, in order of appearance).

FIG. 8B shows alignment of the light chain variable region (SEQ ID NOS 98, 99, 88, 86, 84, 87, 91, 85, 89, 89, 88, 92, 90, 88 and 88, respectively, in order of appearance).

DETAILED DESCRIPTION OF THE INVENTION

Figure 3A:
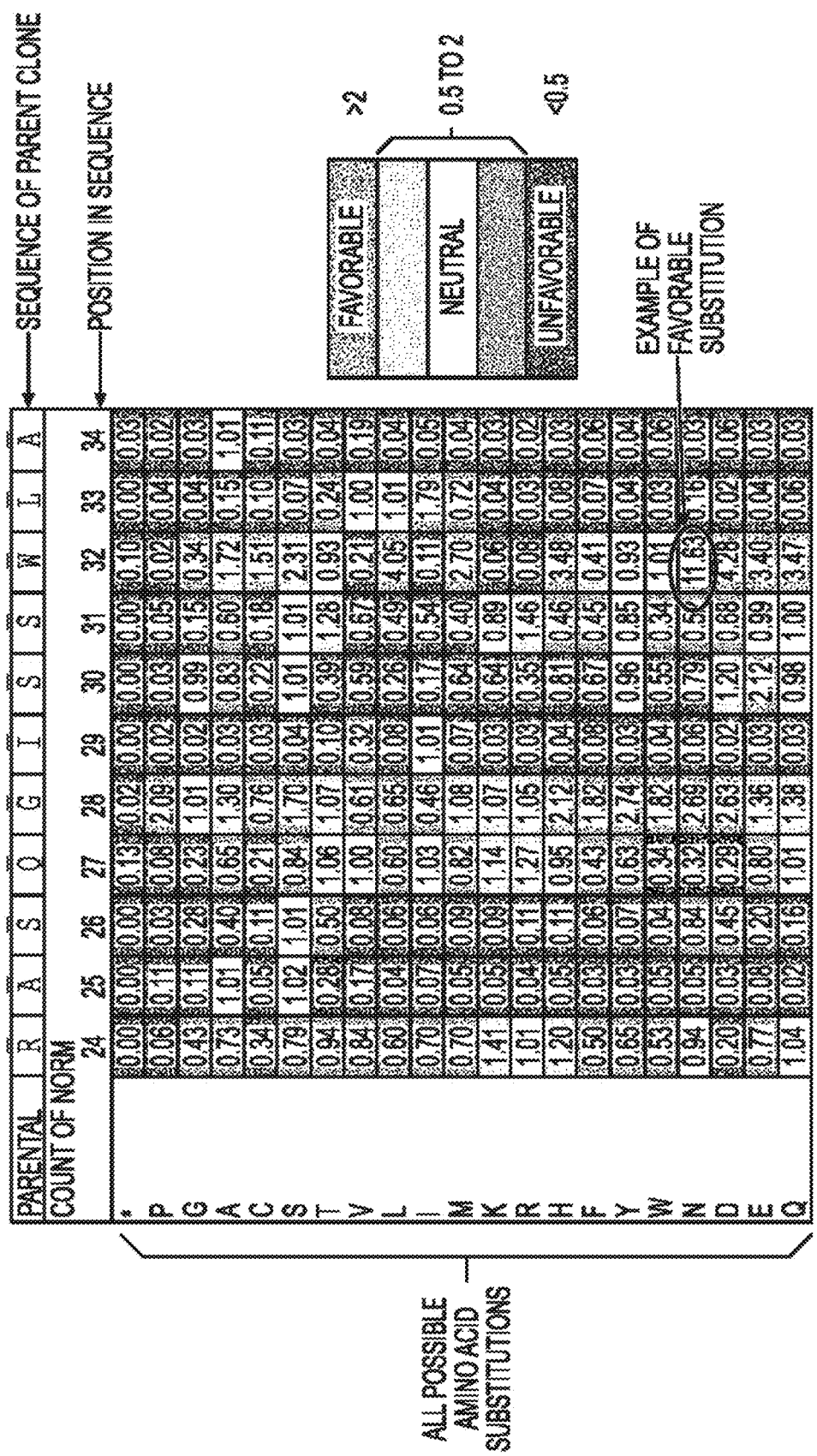

The present invention provides novel antibodies or antigen binding peptides that bind to selective FXIa inhibitors and/or dual inhibitors of FXIa and plasma kallikrein. As used herein, FXIa inhibitors are compounds set forth in Formula (I) and have the ability to inhibit the activity or function of FXIa. Accordingly, in some embodiments, the antigen binding peptide, such as, but not limited to, an antibody or antibody fragment, provided herein specifically binds to the compound set forth in Formula (I) or a stereoisomer or a tautomer thereof. In some embodiments, the $R^1$ in Formula (I) is $C_{1-4}$ alkyl; $R^2$ in Formula (I) is independently selected from F, Cl, $CF_3$, $CHF_2$, $CH_2F$, $CH_3$; the $R^3$ in Formula (I) is independently selected from $CF_3$, $CHF_2$, $CH_2F$, and $CH_3$; the $R^4$ in Formula (I) is H; and the $R^5$ in Formula (I) is independently selected from F and Cl. In certain embodiments, the antigen binding peptide, such as, but not limited to, an antibody or antibody fragment, provided herein specifically binds to the compound set forth in Formula (II). As used herein, the term the compound of Formula (I) or (II) encompasses all the compounds with the Formula (I) or (II), or a stereoisomer or a tautomer thereof.

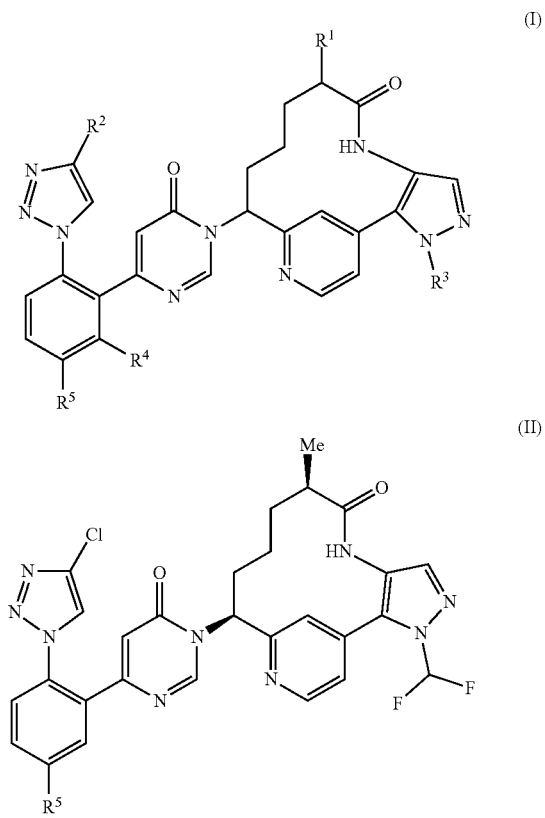

In a specific embodiment, the antigen to be sequester by the antigen binding peptides of the present invention is compound of Formula (II) (also referred to as Compound A herein and known as milvexian). Milvexian is a direct-acting, reversible, small molecule therapeutic agent that binds to and inhibits the activated form of human coagulation Factor XI (FXIa) with high affinity and selectivity. Milvexian has the chemical name (5R,9S)-9-(4-(5-chloro-2-(4-chloro-1H-1,2,3-triazol-1-yl)phenyl)-6-oxopyrimidin-1(6H)-yl)-21-(difluoromethyl)-5-methyl-21H-3-aza-1(4,2)-pyridina-2(5,4)-pyrazolacyclononaphan-4-one. Milvexian and a method of preparing milvexian are described in U.S. Pat. No. 9,453,018, which is hereby incorporated by reference in its entirety.

As used herein, FXIa refers to a serine protease in the intrinsic pathway involved in the regulation of blood coagulation. The structure and physiologic function of FXIa are generally well known in the art. It is primarily synthesized by hepatocytes and circulates in a zymogen form, FXI. FXI is then physiologically activated by FXIIa and thrombin. See Mohammed B. et al. Thromb Res., 161:94-105 (2018), which is incorporated by reference.

As used herein, the term "antigen binding peptide" refers to a protein or polypeptide molecule that recognizes and specifically binds to a target molecule (i.e., antigen). Examples of the target molecules include but are not limited to, a small molecule compound, protein, polypeptide, peptide, carbohydrate, polynucleotide, lipid, or any portion or combination of the foregoing.

In some embodiments, the antigen binding peptide of the present invention is an antibody or an antibody fragment, such as, but not limited to, (Fab), Fab', F(ab')$_2$, Fd, single chain Fv or scFv, disulfide linked Fv, V-NAR domain, IgNar, intrabody, IgGACH2, minibody, F(ab')$_3$, tetrabody, triabody, diabody, single-domain antibody, DVD-Ig, Fcab, mAb$^2$, (scFv)$_2$, scFv-Fc, or a tandem Fab.

In some embodiments, the antigen binding peptides, e.g., antibody or Fab fragment, of the present invention may be isolated. As used herein, the term "isolate" means that the nucleic acid, peptide or protein is removed from its native environment, for example from a cell or organism producing it, or from a fluid in which the nucleic acid, peptide or protein occurs naturally. For peptides or proteins with novel, non-naturally occurring amino acid sequences, an "isolate" peptide or protein means that the protein or peptide has been removed from the engineered cell producing the peptide or protein. For purposes of the present invention, the peptide or protein can still be considered as isolated if the peptide or protein is a component of a mixture or composition, e.g., a pharmaceutical formulation, provided that the protein or peptide is not within the cell producing the peptide or protein and is not otherwise in its native environment.

In one specific embodiment of the present invention, a Fab is provided as the antigen binding peptide. As used herein, the term "Fab" or "antibody Fab fragment" is a well-known term and refers to the region on a full length antibody that binds to antigens. In some embodiments, an antibody Fab fragment is composed of at least the full length light chain and the N-terminal portion of the heavy chain. As used herein, the full length light chain comprises at least the light chain constant region (CL) and the light chain variable region (VL); and the N-terminal portion of the heavy chain comprises at least the CH1 domain of the heavy chain constant region and the heavy chain variable region (VH).

In one specific embodiment of the present invention, a tandem Fab is provided as the antigen binding peptide. A tandem Fab, as provided herein, comprises at least one N-terminal portion of the heavy chain (VH-CH1) and at least one full length light chain (VL-CL). In some embodiments, the tandem Fab provided herein comprises two or more N-terminal portions of the heavy chain linked via a linker (e.g., VH-CH1-linker-CH1-VH or VH-CH1-linker-VH-CH1), each paired with one full length light chain (VL-CL). In an exemplary embodiment, the tandem Fab provided herein comprises two N-terminal portions of the heavy chains linked via a linker (e.g., VH-CH1-linker-CH1-VH or VH-CH1-linker-VH-CH1), each paired with one full length light chain (VL-CL). In some embodiments, the linker is a polypeptide linker. Exemplary tandem Fab are provided in Table 4 of the present invention. The terms "tandem Fab", "antibody tandem Fab fragment" and "antibody TanFab fragment" are used interchangeably herein.

A "variable region" of an antibody is a well-known term of art and refers to the end of the light chain or the heavy chains that contributes to an antibody's specificity for binding its antigen. The terms "heavy chain variable region," "variable heavy chain," and "VH" are used interchangeably and refer to the end of the heavy chain that contributes to an antibody's specificity for binding its antigen. Likewise, the terms "light chain variable region," "variable light chain," and "VL" are used interchangeably and refer to the end of the light chain that contributes to an antibody's specificity for binding its antigen.

The variable regions of the heavy chain and light chain each generally consist of four framework regions (FRs) connected by three complementarity determining regions (CDRs), also known as hypervariable regions. The CDRs in each chain are held together in close proximity by the FRs and, with the CDRs from the other chain, contribute to the formation of the antigen-binding domain of antibodies. The techniques for determining CDRs are generally known in the art. For example, there are at least two techniques for determining CDRs: (1) an approach based on cross-species sequence variability; and (2) an approach based on crystallographic studies of antigen-antibody complexes. In addition, combinations of these two approaches are sometimes used in the art to determine CDRs. The CDRs of each chain are numbered CDR1, CDR2 and CDR3 numbered in the direction from the amino terminal end to the carboxy terminal end.

A "constant region" of an antibody is a well-known term of art and refers to the part of the antibody that is relatively constant in amino acid sequence between different antibody molecules. Typically, the heavy chain constant region is composed of three distinct regions, termed CH1, CH2, and CH3, numbered in the direction from the amino terminal (N-terminal) end to the carboxy terminal (C-terminal) end. A typical light chain has only one constant region, termed CL. The constant region of an antibody determines its particular effector function. One of skill in the art will readily understand the terminology and structural features of constant regions of antibodies.

In some embodiments, the antigen binding peptide encompasses any modified polypeptide molecule comprising at least one antigen recognition site as long as the modified polypeptide molecule exhibits the desired antigen binding activity. The antigen binding peptides provided herein may or may not be conjugated to other molecules, such as toxins, radioisotopes, fluorescent labels, etc.

As used herein, the term "antibody" is a well-known term of art and refers to an immunoglobulin molecule that recognizes and specifically binds to a target molecule through at least one antigen recognition site within at least a portion of the variable region of the immunoglobulin molecule. The structure of an antibody is generally known in the art and is often composed of at least two full length heavy chains. The majority of antibodies, with the most notable exception being camelid antibodies, are composed of at least two full length heavy chains and at least two full length light chains. As used herein, an antibody encompasses polyclonal antibodies, monoclonal antibodies (also referred to herein as "mAbs"), multispecific antibodies such as bispecific antibodies generated from at least two antibodies, chimeric antibodies, humanized antibodies, human antibodies, and non-human antibodies. An "antibody" as used herein can be any of the five major classes of immunoglobulins: IgA, IgD, IgE, IgG, and IgM, or subclasses (isotypes) thereof (e.g. IgG1, IgG2, IgG3, IgG4, IgA1, and IgA2), based on the identity of their heavy-chain constant domains referred to as alpha, delta, epsilon, gamma, and mu, respectively. The different classes of immunoglobulins have different and well known subunit structures and three-dimensional configurations.

The Kabat numbering system is generally used when referring to a residue in the heavy chain variable domain or light chain variable domains (approximately residues 1-107 of the light chain and residues 1-113 of the heavy chain). See Kabat et al., Sequences of Proteins of Immunological Interest, 5th Ed. Public Health Service, National Institutes of Health, Bethesda, MD (1991). The antigen interacting residues of CDRs can also be determined by crystallographic studies of antigen-antibody complexes.

The terms "polypeptide," "peptide," and "protein" are used interchangeably herein to refer to polymers of amino acids of any length. The amino acid polymer can be linear or branched, it can comprise modified amino acids, and it can be interrupted by non-amino acids. The terms also encompass an amino acid polymer that has been modified naturally or by intervention. In some embodiments, the amino acid polymer is modified by disulfide bond formation, glycosylation, lipidation, acetylation, phosphorylation, or any other manipulation or modification. In some embodiments, the amino acid polymer is modified by conjugation with a labeling component. Also included within the definition are peptides containing one or more analogs of an amino acid known in the art, as well as unnatural amino acids.

The term "specifically binds to" (or "specific binding") is well-known in the art and generally means that the antigen binding portion of an antigen binding peptide, such as, but not limited to, an antibody or antibody fragment, specifically recognizing an antigen via its antigen binding domain, and that the binding entails at least some complementarity between the antigen binding domain and the antigen. According to this definition, the antigen binding peptide, such as, but not limited to, an antibody or antibody fragment, is said to "specifically bind" to the epitope of an antigen, via its antigen binding domain more readily than it would bind to a random, unrelated antigen.

In some embodiments, the antibody or antibody fragment of the present invention comprises the combinations of VH and VL CDR sequences provided in Table 1. In some embodiments, the antibody or antibody fragment of the present invention provided herein specifically binds to the FXIa inhibitors disclosed herein, such as, but not limited to, the FXIa inhibitors of Formula (I), and comprises VH and VL CDRs wherein each CDR independently has up to four (i.e., 0, 1, 2, 3, or 4) conservative amino acid substitutions from the corresponding CDR disclosed in Table 1.

TABLE 1

Variable heavy chain (VH) and light chain (VL) CDR amino acid sequences

| Fab/mAb Name | VH-CDR1 | VH-CDR2 | VH-CDR3 | VL-CDR1 | VL-CDR2 | VL-CDR3 |
|---|---|---|---|---|---|---|
| 26D5-75229-343-A10 | SNAMS (SEQ ID NO: 1) | YIYPGGRTYYADSVKG (SEQ ID NO: 13) | AGFGGPDY (SEQ ID NO: 23) | RASQGISSNLA (SEQ ID NO: 29) | AASSLQS (SEQ ID NO: 38) | QQANQFPLT (SEQ ID NO: 44) |
| 26D5-75214-343-F06 | SNAMS (SEQ ID NO: 1) | FIYPGGRTYYADSVKG (SEQ ID NO: 14) | AGFGGPDY (SEQ ID NO: 23) | RASQGISSNLA (SEQ ID NO: 29) | AASSLQS (SEQ ID NO: 38) | QQANEFPLT (SEQ ID NO: 45) |
| 26D5-75202-343-A09 | SNAMS (SEQ ID NO: 1) | YIYPGGRTYYADSVKG (SEQ ID NO: 13) | AGFGGGDY (SEQ ID NO: 24) | RASQGIYSNLA (SEQ ID NO: 30) | AASSLQS (SEQ ID NO: 38) | QQANEFPLT (SEQ ID NO: 45) |
| 26D5-75203-343-B09 | SNAMS (SEQ ID NO: 1) | YIYPGGRTYYADSVKG (SEQ ID NO: 13) | AGFGGGDY (SEQ ID NO: 24) | RASQGISSNLA (SEQ ID NO: 29) | AASTLQS (SEQ ID NO: 39) | QQANEFPLT (SEQ ID NO: 45) |
| 26D5-75616-348-F10 | SNAMS (SEQ ID NO: 1) | FIYPGGRTYYADSVKG (SEQ ID NO: 14) | AEFGLEDI (SEQ ID NO: 25) | RASQGISSNLA (SEQ ID NO: 29) | AASSLQS (SEQ ID NO: 38) | QQANSFPLT (SEQ ID NO: 46) |
| 26D5-75768-348-A10 | SNAVS (SEQ ID NO: 2) | YIYPGGRTYYADSVKG (SEQ ID NO: 13) | GGFGGGDY (SEQ ID NO: 26) | RASQGISSNNQ (SEQ ID NO: 31) | YASSLQS (SEQ ID NO: 40) | QQGNEFPLT (SEQ ID NO: 47) |
| 26D5-75747-348-D07 | SNAFS (SEQ ID NO: 3) | YIYSGGRTYYADSVKG (SEQ ID NO: 15) | AGFGGGDY (SEQ ID NO: 24) | RASQGISSQVA (SEQ ID NO: 32) | YASSLQS (SEQ ID NO: 40) | QQGNEFPLT (SEQ ID NO: 47) |
| 26D5-75602-348-F04 | SNQFS (SEQ ID NO: 4) | YFYPGGRTYYADSVKG (SEQ ID NO: 16) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-75576-348-B03 | SNDMS (SEQ ID NO: 5) | YIYSGGRTYYADSVKG (SEQ ID NO: 15) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-75017-343-F04 | SNAMS (SEQ ID NO: 1) | FIYPGGRTYYADSVKG (SEQ ID NO: 14) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-75592-348-A04 | SNAIA (SEQ ID NO: 6) | YIYPGGRTYYADSVKG (SEQ ID NO: 13) | AGFGGGDY (SEQ ID NO: 24) | RASQGISSNNQ (SEQ ID NO: 31) | YASSLQS (SEQ ID NO: 40) | QQGNEFPLT (SEQ ID NO: 47) |

TABLE 1-continued

Variable heavy chain (VH) and light chain (VL) CDR amino acid sequences

| Fab/mAb Name | VH-CDR1 | VH-CDR2 | VH-CDR3 | VL-CDR1 | VL-CDR2 | VL-CDR3 |
|---|---|---|---|---|---|---|
| 26D5-75746-348-C07 | SNAFS (SEQ ID NO: 3) | YIYSGGRTYYADSVKG (SEQ ID NO: 15) | AGFGGGDY (SEQ ID NO: 24) | RASQGISSQVA (SEQ ID NO: 32) | PASNLWS (SEQ ID NO: 41) | QQANNFPLT (SEQ ID NO: 48) |
| 26D5-296-A07 | SNAMS (SEQ ID NO: 1) | FIYPGGRTYYADSVKG (SEQ ID NO: 14) | AGFGGGDY (SEQ ID NO: 24) | RASQGISSWLA (SEQ ID NO: 33) | AASSLQS (SEQ ID NO: 38) | QQHNSFPLT (SEQ ID NO: 49) |
| 26D5-295-B08 | SNAMS (SEQ ID NO: 1) | FIYPGGRTYYADSVKG (SEQ ID NO: 14) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-295-C08 | SNAMS (SEQ ID NO: 1) | FIYPGGRTYYADSVKG (SEQ ID NO: 14) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-H03 | SNAMS (SEQ ID NO: 1) | FIYPGGRTYYADSVKG (SEQ ID NO: 14) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-295-F07 | ENAMS (SEQ ID NO: 7) | FIYSGGRTYYADSVKG (SEQ ID NO: 17) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-G07 | ENYMS (SEQ ID NO: 8) | FIYSGGRTYYADSVKG (SEQ ID NO: 17) | AGFGGGDY (SEQ ID NO: 24) | RASQYISSNLA (SEQ ID NO: 34) | AASSLQS (SEQ ID NO: 38) | QQANSFPLT (SEQ ID NO: 46) |
| 26D5-295-E07 | SNAMS (SEQ ID NO: 1) | FIYSGGRTYYADSVKG (SEQ ID NO: 17) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-C08 | SNAMS (SEQ ID NO: 1) | FIYSGGRTYYADSVKG (SEQ ID NO: 17) | GGFGGGDY (SEQ ID NO: 26) | RASQYIESNLA (SEQ ID NO: 35) | AASSLQS (SEQ ID NO: 38) | QQANSFPLT (SEQ ID NO: 46) |
| 26D5-295-C07 | SNAMS (SEQ ID NO: 1) | FIYSGGRTYYADSVKG (SEQ ID NO: 17) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-B07 | SNAMS (SEQ ID NO: 1) | FIYSGGRTYYADSVKG (SEQ ID NO: 17) | AGFGGGDY (SEQ ID NO: 24) | RASQGISSWLA (SEQ ID NO: 33) | AASSLQS (SEQ ID NO: 38) | QQHNSFPLT (SEQ ID NO: 49) |
| 26D5-295-G07 | SNYMS (SEQ ID NO: 9) | FIYPGGRTYYADSVKG (SEQ ID NO: 14) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-D08 | SNYMS (SEQ ID NO: 9) | FIYPGGRTYYADSVKG (SEQ ID NO: 14) | GGFGGGDY (SEQ ID NO: 26) | RASQYIESNLA (SEQ ID NO: 35) | AASSLQS (SEQ ID NO: 38) | QQANSFPLT (SEQ ID NO: 46) |
| 26D5-296-F03 | SNYMS (SEQ ID NO: 9) | FIYSGGRTYYADSVKG (SEQ ID NO: 17) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-296-G08 | SNYMS (SEQ ID NO: 9) | FIYSGGRTYYADSVKG (SEQ ID NO: 17) | AGFGGGDY (SEQ ID NO: 24) | RASQYIESNLA (SEQ ID NO: 35) | AASSLQS (SEQ ID NO: 38) | QQANSFPLT (SEQ ID NO: 46) |
| 26D5-295-H07 | SNYMS (SEQ ID NO: 9) | FIYSGGRTYYADSVKG (SEQ ID NO: 17) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-296-F07 | SNYMS (SEQ ID NO: 9) | FIYSGGRTYYADSVKG (SEQ ID NO: 17) | AGFGGGDY (SEQ ID NO: 24) | RASQYISSNLA (SEQ ID NO: 34) | AASSLQS (SEQ ID NO: 38) | QQANSFPLT (SEQ ID NO: 46) |

TABLE 1-continued

Variable heavy chain (VH) and light chain (VL) CDR amino acid sequences

| Fab/mAb Name | VH-CDR1 | VH-CDR2 | VH-CDR3 | VL-CDR1 | VL-CDR2 | VL-CDR3 |
|---|---|---|---|---|---|---|
| 26D5-296-G03 | SNYMS (SEQ ID NO: 9) | FIYPGGRTYYADSVKG (SEQ ID NO: 14) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-296-F08 | SNYMS (SEQ ID NO: 9) | FIYPGGETYYADSVKG (SEQ ID NO: 18) | GGFGGGDY (SEQ ID NO: 26) | RASQYIESNLA (SEQ ID NO: 35) | AASSLQS (SEQ ID NO: 38) | QQANSFPLT (SEQ ID NO: 46) |
| 26D5-295-A08 | ENYMS (SEQ ID NO: 8) | FIYPGGRTYYADSVKG (SEQ ID NO: 14) | AGFGGGDY (SEQ ID NO: 24) | RASQGISSNLA (SEQ ID NO: 29) | AASSLQS (SEQ ID NO: 38) | QQANSFPLT (SEQ ID NO: 46) |
| 26D5-295-D07 | ENYMS (SEQ ID NO: 8) | FIYSGGRTYYADSVKG (SEQ ID NO: 17) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-D03 | SNYMS (SEQ ID NO: 9) | FIYSGGETFYADSVKG (SEQ ID 19) | GGFGGGDY (SEQ ID NO: 26) | RASQGISSNLA (SEQ ID NO: 29) | AASSLQS (SEQ ID NO: 38) | QQANSFPLT (SEQ ID NO: 46) |
| 26D5-296-C07 | SNYMS (SEQ ID NO: 9) | FIYSGGRTYYADSVKG (SEQ ID NO: 17) | GGFGGGDY (SEQ ID NO: 26) | RASQYISSNLA (SEQ ID NO: 34) | AASSLQS (SEQ ID NO: 38) | QQANSFPLT (SEQ ID NO: 46) |
| 9C8-VGSKE | SGYYWG (SEQ ID NO: 10) | SIYHSGNTYYSPSLQS (SEQ ID NO: 20) | GGDFDILTGYYKGWFEP (SEQ ID NO: 27) | RASQGISSALA (SEQ ID NO: 36) | DASSLES (SEQ ID NO: 42) | QQFNSYPQT (SEQ ID NO: 50) |
| 1H2-K | SGHYWS (SEQ ID NO: 11) | GIYHSGTTYYNPSLKS (SEQ ID NO: 21) | DGYYDILTGYYNQYFQH (SEQ ID NO: 28) | RASQSVSSSYLA (SEQ ID NO: 37) | GASSRAT (SEQ ID NO: 43) | QQYGSSPFT (SEQ ID NO: 51) |
| 24H1-GQTV | RNYMS (SEQ ID NO: 12) | FIYSGGSTYYADSVKG (SEQ ID NO: 22) | GGFGGGDY (SEQ ID NO: 26) | RASQGISSWLA (SEQ ID NO: 33) | AASSLQS (SEQ ID NO: 38) | QQANSFPLT (SEQ ID NO: 46) |
| 26D5-GVR-Q-FT | RNYMS (SEQ ID NO: 12) | FIYSGGRTYYADSVKG (SEQ ID NO: 17) | GGFGGGDY (SEQ ID NO: 26) | RASQGISSWLA (SEQ ID NO: 33) | AASSLQS (SEQ ID NO: 38) | QQANSFPLT (SEQ ID NO: 46) |
| 26D5-GVR-H | RNYMS (SEQ ID NO: 12) | FIYSGGRTYYADSVKG (SEQ ID NO: 17) | GGFGGGDY (SEQ ID NO: 26) | RASQGISSWLA (SEQ ID NO: 33) | AASSLQS (SEQ ID NO: 38) | QQANSFPLT (SEQ ID NO: 46) |
| 26D5-GV-Q | SNYMS (SEQ ID NO: 9) | FIYSGGRTYYADSVKG (SEQ ID NO: 17) | GGFGGGDY (SEQ ID NO: 26) | RASQGISSWLA (SEQ ID NO: 33) | AASSLQS (SEQ ID NO: 38) | QQANSFPLT (SEQ ID NO: 46) |
| 26D5 | SNYMS (SEQ ID NO: 9) | FIYSGGRTYYADSVKG (SEQ ID NO: 17) | GGFGGGDY (SEQ ID NO: 26) | RASQGISSWLA (SEQ ID NO: 33) | AASSLQS (SEQ ID NO: 38) | QQANSFPLT (SEQ ID NO: 46) |

In some embodiments, the antibody or antibody fragment of the present invention comprises the combinations of VH and VL amino acid sequences provided in Table 2. In some embodiments, the antibody or antibody fragment of the present invention comprises the combinations of partial heavy chain amino acid sequences and full length light chain amino acid sequences provided in Table 3. In some embodiments, the antibody or antibody fragment of the present invention comprises the combinations of tandem partial heavy chain amino acid sequences and full length light chain amino acid sequences provided in Table 4.

In some embodiments, the antibody or antibody fragment of the present invention comprises one or more of the individual variable light chains or variable heavy chains described herein. In some embodiments, the antibody or antibody fragment of the present invention comprises both a variable light chain and a variable heavy chain described herein. In some embodiments, the antibody or antibody fragment of the present invention comprises one variable heavy chain, paired with one variable light chain described herein. In some embodiments, the antibody or antibody fragment of the present invention comprises more than one variable heavy chains, each paired with one variable light chain described herein. In some embodiments, the antibody or antibody fragment of the present invention comprise two variable heavy chains, each paired with one variable light chains described herein.

The present invention also encompasses antibodies or antibody fragments that comprise VH and VL sequences that are at least about 80%, 85%, 89%, 90%, 95%, or 99% identical to the VH and VL sequences disclosed herein in Table 2.

TABLE 2

Heavy chain and light chain variable chain amino acid sequences
(the underlined portions are the CDRs and the
non-underlined portions are the framework regions)

| Fab/mAb Name | Heavy Chain Variable Domain (VH) | Light Chain Variable Domain (VL) |
|---|---|---|
| 26D5-75229-343-A10 | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSS (SEQ ID NO: 52) | DIQMTQSPSSVSASVGDRVTITCRASQGISSNLAWYQQKPGKAPKLLIYAASSLQSGVPSRFSGSGSGTDFTLTISSLQPEDFATYYCQQANQFPLTFGGGTKVEIK (SEQ ID NO: 84) |
| 26D5-75214-343-F06 | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAGFGGPDYWGQGTLVTVSS (SEQ ID NO: 53) | DIQMTQSPSSVSASVGDRVTITCRASQGISSNLAWYQQKPGKAPKLLIYAASSLQSGVPSRFSGSGSGTDFTLTISSLQPEDFATYYCQQANEFPLTFGGGTKVEIK (SEQ ID NO: 85) |
| 26D5-75202-343-A09 | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGGDYWGQGTLVTVSS (SEQ ID NO: 54) | DIQMTQSPSSVSASVGDRVTITCRASQGIYSNLAWYQQKPGKAPKLLIYAASSLQSGVPSRFSGSGSGTDFTLTISSLQPEDFATYYCQQANEFPLTFGGGTKVEIK (SEQ ID NO: 86) |
| 26D5-75203-343-B09 | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGGDYWGQGTLVTVSS (SEQ ID NO: 54) | DIQMTQSPSSVSASVGDRVTITCRASQGISSNLAWYQQKPGKAPKLLIYAASTLQSGVPSRFSGSGSGTDFTLTISSLQPEDFATYYCQQANEFPLTFGGGTKVEIK (SEQ ID NO: 87) |
| 26D5-75616-348-F10 | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAEFGLEDIWGQGTLVTVSS (SEQ ID NO: 55) | DIQMTQSPSSVSASVGDRVTITCRASQGISSNLAWYQQKPGKAPKLLIYAASSLQSGVPSRFSGSGSGTDFTLTISSLQPEDFATYYCQQANSFPLTFGGGTKVEIK (SEQ ID NO: 88) |
| 26D5-75768-348-A10 | EVQLVESGGGLIQPGGSLRLSCAASGFTVSSNAVSIVRQAPGKGLEWVAYIYPGGRTYYADSVKGRFTISRDNSKNTLYLQMNSLRAEDTAVYYCTIGGFGGGDYWGQGTLVTVSS (SEQ ID NO: 56) | DIQMTQSPSSVSASVGDRVTITCRASQGISSNNQWYQQKPGKAPKLLIYYASSLQSGVPSRFSGSGSGTDFTLTISSLQPEDFATYYCQQGNEFPLTFGGGTKVEIK (SEQ ID NO: 89) |
| 26D5-75747-348-D07 | EVQLVESGGGLIQPGGSLRLSCAASGFTVSSNAFSWVRQAPGKGLEWVSYIYSGGRTYYADSVKGRFTISRDNSKNTLYLQMNSLRAEDTAVYYCAAAGFGGGDYWGQGTLVTVSS (SEQ ID NO: 57) | DIQMTQSPSSVSASVGDRVTITCRASQGISSQVAWYQQKPGKAPKLLIYYASSLQSGVPSRFSGSGSGTDFTLTISSLQPEDFATYYCQQGNEFPLTFGGGTKVEIK (SEQ ID NO: 90) |
| 26D5-75602-348-F04 | EVQLVESGGGLIQPGGSLRLSCAASGFTVSSNQFSWVRQAPGKGLEWVSYFYPGGRTYYADSVKGRFTISRDNSKNTLYLQMNSLRAEDTAVYYCAKAGFGGGDYWGQGTLVTVSS (SEQ ID NO: 58) | DIQMTQSPSSVSASVGDRVTITCRASQGISSNLAWYQQKPGKAPKLLIYAASSLQSGVPSRFSGSGSGTDFTLTISSLQPEDFATYYCQQANSFPLTFGGGTKVEIK (SEQ ID NO: 88) |
| 26D5-75576-348-B03 | EVQLVESGGGLIQPGGSLRLSCAASGFTVSSNDMSYVRQAPGKGLEWVAYIYSGGRTYYADSVKGRFTISRDNSKNTLYLQMNSLRAEDTAVYYCVTAGFGGGDYWGQGTLVTVSS (SEQ ID NO: 59) | DIQMTQSPSSVSASVGDRVTITCRASQGISSNLAWYQQKPGKAPKLLIYAASSLQSGVPSRFSGSGSGTDFTLTISSLQPEDFATYYCQQANSFPLTFGGGTKVEIK (SEQ ID NO: 88) |
| 26D5-75017-343-F04 | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAGFGGGDYWGQGTLVTVSS (SEQ ID NO: 60) | DIQMTQSPSSVSASVGDRVTITCRASQGISSNLAWWQQKPGKAPKLLIYAASSLQSGVPSRFSGSGSGTDFTLTISSLQPEDFATYYCQQANSFPLTFGGGTKVEIK (SEQ ID NO: 91) |
| 26D5-75592-348-A04 | EVQLVESGGGLIQPGGSLRLSCAASGFTVSSNAIAWVRQAPGKGLEWVAYIYPGGRTYYADSVKGRFTISRDNSKNTLYLQMNSLRAEDTAVYYCVTAGFGGGDYWGQGTLVTVSS (SEQ ID NO: 61) | DIQMTQSPSSVSASVGDRVTITCRASQGISSNNQWYQQKPGKAPKLLIYYASSLQSGVPSRFSGSGSGTDFTLTISSLQPEDFATYYCQQGNEFPLTFGGGTKVEIK (SEQ ID NO: 89) |
| 26D5-75746-348-C07 | EVQLVESGGGLIQPGGSLRLSCAASGFTVSSNAFSWVRQAPGKGLEWVSYIYSGGRTYYADSVKGRFTISRDNSKNTLYLQMNSLRAEDTAVYYCAAAGFGGGDYWGQGTLVTVSS (SEQ ID NO: 57) | DIQMTQSPSSVSASVGDRVTITCRASQGISSQVAWYQQKPGKAPKLLIYPASNLWSGVPSRFSGSGSGTDFTLTISSLQPEDFATYYCQQANNFPLTFGGGTKVEIK (SEQ ID NO: 92) |
| 26D5-296-A07 | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAGFGGGDYWGQGTLVTVSS (SEQ ID NO: 60) | DIQMTQSPSSVSASVGDRVTITCRASQGISSWLAWYQQKPGKAPKLLIYAASSLQSGVPSRFSGSGSGTDFTLTISSLQPEDFATYYCQQHNSFPLTFGGGTKVEIK (SEQ ID NO: 93) |
| 26D5-295-B08 | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAGFGGGDYWGQGTLVTVSS (SEQ ID NO: 60) | DIQMTQSPSSVSASVGDRVTITCRASQGISSNLAWYQQKPGKAPKLLIYAASSLQSGVPSRFSGSGSGTDFTLTISSLQPEDFATYYCQQANSFPLTFGGGTKVEIK (SEQ ID NO: 88) |

TABLE 2-continued

Heavy chain and light chain variable chain amino acid sequences
(the underlined portions are the CDRs and the
non-underlined portions are the framework regions)

| Fab/mAb Name | Heavy Chain Variable Domain (VH) | Light Chain Variable Domain (VL) |
|---|---|---|
| 26D5-295-C08 | EVQLVESGGGLIQPGGSLRLSCAASGFQVSSNAMSWVRQ APGKGLEWVSFIYPGGRTYYADSVKGRFTISRDNSKNTL YLQMNSLRAEDTAVYYCARGGFGGGDYWGQGTLVTVSS (SEQ ID NO: 62) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-H03 | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARGGFGGGDYWGQGTLVTVSS (SEQ ID NO: 63) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-295-F07 | EVQLVESGGGLIQPGGSLRLSCAASGFTVSENAMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 64) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-G07 | EVQLVESGGGLIQPGGSLRLSCAASGFTVSENYMSWVRQ APGKGLEWVSFIYSGGRTYYADSVKGRFTISRDNSKNTL YLQMNSLRAEDTAVYYCARAGFGGGDYWGQGTLVTVSS (SEQ ID NO: 65) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIK (SEQ ID NO: 94) |
| 26D5-295-E07 | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 66) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-C08 | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 66) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIK (SEQ ID NO: 95) |
| 26D5-295-C07 | EVQLVESGGGLIQPGGSLRLSCAASGFTVSSNAMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 67) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-B07 | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARAGFGGGDYWGQGTLVTVSS (SEQ ID NO: 68) | DIQMTQSPSSVSASVGDRVTITCRASQGISSWLAWYQQ KPGKAPKLLIYAASSLQSGVPSRFSGSGSGTDFTLTIS SLQPEDFATYYCQQHNSFPLTFGGGTKVEIK (SEQ ID NO: 93) |
| 26D5-295-G07 | EVQLVESGGGLIQPGGSLRLSCAASGFTVSSNYMSWVRQ APGKGLEWVSFIYPGGRTYYADSVKGRFTISRDNSKNTL YLQMNSLRAEDTAVYYCARGGFGGGDYWGQGTLVTVSS (SEQ ID NO: 69) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-D08 | EVQLVESGGGLIQPGGSLRLSCAASGFTVSSNYMSWVRQ APGKGLEWVSFIYPGGRTYYADSVKGRFTISRDNSKNTL YLQMNSLRAEDTAVYYCARGGFGGGDYWGQGTLVTVSS (SEQ ID NO: 69) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIK (SEQ ID NO: 95) |
| 26D5-296-F03 | EVQLVESGGGLIQPGGSLRLSCAASGFQVSSNYMSWVRQ APGKGLEWVSFIYSGGRTYYADSVKGRFTISRDNSKNTL YLQMNSLRAEDTAVYYCARAGFGGGDYWGQGTLVTVSS (SEQ ID NO: 70) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-G08 | EVQLVESGGGLIQPGGSLRLSCAASGFQVSSNYMSWVRQ APGKGLEWVSFIYSGGRTYYADSVKGRFTISRDNSKNTL YLQMNSLRAEDTAVYYCARAGFGGGDYWGQGTLVTVSS (SEQ ID NO: 70) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIK (SEQ ID NO: 95) |
| 26D5-295-H07 | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARAGFGGGDYWGQGTLVTVSS (SEQ ID NO: 71) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-F07 | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARAGFGGGDYWGQGTLVTVSS (SEQ ID NO: 71) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIK (SEQ ID NO: 94) |

TABLE 2-continued

Heavy chain and light chain variable chain amino acid sequences
(the underlined portions are the CDRs and the
non-underlined portions are the framework regions)

| Fab/mAb Name | Heavy Chain Variable Domain (VH) | Light Chain Variable Domain (VL) |
|---|---|---|
| 26D5-296-G03 | EVQLVESGGGLIQPGGSLRLSCAASGFQVSSNYMSWVRQ APGKGLEWVSFIYPGGRTYYADSVKGRFTISRDNSKNTL YLQMNSLRAEDTAVYYCARAGFGGGDYWGQGTLVTVSS (SEQ ID NO: 72) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-F08 | EVQLVESGGGLIQPGGSLRLSCAASGFTVSSNYMSWVRQ APGKGLEWVSFIYPGGETYYADSVKGRFTISRDNSKNTL YLQMNSLRAEDTAVYYCARGGFGGGDYWGQGTLVTVSS (SEQ ID NO: 73) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIK (SEQ ID NO: 95) |
| 26D5-295-A08 | EVQLVESGGGLIQPGGSLRLSCAASGFTVSENYMSWVRQ APGKGLEWVSFIYPGGRTYYADSVKGRFTISRDNSKNTL YLQMNSLRAEDTAVYYCARAGFGGGDYWGQGTLVTVSS (SEQ ID NO: 74) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-295-D07 | EVQLVESGGGLIQPGGSLRLSCAASGFQVSENYMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 75) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-D03 | EVQLVESGGGLIQPGGSLRLSCAASGFTVSSNYMSWVRQ APGKGLEWVSFIYSGGETFYADSVKGRFTISRDNSKNTL YLQMNSLRAEDTAVYYCARGGFGGGDYWGQGTLVTVSS (SEQ ID NO: 76) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIK (SEQ ID NO: 88) |
| 26D5-296-C07 | EVQLVESGGGLIQPGGSLRLSCAASGITVSSNYMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 77) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIK (SEQ ID NO: 94) |
| 9C8-VGSKE | QVQLQESGPGLVKPSETLSLTCAVSGYSISSGYYWGWIR QPPGKGLEWIGSIYHSGNTYYSPSLQSRVTISVDTSKNQ FSLKLSSVTAADTAVYYCARGGDFDILTGYYKGWFEPWG QGTLVTVSS (SEQ ID NO: 78) | AIQLTQSPSSLSASVGDRVTITCRASQGISSALAWYQQ KPGKAPKLLIYDASSLESGVPSRFSGSGSGTDFTLTIS SLQPEDFATYYCQQFNSYPQTFGQGTKVEIK (SEQ ID NO: 96) |
| 1H2-K | QVQLQESGPGLVKPSETLSLICAVSGYSISSGHYWSWIR QPPGKGLEWIGGIYHSGTTYYNPSLKSRVTISVDTSKNQ FSLKLSSVTAADTAVYYCARDGYYDILTGYYNQYFQHWG QGTLVTVSS (SEQ ID NO: 79) | EIVLTQSPGILSLSPGERATLSCRASQSVSSSYLAWYQ QKPGQAPRLLIYGASSRATGIPDRFSGSGSGTDFTLTI SRLEPEDFAVYYCQQYGSSPFTFGPGTKVDIK (SEQ ID NO: 97) |
| 24H1-GQTV | EVQLVESGGGLIQPGGSLRLSCAASGFTVSRNYMSWVRQ APGKGLEWVSFIYSGGSTYYADSVKGRFTISRDNSKNTL YLQMNSLRAEDTAVYYCARGGFGGGDYWGQGTLVTVSS (SEQ ID NO: 80) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIK (SEQ ID NO: 98) |
| 26D5-GVR-Q-FT | EVQLVESGGGLIQPGGSLRLSCAASGFTVSRNYMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 81) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIK (SEQ ID NO: 99) |
| 26D5-GVR-H | EVQLVESGGGLIQPGGSLRLSCAASGFTVSRNYMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 81) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIK (SEQ ID NO: 98) |
| 26D5-GV-Q | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARGGFGGGDYWGQGTLVTVSS (SEQ ID NO: 82) | DIQMTQSPSSVSASVGDRVTITCRASQGISSWLAWYQQ KPGKAPKLLIYAASSLQSGVPSRFSGSGSGTDFTLTIS SLQPEDFATYYCQQANSFPLTFGGGTKVEIK (SEQ ID NO: 99) |
| 26D5 | EVQLVESGGALIQPGGSLRLSCAASGFTVSSNYMSWVRQ APGKGLEWVSFIYSGGRTYYADSVKGRFTISRDNSKNTL YLQMNSLRAEDTAMYYCARGGFGGGDYWGQGTLVTVSS (SEQ ID NO: 83) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIK (SEQ ID NO: 98) |

The present invention also encompasses antibodies or antibody fragments that comprise partial heavy chain amino acid sequences and full length light chain amino acid sequences that are at least about 80%, 85%, 89%, 90%, 95%, or 99% identical to the partial heavy chain amino acid sequences and full length light chain amino acid sequences disclosed herein in Table 3. The present invention also encompasses antibodies or antibody fragments, e.g., antibody Fab fragments, that comprise, consist essentially of, or consist of any one of the N-terminal portion of the heavy chains in Table 3 in combination with any one of the full length light chains in Table 3. The present invention also encompasses antibodies or antibody fragments, e.g., antibody Fab fragments, that comprise, consist essentially of, or consist of any one of the indicated pairs of an N-terminal Portion of the heavy chain in Table 3 and a full length light chain in Table 3. The present invention also encompasses antibodies or antibody fragments, e.g., antibody Fab fragments, that comprise, consist essentially of, or consist of the sequence of SEQ ID NO: 106 and the sequence of SEQ ID NO: 164. The present invention also encompasses antibodies or antibody fragments, e.g., antibody Fab fragments, that comprise the sequence of SEQ ID NO: 106 and the sequence of SEQ ID NO: 164. The present invention also encompasses antibodies or antibody fragments, e.g., antibody Fab fragments, that consist essentially of the sequence of SEQ ID NO: 106 and the sequence of SEQ ID NO: 164. The present invention also encompasses antibodies or antibody fragments, e.g., antibody Fab fragments, that consist of the sequence of SEQ ID NO: 106 and the sequence of SEQ ID NO: 164.

TABLE 3

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 26D5-75229-343-A10-Fab-SHORT | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 100) | DIQMTQSPSSVSASVGDRVTITCRASQGISSNLAWYQQ KPGKAPKLLIYAASSLQSGVPSRFSGSGSGTDFTLTIS SLQPEDFATYYCQQANQFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 160) |
| 26D5-75229-343-A10-Fab-LONG | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 101) | DIQMTQSPSSVSASVGDRVTITCRASQGISSNLAWYQQ KPGKAPKLLIYAASSLQSGVPSRFSGSGSGTDFTLTIS SLQPEDFATYYCQQANQFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 160) |
| 26D5-75214-343-F06-Fab-SHORT | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 102) | DIQMTQSPSSVSASVGDRVTITCRASQGISSNLAWYQQ KPGKAPKLLIYAASSLQSGVPSRFSGSGSGTDFTLTIS SLQPEDFATYYCQQANEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 161) |
| 26D5-75214-343-F06-Fab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 103) | DIQMTQSPSSVSASVGDRVTITCRASQGISSNLAWYQQ KPGKAPKLLIYAASSLQSGVPSRFSGSGSGTDFTLTIS SLQPEDFATYYCQQANEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 161) |
| 26D5-75202-343-A09-Fab-SHORT | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 104) | DIQMTQSPSSVSASVGDRVTITCRASQGIYSNLAWYQQ KPGKAPKLLIYAASSLQSGVPSRFSGSGSGTDFTLTIS SLQPEDFATYYCQQANEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 162) |
| 26D5-75202-343-A09-Fab-LONG | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 105) | DIQMTQSPSSVSASVGDRVTITCRASQGIYSNLAWYQQ KPGKAPKLLIYAASSLQSGVPSRFSGSGSGTDFTLTIS SLQPEDFATYYCQQANEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 162) |
| 26D5-75203-343-B09-Fab-SHORT | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 104) | DIQMTQSPSSVSASVGDRVTITCRASQGISSNLAWYQQ KPGKAPKLLIYAASSLQSGVPSRFSGSGSGTDFTLTIS SLQPEDFATYYCQQANEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 163) |
| 26D5-75203-343-B09-Fab-LONG | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS | DIQMTQSPSSVSASVGDRVTITCRASQGISSNLAWYQQ KPGKAPKLLIYAASTLQSGVPSRFSGSGSGTDFTLTIS SLQPEDFATYYCQQANEFPLTFGGGTKVEIKRTVAAPS VFIFPPSDEQLKSGTASVVCLLNNFYPREAKVQWKVDN |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| | WNSGALTSGVHTFPAVLQSSGLYSLSSVVTVPSSSLGTQ TYICNVNHKPSNTKVDKRVEPKSCDKTH (SEQ ID NO: 105) | ALQSGNSQESVTEQDSKDSTYSLSSTLTLSKADYEKHK VYACEVTHQGLSSPVTKSFNRGEC (SEQ ID NO: 163) |
| 26D5-75616-348-F10-Fab-SHORT | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAEFGLEDIWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 106) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-75616-348-F10-Fab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAEFGLEDIWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 107) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-75768-348-A10-Fab-SHORT | EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 108) | DIQMTQSPSSVSASVGDRVTITCRASQGISSNNQWYQQ KPGKAPKLLIYAASSLQSGVPSRFSGSGSGTDFTLTIS SLQPEDFATYYCQQGNEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 165) |
| 26D5-75768-348-A10-Fab-LONG | EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 109) | DIQMTQSPSSVSASVGDRVTITCRASQGISSNNQWYQQ KPGKAPKLLIYAASSLQSGVPSRFSGSGSGTDFTLTIS SLQPEDFATYYCQQGNEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 165) |
| 26D5-75747-348-D07-Fab-SHORT | EVQLVESGGGLIQPGGSLRLSCAASGFTVSSNAFSWVRQ APGKGLEWVSYIYSGGRTYYADSVKGRFTISRDNSKNTL YLQMNSLRAEDTAVYYCAAAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 110) | DIQMTQSPSSVSASVGDRVTITCRASQGISSQVAWYQQ KPGKAPKLLIYAASSLQSGVPSRFSGSGSGTDFTLTIS SLQPEDFATYYCQQGNEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 166) |
| 26D5-75747-348-D07-Fab-LONG | EVQLVESGGGLIQPGGSLRLSCAASGFTVSSNAFSWVRQ APGKGLEWVSYIYSGGRTYYADSVKGRFTISRDNSKNTL YLQMNSLRAEDTAVYYCAAAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 111) | DIQMTQSPSSVSASVGDRVTITCRASQGISSQVAWYQQ KPGKAPKLLIYAASSLQSGVPSRFSGSGSGTDFTLTIS SLQPEDFATYYCQQGNEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 166) |
| 26D5-75602-348-F04-Fab-SHORT | EVQLVESGGGLIQPGGSLRLSCAASGFTVSSNQFSWVRQ APGKGLEWVSYFYPGGRTYYADSVKGRFTISRDNSKNTL YLQMNSLRAEDTAVYYCAKAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 112) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-75602-348-F04-Fab-LONG | EVQLVESGGGLIQPGGSLRLSCAASGFTVSSNQFSWVRQ APGKGLEWVSYFYPGGRTYYADSVKGRFTISRDNSKNTL YLQMNSLRAEDTAVYYCAKAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 113) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |

TABLE 3-continued

Fab Sequences (the non-bolded portions are the variable regions with CDRs being underlined and
framework regions not being underlined; bolded amino acids are the constant regions for
each of the heavy and light chain portions of the Fab)

| Fab/mAb Name | N-terminal Portion of the Heavy Chain | Full Length Light Chain |
| --- | --- | --- |
| 26D5-75576-348-B03-Fab-SHORT | EVQLVESGGGLIQPGGSLRLSCAASGFTVSSNDMSYVRQ APGKGLEWVAYIYSGGRTYYADSVKGRFTISRDNSKNTL YLQMNSLRAEDTAVYYCVTAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 114) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-75576-348-B03-Fab-LONG | EVQLVESGGGLIQPGGSLRLSCAASGFTVSSNDMSYVRQ APGKGLEWVAYIYSGGRTYYADSVKGRFTISRDNSKNTL YLQMNSLRAEDTAVYYCVTAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 115) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-75017-343-F04-Fab-SHORT | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 116) | DIQMTQSPSSVSASVGDRVTITCRASQGISSNLAWWQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 167) |
| 26D5-75017-343-F04-Fab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 117) | DIQMTQSPSSVSASVGDRVTITCRASQGISSNLAWWQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 167) |
| 26D5-75592-348-A04-Fab-SHORT | EVQLVESGGGLIQPGGSLRLSCAASGFTVSSNAIAWVRQ APGKGLEWVAYIYPGGRTYYADSVKGRFTISRDNSKNTL YLQMNSLRAEDTAVYYCVTAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 118) | DIQMTQSPSSVSASVGDRVTITCRASQGISSNNQWYQQ KPGKAPKLLIYAASSLQSGVPSRFSGSGSGTDFTLTIS SLQPEDFATYYCQQGNEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 165) |
| 26D5-75592-348-A04-Fab-LONG | EVQLVESGGGLIQPGGSLRLSCAASGFTVSSNAIAWVRQ APGKGLEWVAYIYPGGRTYYADSVKGRFTISRDNSKNTL YLQMNSLRAEDTAVYYCVTAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 119) | DIQMTQSPSSVSASVGDRVTITCRASQGISSNNQWYQQ KPGKAPKLLIYAASSLQSGVPSRFSGSGSGTDFTLTIS SLQPEDFATYYCQQGNEFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 165) |
| 26D5-75746-348-C07-Fab-SHORT | EVQLVESGGGLIQPGGSLRLSCAASGFTVSSNAFSWVRQ APGKGLEWVSYIYSGGRTYYADSVKGRFTISRDNSKNTL YLQMNSLRAEDTAVYYCAAAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 110) | DIQMTQSPSSVSASVGDRVTITCRASQGISSQVAWYQQ KPGKAPKLLIYPASNLWSGVPSRFSGSGSGTDFTLTIS SLQPEDFATYYCQQANNFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 168) |
| 26D5-75746-348-C07-Fab-LONG | EVQLVESGGGLIQPGGSLRLSCAASGFTVSSNAFSWVRQ APGKGLEWVSYIYSGGRTYYADSVKGRFTISRDNSKNTL YLQMNSLRAEDTAVYYCAAAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 111) | DIQMTQSPSSVSASVGDRVTITCRASQGISSQVAWYQQ KPGKAPKLLIYPASNLWSGVPSRFSGSGSGTDFTLTIS SLQPEDFATYYCQQANNFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 168) |
| 26D5-296-A07-Fab-SHORT | EVQLVESGGGLIQPGGSLRLSCAASGFTVSSNAMSWVRQ APGKGLEWVAYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 116) | DIQMTQSPSSVSASVGDRVTITCRASQGISSWLAWYQQ KPGKAPKLLIYAASSLQSGVPSRFSGSGSGTDFTLTIS SLQPEDFATYYCQQHNSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 169) |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 26D5-296-A07-Fab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 117) | DIQMTQSPSSVSASVGDRVTITCRASQGISSWLAWYQQ KPGKAPKLLIYAASSLQSGVPSRFSGSGSGTDFTLTIS SLQPEDFATYYCQQHNSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 169) |
| 26D5-295-B08-Fab-SHORT | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 116) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-B08-Fab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 117) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-C08-Fab-SHORT | EVQLVESGGGLIQPGGSLRLSCAASGFQVSSNAMSWVRQ APGKGLEWVSFIYPGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 120) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-C08-Fab-LONG | EVQLVESGGGLIQPGGSLRLSCAASGFQVSSNAMSWVRQ APGKGLEWVSFIYPGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 121) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-H03-Fab-SHORT | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 122) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-H03-Fab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 123) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-F07-Fab-SHORT | EVQLVESGGGLIQPGGSLRLSCAASGFTVSENAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 124) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-F07-Fab-LONG | EVQLVESGGGLIQPGGSLRLSCAASGFTVSENAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 125) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 26D5-296-G07-Fab-SHORT | EVQLVESGGGLIQPGGSLRLSCAASGFTVSENYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 126) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 170) |
| 26D5-296-G07-Fab-LONG | EVQLVESGGGLIQPGGSLRLSCAASGFTVSENYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 127) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 170) |
| 26D5-295-E07-Fab-SHORT | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 128) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-E07-Fab-LONG | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 129) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-C08-Fab-SHORT | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 128) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-296-C08-Fab-LONG | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 129) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-295-C07-Fab-SHORT | EVQLVESGGGLIQPGGSLRLSCAASGFTVSSNAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 130) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-C07-Fab-LONG | EVQLVESGGGLIQPGGSLRLSCAASGFTVSSNAMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 131) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-B07-Fab-SHORT | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 132) | DIQMTQSPSSVSASVGDRVTITCRASQGISSWLAWYQQ KPGKAPKLLIYAASSLQSGVPSRFSGSGSGTDFTLTIS SLQPEDFATYYCQQHNSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 169) |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 26D5-296-B07-Fab-LONG | EVQLVESGGGLIQPGGSLRLSCAASGFQVSSNAMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 133) | DIQMTQSPSSVSASVGDRVTITCRASQGISSWLAWYQQ KPGKAPKLLIYAASSLQSGVPSRFSGSGSGTDFTLTIS SLQPEDFATYYCQQHNSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 169) |
| 26D5-295-G07-Fab-SHORT | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 134) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-G07-Fab-LONG | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 135) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-D08-Fab-SHORT | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 134) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-296-D08-Fab-LONG | EVQLVESGGGLIQPGGSLRLSCAASGFTVSSNYMSWVRQ APGKGLEWVSFIYPGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 135) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-296-F03-Fab-SHORT | EVQLVESGGGLIQPGGSLRLSCAASGFQVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 136) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-F03-Fab-LONG | EVQLVESGGGLIQPGGSLRLSCAASGFQVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 137) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-G08-Fab-SHORT | EVQLVESGGGLIQPGGSLRLSCAASGFQVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 136) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-296-G08-Fab-LONG | EVQLVESGGGLIQPGGSLRLSCAASGFQVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 137) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 26D5-295-H07-Fab-SHORT | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 138) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-H07-Fab-LONG | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 139) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-F07-Fab-SHORT | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 138) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 170) |
| 26D5-296-F07-Fab-LONG | EVQLVESGGGLIQPGGSLRLSCAASGFTVSSNYMSWVRQ APGKGLEWVSFIYSGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 139) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 170) |
| 26D5-296-G03-Fab-SHORT | EVQLVESGGGLIQPGGSLRLSCAASGFQVSSNYMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 140) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-G03-Fab-LONG | EVQLVESGGGLIQPGGSLRLSCAASGFQVSSNYMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 141) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-F08-Fab-SHORT | EVQLVESGGGLIQPGGSLRLSCAASGFTVSSNYMSWVRQ APGKGLEWVSFIYPGGETYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 142) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-296-F08-Fab-LONG | EVQLVESGGGLIQPGGSLRLSCAASGFTVSSNYMSWVRQ APGKGLEWVSFIYPGGETYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 143) | DIQMTQSPSSVSASVGDRVTITCRASQYIESNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 171) |
| 26D5-295-A08-Fab-SHORT | EVQLVESGGGLIQPGGSLRLSCAASGFTVSENYMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 144) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 26D5-295-A08-Fab-LONG | EVQLVESGGGLIQPGGSLRLSCAASGFTVSENYMSWVRQ APGKGLEWVSFIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 145) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-D07-Fab-SHORT | EVQLVESGGGLIQPGGSLRLSCAASGFQVSENYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 146) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-295-D07-Fab-LONG | EVQLVESGGGLIQPGGSLRLSCAASGFQVSENYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 147) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-D03-Fab-SHORT | EVQLVESGGGLIQPGGSLRLSCAASGFTVSSNYMSWVRQ APGKGLEWVSFIYSGGETFYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 148) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-D03-Fab-LONG | EVQLVESGGGLIQPGGSLRLSCAASGFTVSSNYMSWVRQ APGKGLEWVSFIYSGGETFYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 149) | DIQMTQSPSSVSASVGDRVTITCRASQGISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 164) |
| 26D5-296-C07-Fab-SHORT | EVQLVESGGGLIQPGGSLRLSCAASGITVSSNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 150) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 170) |
| 26D5-296-C07-Fab-LONG | EVQLVESGGGLIQPGGSLRLSCAASGITVSSNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 151) | DIQMTQSPSSVSASVGDRVTITCRASQYISSNLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 170) |
| 9C8-VGSKE-Fab-SHORT | QVQLQESGPGLVKPSETLSLTCAVSGYSISSGYYWGWIR QPPGKGLEWIGSIYHSGNTYYSPSLQSRVTISVDTSKNQ FSLKLSSVTAADTAVYYCARGGDFDILTGYYKGWFEPWG QGTLVIVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKRVEPKSC (SEQ ID NO: 152) | AIQLTQSPSSLSASVGDRVTITCRASQGISSALAWYQQ KPGKAPKLLIYDASSLESGVPSRFSGSGSGTDFTLTIS SLQPEDFATYYCQQFNSYPQTFGQGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 172) |
| 9C8-VGSKE-Fab-LONG | QVQLQESGPGLVKPSETLSLTCAVSGYSISSGYYWGWIR QPPGKGLEWIGSIYHSGNTYYSPSLQSRVTISVDTSKNQ FSLKLSSVTAADTAVYYCARGGDFDILTGYYKGWFEPWG QGTLVIVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKRVEPKSCDKTH (SEQ ID NO: 153) | AIQLTQSPSSLSASVGDRVTITCRASQGISSALAWYQQ KPGKAPKLLIYDASSLESGVPSRFSGSGSGTDFTLTIS SLQPEDFATYYCQQFNSYPQTFGQGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 172) |

TABLE 3-continued

Fab Sequences (the non-bolded portions are the variable regions with CDRs being underlined and framework regions not being underlined; bolded amino acids are the constant regions for each of the heavy and light chain portions of the Fab)

| Fab/mAb Name | N-terminal Portion of the Heavy Chain | Full Length Light Chain |
|---|---|---|
| 1H2-K-Fab-SHORT | QVQLQESGPGLVKPSETLSLTCAVSGYSISSGHYWSWIR QPPGKGLEWIGGIYHSGTTYYNPSLKSRVTISVDTSKNQ FSLKLSSVTAADTAVYYCARDGYYDILTGYYNQYFQHWG QGTLVIVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKRVEPKSC (SEQ ID NO: 154) | EIVLTQSPGILSLSPGERATLSCRASQSVSSSYLAWYQ QKPGQAPRLLIYGASSRATGIPDRFSGSGSGTDFTLTI SRLEPEDFAVYYCQQYGSSPFTFGPGTKVDIKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC (SEQ ID NO: 173) |
| 1H2-K-Fab-LONG | QVQLQESGPGLVKPSETLSLICAVSGYSISSGHYWSWIR QPPGKGLEWIGGIYHSGTTYYNPSLKSRVTISVDTSKNQ FSLKLSSVTAADTAVYYCARDGYYDILTGYYNQYFQHWG QGTLVIVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKRVEPKSCDKTH (SEQ ID NO: 155) | EIVLTQSPGILSLSPGERATLSCRASQSVSSSYLAWYQ QKPGQAPRLLIYGASSRATGIPDRFSGSGSGTDFTLTI SRLEPEDFAVYYCQQYGSSPFTFGPGTKVDIKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC (SEQ ID NO: 173) |
| 24H1-GQTV-Fab-SHORT | EVQLVESGGGLIQPGGSLRLSCAASGFTVSRNYMSWVRQ APGKGLEWVSFIYSGGSTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 156) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 174) |
| 24H1-GQTV-Fab-LONG | EVQLVESGGGLIQPGGSLRLSCAASGFTVSRNYMSWVRQ APGKGLEWVSFIYSGGSTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 157) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 174) |
| 26D5-GVR-Q-FT-Fab-SHORT | EVQLVESGGGLIQPGGSLRLSCAASGFTVSRNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 158) | DIQMTQSPSSVSASVGDRVTITCRASQGISSWLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 175) |
| 26D5-GVR-Q-FT-Fab-LONG | EVQLVESGGGLIQPGGSLRLSCAASGFTVSRNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 159) | DIQMTQSPSSVSASVGDRVTITCRASQGISSWLAWYQQ KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 175) |
| 26D5-GVR-H-Fab-SHORT | EVQLVESGGGLIQPGGSLRLSCAASGFTVSRNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 158) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 174) |
| 26D5-GVR-H-Fab-LONG | EVQLVESGGGLIQPGGSLRLSCAASGFTVSRNYMSWVRQ APGKGLEWVSFIYSGGRTYYADSVKGRFTISRDNSKNTL YLQMNSLRAEDTAVYYCARGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTH (SEQ ID NO: 159) | DIQMTQSPSSVSASVGDRVTITCRASQGISSWLAWYQH KPGKAPKLLIYAASSLQSGVPSRFSGSGSGTDFTLTIS SLQPEDFATYYCQQANSFPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 174) |

The present invention also encompasses antibodies or antibody fragments that comprise tandem partial heavy chain amino acid sequences and full length light chain amino acid sequences that are at least about 80%, 85%, 89%, 90%, 95%, or 99% identical to the partial heavy chain amino acid sequences and full length light chain amino acid sequences disclosed herein in Table 4.

TABLE 4

Tandem Fab sequences (the non-bolded portions are the variable chains with CDRs being underlined and framework regions not being underlined; bolded amino acids are the constant regions for each of the heavy and light chain portions of the Fab; the double underlined portions are the linker sequences)

| Construct Name | Tandem Fab Heavy Chain | Tandem Fab Light Chain |
|---|---|---|
| 26D5-75229-343-A10-TanFab | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCASTKGPEVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC (SEQ ID NO: 176) | DIQMTQSPSSVSASVGDRVTITCRASQGISSNLAWYQQKPGKAPKLLIYAASSLQSGVPSRFSGSGSGTDFTLTISSLQPEDFATYYCQQANQFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 160) |
| 26D5-75229-343-A10-TanFab-long | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCASTKGPSVFPLAPEVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC (SEQ ID NO: 177) | DIQMTQSPSSVSASVGDRVTITCRASQGISSNLAWYQQKPGKAPKLLIYAASSLQSGVPSRFSGSGSGTDFTLTISSLQPEDFATYYCQQANQFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 160) |
| 26D5-75229-343-A10-TanFab-ELQ | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDERVEPKSCELQLEESAAEAQEGELEEVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNIMPSNTKVDKRVEPKSC (SEQ ID NO: 178) | DIQMTQSPSSVSASVGDRVTITCRASQGISSNLAWYQQKPGKAPKLLIYAASSLQSGVPSRFSGSGSGTDFTLTISSLQPEDFATYYCQQANQFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 160) |
| 26D5-75229-343-A10-TanFab-G45 | EVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGGGGSGGGGSGGGGSEVQLVESGGGLIQPGGSLRLSCAASGFTVSSNAMSWVRQAPGKGLEWVSYIYPGGRTYYADSVKGRFTISRDNSKNTLYLQMNSLRAEDTAVYYCARAGFGGPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC (SEQ ID NO: 179) | DIQMTQSPSSVSASVGDRVTITCRASQGISSNLAWYQQKPGKAPKLLIYAASSLQSGVPSRFSGSGSGTDFTLTISSLQPEDFATYYCQQANQFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 160) |
| 26D5-75616-348-F10-TanFab | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAEFGLEDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNIMPSNTKVDKRVEPKSCASTKGPEVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAEFGLEDIWGQGTLVTVSSASTKGPSVFPLAPSSKSTSGGTAALGCLVKDYFPEPVTVSWNSGALTSGVHTFPAVLQSSGLYSLSSVVIVPSSSLGTQTYICNVNHKPSNTKVDKRVEPKSC (SEQ ID NO: 180) | DIQMTQSPSSVSASVGDRVTITCRASQGISSNLAWYQQKPGKAPKLLIYAASSLQSGVPSRFSGSGSGTDFTLTISSLQPEDFATYYCQQANSFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 164) |
| 26D5-75616-348-F10-TanFab-long | EVQLVESGGGLIQPGGSLRLSCAASGFTVSSNAMSWVRQAPGKGLEWVSFIYPGGRTYYADSVKGRFTISRDNSKNTLYLQMNSLRAEDTAVYYCARAEFGLEDIWGQGTLVTVSSASTKGPSVFPLAPSSKSTSGGTAALGCLVKDYFPEPVTVSWNSGALTSGVHTFPAVLQSSGLYSLSSVVTVPSSSLGTQ | DIQMTQSPSSVSASVGDRVTITCRASQGISSNLAWYQQKPGKAPKLLIYAASSLQSGVPSRFSGSGSGTDFTLTISSLQPEDFATYYCQQANSFPLTFGGGTKVEIKRTVAAPSVFIFPPSDEQLKSGTASVVCLLNNFYPREAKVQWKVDNALQSGNSQESVTEQDSKD |

TABLE 4-continued

Tandem Fab sequences (the non-bolded portions are the variable chains with CDRs being underlined and framework regions not being underlined; bolded amino acids are the constant regions for each of the heavy and light chain portions of the Fab; the double underlined portions are the linker sequences)

| Construct Name | Tandem Fab Heavy Chain | Tandem Fab Light Chain |
|---|---|---|
| | TYICNVNHKPSNTKVDKRVEPKSCASTKGPSVFPLAPEV QLVESGGGLIQPGGSLRLSCAASGFTVSSNAMSWVRQAP GKGLEWVSFIYPGGRTYYADSVKGRFTISRDNSKNTLYL QMNSLRAEDTAVYYCARAEFGLEDIWGQGTLVTVSSAST KGPSVFPLAPSSKSTSGGTAALGCLVKDYFPEPVTVSWN SGALTSGVHTFPAVLQSSGLYSLSSVVTVPSSSLGTQTY ICNVNHKPSNTKVDKRVEPKSC (SEQ ID NO: 181) | STYSLSSTLTLSKADYEKHKVYACEVTHQGLSSP VTKSFNRGEC (SEQ ID NO: 164) |
| 26D5-75616-348-F10-TanFab-ELQ | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAEFGLEDIWGQGTLVTVSSASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDERVEPKSCELQLEESAAEAQEGE LEEVQLVESGGGLIQPGGSLRLSCAASGFTVSSNAMSWV RQAPGKGLEWVSFIYPGGRTYYADSVKGRFTISRDNSKN TLYLQMNSLRAEDTAVYYCARAEFGLEDIWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSC (SEQ ID NO: 182) | DIQMTQSPSSVSASVGDRVTITCRASQGISSNLA WYQQKPGKAPKLLIYAASSLQSGVPSRFSGSGSG TDFTLTISSLQPEDFATYYCQQANSFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 164) |
| 26D5-75616-348-F10-TanFab-G4S | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAEFGLEDIWGQGTLVTVSSASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCGGGGSGGGGSGGGGS EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAEFGLEDIWGQGTLVTVSSASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 183) | DIQMTQSPSSVSASVGDRVTITCRASQGISSNLA WYQQKPGKAPKLLIYAASSLQSGVPSRFSGSGSG TDFTLTISSLQPEDFATYYCQQANSFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 164) |
| 26D5-75203-343-B09-TanFab | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSASTKGPSVFPLAPSSKSTSGGTAALGCLVKDYFPEPVTVS WNSGALTSGVHTFPAVLQSSGLYSLSSVVTVPSSSLGTQ TYICNVNIMPSNTKVDKRVEPKSCASTKGPEVQLVESGG GLIQPGGSLRLSCAASGFTVSSNAMSWVRQAPGKGLEWV SYIYPGGRTYYADSVKGRFTISRDNSKNTLYLQMNSLRA EDTAVYYCARAGFGGGDYWGQGTLVIVSSASTKGPSVFP LAPSSKSTSGGTAALGCLVKDYFPEPVTVSWNSGALTSG VHTFPAVLQSSGLYSLSSVVTVPSSSLGTQTYICNVNHK PSNTKVDKRVEPKSC (SEQ ID NO: 184) | DIQMTQSPSSVSASVGDRVTITCRASQGISSNLA WYQQKPGKAPKLLIYAASTLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 163) |
| 26D5-75203-343-B09-TanFab-long | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSASTKGPSVFPLAPSSKSTSGGTAALGCLVKDYFPEPVTVS WNSGALTSGVHTFPAVLQSSGLYSLSSVVTVPSSSLGTQ TYICNVNIMPSNTKVDERVEPKSCASTKGPSVFPLAPEV QLVESGGGLIQPGGSLRLSCAASGFTVSSNAMSWVRQAP GKGLEWVSYIYPGGRTYYADSVKGRFTISRDNSKNTLYL QMNSLRAEDTAVYYCARAGFGGGDYWGQGTLVTVSSAST KGPSVFPLAPSSKSTSGGTAALGCLVKDYFPEPVTVSWN SGALTSGVHTFPAVLQSSGLYSLSSVVTVPSSSLGTQTY ICNVNHKPSNTKVDKRVEPKSC (SEQ ID NO: 185) | DIQMTQSPSSVSASVGDRVTITCRASQGISSNLA WYQQKPGKAPKLLIYAASTLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 163) |
| 26D5-75203-343-B09-TanFab-ELQ | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDERVEPKSCELQLEESAAEAQEGE LEEVQLVESGGGLIQPGGSLRLSCAASGFTVSSNAMSWV RQAPGKGLEWVSYIYPGGRTYYADSVKGRFTISRDNSKN TLYLQMNSLRAEDTAVYYCARAGFGGGDYWGQGTLVTVS SASTKGPSVFPLAPSSKSTSGGTAALGCLVKDYFPEPVT | DIQMTQSPSSVSASVGDRVTITCRASQGISSNLA WYQQKPGKAPKLLIYAASTLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 163) |

TABLE 4-continued

Tandem Fab sequences (the non-bolded portions are the variable chains with CDRs being underlined and framework regions not being underlined; bolded amino acids are the constant regions for each of the heavy and light chain portions of the Fab; the double underlined portions are the linker sequences)

| Construct Name | Tandem Fab Heavy Chain | Tandem Fab Light Chain |
|---|---|---|
| | VSWNSGALTSGVHTFPAVLQSSGLYSLSSVVTVPSSSLG TQTYICNVNHKPSNTKVDKRVEPKSC (SEQ ID NO: 186) | |
| 26D5-75203-343-B09-TanFab-G4S | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCGGGGSGGGGSGGGGS EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 187) | DIQMTQSPSSVSASVGDRVTITCRASQGISSNLA WYQQKPGKAPKLLIYAASTLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 163) |
| 26D5-75202-343-A09-TanFab | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDERVEPKSCASTKGPEVQLVESGG GLIQPGGSLRLSCAASGFTVSSNAMSWVRQAPGKGLEWV SYIYPGGRTYYADSVKGRFTISRDNSKNTLYLQMNSLRA EDTAVYYCARAGFGGGDYWGQGTLVIVSSASTKGPSVFP LAPSSKSTSGGTAALGCLVKDYFPEPVTVSWNSGALTSG VHTFPAVLQSSGLYSLSSVVIVPSSSLGTQTYICNVNHK PSNTKVDKRVEPKSC (SEQ ID NO: 184) | DIQMTQSPSSVSASVGDRVTITCRASQGIYSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 162) |
| 26D5-75202-343-A09-TanFab-LONG | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNIMPSNTKVDERVEPKSCASTKGPSVFPLAPEV QLVESGGGLIQPGGSLRLSCAASGFTVSSNAMSWVRQAP GKGLEWVSYIYPGGRTYYADSVKGRFTISRDNSKNTLYL QMNSLRAEDTAVYYCARAGFGGGDYWGQGTLVTVSSAST KGPSVFPLAPSSKSTSGGTAALGCLVKDYFPEPVTVSWN SGALTSGVHTFPAVLQSSGLYSLSSVVTVPSSSLGTQTY ICNVNHKPSNTKVDKRVEPKSC (SEQ ID NO: 185) | DIQMTQSPSSVSASVGDRVTITCRASQGIYSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 162) |
| 26D5-75202-343-A09-TanFab-ELQ | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDERVEPKSCELQLEESAAEAQEGE LEEVQLVESGGGLIQPGGSLRLSCAASGFTVSSNAMSWV RQAPGKGLEWVSYIYPGGRTYYADSVKGRFTISRDNSKN TLYLQMNSLRAEDTAVYYCARAGFGGGDYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSC (SEQ ID NO: 186) | DIQMTQSPSSVSASVGDRVTITCRASQGIYSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 162) |
| 26D5-75202-343-A09-TanFab-G4S | EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCGGGGSGGGGSGGGGS EVQLVESGGGLIQPGGSLRLSCAASGFTVSSNAMSWVRQ APGKGLEWVSYIYPGGRTYYADSVKGRFTISRDNSKNTL YLQMNSLRAEDTAVYYCARAGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 187) | DIQMTQSPSSVSASVGDRVTITCRASQGIYSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 162) |

TABLE 4-continued

Tandem Fab sequences (the non-bolded portions are the variable chains with CDRs being underlined and framework regions not being underlined; bolded amino acids are the constant regions for each of the heavy and light chain portions of the Fab; the double underlined portions are the linker sequences)

| Construct Name | Tandem Fab Heavy Chain | Tandem Fab Light Chain |
| --- | --- | --- |
| 26D5-75768-348-A10-TanFab | EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNIMPSNTKVDKRVEPKSCASTKGPEVQLVESGG GLIQPGGSLRLSCAASGFTVSSNAVSIVRQAPGKGLEWV AYIYPGGRTYYADSVKGRFTISRDNSKNTLYLQMNSLRA EDTAVYYCTIGGFGGGDYWGQGTLVTVSSASTKGPSVFP LAPSSKSTSGGTAALGCLVKDYFPEPVTVSWNSGALTSG VHTFPAVLQSSGLYSLSSVVTVPSSSLGTQTYICNVNHK PSNTKVDKRVEPKSC (SEQ ID NO: 188) | DIQMTQSPSSVSASVGDRVTITCRASQGISSNNQ WYQQKPGKAPKLLIYYASSLQSGVPSRFSGSGSG TDFTLTISSLQPEDFATYYCQQGNEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 165) |
| 26D5-75768-348-A10-TanFab-Long | EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCASTKGPSVFPLAPEV QLVESGGGLIQPGGSLRLSCAASGFTVSSNAVSIVRQAP GKGLEWVAYIYPGGRTYYADSVKGRFTISRDNSKNTLYL QMNSLRAEDTAVYYCTIGGFGGGDYWGQGTLVTVSSAST KGPSVFPLAPSSKSTSGGTAALGCLVKDYFPEPVTVSWN SGALTSGVHTFPAVLQSSGLYSLSSVVTVPSSSLGTQTY ICNVNHKPSNTKVDKRVEPKSC (SEQ ID NO: 189) | DIQMTQSPSSVSASVGDRVTITCRASQGISSNNQ WYQQKPGKAPKLLIYYASSLQSGVPSRFSGSGSG TDFTLTISSLQPEDFATYYCQQGNEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 165) |
| 26D5-75768-348-A10-TanFab-ELQ | EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNIMPSNTKVDKRVEPKSCELQLEESAAEAQEGE LEEVQLVESGGGLIQPGGSLRLSCAASGFTVSSNAVSIV RQAPGKGLEWVAYIYPGGRTYYADSVKGRFTISRDNSKN TLYLQMNSLRAEDTAVYYCTIGGFGGGDYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSC (SEQ ID NO: 190) | DIQMTQSPSSVSASVGDRVTITCRASQGISSNNQ WYQQKPGKAPKLLIYYASSLQSGVPSRFSGSGSG TDFTLTISSLQPEDFATYYCQQGNEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 165) |
| 26D5-75768-348-A10-TanFab-G45 | EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCGGGGSGGGGSGGGGS EVQLVESGGGLIQPGGSLRLSCAASGFTVSSNAVSIVRQ APGKGLEWVAYIYPGGRTYYADSVKGRFTISRDNSKNTL YLQMNSLRAEDTAVYYCTIGGFGGGDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 191) | DIQMTQSPSSVSASVGDRVTITCRASQGISSNNQ WYQQKPGKAPKLLIYYASSLQSGVPSRFSGSGSG TDFTLTISSLQPEDFATYYCQQGNEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 165) |
| 26D5-75214-343-F06-TanFab | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDERVEPKSCASTKGPEVQLVESGG GLIQPGGSLRLSCAASGFTVSSNAMSWVRQAPGKGLEWV SFIYPGGRTYYADSVKGRFTISRDNSKNTLYLQMNSLRA EDTAVYYCARAGFGGPTINGQGTLVIVSSASTKGPSVFP LAPSSKSTSGGTAALGCLVKDYFPEPVTVSWNSGALTSG VHTFPAVLQSSGLYSLSSVVIVPSSSLGTQTYICNVNHK PSNTKVDKRVEPKSC (SEQ ID NO: 192) | DIQMTQSPSSVSASVGDRVTITCRASQGISSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 161) |
| 26D5-75214-343-F06-TanFab-LONG | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ | DIQMTQSPSSVSASVGDRVTITCRASQGISSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD |

TABLE 4-continued

Tandem Fab sequences (the non-bolded portions are the variable chains with CDRs being underlined and framework regions not being underlined; bolded amino acids are the constant regions for each of the heavy and light chain portions of the Fab; the double underlined portions are the linker sequences)

| Construct Name | Tandem Fab Heavy Chain | Tandem Fab Light Chain |
|---|---|---|
| | TYICNVNHKPSNTKVDKRVEPKSCASTKGPSVFPLAPEV QLVESGGGLIQPGGSLRLSCAASGFTVSSNAMSWVRQAP GKGLEWVSFIYPGGRTYYADSVKGRFTISRDNSKNTLYL QMNSLRAEDTAVYYCARAGFGGPDYWGQGTLVTVSSAST KGPSVFPLAPSSKSTSGGTAALGCLVKDYFPEPVTVSWN SGALTSGVHTFPAVLQSSGLYSLSSVVTVPSSSLGTQTY ICNVNHKPSNTKVDKRVEPKSC (SEQ ID NO: 193) | STYSLSSTLTLSKADYEKHKVYACEVTHQGLSSP VTKSFNRGEC (SEQ ID NO: 161) |
| 26D5-75214-343-F06-TanFab-ELQ | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDERVEPKSCELQLEESAAEAQEGE LEEVQLVESGGGLIQPGGSLRLSCAASGFTVSSNAMSWV RQAPGKGLEWVSFIYPGGRTYYADSVKGRFTISRDNSKN TLYLQMNSLRAEDTAVYYCARAGFGGPDYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNIMPSNTKVDKRVEPKSC (SEQ ID NO: 194) | DIQMTQSPSSVSASVGDRVTITCRASQGISSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 161) |
| 26D5-75214-343-F06-TanFab-G45 | EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCGGGGSGGGGSGGGGS EVQLVESGGGLIQPGGSLRLSCAASGFTVSSNAMSWVRQ APGKGLEWVSFIYPGGRTYYADSVKGRFTISRDNSKNTL YLQMNSLRAEDTAVYYCARAGFGGPDYWGQGTLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSC (SEQ ID NO: 195) | DIQMTQSPSSVSASVGDRVTITCRASQGISSNLA WYQQKPGKAPKLLIYAASSLQSGVPSRFSGSGSG TDFTLTISSLQPEDFATYYCQQANEFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC (SEQ ID NO: 161) |

"Identity" per se has an art-recognized meaning and can be calculated using published techniques. See, e.g., COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991).) While there exist a number of methods to measure identity between two polynucleotide or polypeptide sequences, the term "identity" is well known to skilled artisans. (Carillo, H., and Lipton, D., SIAM J. Applied Math. 48:1073 (1988).) Methods commonly employed to determine identity or similarity between two sequences include, but are not limited to, those disclosed in "Guide to Huge Computers," Martin J. Bishop, ed., Academic Press, San Diego, (1994), and Carillo, H., and Lipton, D., SIAM J. Applied Math. 48:1073 (1988). Methods for aligning polynucleotides or polypeptides are codified in computer programs, including the GCG program package (Devereux, J., et al., Nucleic Acids Research 12(1):387 (1984)), BLASTP, BLASTN, FASTA (Atschul, S. F. et al., J. Mol. Biol. 215:403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, Advances in Applied Mathematics 2:482 489 (1981)).

By a polynucleotide being at least, for example, 95% "identical" to a reference nucleotide sequence, respectively, it is intended that the nucleotide sequence of the polynucleotide is identical to the reference sequence, except that the polynucleotide sequence may include up to five mutations per each 100 nucleotides of the reference nucleotide sequence. For example, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 80%, 85%, 89%, 90%, 95%, or 99% identical to a nucleotide sequence of the presence invention can be determined using known computer programs. One method for determining the best overall match between a query sequence and a reference sequence, also referred to as a global sequence alignment, can be determined using the FASTDB computer program based on the algorithm of Brutlag et al. (Comp. App. Biosci. 6:237-245 (1990)). In a conventional nucleotide sequence alignment, the query and reference sequences are both DNA sequences; however, an RNA sequence can be compared by converting Us to T's.

The results of the global sequence alignment are reported in terms of percent identity. In one embodiment of the present invention, the parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the reference sequence is shorter than the query sequence because of, for example, 5' or 3' deletions, not because of internal deletions, a manual correction must be made to the results. This is because the FASTDB program does not account for 5' and 3' truncations of the reference sequence when calculating percent identity. For reference sequences truncated at the 5' or 3' ends, relative to the query sequence, the percent identity is corrected by calculating the number of bases of the query sequence that are 5' and 3' of the reference sequence, which are not matched/aligned, as a percent of the total bases of the query sequence. This percentage is then subtracted from the percent identity, calculated for example by the FASTDB program, using the specified parameters, to arrive at a final percent identity score. This corrected score is what is used for the purposes of the present invention. Only bases outside the 5' and 3' bases of the reference sequence, as displayed by the FASTDB alignment, which are not matched/aligned with the query sequence, are calculated for the purposes of manually adjusting the percent identity score.

For example, a 90 base reference sequence is aligned to a 100 base query sequence to determine percent identity. The deletions occur at the 5' end of the reference sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base reference sequence is compared with a 100 base query sequence. This time the deletions are internal deletions so that there are no bases on the 5' or 3' of the reference sequence which are not matched/aligned with the query. In this case, the percent identity calculated by FASTDB is not manually corrected. Once again, only bases 5' and 3' of the reference sequence which are not matched/aligned with the query sequence are manually corrected for.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the reference sequence may be inserted, deleted or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 89%, 90%, 95%, or 99% identical to, for instance, the amino acid sequences shown in any of the Tables 1-4, can be determined conventionally using known computer programs. A preferred method for determining the best overall match between a query sequence (a sequence of the present invention) and a reference sequence, also referred to as a global sequence alignment, can be determined using the FASTDB computer program mentioned above. In a sequence alignment the query and reference sequences are both amino acid sequences. The result of said global sequence alignment is in percent identity. In one embodiment of the present invention, the parameters used in a FASTDB alignment of amino acid sequences to calculate percent identity are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the reference sequence is shorter than the query sequence due to N- or C-terminal deletions, not because of internal deletions, a manual correction must be made to the results. This is because the FASTDB program does not account for N- and C-terminal truncations of the reference sequence when calculating global percent identity. For reference sequences truncated at the N- and C-termini, relative to the query sequence, the percent identity is corrected by calculating the number of residues of the query sequence that are N- and C-terminal of the reference sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-terminal of the reference sequence, which are not matched/aligned with the query sequence, are considered for the purposes of manually adjusting the percent identity score. That is, only query residue positions outside the farthest N- and C-terminal residues of the reference sequence.

For example, a 90 amino acid residue reference sequence is aligned with a 100 residue query sequence to determine percent identity. The deletion occurs at the N-terminus of the reference sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue reference sequence is compared with a 100 residue query sequence. This time the deletions are internal deletions so there are no residues at the N- or C-termini of the reference sequence which are not matched/aligned with the query. In this case the percent identity calculated by FASTDB is not manually corrected. Once again, only residue positions outside the N- and C-terminal ends of the reference sequence, as displayed in the FASTDB alignment, which are not matched/aligned with the query sequence are manually corrected.

Within the confines of the disclosed percent identity, the invention also relates to substitution variants of disclosed polypeptides of the invention. Substitution variants include those polypeptides in which one or more amino acid residues are removed and replaced with alternative residues. In one aspect, while the percent identity as disclosed above relates to the overall sequence of the specific sequence identified, the amino acid residues that are to remain constant and are not subject to variation would be those of the CDRs, and the amino acid residues that framework would be subject to variation. For example, in one specific embodiment, when the antigen binding peptide, such as, but not limited to, an antibody or antibody fragment, of the present invention comprises at least one VH comprising an amino acid sequence that is at least about 80%, 85%, 90%, 95%, or 99% identical to the amino acid sequence of SEQ ID NO: 64, the CDR regions of the VH are to remain constant and the framework regions are permitted to be variable, provided the overall percentage identity of SEQ ID NO:64 falls within the confines of the embodiment. In one aspect, the variations are substitutions that are conservative in nature; however, the invention embraces substitutions that are also non-conservative. Conservative substitutions for the purpose of the present invention may be defined as set out in Tables 5-7 below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE 5

Conservative Substitutions

| Side Chain Characteristic | Amino Acid |
| --- | --- |
| Aliphatic | |
| Non-polar | Gly, Ala, Pro, Ile, Leu, Val, Met |
| Polar-uncharged | Cys, Ser, Thr, Asn, Gln |
| Polar-charged | Asp, Glu, Lys, Arg |
| Aromatic | His, Phe, Trp, Tyr |

Alternatively, conservative amino acids can be grouped as described in Lehninger (1975) Biochemistry, Second Edition; Worth Publishers, pp. 71-77, as set forth below.

TABLE 6

Conservative Substitutions

| Side Chain Characteristic | Amino Acid |
| --- | --- |
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hyroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic) | Asp, Glu |

And still other alternative, exemplary conservative substitutions are set out below.

TABLE 7

Conservative Substitutions

| Original Residue | Exemplary Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (5) | Thr |
| Thr (T) | Ser |
| Trp (W) | Tyr |
| Tyr (Y) | Trp, Phe, Thr, Ser |
| Val (V) | Ile, Leu, Met, Phe, Ala |

In some embodiments of the antibodies or antibody fragments of the present invention, the CH1 domain comprises a partial heavy chain constant region with amino acid sequence of: ASTKGPSVFPLAPSSKSTSGGTAAL-GCLVKDYFPEPVTVSWNSGALTSGVHTFPAVLQSSGL YSLSSVVTVPSSSLGTQTYICNVNHKPSNTKVDKRVE-PKSC (SEQ ID NO: 202). The present invention also encompasses antibodies or antibody fragment of the present invention that comprise a CH1 domain with an amino acid sequence that is at least about 80%, 85%, 89%, 90%, 95%, or 99% identical to the CH1 domain of SEQ ID NO:202. In some embodiments of the antibodies or antibody fragments of the present invention, the CH1 domain comprises a partial heavy chain constant region with amino acid sequence of: ASTKGPSVFPLAPSSKSTSGGTAALGCLVKDYF-PEPVTVSWNSGALTSGVHTFPAVLQSSGL YSLSSVVTVPSSSLGTQTYICNVNHKPSNTKVDKRVE-PKSCDKTH (SEQ ID NO: 203). The present invention also encompasses antibodies or antibody fragments that comprise a CH1 domain with an amino acid sequence that is at least about 80%, 85%, 89%, 90%, 95%, or 99% identical to the CH1 domain of SEQ ID NO:203. In some embodiments of the antibodies or antibody fragments of the present invention, the CL domain comprises a light chain constant region with amino acid sequence of: RTVAAPSVFIFPPS-DEQLKSGTASVVCLLNNFYPREAKVQWKVD-NALQSGNSQESVTEQDSK DSTYSLSSTLTL-SKADYEKHKVYACEVTHQGLSSPVTKSFNRGEC (SEQ ID NO: 204). The present invention also encompasses antibodies or antibody fragments that comprise a CL domain with an amino acid sequence that is at least about 80%, 85%, 89%, 90%, 95%, or 99% identical to the CH1 domain of SEQ ID NO:204.

In some embodiments, the antibody or antibody fragment of the present invention comprises one or more of the individual N-terminal portion of the heavy chains and full length light chains described herein. In some embodiments, the antigen binding peptide, such as, but not limited to, an antibody or antibody fragment, comprises both an N-terminal portion of the heavy chain and a full length light chain sequences described herein. In some embodiments, the antibody or antibody fragment of the present invention comprises one N-terminal portion of the heavy chain, paired with one full length light chain described herein. In some embodiments, the antibody or antibody fragment of the present invention comprises more than one N-terminal portion of the heavy chain, each paired with one full length light chain described herein. In some embodiments, the antibody or antibody fragment of the present invention comprise two N-terminal portions of the heavy chains, each paired with one full length light chain described herein. In certain embodiments, the two N-terminal portions of the heavy chains are linked via a linker.

Table 4 provides sequences for heavy chains and light chains of exemplary tandem Fabs of the present invention. In some embodiments, the heavy chain of the tandem Fab comprises one or two N-terminal portions of the heavy chain of an antibody linked via a linker, and the light chain of the tandem Fab comprises a full length light chain (VL-CL) of an antibody. In some embodiments, the heavy chain of the tandem Fab can be expressed as VH-CH1-linker-CH1-VH or VH-CH1-linker-VH-CH1.

The linker encompassed by the present invention can be any suitable molecule of various structures. In certain embodiments, the linker is a polypeptide linker. The polypeptide linker can have various lengths. In some embodiments, the linker is a polypeptide comprising about 20 amino acids or fewer. Exemplary polypeptide linker sequences are provided in Table 8 and double underlined in Table 4.

TABLE 8

Exemplary linker sequences

| Linker sequence | SEQ ID NO |
| --- | --- |
| ASTKGP | SEQ ID NO: 196 |
| ASTKGPSVFPLAP | SEQ ID NO: 197 |
| ELQLEESAAEAQEGELE | SEQ ID NO: 198 |
| GGGGSGGGGSGGGGS | SEQ ID NO: 199 |

TABLE 9 mAb sequences

| Name | Sequence |
| --- | --- |
| Human IgG1f mAb heavy chain constant region | ASTKGPSVFPLAPSSKSTSGG TAALGCLVKDYFPEPVTVSW NSGALTSGVHTFPAVLQSSG LYSLSSVVTVPSSSLGTQTY ICNVNHKPSNTKVDKRVEPK SCDKTHTCPPCPAPELLGGP SVFLFPPKPKDTLMISRTPE VICVVVDVSHEDPEVKFNWY VDGVEVHNAKTKPREEQYNS TYRVVSVLTVLHQDWLNGKE YKCKVSNKALPAPIEKTISK AKGQPREPQVYTLPPSREEM TKNQVSLTCLVKGFYPSDIA VEWESNGQENNYKTIPPVLD SDGSFFLYSKLTVDKSRWQQ GNVFSCSVMHEALHNHYTQK SLSLSPG (SEQ ID NO: 200) |
| 26D5-75616-348-F10-mAb heavy chain | EVQLVESGGGLIQPGGSLRL SCAASGFTVS<u>SNAMSW</u>VRQA PGKGLEWVS<u>FIYPGGRTYYA DSVKGRF</u>TISRDNSKNTLYL QMNSLRAEDTAVYYC<u>ARAEF GLEDI</u>WGQGTLVTVSS<ins>ASTK GPSVFPLAPSSKSTSGG</ins>TAA LGCLVKDYFPEPVTVSWNSG |

TABLE 9-continued mAb sequences

| Name | Sequence |
| --- | --- |
| | ALTSGVHTFPAVLQSSGLYS LSSVVTVPSSSLGTQTYICN VNHKPSNTKVDKRVEPKSCD KTHTCPPCPAPELLGGPSVF LFPPKPKDTLMISRIPEVIC VVVDVSHEDPEVKFNWYVDG VEVHNAKTKPREEQYNSTYR VVSVLTVLHQDWLNGKEYKC KVSNKALPAPIEKTISKAKG QPREPQVYTLPPSREEMTKN QVSLTCLVKGFYPSDIAVEW ESNGQENNYKTIPPVLDSDG SFFLYSKLTVDKSRWQQGNV FSCSVMHEALHNHYTQKSLS LSPG (SEQ ID NO: 201) |

In some embodiments, the present invention provides an antigen binding peptide comprising the amino acid sequence of SEQ ID NO: 201.

In some embodiments, the present invention provides an antigen binding peptide, such as, but not limited to, an antibody or antibody fragment, comprising at least one VH and at least one VL. In some embodiments, the at least one VH comprises a VH complementarity-determining region 1 (VH-CDR1) comprising an amino acid sequence selected from the group comprising SEQ ID NOs: 1-12; a VH-CDR2 comprising an amino acid sequence selected from the group comprising SEQ ID NOs: 13-22; or a VH-CDR3 comprising an amino acid sequence selected from the group comprising SEQ ID NOs: 23-28. In some embodiments, the at least one VL comprises at least one of: a VL-CDR1 comprising an amino acid sequence selected from the group comprising SEQ ID NOs: 29-37; a VL-CDR2 comprising an amino acid sequence selected from the group comprising SEQ ID NOs: 38-43; or a VL-CDR3 comprising an amino acid sequence selected from the group comprising SEQ ID NOs: 44-51. In some embodiments, the antigen binding peptide, such as, but not limited to, an antibody or antibody fragment, of the present invention comprises VH-CDR1, VH-CDR2, VH-CDR3, VL-CDR1, VL-CDR2, and VL-CDR3 that have 1, 2, 3, or 4 conservative amino acid substitutions thereof.

In some embodiments, the antigen binding peptide, such as, but not limited to, an antibody or antibody fragment, comprises at least one VH comprising an amino acid sequence at least about 80%, 85%, 90%, 95%, or 99% identical to a sequence selected from the group comprising SEQ ID NOs: 52-83; and at least one VL comprising an amino acid sequence at least about 80%, 85%, 90%, 95%, or 99% identical to a sequence selected from the group comprising SEQ ID NOs: 84-99.

In some embodiments, the at least one VH region and the at least one VL region disclosed in Table 2 herein also encompass variant sequences comprising 1, 2, 3, or 4 conservative amino acid substitutions.

In some embodiments, the tandem Fab of the present invention comprises sequences that are at least about 80%, 85%, 90%, 95%, and 99% identical to the sequences to in Table 4.

The present invention further encompasses a polynucleotide comprising a nucleic acid sequence that encodes partly or wholly the antigen binding peptide, such as, but not limited to, an antibody or antibody fragment, provided herein.

In some embodiments, the polynucleotides comprise a nucleic acid sequence encoding any one of the CDR sequences provided in Table 1. In some embodiments, the polynucleotides comprise a nucleic acid sequence encoding any one of the VHs or the VLs provided in Table 2. In some embodiments, the polynucleotides comprise a nucleic acid sequence encoding any one of the N-terminal portion of the heavy chains or full length light chains provided in Table 3. In some embodiments, the polynucleotides comprise a nucleic acid sequence encoding any one of the tandem Fab heavy chain and light chain sequences provided in Table 4.

The present invention also encompasses polynucleotides having at least about 80%, at least about 85%, at least about 90%, at least about 95%, at least about 96%, at least about 97%, at least about 98%, or at least about 99% sequence identity to any of the polynucleotides disclosed herein. The present invention further provides variants of the polynucleotides encoding fragments, analogs, and derivatives of the antigen binding peptide, such as, but not limited to, an antibody or antibody fragment, disclosed herein. The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, the polynucleotide variants are produced by silent substitutions due to the degeneracy of the genetic code. Polynucleotide variants can be produced for a variety of reasons, e.g., to optimize codon expression for a particular host.

In certain embodiments, the polynucleotides of the present invention comprise the coding sequence for the mature polypeptide fused in the same reading frame to a polynucleotide encoding a polypeptide which aids, for example, in the expression and secretion of a polypeptide from a host cell. In some embodiments, the mature polypeptide is the antigen binding peptide, such as, but not limited to, an antibody or antibody fragment, disclosed herein. In certain embodiments, the polynucleotides comprise a sequence encoding a leader polpeptide sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature polypeptide having a prosequence is a proprotein and is an inactive form of the protein. Once the prosequence is cleaved, an active mature protein remains. In certain embodiments, the polynucleotides comprise the coding sequence for the mature polypeptide fused in the same reading frame to a marker sequence that allows, for example, for purification of the encoded polypeptide.

In some embodiments, the present invention provides a vector comprising any one of the polynucleotides provided herein. As used herein, the term "vector" refers to a construct, which is capable of delivering, and optionally expressing, one or more polynucleotides, proteins, or sequences of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The present invention further provides host cells comprising the vectors provided herein. In some embodiments, the host cell is an isolated cell. In some embodiments, the isolated host cell produces the antigen binding peptide, such as, but not limited to, an antibody or antibody fragment, provided herein. Suitable host cells include prokaryotes, yeast, insect or higher eukaryotic cells. Prokaryotes include gram negative or gram positive organisms, for example E. coli or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are generally known in the art. Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, L cells, C127, 3T3, Chinese hamster ovary (CHO), HeLa, and BHK cell lines. In addition, baculovirus systems for production of heterologous proteins in insect cells are generally known in the art.

The antigen binding peptide, such as, but not limited to, an antibody or antibody fragment, of the present invention produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO:221), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance, mass spectrometry and x-ray crystallography. Methods for purifying antibodies and other proteins are generally known in the art.

In certain embodiments, the present invention provides a method of making an antigen binding peptide, such as, but not limited to, an antibody or antibody fragment, disclosed herein. In an exemplary embodiment, the method comprises: (a) culturing the host cell provided hereinabove under culture conditions that promote protein production such that the host cell produces the antigen binding peptide, such as, but not limited to, an antibody or antibody fragment; and (b) isolating the antigen binding peptide, such as, but not limited to, an antibody or antibody fragment, from the cultured cell. Methods for making antigen binding peptides that are generally known in the art can be used to produce the antigen binding peptide, such as, but not limited to, an antibody or antibody fragment, of the present invention.

In some embodiments, the antigen binding peptide, such as, but not limited to, an antibody or antibody fragment, provided herein can be used as a detection reagent. In some embodiments, the antigen binding peptide, such as, but not limited to, an antibody or antibody fragment, is detectably labeled. The term "label" when used herein refers to a detectable compound which is conjugated directly or indirectly to the antigen binding peptide, such as, but not limited to, an antibody or antibody fragment. The label can be detectable by itself (e.g. radioisotope labels or fluorescent labels), or, in the case of an enzymatic label, can catalyze chemical alteration of a substrate which is detectable. In certain embodiments, the label is selected from the group consisting of an immunofluorescent label, a chemiluminescent label, a phosphorescent label, an enzyme label, a radiolabel, avidin/biotin, a colloidal gold particle, a colored particle, and a magnetic particle.

In some embodiments, the antigen binding peptide, such as, but not limited to, an antibody or antibody fragment, forms a bound complex with the compound of Formula (I) or (II) in vitro or in vivo. In some embodiments, the bound complex is an immunocomplex. In general, the detection of immunocomplex formation is well known in the art and can be achieved through the application of numerous approaches. In some embodiments, the detection is performed by an immunological assay, or immunoassay.

As used herein, an immunological assay refers to any assay that capitalizes on the specificity of the antibody-antigen binding in vitro or in vivo. In some embodiments, the assay can be used to identify the presence or absence of a target molecule in a biological sample. In some embodiments, the assay can be used to measure the amount or level of a target molecule. In some embodiments, the target molecule is an immunocomplex of the antigen binding peptide, such as, but not limited to, an antibody or antibody fragment, formed with the compound of Formula (I) or (II) in vitro or in vivo. In some embodiments, the target molecule is the compound of Formula (I) or (II) itself. In some exemplary embodiments, the immunological assay includes, but is not limited to, radioimmunoassay, immunohistochemistry, chemiluminescenceimmunoassay (CLIA), Enzyme Immunoassays (EIA) or Enzyme-Linked Immuno Sorbent Assay (ELISA), Western blot, counting immunoassay, flow cytometry, fluoroimmnoassay, and fluorescence-activated cell sorting (FACS).

A biological sample as used herein can be any sample derived from a subject. In some embodiments, the biological sample is urine, feces, saliva, whole blood, plasma, organ tissue, hair, skin, cells, or cell cultures. In some embodiments, the biological sample is a liquid sample. In some embodiments, the biological sample can be fixed with a fixative. For example, aldehyde fixatives such as formalin (formaldehyde) and glutaraldehyde are typically used.

The present invention further provides a method of reducing the antithrombotic effect of an FXIa inhibitor, or a dual inhibitor of FXIa and plasma kallikrein, in a subject in need thereof. In some embodiments, the present invention relates to a method of reducing the antithrombotic effect of an FXIa inhibitor. In certain embodiments, the FXIa inhibitor is the compound of Formula (I) or II. In some embodiments, the method comprises administering to the subject a pharmaceutically effective dose of the antigen binding peptide, such as, but not limited to, an antibody or antibody fragment, provided herein. In some embodiments, the antigen binding peptide, such as, but not limited to, an antibody or antibody fragment, can bind to the compound of Formula (I) or (II) with high affinity and reverse its antithrombotic effect in vitro or in vivo. In some embodiments, the binding of the antigen binding peptide, such as, but not limited to, an antibody or antibody fragment, to the compound of Formula (I) or (II) can neutralize its antithrombotic effect in vitro or in vivo. In some embodiments, the antigen binding peptide binds to the FXIa inhibitor, e.g., the compound of Formula (I) or (II), and thereby prevents the FXIa inhibitor from binding to FXIa.

The term "subject" refers to any animal including, but not limited to, humans, non-human primates, and the like. In some embodiments, a subject is the recipient of a particular treatment. In some embodiments, the subject is a human. In certain embodiments, the subject is a human patient who is in need of the treatment provided herein. In some embodiments, the terms "subject" and "patient" are used interchangeably herein.

Terms such as "treating," "treatment," or "to treat" are used interchangeably and refer to therapeutic measures that cure, slow down, reduce or lessen symptoms of, reverse or neutralize the effect of, and/or halt progression of a pathologic condition. As used herein, the term treatment is used to mean receiving at least one of the antigen binding peptides, such as, but not limited to, an antibody or antibody fragment, of the present invention. The term "prevent" or "reduce the risk" are used to mean prophylactic or preventative measures that prevent and/or slow the development of a targeted pathologic condition, or lessen the risk that a subject will acquire an abnormal condition as compared to an individual not receing the treatment. Thus, subjects in need of treatment include those already with the condition (such as thrombosis), those prone to have the condition, and those in whom the condition is to be prevented.

The present invention also provides pharmaceutical compositions comprising the antigen binding peptide, such as, but not limited to, an antibody or antibody fragment, disclosed herein. In some embodiments, the pharmaceutical compositions of the present invention encompass therapeutic compositions and/or prophylactic compositions. In some embodiments, the pharmaceutical compositions comprise a therapeutically effective dose of the antigen binding peptide, such as, but not limited to, an antibody or antibody fragment, and a pharmaceutically acceptable carrier or excipient. Such pharmaceutically acceptable excipients are generally known in the art. Common excipients include, but are not limited to, preserving agents, solubilising agents, stabilising agents, wetting agents, emulsifiers, disintegrants, glidants, lubricants, sorbents, vehicles, sweeteners, flavors, colourants, odourants, salts (substances of the present invention may themselves be provided in the form of a pharmaceutically acceptable salt), buffers, coating agents, and antioxidants. Exemplary excipients include, but are not limited to, saline, buffered saline, dextrose, water, glycerol, ethanol, sucrose, sorbitol and any combinations thereof. In some embodiments, the pharmaceutically acceptable excipients are inactive ingredients. However, it is understood that the pharmaceutically acceptable excipients can sometimes have impact on the manufacture, quality, safety, or efficacy of the pharmaceutical compositions. In some embodiments, the pharmaceutical compositions may also contain therapeutically active agents in addition to the antigen binding peptide, such as, but not limited to, an antibody or antibody fragment, of the present invention.

The pharmaceutical compositions of the present invention may be presented in unit-dose or multi-dose containers, for example, sealed ampoules and vials, and may be stored in a freeze-dried (lyophilized) condition requiring only the addition of the sterile liquid carrier, for example, water or saline for injections, immediately prior to use. Extemporaneous injection solutions and suspensions may be prepared from sterile powders, granules, and tablets.

The pharmaceutical compositions may be administered in a convenient and suitable manner according to the use. In some embodiments, the pharmaceutical compositions may be administered by parenteral routes. In some embodiments, the parenteral administration routes may be intravenous, intraperitoneal, intramuscular, intratumor, subcutaneous, intranasal, or intradermal routes.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6):318 (1986).

Pharmaceutical compositions adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for parenteral administration may include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine, and vegetable oils, for example.

The terms "effective dose," "therapeutically effective dose," and "pharmaceutically effective dose" are used interchangeably herein and refer to a dose sufficient to produce a physiological effect. In some embodiments, a pharmaceutically effective dose of the antigen binding peptide, such as, but not limited to, an antibody or antibody fragment, provided herein refers to an amount of the antigen binding peptide, such as, but not limited to, an antibody or antibody fragment, effective to reduce or neutralize the antithrombotic effect of the compounds disclosed herein in a subject in need thereof. In some embodiments, the administration of one pharmaceutically effective dose of the antigen binding peptide, such as, but not limited to, an antibody or antibody fragment, can immediately reverse the antithrombotic effect of the compound of Formula (I) or (II) in a subject with serious bleeding. In some embodiments, the administration of one pharmaceutically effective dose of the antigen binding peptide, such as, but not limited to, an antibody or antibody fragment, has a limited duration of action. In certain embodiments, a single pharmaceutically effective dose of the antigen binding peptide, such as, but not limited to, an antibody or antibody fragment, has a duration of action long enough to reverse the antithrombotic effect of the compound of Formula (I) or (II). In the meantime, the single pharmaceutically effective dose of the antigen binding peptide, such as, but not limited to, an antibody or antibody fragment, has a duration of action short enough to allow resumption of antithrombotic therapy soon after the administration of the single pharmaceutically effective dose and to minimize the period of increased risk for thromboembolic events.

In some embodiments, a pharmaceutically effective dose can be determined empirically and in a routine manner, in relation to the stated purpose. For example, in some embodiments, the dose of the compound of Formula (II) ranges from about 25 milligrams (mg) quaque die (q.d., or once a day) to about 375 mg bis in die (b.i.d., or twice a day). In some embodiments, the pharmaceutically effective dose of the antigen binding peptide, such as, but not limited to, an antibody or antibody fragment, is about 25 mg q.d. In some embodiments, the pharmaceutically effective dose of the antigen binding peptide, such as, but not limited to, an antibody or antibody fragment, is about 50 mg q.d. In some embodiments, the pharmaceutically effective dose of the antigen binding peptide, such as, but not limited to, an antibody or antibody fragment, is about 75 mg q.d. In some embodiments, the pharmaceutically effective dose of the antigen binding peptide, such as, but not limited to, an antibody or antibody fragment, is about 100 mg q.d. In some embodiments, the pharmaceutically effective dose of the antigen binding peptide, such as, but not limited to, an antibody or antibody fragment, is about 125 mg q.d. In some embodiments, the pharmaceutically effective dose of the antigen binding peptide, such as, but not limited to, an antibody or antibody fragment, is about 150 mg q.d. In some embodiments, the pharmaceutically effective dose of the antigen binding peptide, such as, but not limited to, an antibody or antibody fragment, is about 175 mg q.d. In some embodiments, the pharmaceutically effective dose of the antigen binding peptide, such as, but not limited to, an antibody or antibody fragment, is about 200 mg q.d. In some embodiments, the pharmaceutically effective dose of the antigen binding peptide, such as, but not limited to, an antibody or antibody fragment, is about 375 mg q.d.

In some embodiments, the pharmaceutically effective dose of the antigen binding peptide, such as, but not limited to, an antibody or antibody fragment, is about 25 mg b.i.d. In some embodiments, the pharmaceutically effective dose of the antigen binding peptide, such as, but not limited to, an antibody or antibody fragment, is about 50 mg b.i.d. In some embodiments, the pharmaceutically effective dose of the antigen binding peptide, such as, but not limited to, an antibody or antibody fragment, is about 75 mg b.i.d. In some embodiments, the pharmaceutically effective dose of the antigen binding peptide, such as, but not limited to, an antibody or antibody fragment, is about 100 mg b.i.d. In some embodiments, the pharmaceutically effective dose of the antigen binding peptide, such as, but not limited to, an antibody or antibody fragment, is about 125 mg b.i.d. In some embodiments, the pharmaceutically effective dose of the antigen binding peptide, such as, but not limited to, an antibody or antibody fragment, is about 150 mg b.i.d. In some embodiments, the pharmaceutically effective dose of the antigen binding peptide, such as, but not limited to, an antibody or antibody fragment, is about 175 mg b.i.d. In some embodiments, the pharmaceutically effective dose of the antigen binding peptide, such as, but not limited to, an antibody or antibody fragment, is about 200 mg b.i.d. In some embodiments, the pharmaceutically effective dose of the antigen binding peptide, such as, but not limited to, an antibody or antibody fragment, is about 375 mg b.i.d.

In some embodiments of the present invention, the pharmaceutically effective dose of the antigen binding peptide, such as, but not limited to, an antibody or antibody fragment, is determined primarily in relation to the dose of the compound of Formula (I) or (II) administered before. In some embodiments, a pharmaceutically effective dose comprises the antigen binding peptide, such as, but not limited to, an antibody or antibody fragment, at an at least about 1:1 molar ratio to the dose of the compound of Formula (I) or (II) administered to the subject before. In some embodiments, a pharmaceutically effective dose comprises the antigen binding peptide, such as, but not limited to, an antibody or antibody fragment, at an at least about 2:1 to about 10:1 molar ratio to the dose of the compound of Formula (I) or (II) administered to the subject. In some embodiments, a pharmaceutically effective dose comprises the antigen binding peptide, such as, but not limited to, an antibody or antibody fragment, at an at least about 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1 molar ratio to the dose of the compound of Formula (I) or (II) administered to the subject before.

In some embodiments, a pharmaceutically effective dose comprises the antigen binding peptide, such as, but not limited to, an antibody or antibody fragment, at an at least about 1:1 molar ratio to the amount of the compound of Formula (I) or (II) present in a subject. In some embodiments, a pharmaceutically effective dose comprises the antigen binding peptide, such as, but not limited to, an antibody or antibody fragment, at an at least about 2:1 to about 10:1 molar ratio to the amount of the compound of Formula (I) or (II) present in the subject. In some embodiments, a pharmaceutically effective dose comprises the antigen binding peptide, such as, but not limited, to an antibody or antibody fragment, at an at least about 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1 molar ratio to the amount of the compound of Formula (I) or (II) present in the subject.

In some embodiments, the pharmaceutically effective dose of the antigen binding peptide, such as, but not limited to, an antibody or antibody fragment, is calculated in mass ratio. For example, the molecular weight (MW) of the antigen binding peptide, such as, but not limited to an antibody or antibody fragment, may be about 75 times the MW of the compound of Formula (II). In this example, for every about 100 mg of the compound of Formula (II), equal molar of the antigen binding peptide, such as, but not limited to, an antibody or antibody fragment, is about 7.5 grams. Thus, one skilled in the art can readily calculate the mass ratio of the antigen binding peptide, such as, but not limited to, an antibody or antibody fragment, to the compound of Formula (I) or (II) since their molar masses are readily available according to the present invention.

In some embodiments, the dose of the antigen binding peptide, such as, but not limited to, an antibody or antibody fragment, will be determined in clinical studies. Prior to those studies, computational modeling and simulation are performed which incorporate (1) human pharmacokinetic and pharmacodynamic information (from Phase 1 studies), (2) binding kinetics and (3) predicted human PK parameters.

The antigen binding peptide, such as, but not limited to, an antibody or antibody fragment, of the present invention can be administered concurrently with or after the administration of the compound of Formula (I) or (II). In some embodiments, the antigen binding peptide, such as, but not limited to, an antibody or antibody fragment, is administered concurrently with the administration of the compound of Formula (I) or (II). In some embodiments, the antigen binding peptide, such as, but not limited to, an antibody or antibody fragment, is administered immediately after the administration of the compound of Formula (I) or (II). In an exemplary embodiment, the antigen binding peptide, such as, but not limited to, an antibody or antibody fragment, is administered about 30 minutes after the beginning of the administration of the compound of Formula (I) or (II). In some exemplary embodiments, the antigen binding peptide, such as, but not limited to, an antibody or antibody fragment, is administered about 20 minutes after the administration of the compound of Formula (I) or (II) has finished. However, the administration of the antigen binding peptide, such as, but not limited to, an antibody or antibody fragment, and the compound of Formula (I) or (II) can be concurrent or consecutive in any order as deemed appropriate by a person skilled in the art.

The antigen binding peptide, such as, but not limited to, an antibody or antibody fragment, of the present invention can be administered by any route a skilled person deems suitable. In one embodiment, the antigen binding peptide, such as, but not limited to, an antibody or antibody fragment, is administered intravenously, intramuscularly, or subcutaneously. In some embodiments, the antigen binding peptide, such as, but not limited to, an antibody or antibody fragment, is administered once a day. In some embodiments, the antigen binding peptide, such as, but not limited to, an antibody or antibody fragment, is administered more than once a day. In some embodiments, the antigen binding peptide, such as, but not limited to, an antibody or antibody fragment, is administered over a period of about 10 minutes. In some embodiments, the antigen binding peptide, such as, but not limited to, an antibody or antibody fragment, is administered over a period of about less than about 10 minutes. In some embodiments, the antigen binding peptide, such as, but not limited to, an antibody or antibody fragment, is administered over a period of about more than about 10 minutes.

The present invention further provides a method of detecting the level of a compound of Formula (I) or (II) in a biological sample. In some embodiments, the method comprises contacting a biological sample with the antigen binding peptide, such as, but not limited to, an antibody or antibody fragment. In some embodiments, the method comprises detecting the level of a bound complex of the compound of Formula (I) or (II) and the antigen binding peptide, such as, but not limited to, an antibody or antibody fragment. In some embodiments, the method comprises contacting a biological sample with the antigen binding peptide, such as, but not limited to, an antibody or antibody fragment, and then detecting the level of a bound complex of the compound and the antigen binding peptide, such as, but not limited to, an antibody or antibody fragment.

The breadth and scope of the present disclosure should not be limited by any of the above-described exemplary aspects, but should be defined only in accordance with the following claims and their equivalents.

The contents of all cited references (including literature references, patents, patent applications, and websites) that may be cited throughout this application are hereby expressly incorporated by reference in their entirety for any purpose, as are the references cited therein.

EXAMPLES

Example 1: Generation of Human Monoclonal Antibodies Against Compound A Using Transgenic Mice that Express Human Antibody Genes Preparation of Antigen and Related Compounds Fully human monoclonal antibodies to Compound A, a specific inhibitor of Factor XIa, were prepared by immunizing transgenic mice with Keyhole limpet haemocyanin (KLH) conjugated versions of Compound A (shown below).

Compound A

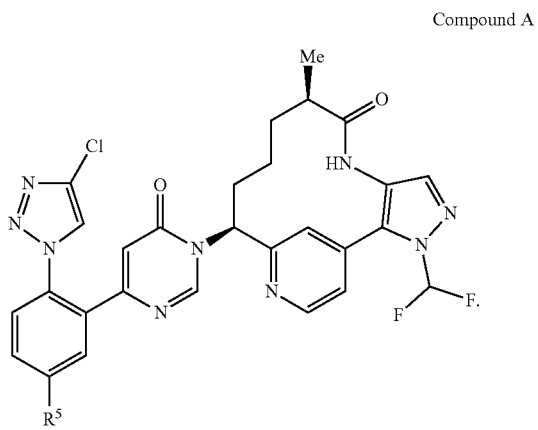

Example 1A. Synthesis of Compound 3

Step 1: Synthesis of tert-butyl 1-(4-chloro-2-(1-((5R,9S)-21-(difluoromethyl)-5-methyl-4-oxo-21H-3-aza-1(4,2)-pyridina-2(5,4)-pyrazolacyclonon-aphane-9-yl)-6-oxo-1,6-dihydropyrimidin-4-yl)phenyl)-1H-1,2,3-triazole-4-carboxylate (Compound 1)

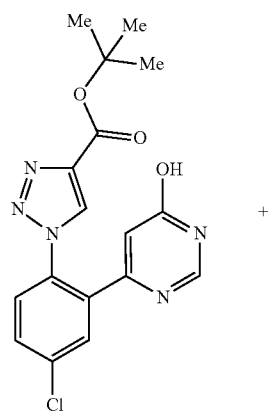

+

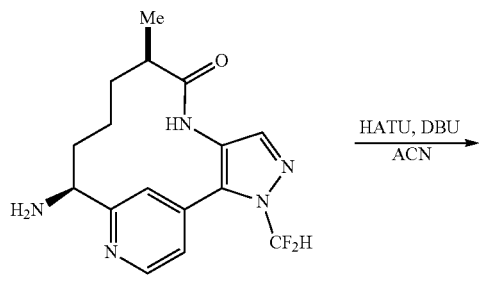

HATU, DBU
———————→
ACN

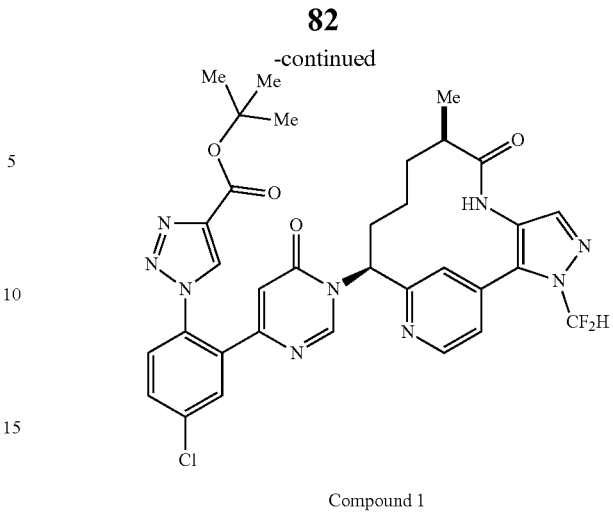

Compound 1

To a 100 mL flask containing a white suspension of tert-butyl 1-(4-chloro-2-(6-hydroxypyrimidin-4-yl)phenyl)-1H-1,2,3-triazole-4-carboxylate (105 mg, 0.28 mmol) in acetonitrile (3.7 mL) was added HATU (1-[Bis(dimethyl-amino)methylene]-1H-1,2,3-triazolo[4,5-b]pyridinium 3-oxide hexafluorophosphate) (117 mg, 0.31 mmol) and DBU (1,8-Diazabicyclo[5.4.0]undec-7-ene) (55.0 µl, 0.37 mmol). The resulting clear, yellow solution was stirred at room temperature for 5 minutes. (5R,9S)-9-amino-21-(difluoromethyl)-5-methyl-21H-3-aza-1(4,2)-pyridina-2(5,4)-pyrazolacyclononaphan-4-one (94 mg, 0.281 mmol) was added and the resulting suspension was stirred at room temperature for 3 hours, at which point it was concentrated to dryness. The residue was dissolved in 1 mL EtOAc and was loaded onto a 40 g Isco column. The product was eluted with a linear gradient of 0% to 100% EtOAc in hexanes over 35 minutes. Product eluted right at 100% EtOAc. Tert-butyl 1-(4-chloro-2-(1-((5R,9S)-21-(difluoromethyl)-5-methyl-4-oxo-21H-3-aza-1(4,2)-pyridina-2(5,4)-pyrazolacyclonon-aphane-9-yl)-6-oxo-1,6-dihydropyrimidin-4-yl)phenyl)-1H-1,2,3-triazole-4-carboxylate (161 mg, 0.233 mmol, 83% yield) was isolated as a white solid.

Step 2: Synthesis of 1-(4-chloro-2-(1-((5R,9S)-21-(difluoromethyl)-5-methyl-4-oxo-21H-3-aza-1(4,2)-pyridina-2(5,4)-pyrazolacyclononaphane-9-yl)-6-oxo-1,6-dihydropyrimidin-4-yl)phenyl)-1H-1,2,3-triazole-4-carboxylic Acid Hydrochloride (Compound 1A)

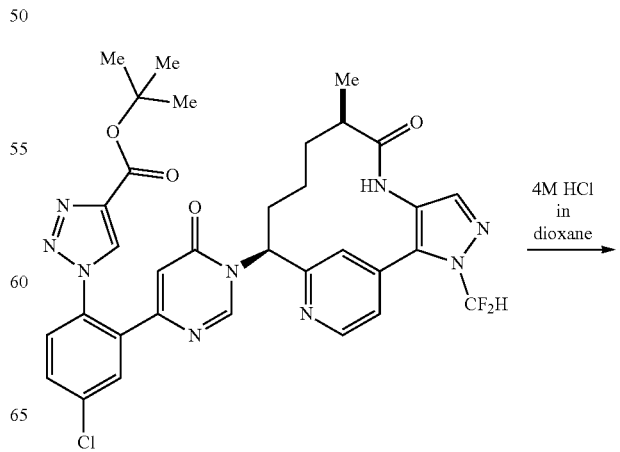

4M HCl
in
dioxane
———————→

-continued

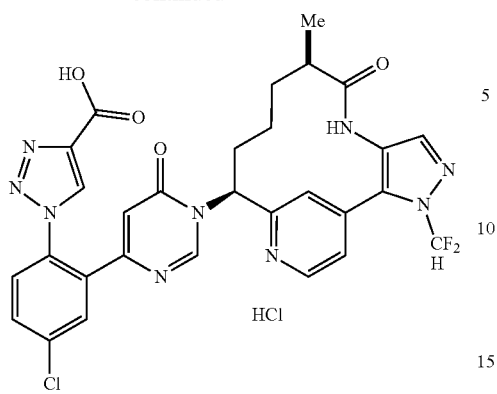

Compound 1A

Tert-butyl 1-(4-chloro-2-(1-((5R,9S)-21-(difluoromethyl)-5-methyl-4-oxo-21H-3-aza-1(4,2)-pyridina-2(5,4)-pyrazolacyclononaphane-9-yl)-6-oxo-1,6-dihydropyrimidin-4-yl)phenyl)-1H-1,2,3-triazole-4-carboxylate (161 mg, 0.233 mmol) was dissolved in HCl in dioxane (3 ml, 12.00 mmol) and stirred for 2 hours at which point the deprotection was complete by LCMS. The reaction mixture was concentrated to dryness and further dried overnight in vacuo. 1-(4-chloro-2-(1-((5R,9S)-21-(difluoromethyl)-5-methyl-4-oxo-21H-3-aza-1(4,2)-pyridina-2(5,4)-pyrazolacyclononaphane-9-yl)-6-oxo-1,6-dihydropyrimidin-4-yl)phenyl)-1H-1,2,3-triazole-4-carboxylic acid hydrochloride (150 mg, 0.223 mmol, 96% yield) was isolated as a pale yellow solid.

Step 3: Synthesis of 3-(2-(2-(1-(4-chloro-2-(1-((5R,9S)-21-(difluoromethyl)-5-methyl-4-oxo-21H-3-aza-1(4,2)-pyridina-2(5,4)-pyrazolacyclononaphane-9-yl)-6-oxo-1,6-dihydropyrimidin-4-yl)phenyl)-1H-1,2,3-triazole-4-carboxamido)ethoxy)ethoxy)propanoic Acid (Compound 1B)

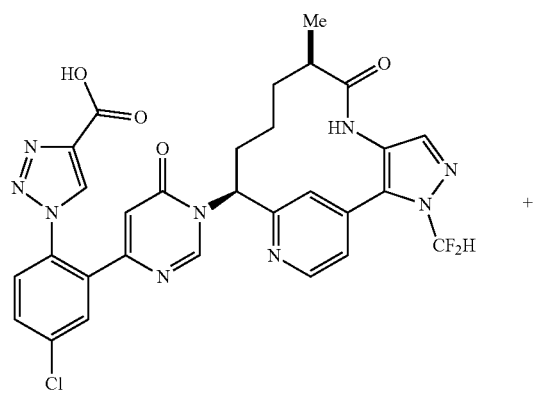

+

-continued

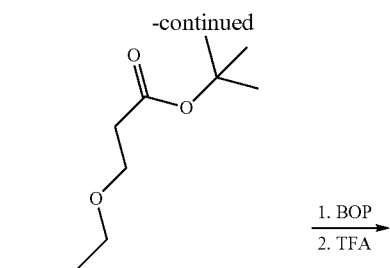

1. BOP
2. TFA

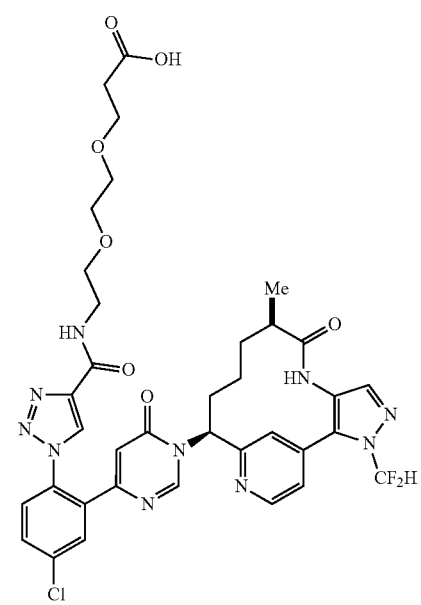

Compound 1B 1-(4-chloro-2-(1-((5R,9S)-21-(difluoromethyl)-5-methyl-4-oxo-21H-3-aza-1(4,2)-pyridina-2(5,4)-pyrazolacyclononaphane-9-yl)-6-oxo-1,6-dihydropyrimidin-4-yl)phenyl)-1H-1,2,3-triazole-4-carboxylic acid hydrochloride (40 mg, 0.063 mmol), tert-butyl 3-(2-(2-aminoethoxy)ethoxy)propanoate (14.67 mg, 0.063 mmol) and triethylamine (8.77 µl, 0.063 mmol) were dissolved in DMF (N,N-dimethylformamide) (2 mL). BOP (benzotriazol-1-yloxytris(dimethylamino)phosphonium hexafluorophosphate) (27.8 mg, 0.063 mmol) was added and the resulting mixture stirred for 4 hours at room temperature. The residue was concentrated to dryness and subsequently diluted with $CH_2Cl_2$ (4 mL) and TFA (trifluoroacetic acid) (2 mL). The reaction mixture was stirred for 2 hours at room temperature and then concentrated to a dry residue.

Purification of COMPOUND 1 was accomplished by prep HPLC.

Prep HPLC—Column=Sunfire Prep C18 OBD 5 micron (30×100 mm)

Solvent A=10% MeOH, 90% water, 10 mM ammonium acetate

Solvent B=90% MeOH, 10% water, 10 mM ammonium acetate

Linear gradient of 25% B to 100% B

Example 1B. Synthesis of Compound 2 and 3

Synthesis of 3-(2-(2-(2-(((5R,9S)-9-(4-(5-chloro-2-(4-chloro-1H-1,2,3-triazol-1-yl)phenyl)-6-oxopyrimidin-1(6H)-yl)-5-methyl-4-oxo-21H-3-aza-1(4,2)-pyridina-2(3,4)-pyrazolacyclononaphane-21-yl)ethoxy)ethoxy)ethoxy)propanoic Acid (Compound 2) and 3-(2-(2-(2-(((5R,9S)-9-(4-(5-chloro-2-(4-chloro-1H-1,2,3-triazol-1-yl)phenyl)-6-oxopyrimidin-1(6H)-yl)-5-methyl-4-oxo-21H-3-aza-1(4,2)-pyridina-2(5,4)-pyrazolacyclononaphane-21-yl)ethoxy)ethoxy)ethoxy)propanoic Acid (Compound 3)

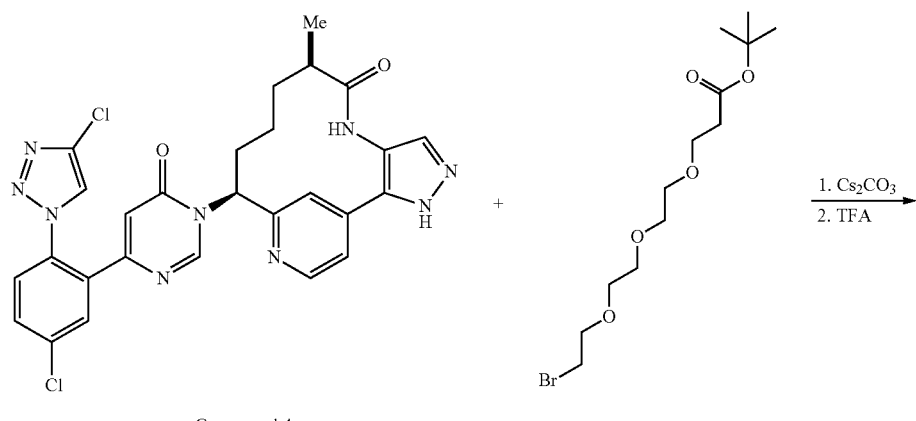

Compound 4

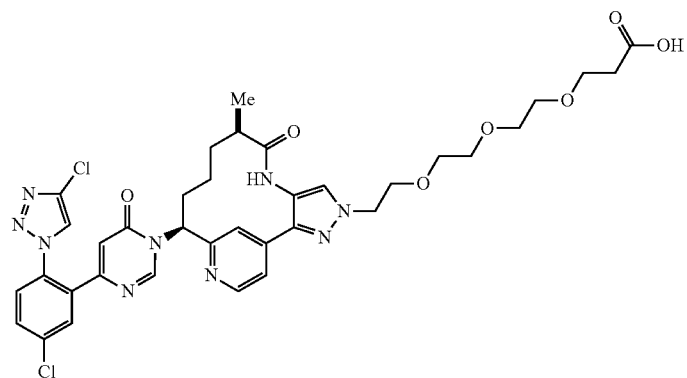

Compound 2

+

-continued

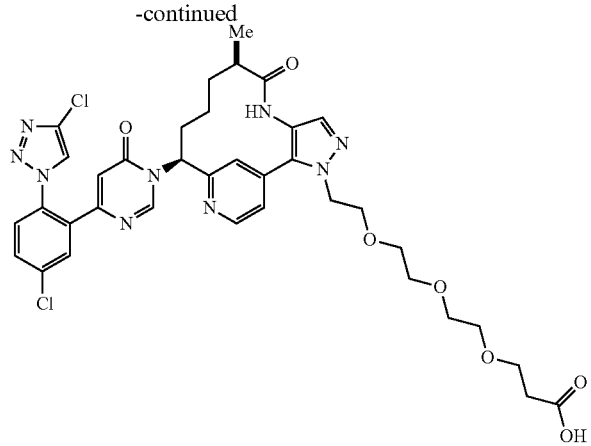

Compound 3

(5R,9S)-9-(4-(5-chloro-2-(4-chloro-1H-1,2,3-triazol-1-yl)phenyl)-6-oxopyrimidin-1(6H)-yl)-5-methyl-21H-3-aza-1(4,2)-pyridina-2(5,4)-pyrazolacyclononaphan-4-one (COMPOUND 4) (70 mg, 0.121 mmol), tert-butyl 3-(2-(2-(2-bromoethoxy)ethoxy)ethoxy)propanoate (41.4 mg, 0.121 mmol), and cesium carbonate (39.6 mg, 0.121 mmol) were heated to 60° C. in DMF (N,N-dimethylformamide) (3 mL) for 1 hour and then cooled to room temperature. The reaction mixture was filtered and then concentrated to dryness. The residue was diluted with CH$_2$Cl$_2$ (4 mL) and TFA (2 mL) and then stirred for 1 hour at room temperature. Purification of resulting COMPOUND 2 and COMPOUND 3 was accomplished by prep HPLC.

Prep HPLC—Column=Sunfire Prep C18 OBD 5 micron (30×100 mm)

Solvent A=10% MeOH, 90% water, 10 mM ammonium acetate

Solvent B=90% MeOH, 10% water, 10 mM ammonium acetate

Linear gradient of 25% B to 100% B

COMPOUND 2 (40 mg, 0.051 mmol, 41.8% yield) and COMPOUND 3 (15 mg, 0.019 mmol, 15.51% yield) were isolated as white solids.

COMPOUND 2, COMPOUND 3 and COMPOUND 1 were conjugated to BSA and KLH for immunization and ELISA screening.

Conjugation to KLH: A 2 mg sample of the COMPOUND 1, 2 or 3 was dissolved with 90 μL of DMSO followed by 390 μL of MES buffer and mixed by vortex. Then 200 μL of KLH (10 mg/mL stock) was added to the mixture. Finally 50 μL of EDC (20 mg/mL stock) was added. The samples were Incubated at room temperature for 3 hr in the dark and then dialyzed against 5 L of 1×DPBS (Lonza, cat #17-512Q).

Conjugation BSA: A 2 mg sample of the compound (COMPOUND 2, COMPOUND 3, or COMPOUND 1) was dissolved with 200 μL of DMSO followed by 200 μL of MES Conjugation buffer (MES pH4.7) and mixed by vortex. Then 400 μL of BSA (5 mg/mL stock) was added to the mixture. Finally, 50 μL of EDC (20 mg/mL stock) was added. (Ratios added were 10× compound:1× carrier:2× activating agent.) The samples were incubated at room temperature for 3 hr in the dark and then dialyzed against 5 L of 1×DPBS (Lonza, cat #17-512Q).

COMPOUND 5 (a biotin-labeled version of COMPOUND 2) has the following structure:

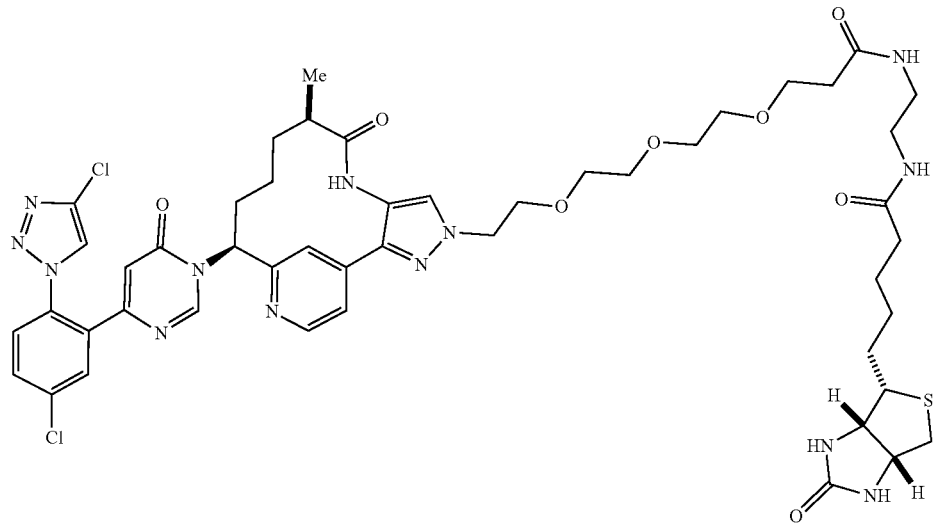 [SMILES: C[C@@H]1CCC[C@H](n2cnc(-c3cc(Cl)ccc3-n3cc(Cl)nn3)cc2=O)c2cc(ccn2)-c2nn(CCOCCOCCOCCC(=O)NCCNC(=O)CCCC[C@@H]3SC[C@@H]4NC(=O)N[C@@H]43)cc2NC1=O]

Synthesis of: N-(1-((5R,9S)-9-(4-(5-chloro-2-(4-chloro-1H-1,2,3-triazol-1-yl)phenyl)-6-oxopyrimidin-1(6H)-yl)-5-methyl-4-oxo-21H-3-aza-1(4,2)-pyridina-2(3,4)-pyrazolacyclononaphane-21-yl)-12-oxo-3,6,9-trioxa-13-azapentadecan-15-yl)-5-((3aS, 4S,6aR)-2-oxohexahydro-1H-thieno[3,4-d]imidazol-4-yl)pentanamide (Compound 5)

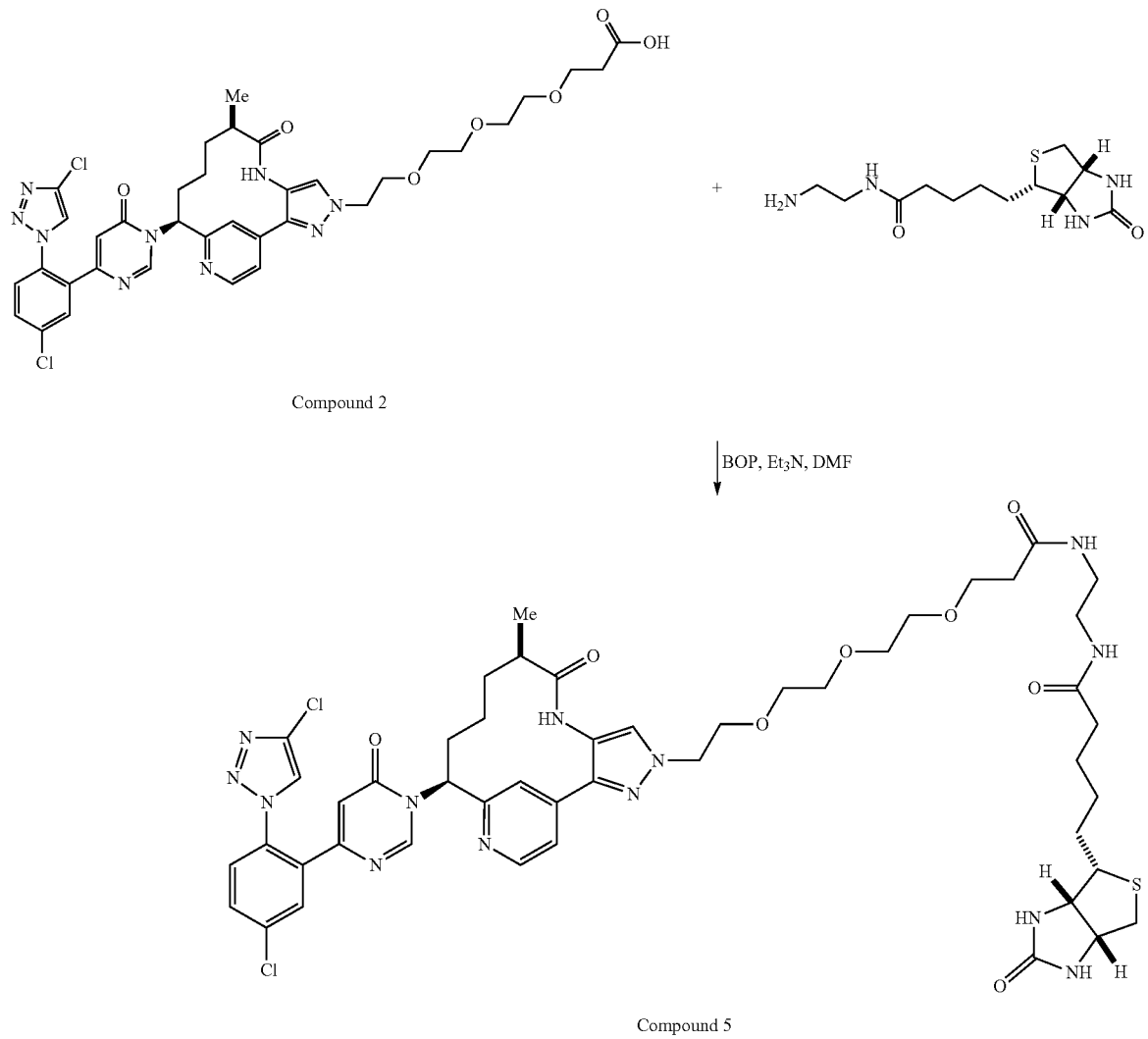

Compound 2

BOP, Et₃N, DMF

Compound 5

COMPOUND 2 (16 mg, 0.02 mmol), N-(2-aminoethyl)-5-43aS,4S,6aR)-2-oxohexahydro-1H-thieno[3,4-d]imidazol-4-yl)pentanamide (5.9 mg, 0.02 mmol), biotin and triethylamine (2.9 µl, 0.02 mmol) were dissolved in DMF (2 mL). BOP (9.1 mg, 0.02 mmol) was added and the reaction mixture was stirred for 4 hours at rt. The reaction mixture was then purified by prep HPLC.

Prep HPLC—Column=Sunfire Prep C18 OBD 5 micron (30×100 mm)
Solvent A=10% MeOH, 90% water, 10 mM ammonium acetate
Solvent B=90% MeOH, 10% water, 10 mM ammonium acetate
Linear gradient of 25% B to 100% B COMPOUND 5 (18 mg, 80%) was isolated as a white solid.

Example 2: Generation of Human Monocloncal Antibodies Against Compound A Using Transgenic Mice that Express Human Antibody Genes
Immunization of Mice Human anti-Compound A antibodies were generated by immunizing mice of human Ig transgenic mouse strain HCo42:01 KCo5:01 [J/K] (Lonberg, Handbook of Experimental Pharmacology 113:49, 1994; Lonberg et al. Nature 368:856, 1994). The immunogen was a mixture of the three KLH-compound conjugated forms: COMPOUND 1-KLH, COMPOUND 2-KLH, and COMPOUND 3-KLH, together with Ribi adjuvant (RA). The immunization protocol consisted of foot pad injections of the immunogen mixture in Ribi adjuvant. Mice were immunized every three to five days for three weeks with a total of seven injections, and the lymph nodes harvested after a pre-fusion boost the day prior to tissue collection. In vivo experiments were conducted in accordance with the regulations of the Animal Care and Use Committee of the Bristol-Myers Squibb Company. Lymph nodes from three immunized mice were harvested, homogenized and pooled. Hybridomas were generated by electrofusion with the mouse myeloma fusion partner SP2/0-Ag14 (ATCC CRL-1581™) by electric field-based electrofusion. Fused cells were plated into multi-well plates in selective HAT medium for 7 days and subsequently screened by ELISA for antigen binding. Based on these results, hybridoma clones 1H2, 9C8, 24H1, and 26D5 from fusion 6938 were selected for further analysis, subcloning, and sequencing. Subcloned hybridomas were expanded to 400 ml cultures for purification. Secreted fully human antibodies were purified via Protein A affinity chromatography. The best performing fully human antibody from hybridoma subclone 1873.6938.26D5.D12 (referred to as '26D5' herein) was ultimately advanced to affinity maturation.

Example 3: Affinity Maturation of Antibodies

Figure 8B:
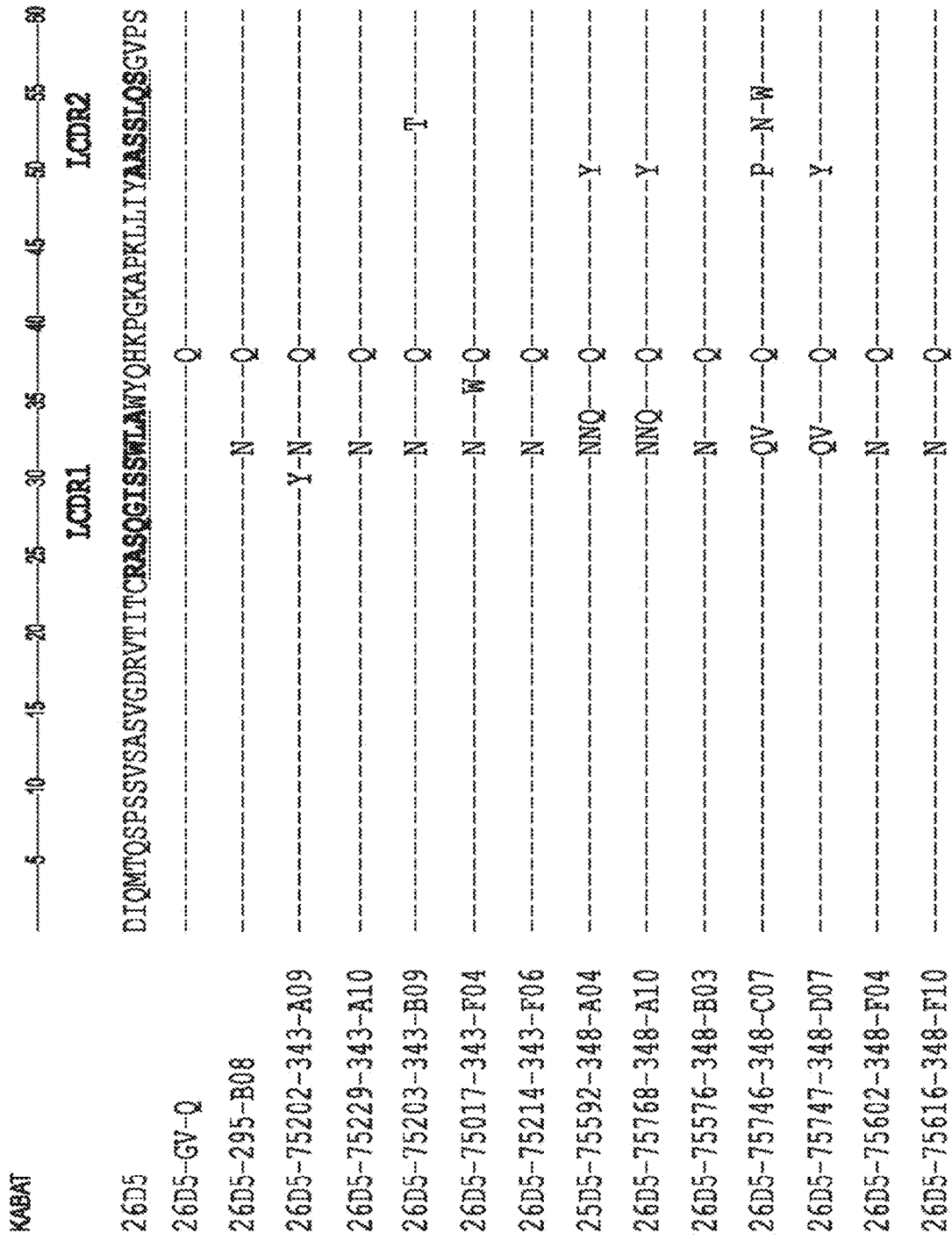

An affinity maturation campaign was conducted on human mAb 26D5 in order to improve its affinity for Compound A. First, the mAb 26D5 sequence was compared to the closest human germline V and J gene sequences (FIG. 1A-B). In order to reduce the risk of immunogenicity in humans, the framework positions that differed from germline were mutated or reverted back to germline sequence, generating human mAb 26D5-GV-Q (which in its fully human antibody format is also referred to herein as P1-072226), which retained similar binding to Compound A. mAb 26D5-GV-Q (P1-072226) was then the starting point for a mutational scan, which measured the relative fitness of every possible single amino acid substitution in the antibody CDR positions shown in FIG. 2. Deep mutational scanning approaches have been described in Araya et al., *Trends in Biotechnology* 29:435, 2001; Forsynth et al., *mAbs* 5:523, 2013; and Wrenbeck et al., *Curr. Opin. Struct. Biol.* 45:36, 2017. First, an scFv (single chain) library was created where each individual amino acid substitution was generated using NNK oligonucleotides at the CDR positions shown in FIG. 2. In generating this library of single mutants, multiple oligonucleotides were designed that each individually incorporated an NNK codon at a single position, where N=A, C, G, T, and K=G, T. The use of these degenerate codons allowed encoding of all 20 naturally-occurring amino acids (plus a stop codon) at the position where the NNK codon was incorporated. The Kabat definition was used for all CDRs except HCDR1, where the AbM definition was used (Abhinandan and Martin, *Mol. Immunol.* 45:3832, 2008; Swindells et al., *J. Mol. Biol.* 429:356, 2017), and positions 60-65 of HCDR2 were not included in the analysis. Next, using mRNA display (Xu et al., *Chemistry & Biology* 9: 933, 2002; Roberts and Szostak, *Proc. Natl. Acad. Sci. USA* 94:12297, 1997; Kurz et al., *Nucleic Acids Res.* 28: E83, 2000), the DNA library was taken through a single round of in vitro transcription and translation, during which the encoding mRNA was fused to its own scFv protein molecule via a puromycin linkage. During selection, any scFvs that bound COMPOUND 5 (a biotin-labeled version of COMPOUND 2) were captured by magnetic streptavidin beads, eluted, and amplified by PCR. Finally, both the initial DNA library generated and the eluted DNA (encoding scFvs binding to COMPOUND 5) were sequenced using next generation sequencing (NGS).

For the analysis of the NGS data, paired-end forward and reverse read sequences from NGS were assembled using FLASH (Magor and Salzberg, *Bioinformatics* 27:2957, 2011) and binned according to mutation position and identity of the mutated amino acid. All sequences of poor quality and those containing multiple mutation sites were eliminated from the analysis. Next, the frequency of each sequence in the post-selection population was divided by the frequency in the starting population to derive an enrichment ratio (ER). In other words, the enrichment ratio is the counts of a particular sequence variant in the COMPOUND 5-bound sample divided by the counts in the initial library. This was then normalized to the enrichment ratio of the parental 26D5-GV-Q mAb. In this manner, the effect on COMPOUND 5 binding (and thus, by inference, A) of every single amino acid substitution in the CDR regions as discussed herein was assessed. FIG. 3A shows the LCDR1 heat map that was generated using the mutational scan data analysis, and allows for the interpretation of the sequence-activity relationship of single amino acid substitutions. Generally, the error in this method is approximately two-fold. Thus, enrichment ratio (ER) values from 0.5 to 2 are considered to be neutral substitutions, i.e., substitutions that maintain binding properties to COMPOUND 5. ER values greater than 2 are considered favorable or preferred for binding, and ER values less than 0.5 are considered unfavorable for binding. FIGS. 3B-E show the heat maps for the remaining CDRs.

Based on the calculated enrichment ratios from the NGS data, variable region genes for single and combinations of favorable amino acid substitutions were synthesized and cloned into IgG expression vectors with the human IgG1f Fc region and human LC kappa region (CK). The vectors were transiently transfected into Expi293 HEK cells at a small scale (2 ml culture) and purified using a Protein A filter plate. The IgG proteins were assessed using SPR (surface plasmon resonance) and functional activity (see data below). Sequences of the antibodies of interest that were identified following this assessment are shown in FIG. 4A-B.

In particular, progeny 26D5-295-B08 was chosen for further affinity maturation using three different library designs. For the first design, a second mutational scan was performed on 26D5-295-B08, randomizing the residues shown in FIG. 5. In this second mutational scan, positions outside of the Kabat and/or AbM CDR definitions were randomized, based on their proximity to Compound A in the co-crystal structure. The heat maps from the mutational scan of 26D5-295-B08 are shown in FIGS. 6A-F. As previously, variable region genes for single and combinations of favorable amino acid substitutions were synthesized and cloned into IgG1f expression vectors for assays. MAbs of interest that were identified from the mutational scan of 26D5-295-B08 included: 26D5-75202-343-A09, 26D5-75229-343-A10, 26D5-75203-343-B09, 26D5-75017-343-F04, and 26D5-75214-343-F06 (see Tables 1-3 for sequences). All human antibodies disclosed in the Examples were in IgG1f (e.g., SEQ ID NO: 200) and human LC kappa format (e.g., SEQ ID NO: 204), unless specifically indicated otherwise.

In addition, two complex libraries (chip and doped) based on 26D5-295-B08 were constructed to more fully randomize positions of interest (FIG. 7A-B). The chip library was designed to contain single and double substitutions to all amino acids (except cysteine and methionine) within a CDR and flanking framework positions, with some additional modifications as noted in FIG. 7A. The design also removed sequences containing chemical liabilities and was synthesized via chip oligonucleotides (Twist Bioscience). The doped library focused randomization on HCDR3 and surrounding framework residues in order to access more than two mutations within a single CDR. The DNA oligonucleotides encoding this library were generated by "doping" the randomized region based on the 26D5-295-B08 DNA sequence. For each nucleotide in the randomized region, the oligo contained 70% of the 26D5-295-B08 DNA base, and 10% each of the other bases. For example, if the 26D5-295-B08 DNA had a G at a particular position, then the doped oligo would contain 70% G, 10% A, 10% C, and 10% Tat that position. This allows deeper randomization of the regions of interest while still biasing the library toward the original parent sequence. The oligos were used to generate separate chip and doped DNA scFv libraries. These libraries were selected using mRNA display according to the above protocol, but with multiple successive rounds incorporating off-rates in later rounds. The resulting populations were sequenced using NGS, and the data were analyzed to pick variable regions for synthesis and cloning into IgG expression vectors for testing. MAbs of interest that were identified from the chip library include: 26D5-75592-348-A04, 26D5-75768-348-A10, 26D5-75576-348-B03, 26D5-75746-348-007, 26D5-75747-348-D07, and 26D5-75602-348-F04 (see Tables 1-3 for sequences). MAb 26D5-75616-348-F10 was identified as an antibody of interest from the doped library. FIGS. 8A-B show the sequences of interest from the affinity maturation of mAb 26D5-295-B08.

For confirmation of small-scale results, the expression vectors of antibodies of interest were transiently transfected into Expi293 HEK cells at a 340 mL scale and purified using a prepacked 20 mL POROS A column, buffer exchanged into PBS using an Amicon 30K MWCO filter, sterile filtered over 0.2 μm PES filter, aliquoted and stored at −80° C. Each sample was mass confirmed by LC/MS and characterized by analytical SEC.

Example 4: Characterization of mAbs by a Chromogenic Enzymatic Assay

Figure 9:
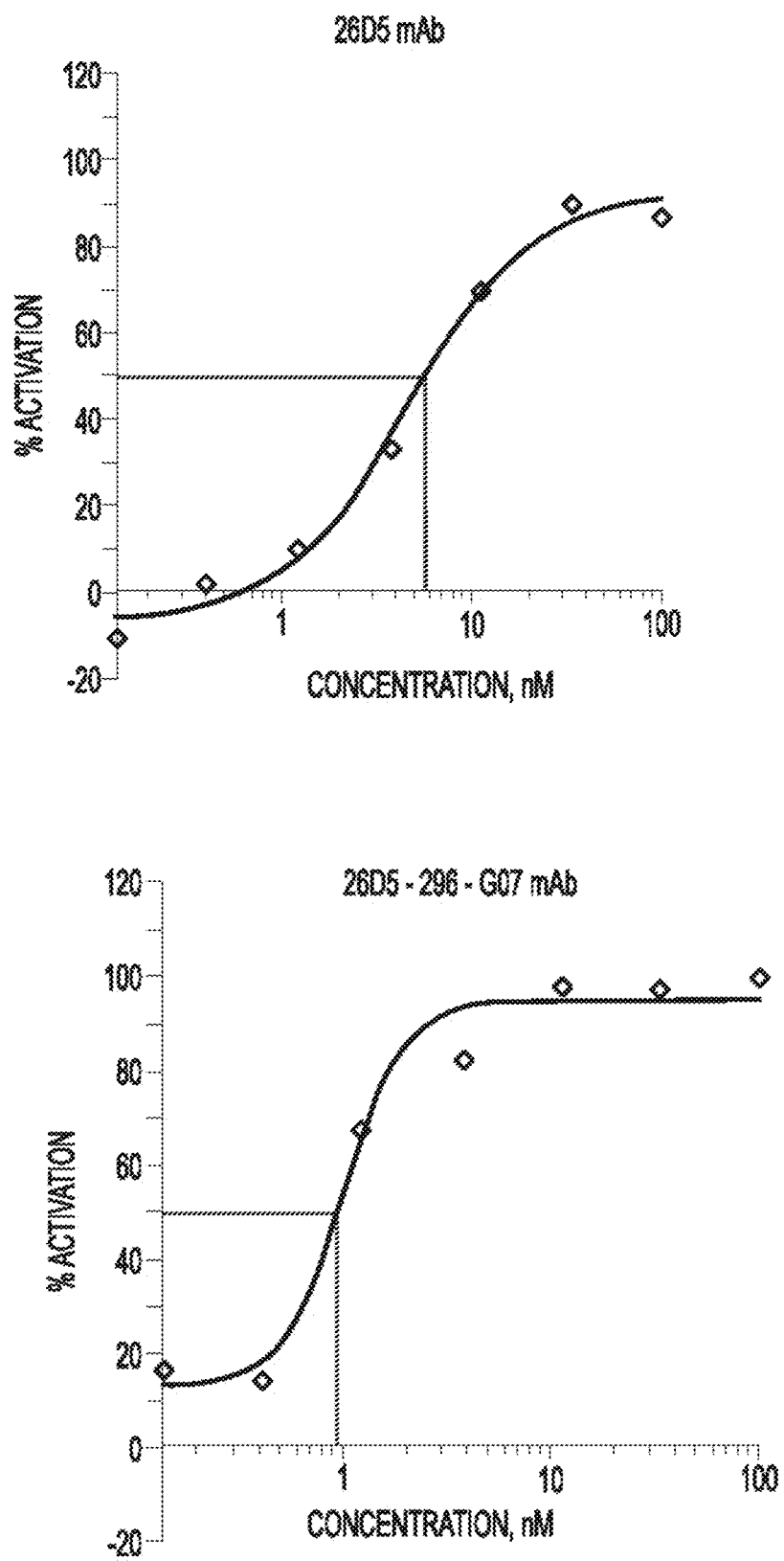
FIG. 9 depicts results from a chromogentic enzymatic assay for determining the amount of antibodies needed for equal to or greater than 50% reversal of activity of Compound A. The activity of Factor XIa enzymatic activity (y-axis) was plotted as a function of the concentration of representative affinity matured mAbs (x-axis), while the concentrations of Factor XIa substrate and Compound A was kept constant. The top graph shows data derived from the use of the mAb IgG1f version of parent 26D5 (SEQ ID NO: 83 and 98; also referred to herein as P1-072224; indicated as "26D5 mAb" in the figure). The bottom graph shows data derived from the use of mAb IgG1f version of 26D5-296-G07 (SEQ ID NO: 65 and 94; also referred to herein as P1-073056; indicated as "26D5-296-G07 mAb" in the figure).

The ability of mAbs to preserve FXIa enzymatic activity in the presence of Compound A was used as a screening assay for antibodies with improved affinity. The assay used an S-2366 chromogenic peptide from Chromogenix as substrate for the Factor XIa enzyme. Each tested mAb was serially diluted from 100 nM to 1.5 nM and incubated with 2.5 nM Compound A or a control compound for 10 minutes at 37° C. Then the chromogenic substrate S-2366 was added to a final concentration 0.5 mM and human FXIa enzyme (Haematologic Techologies, Inc.; HCZIA-0160) was added to a final concentration 0.2 nM. A concentration of 2.5 nM of Compound A produced ~90% inhibition of FXIa activity, i.e. near full occupancy of FXIa. The assay described here was constructed to produce a meaningful dynamic range. Plates were immediately read at OD 405 nm at 37° C. on a Molecular Devices SPECTRAmax to measure the rate of substrate hydrolysis. The signal was normalized to 0% activation (FXIa enzyme with Compound A) and 100% activation (FXIa enzyme with no inhibitor). An $EC_{50}$ was determined for antibodies that reversed 50% or more of the Compound A induced inhibition. Example results are shown in FIG. 9.

Example 5: Production of Recombinant α-Compound A Antibody Fab Fragments

The selected antibodies were cloned as untagged antibody Fab fragments into the pTT5 vector for Expi293 expression. See SEQ ID NOs for Fab sequences. The optimized DNA sequences were received from GenScript for mammalian expression. For expression at 1 L scale, 900 mL of cells at $3\times10^6$ cells/mL were seeded in a 2 L Corning flask. 0.25 mg of each heavy chain and light chain DNA construct were added to 50 mL of Opti-MEM™. 4.1 mL of Expi-Fectamine™ in 150 mL of Opti-MEM™ was incubated for 5 minutes at room temperature and then 50 mL of the aforesaid 150 mL were added to the DNA/Opti-MEM™ mixture and incubated for 20 minutes at room temperature. This total 100 mL transfection mixture was added to the 900 mL of cells and placed in 37° C. shaker (125 rpm, 8% $CO_2$ in air). Production was fed with 2 mM VPA and 50 ml of CHO CD efficient Feed B on the first day. Cell viability was tested and productions were harvested on day 5. Average cell viability/cell density was 80%/$6\times10^6$ cells/mL. The productions were centrifuged at 2,000 rpm at 4° C. for 20 minutes. The conditioned media supernatant was filtered through 0.2 um filters. A 30 mL rProteinA Sepharose FF column was washed with 2 column volumes (CVs) of 6M Guanidine, 2 CVs of 0.033M HCl, and then equilibrated in 1× Dulbecco's PBS. The supernatant pH was verified to be >7.0 and then loaded at 10 mL/min onto the rProteinA Sepharose column. rProteinA binding via framework proteinA interactions was observed for all of the progeny of 1873.6938.26D5.D12 including affinity matured variants. The column was washed in 1×DPBS until baseline was reached and then eluted with 80 mM Sodium Acetate (pH 2.8) into a container filled with ~20 ml Tris HCl (pH 8.0) so protein could neutralize while eluting. The column was then neutralized with 1×DPBS. The eluted sample was concentrated to <10 mL and loaded onto an equilibrated (1×DPBS) S200 26/600 column at 2.5 mL/min. Five mL fractions were collected at 2.5 mL/min and analyzed by SDS-PAGE and chromatogram for pooling. Typical yields were 150-250 mg/L of purified Antibody Fab Fragment.

Figure 10:
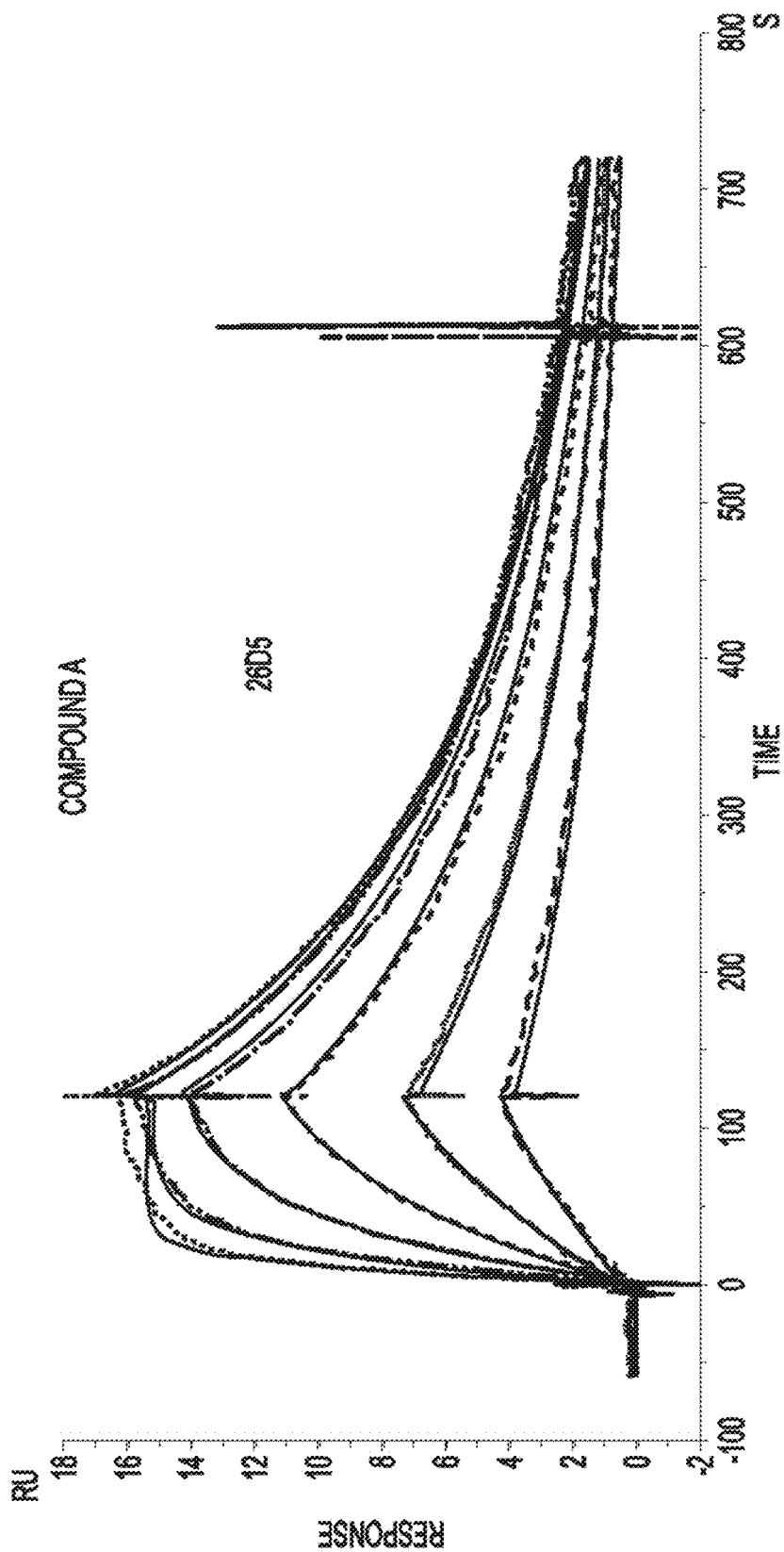
FIG. 10 depicts a surface plasmon resonance (SPR) sensograms indicating the binding affinity of parent mAb 26D5 (P1-072224) (indicated as "26D5 mAb" in the figure) to Compound A, measured at various compound concentrations.

Example 6: Characterization of mAbs and Fabs by Surface Plasmon Resonance (SPR) (Biacore™) Analysis The binding of hybridoma expressed 26D5 parent mAb (VH SEQ ID NO: 83 and VL SEQ ID NO: 98 in IgG1 f format)(P1-072224) and affinity matured mAbs to Compound A was examined by SPR (Biacore™) using a protein A capture method. The running buffer was 1×PBS (phosphate buffered saline, pH 7.4) with 0.05% Tween 20 and 2% DMSO. Binding experiments were carried out at 37° C. Protein A was coated on a CM5 S-series sensor chip (Cytiva, Cat. No. 29149603) at high density (2000+ RUs of protein A). The immobilization of protein A was carried out using the standard amine coupling immobilization procedure recommended by the manufacturer. The affinity matured antibody was then captured at a concentration of 2 ug/mL on the protein A surface at a flow rate of 3 uL/min for 2 minutes. Compound A was then injected over the captured antibody at concentrations spanning 100-3 nM (100, 50, 25, 12.5, 6.25, 3.125 nM) (FIG. 10) and for screening concentrations spanning 100-3 nM (100, 33, 11 nM) for 2 minutes at a flow rate of 100 uL/min and allowed to dissociate for at least 450 seconds. The chip surface was regenerated after each cycle with a 40 second pulse of 10 mM Glycine, pH 1.5. Background binding to the protein A surface alone was used to subtract non-specific binding. All experiments were run on a Biacore T200 surface plasmon resonance instrument using Biacore T200 Control software v. 2. Data analysis was performed using Biacore T200 evaluation software v 3.1. Apparent affinities were determined for rank ordering only since dissociation rates were too slow to be measured by Biacore. Example binding assay data are shown in FIG. 10 and binding assay data are reported in Table 10. The names of the mAbs in Table 10 refer to mAbs having the H and L chain sequences of the corresponding Fabs in Table 3 in an IgG1f format.

TABLE 10

SPR data
Biacore Protein A mAb capture

| Name | Ka (1/Ms) | Kd (1/s) | KD (M) | Temperature |
|---|---|---|---|---|
| 26D5-75229-343-A10-mAb | 7.7E5 | <5E−5 | <0.07 nM | 37° C. |
| 26D5-75214-343-F06-mAb | 1.2E6 | <5E−5 | <0.05 nM | 37° C. |
| 26D5-75202-343-A09-mAb | 5.9E5 | <5E−5 | <0.09 nM | 37° C. |
| 26D5-75203-343-B09-mAb | 1.2E6 | <5E−5 | <0.05 nM | 37° C. |
| 26D5-75616-348-F10-mAb | 1.7E6 | <5E−5 | <0.03 nM | 37° C. |
| 26D5-75768-348-A10-mAb | 3.8E6 | <4.1E−4 | <0.1 nM | 37° C. |
| 26D5-75747-348-D07-mAb | 2.0E6 | <5E−5 | <0.02 nM | 37° C. |
| 26D5-75602-348-F04-mAb | 9.1E5 | <5E−5 | <0.05 nM | 37° C. |
| 26D5-75576-348-B03-mAb | 8.8E5 | <5E−5 | <0.06 nM | 37° C. |
| 26D5-075017-343-F04-mAb | 1.5E6 | 1.7E−4 | 0.11 nM | 37° C. |
| 25D5-75592-0348-A04-mAb | 1.0E6 | 1.1E−4 | 0.1 nM | 37° C. |
| 26D5-75017-0343-F04-mAb | 1.5E6 | 1.7E−4 | 0.11 nM | 37° C. |
| 26D5-75602-0348-F04-mAb | 9.1E5 | <5E−5 | <0.05 nM | 37° C. |
| 26D5-75576-0348-B03-mAb | 8.8E5 | <5E−5 | <0.06 nM | 37° C. |
| 26D5-75746-0348-C07-mAb | 2.4E6 | 2.4E−4 | 0.1 nM | 37° C. |
| 26D5-75747-0348-D07-mAb | 2.0E6 | <5E−5 | <0.03 nM | 37° C. |
| 25D5-296-A07-mAb | 1.7E5 | 2.7E−4 | 1.6 nM | 37° C. |
| 26D5-296-H03-mAb | 1.6E5 | 1.8E−4 | 1.1 nM | 37° C. |
| 26D5-295-F07-mAb | 1.8E5 | 1.7E−4 | 0.94 nM | 37° C. |
| 26D5-296-G07-mAb | 8.5E5 | 3.2E−4 | 0.38 nM | 37° C. |
| 26D5-295-E07-mAb | 1.9E5 | 2.3E−4 | 1.2 nM | 37° C. |
| 26D5-296-C08-mAb | 5.3E5 | 3.1E−4 | 0.59 nM | 37° C. |
| 26D5-295-C07-mAb | 2.0E5 | 3.3E−4 | 1.6 nM | 37° C. |
| 26D5-296-B07-mAb | 2.9E5 | 4.2E−4 | 1.8 nM | 37° C. |
| 26D5-295-G07-mAb | 6.3E5 | 4.3E−4 | 0.67 nM | 37° C. |
| 26D5-296-D08-mAb | 7.7E5 | 4.5E−4 | 0.59 nM | 37° C. |
| 26D5-296-F03-mAb | 7.2E5 | 3.9E−4 | 0.54 nM | 37° C. |
| 26D5-296-G08-mAb | 8.0E5 | 3.9E−4 | 0.49 nM | 37° C. |
| 26D5-296-F07-mAb | 7.6E5 | 4.4E−4 | 0.58 nM | 37° C. |
| 26D5-296-G03-mAb | 9.4E5 | 5.8E−4 | 0.61 nM | 37° C. |
| 26D5-296-F08-mAb | 8.7E5 | 6.0E−4 | 0.68 nM | 37° C. |
| 26D5-295-A08-mAb | 1.0E6 | 5.9E−4 | 0.58 nM | 37° C. |
| 26D5-295-D07-mAb | 8.0E5 | 8.1E−4 | 1.0 nM | 37° C. |
| 26D5-296-D03-mAb | 1.7E6 | 1.2E−3 | 0.71 nM | 37° C. |
| 26D5-296-C07-mAb | 9.5E5 | 1.4E−3 | 1.4 nM | 37° C. |

Figure 11:
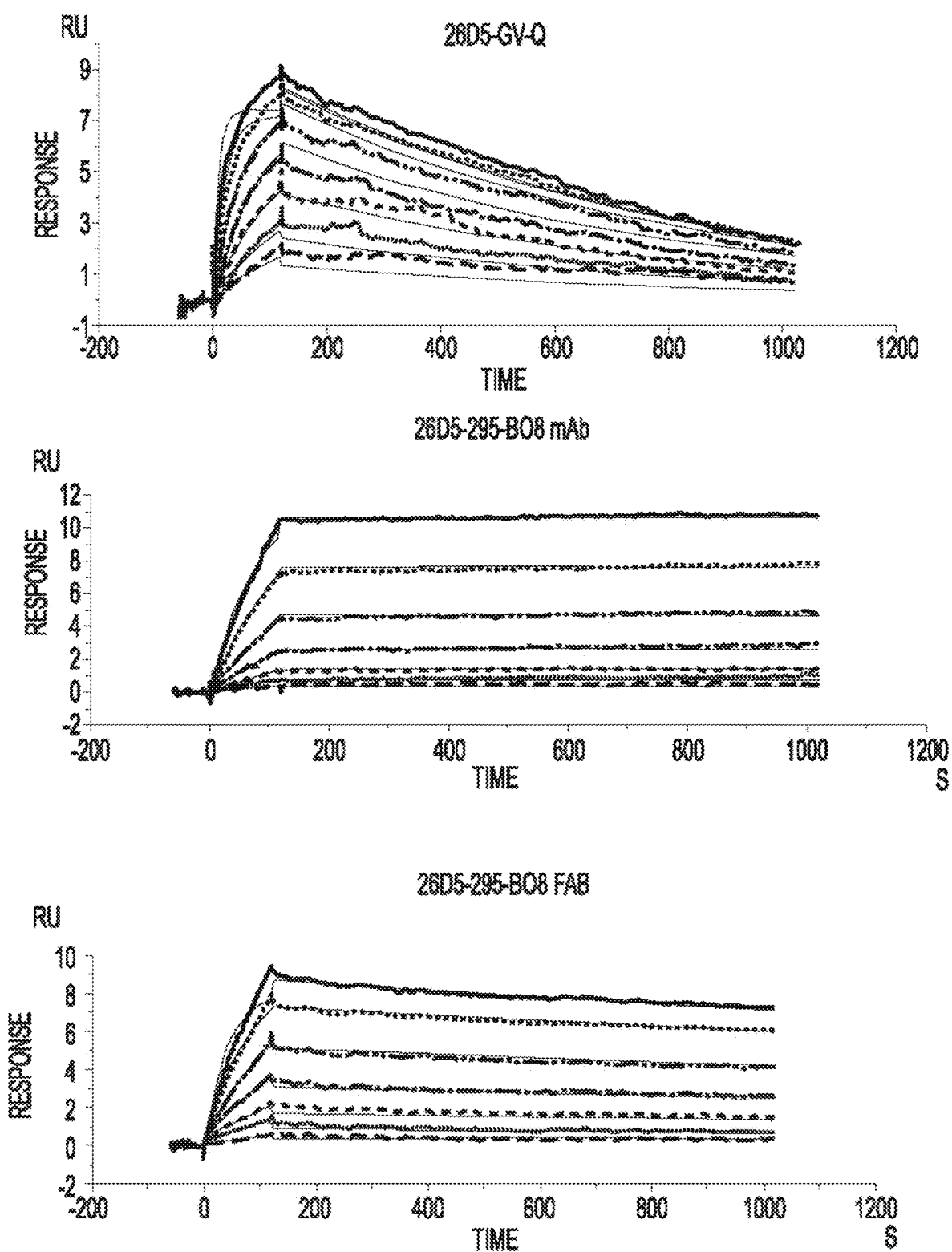
FIG. 11 depicts surface plasmon resonance (SPR) sensograms indicating the binding affinity of (top) mAb 26D5-GV-Q, (middle) mAb 26D5-295-B08 and (bottom) antibody Fab fragment 26D5-295-B08 to COMPOUND 2, measured at various mAb/Fab concentrations.

The binding of the first round affinity matured antibody Fab fragments to conjugated versions of Compound A was examined by SPR (Biacore™) using a CM5 S-series sensor chip (Cytiva, Cat. No. 29149603) coated with BSA previously conjugated to COMPOUND 2, COMPOUND 3 or COMPOUND 1. The immobilization level was 150-250 RUs. The running buffer was 1×PBS (phosphate buffered saline, pH 7.4) with 0.05% Tween 20. Binding experiments were carried out at 25° C. The antibody Fab fragment at a concentration of between 200-0.8 nM was injected over the BSA-compound coated surface for 2 minutes at a flow rate of 30 uL/min. The antibody Fab fragment was then allowed to dissociate for 15 minutes. The chip surface was regenerated after each cycle with a 1 minute pulse of 10 mM Glycine, pH 2, and a 1 minute pulse of 50 mM NaOH. All experiments were run on the same equipment and analyzed with the same software as described before. Apparent affinities were determined for rank ordering only since dissociation rates were too slow to be measured by Biacore. Comparative experiments with selected mAbs were also conducted in a similar fashion (see FIG. 11). Example binding assay data are shown in FIG. 11 and binding assay data for COMPOUND 2-BSA are reported in Table 11. The sequences of the Fabs in Table 11 are indicated in Table 3.

TABLE 11

SPR data

| Name | Ka (1/Ms) | Kd (1/s) | KD (M) | Temperature |
|---|---|---|---|---|
| 26D5-295-B08-Fab-LONG | 2.8E5 | 2.2E−4 | 0.8 nM | 37° C. |
| 26D5-295-C08-Fab-LONG | 2.8E5 | 8.5E−5 | 0.3 nM | 37° C. |
| 9C8-VGSKE-Fab-LONG | 4.0E5 | 8.7E−4 | 2.1 nM | 25° C. |
| 1H2-K-Fab-LONG | 1.8E6 | 1.5E−3 | 0.8 nM | 37° C. |
| 24H1-GQTV-Fab-LONG | 7.9E5 | 1.0E−3 | 1.3 nM | 37° C. |
| 26D5-GVR-Q-FT-Fab-LONG | 1.3E6 | 1.6E−3 | 1.3 nM | 37° C. |
| 26D5-GVR-Q-FT-Fab-SHORT | 1.6E6 | 1.3E−3 | 0.9 nM | 37° C. |
| 26D5-GVR-H-Fab-LONG | 2.8E5 | 1.0E−3 | 3.5 nM | 37° C. |

Figure 12:
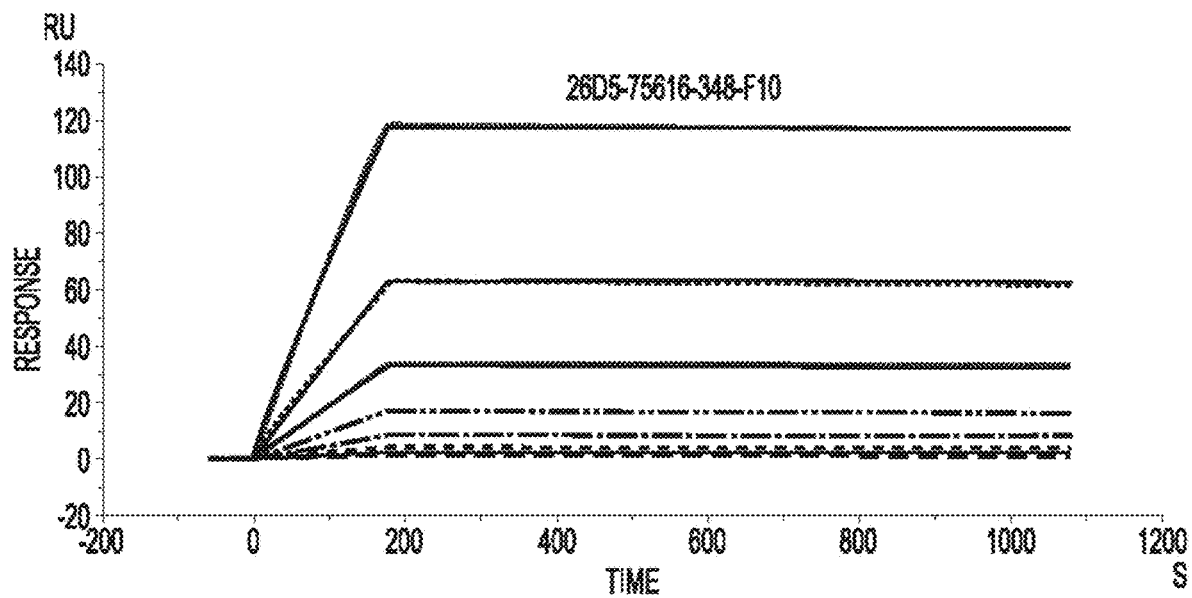
FIG. 12 depicts surface plasmon resonance (SPR) sensograms indicating the binding affinity of (top) antibody tandem Fab (TanFab) fragment 26D5-75616-348-F10-TanFab and (bottom) antibody tandem Fab (TanFab) fragment 26D5-75214-343-F06-TanFab to COMPOUND 5, measured at various TanFab concentrations.
Figure 12:
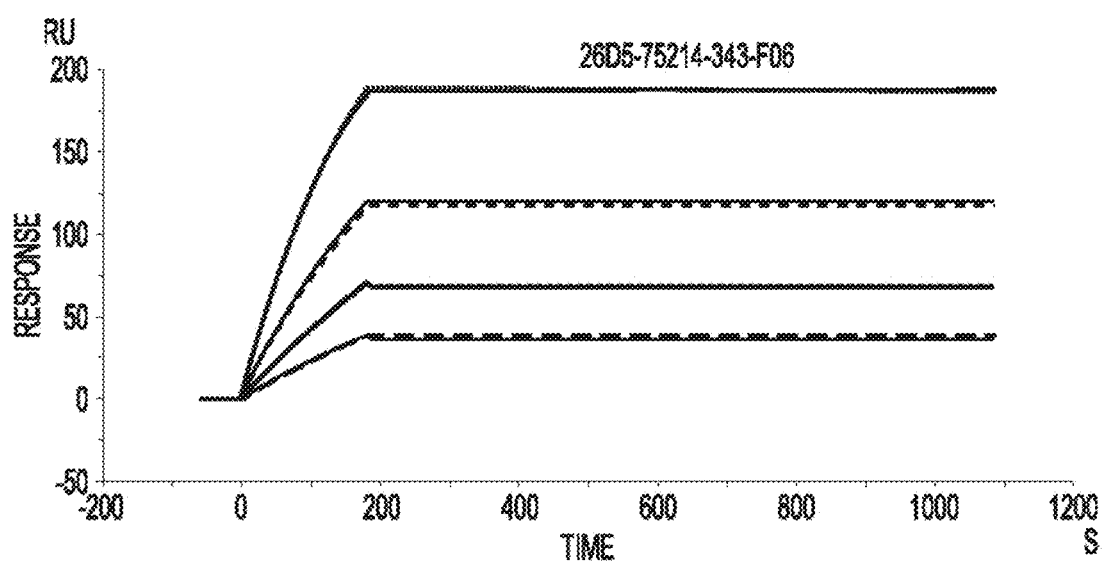

The binding of the first and second round affinity matured antibody Fab fragments to conjugated versions of Compound A was examined by SPR (Biacore™) using a Biotin-CAP S-series sensor chip and kit reagents from Cytiva (Cat No. 28920234). The Biotin-CAP chip was hydrated in buffer overnight. Biotin-CAP reagent at 50% in water was flowed over the chip surface for 150 seconds at a flow rate of 2 uL/min. COMPOUND 5 (a biotinylated version of COMPOUND 2) was captured on the Biotin CAP surface at 0.25 ug/mL at a flow rate of 10 uL/min for a 20 second pulse. The running buffer was 1×PBS (phosphate buffered saline, pH 7.4) with 0.05% Tween 20. Experiments were carried out at 25° C. or 37° C. The antibody Fab fragment at a concentrations of 100-3 nM was injected over the Biotin-CAP-COMPOUND 5 surface for 3 minutes at a flow rate of 30 uL/min. The antibody Fab fragment was allowed to dissociate for 11.7 minutes. The chip surface was regenerated after each cycle with two 2 minute pulses of 6 M Guanidine-HCl in 250 mM NaOH. All experiments were run on the same equipment and analyzed with the same software as described before. Apparent affinities were determined for rank ordering only since dissociation rates were too slow to be measured by Biacore. Example binding assay data are shown in FIG. 12 and binding assay data for antibody TanFab fragments are reported in Table 12. The sequences of the TanFabs in Table 12 are indicated in Table 4.

TABLE 12

SPR data

| mAb/Fab | Ka (1/Ms) | Kd (1/s) | KD (M) | Temperature |
|---|---|---|---|---|
| 26D5-75229-343-A10-TanFab | 1.7E5 | <5E-5 | <0.3 nM | 25° C. |
| 26D5-75229-343-A10-TanFab-long | 1.8E5 | <5E-5 | <0.3 nM | 25° C. |
| 26D5-75229-343-A10-TanFab-ELQ | 1.8E5 | <5E-5 | <0.3 nM | 25° C. |
| 26D5-75229-343-A10-TanFab-G4S | 1.9E5 | <5E-5 | <0.3 nM | 25° C. |
| 26D5-75616-348-F10-TanFab | 1.1E5 | <5E-5 | <0.5 nM | 25° C. |
| 26D5-75203-343-B09-TanFab | 9.2E4 | <5E-5 | <0.5 nM | 25° C. |
| 26D5-75202-343-A09-TanFab | 3.0E5 | <5E-5 | <0.2 nM | 25° C. |
| 26D5-75768-348-A10-TanFab | 1.3E5 | <5E-5 | <0.4 nM | 25° C. |
| 26D5-75214-343-F06-TanFab | 1.2E5 | <5E-5 | <0.4 nM | 25° C. |

Example 7: Characterization of mAbs and Fabs by TR-FRET Assay

A competitive TR-FRET (time-resolved fluorescence resonance energy transfer) assay was developed to rank-order the dissociation of α-Compound A mAbs from Compound A as equilibrium is reached at 37° C. The assay buffer was HBS-N (10 mM HEPES, 150 mM NaCl, pH 7.4; GE Healthcare), 0.1% (w/v) BSA (bovine serum albumin; Sigma), 2% DMSO (dimethyl sulfoxide; Sigma). All reagents were prepared in assay buffer and dispensed in equal volumes into white 384 microplates with final volume of 20 μl per well at the following final concentrations: 4 nM COMPOUND 5, the biotinylated analog of COMPOUND 2, a 100 0.1 nM 7-pt titration of human α-Compound A antibodies, 0.1 nM europium-labeled α-mouse IgG (LANCE Eu-W1024; PerkinElmer), 5 nM streptavidin-D2 (Cisbio), and 4 nM mAb 26D5 VH_A10G_Y33A_S53P_M89V_G95A; VK_W32N_H38Q (P1-075621, the second-round optimization parent 26D5-295-B08 formatted with mouse IgG Fc). COMPOUND 5 and α-Compound A antibody titrations were added first to the microplate, and were subjected to an initial incubation at 37° C., 1000 rpm, for one hour to facilitate antibody binding to the compound. After the initial incubation period, the europium α-mouse IgG, streptavidin-D2, and 26D5-mouse IgG (P1-075621) were added sequentially, then the plate was returned to 37° C., 1000 rpm incubation. Microplates were read using a Perkin Elmer EnVision plate reader, and the measured FRET signal was defined as [665 nm]/[620 nm]*10,000. Microplates were read at 30 minutes (T0) and after 24 hour (T24) intervals. For each antibody titration, the FRET signal was converted to % Inhibition relative to wells without α-Compound A antibody: (100 ((FRET at [antibody concentration]/FRET at 0 nM)*100). The % inhibition antibody titrations were plotted using TIBCO Spotfire (v.7), and the $IC_{50}$ was determined using a 4-parameter model curve fit. The $IC_{50}$s at each timepoint were reported, as well as the $IC_{50}$ curve shift relative to T0. An $IC_{50}$ curve shift indicated α-Compound A antibody dissociation from the biotinylated compound as the assay reached equilibrium, which subsequently allowed 26D5-mouse IgG1 (P1-075621) competitor to bind and generate the FRET signal detected in the assay.

Figure 13:
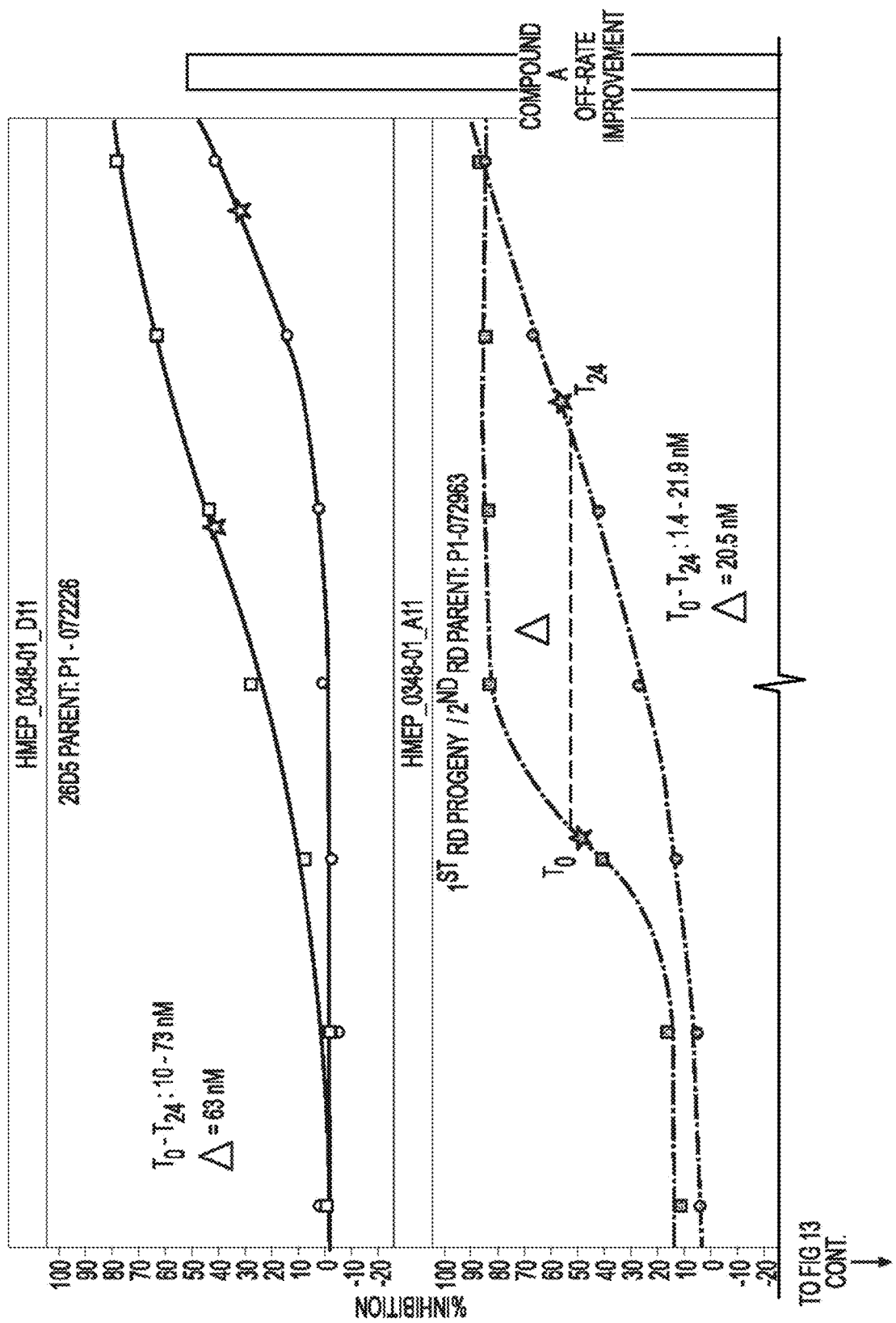
FIG. 13 depicts time-resolved fluorescence energy transfer (TR-FRET) derived competitive binding data of (A) mAb form of 26D5-GVR-Q-FT-Fab-LONG, (B) mAb form of 26D5-295-B08-Fab-LONG and (C) mAb form of 26D5-75747-348-D07-Fab-LONG, each binding to COMPOUND 5.
Figure 13:
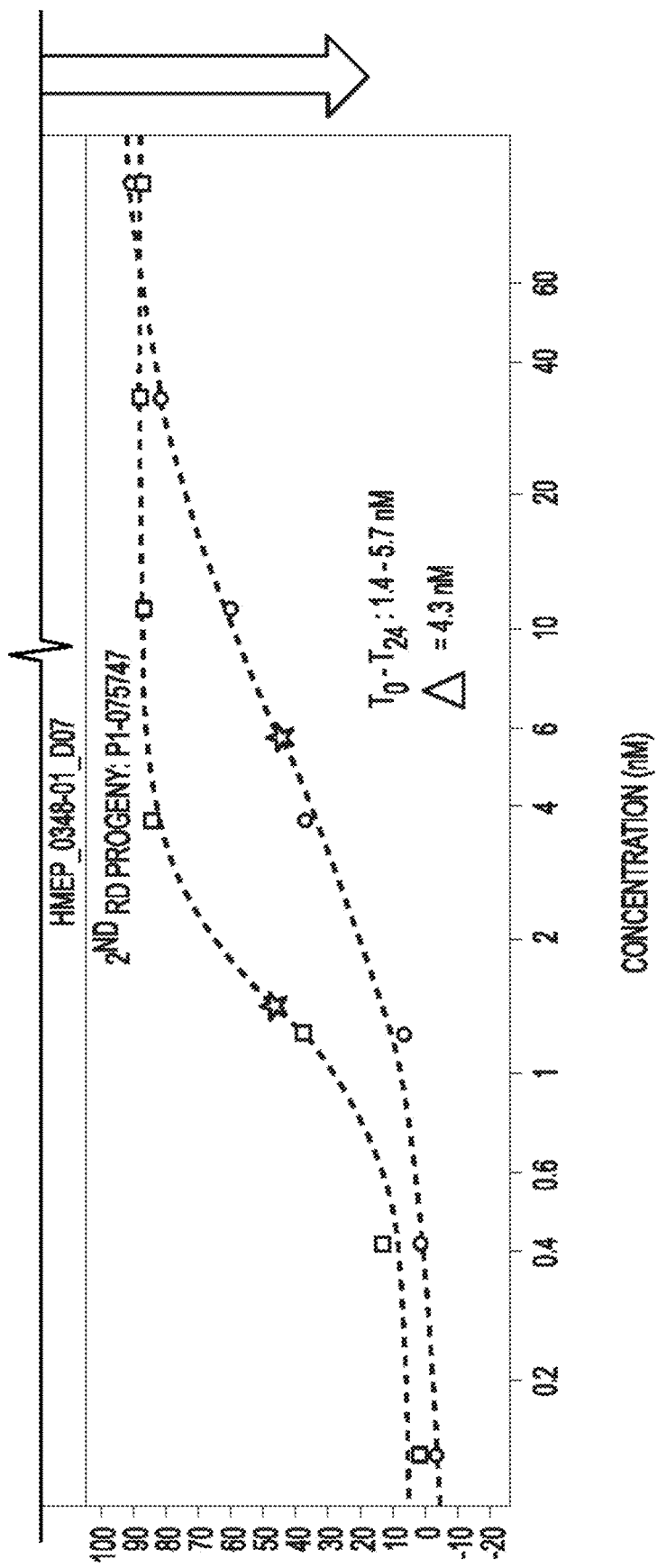

Exemplary competitive FRET data collected from α-Compound A 26D5 affinity optimization screening is shown in FIG. 13. Three representative human antibodies are shown: 1) IgG1f mAb format of 26D5-GVR-Q-FT-Fab-LONG; also referred to herein as P1-072226 (except that R31 in 26D5-GVR-Q-FT HC is 531 in P1-072226 HC), top panel, 2) IgG1f mAb format of first round optimization progeny 26D5-295-B08-Fab-LONG (also referred to herein as P1-072963), middle panel, and 3) IgG1f mAb format of second round optimization progeny 26D5-75747-348-D07-Fab-LONG (also referred to herein as P1-075747), bottom panel. The $IC_{50}$s are annotated along each antibody titration curve with a star. The difference between T0 and T24 $IC_{50}$s is defined as Δ, and the values are reported in each panel. The 26D5-GVR-Q-FT-Fab-LONG mAb parent exhibited the most significant T0-T24 $IC_{50}$ shift, 63 nM. As the Compound A dissociation rate (off-rate) was improved through successive rounds of affinity maturation in subsequent progeny (P1-072963: 20.5 nM, then P1-075747: 4.3 nM), the T0-T24 $IC_{50}$ shift was minimized. The α-Compound A antibodies were rank-ordered by T24 $IC_{50}$ and the $IC_{50}$ shift (Δ) to identify antibodies with improved 37° C. Compound A dissociation rates relative to the mAb 26D5-GVR-Q-FT-Fab-LONG parent and mAb 26D5-295-B08 (P1-072963).

The competitive TR-FRET assay defined above was also modified to assess optimized 26D5 antibody progeny that were reformatted as Fabs. The α-Compound A antibody and Fab titration series were extended to 250 0.244 nM (11-pt titration), and replicates of each concentration were collected in quadruplicate. The assay incubation was extended to include an additional 48 hr timepoint to ensure equilibrium was reached, and T48 hr $IC_{50}$ and $IC_{50}$ shifts were reported. The % inhibition titrations were plotted in Graphpad Prism (v.8) and fit to a 4-parameter model. All other experimental setup conditions were otherwise identical to the antibody TF-FRET assay.

Figure 14:
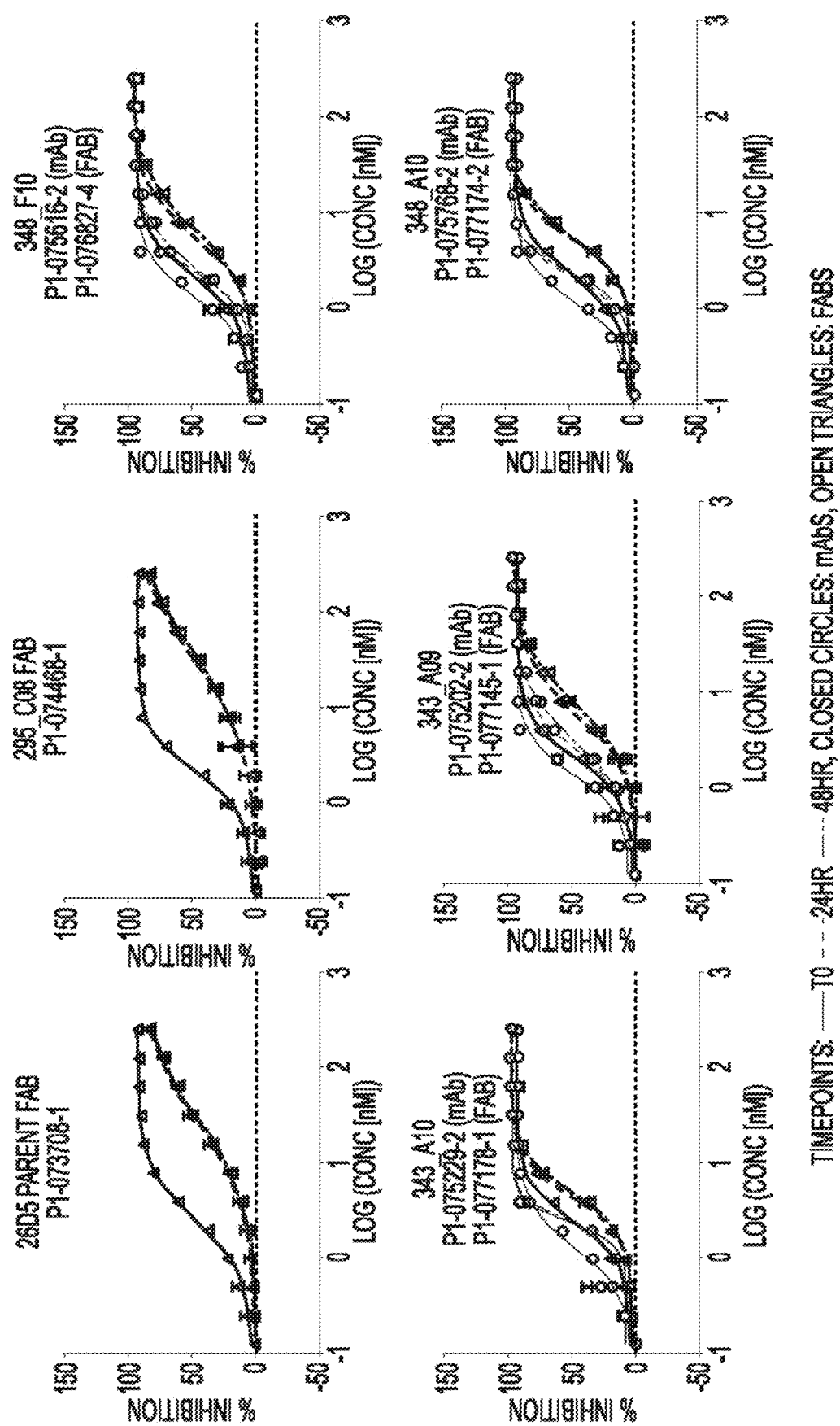
FIG. 14 depicts time-resolved fluorescence energy transfer (TR-FRET) derived competitive binding data of the indicated antibodies and antibody Fab fragments, each binding to COMPOUND 5.

Competitive FRET data collected for affinity-optimized α-Compound A 26D5 progeny comparing human antibodies and Fabs are shown in FIG. 14 and Table 13. Each panel represents a single α-Compound A sequence, with antibody (mAb, solid lines, circles) and Fab (dotted lines, triangles) formats overlaid. The 26D5 parent Fab (Fab 26D5-GV-Q; also referred to herein as P1-073708) and first round optimization progeny Fab 26D5-295-008 (also referred to herein as P1-074468-1) exhibited significant T48 $IC_{50}$ shifts of at least 26 nM. Second round affinity maturated optimized progeny retained slow 37° C. dissociation from Compound A in both antibody and Fab formats, exhibiting minimal T48 $IC_{50}$ shifts. FRET data are provided in Table 13. The names of the mAbs/Fabs in Table 13 refer to the corresponding sequences in Tables 1-3. All mAbs listed in Table 13 were in a human IgG1f/LC kappa format.

TABLE 13

("-1", "-2" etc. refer to lot numbers of otherwise identical mAbs or Fabs)

| Sample | T0 IC$_{50}$ (nM) | T24 hr IC$_{50}$ (nM) | T24 hr IC$_{50}$ shift (nM) | T48 hr IC$_{50}$ (nM) | T48 hr IC$_{50}$ shift (nM) |
|---|---|---|---|---|---|
| P1-075616-2 (26D5-75616-348-F10 mAb) | 1.4 | 2.5 | 1.1 | 2.8 | 1.4 |
| P1-076827-3 (26D5-75616-348-F10 Fab) | 2.8 | 6.6 | 3.8 | 8.8 | 5.9 |
| P1-076827-4 (26D5-75616-348-F10 Fab) | 2.2 | 5.8 | 3.5 | 7.1 | 4.9 |
| P1-075229-2 (26D5-75229-343-A10 mAb) | 1.3 | 2.4 | 1.1 | 2.5 | 1.1 |
| P1-077178-1 (26D5-75229-343-A10 Fab) | 2.5 | 4.5 | 2.0 | 4.9 | 2.5 |
| P1-075202-2 (26D5-75202-343-A09 mAb) | 1.4 | 2.5 | 1.1 | 2.9 | 1.5 |
| P1-077145-1 (26D5-75202-343-A09 Fab) | 2.0 | 5.8 | 3.8 | 7.5 | 5.5 |
| P1-075768-2 (26D5-75768-348-A10 mAb) | 1.2 | 2.2 | 1.0 | 2.3 | 1.1 |
| P1-077174-2 (26D5-75768-348-A10 Fab) | 2.2 | 5.4 | 3.2 | 5.8 | 3.6 |
| P1-075214-2 (26D5-75214-343-F06 mAb) | 1.3 | 2.5 | 1.3 | 2.7 | 1.4 |
| P1-077176-2 (26D5-75214-343-F06 Fab) | 2.6 | 7.3 | 4.7 | 8.7 | 6.1 |
| P1-075203-2 (26D5-75203-343-B09 mAb) | 2.6 | 3.0 | 0.4 | 3.1 | 0.5 |
| P1-077144-1 (26D5-75203-343-B09 Fab) | 2.7 | 6.1 | 3.4 | 8.1 | 5.4 |
| P1-073708-1 (26D5 parent Fab) | 2.6 | >28.2 | >25.7 | >28.8 | >26.2 |
| P1-074468-1 (26D5-295-C08 Fab) | 2.2 | >38.2 | >36.0 | >43.1 | >41.0 |

Example 8: Gel Filtration

Using an Agilent 1260 HPLC system with a Shodex K403-4F and a mobile phase of 100 mM Sodium Phosphate 150 mM Sodium Chloride, pH 7.3, at a flow rate of 0.3 mL/min, aliquots of purified Fab were injected (20 ug) for a run time of 20 minutes. Gel Filtration standards confirmed that most Fabs were at least 98% monomer with greater than 75% recovery.

Example 9: Thermal Stability Analysis of Fabs

Figure 15:
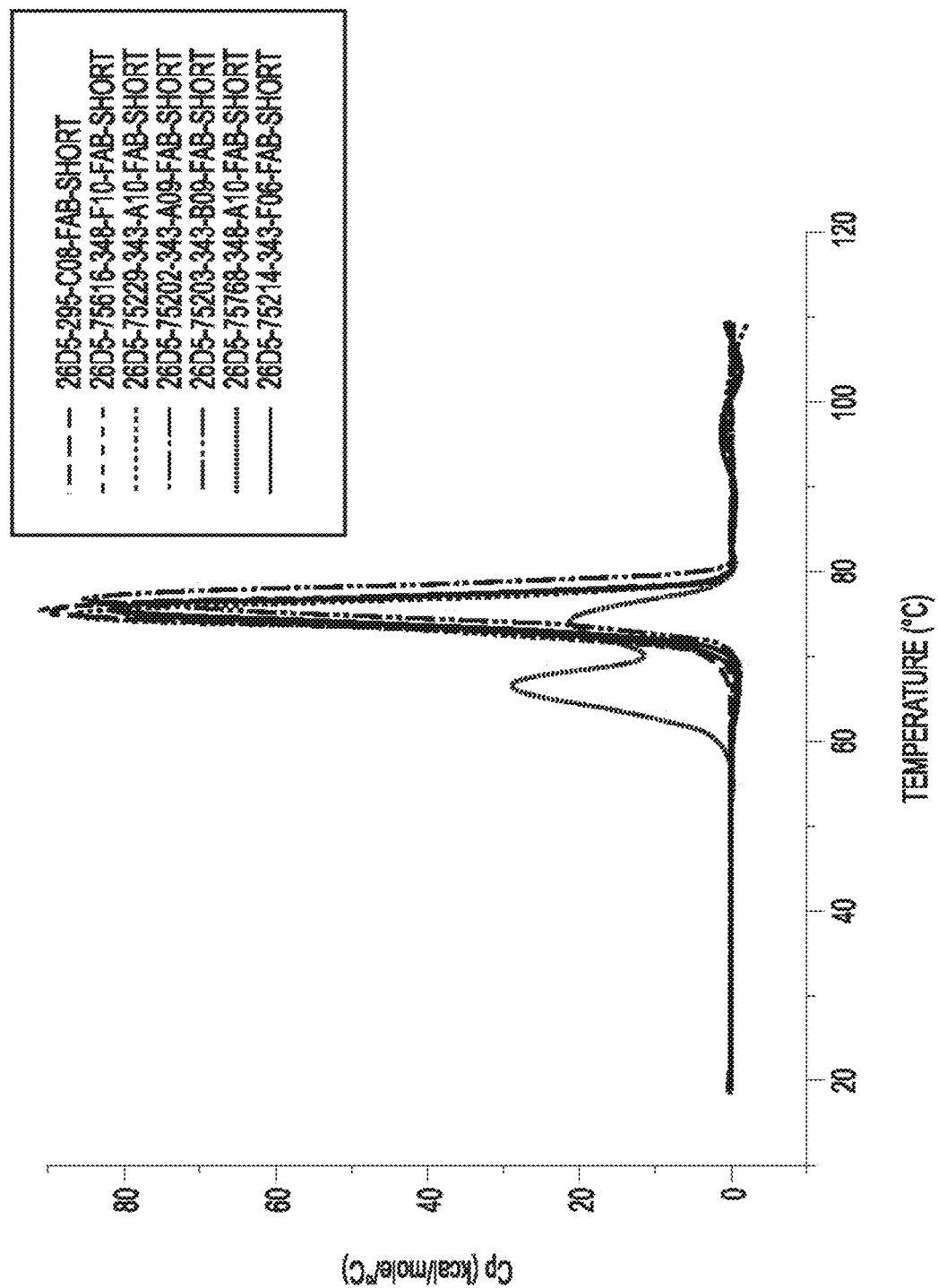
FIG. 15 depicts DSC thermograms of the indicated antibody Fab fragments.

Thermal stability analysis was performed with UNchained Labs UNcle™/Tagg analysis with Fabs at a concentration of 20 uM with or without Compound A at a concentration of 50 uM (or control compound). Capillaries were scanned from 25 to 90° C. at 0.5° C./min. In addition, select Fabs were also analyzed by Differential Scanning calorimetry analysis using the Malvern MicroCal VP-Capillary DSC. Samples were buffer matched and loaded with Fabs at a concentration of 10 uM with or without Compound A at a concentration of 15 uM (or control compound). Scan temperature range was 15-110° C. at a rate of 60° C./Hr (Filter period: 16 sec, Gain: None). Sample analysis was using software provided by the manufacturer for both the UNcle and the Malvern Capillary DSC. FIG. 15 and Table 14 below show representative DSC results. The sequences of the Fabs in Table 14 are indicated in Table 3.

TABLE 14

(Thermal stability by Differential Scanning Calorimetry)

| Sample | Conc (mg/ml) | Tm1 (° C.) | Tm2 (° C.) |
|---|---|---|---|
| 26D5-295-C08-Fab-SHORT | 1 | 75.3 | |
| 26D5-75616-348-F10-Fab-SHORT | 1 | 75.2 | |
| 26D5-75229-343-A10-Fab-SHORT | 1 | 74.9 | |
| 26D5-75202-343-A09-Fab-SHORT | 1 | 75.3 | |
| 26D5-75203-343-B09-Fab-SHORT | 1 | 76.6 | |
| 26D5-75768-348-A10-Fab-SHORT | 1 | 66.3 | 74.1 |
| 26D5-75214-343-F06-Fab-SHORT | 1 | 75.5 | |

Example 10: Kinetic Exclusion Analysis (KinExA)

The solution affinity of the antibody Fab fragments disclosed herein for Compound A was measured using a Kinetic Exclusion Assay (KinExA). Duplicate titrations of Compound A were performed with 26D5 affinity matured antibody Fab fragments at 100, 200, and 300 pM (equilibrated for 24-72 hours). The relative unbound concentration of 26D5 affinity matured antibody Fab fragment was measured by capture on a streptavidin coated bead with COMPOUND 5 followed by detection with a fluorescently labeled antibody that recognizes the human IgG Fab. Kinetic analysis to determine the complex association rate was measured with the same assay format except that a single tube of the mixture was prepared (200 pM Fab and 400 pM Compound A) and time points were removed immediately (no equilibration). Results are shown in Table 15 below. Two Fabs, 26D5-75229-343-A10-Fab-SHORT and 26D5-75616-348-F10-Fab-SHORT, were identified as the top two Fabs by DSC thermal stability and KinExA analysis. Antibody Fab fragment 26D5-75616-348-F10-Fab-SHORT (SEQ ID NO: 106 and SEQ ID NO: 164; see Table 3) was selected for X-ray crystallography as described below and in vivo studies as described in Example 12.

TABLE 15

KinExA (Kinetic Exclusion Analysis)

| Name | KinExA KD (M) | KD 95% Confidence Interval | KinExA Ka (1/Ms) |
|---|---|---|---|
| 26D5-75229-343-A10-Fab-SHORT | 0.22 pM | 8 pM to <1 fM | 5.0E4 |
| 26D5-75214-343-F06-Fab-SHORT | 15 pM | 4 pM to 37 pM | 6.0E5 |
| 26D5-75202-343-A09-Fab-SHORT | 19 pM | 92 pM to <70 fM | 1.5E5 |
| 26D5-75203-343-B09-Fab-SHORT | 10 pM | 35 pM to <15 fM | 1.4E4 |
| 26D5-75616-348-F10-Fab-SHORT | 0.13 pM | 3.8 pM to <1 fM | 9.0E5 |
| 26D5-75768-348-A10-Fab-SHORT | 0.41 pM | 12 pM to <1.5 fM | NM |

Example 11: Crystallization of Fabs

Fab 26D5-GVR-Q-FT-Fab-SHORT with a GGH (SEQ ID NO:222) affinity tag was concentrated to 10 mg/ml in DPBS (Dulbecco's Phosphate Buffered Saline) buffer. The protein was complexed with a 5-fold molar excess of Compound A and incubated overnight at 4° C. The complex was crystallized by sitting drop vapor diffusion. The drops consisted of 1 μl of complex and 1 μl of reservoir. The crystallization reservoir consisted of 20 g PEG 3350 dissolved in water to a total volume of 100 ml and 20 mM of unbuffered sodium citrate. The crystals were prepared for flash-cooling in liquid nitrogen by the serial addition of a mixture of 2.5 µl 40% PEG400:40% glycerol (v/v) with 7.5 µl of the reservoir solution to the drop.

Antibody Fab fragment 26D5-75616-348-F10-Fab-SHORT was concentrated to 20 mg/ml in DPBS buffer. The protein was complexed with a 5-fold molar excess of Compound A and incubated overnight at 4° C. The complex was crystallized by sitting drop vapor diffusion. The drops consisted of 1 µl of complex and 1 µl of reservoir. The crystallization reservoir consist of 100 mM CAPS (N-cyclohexyl-3-aminopropanesulfonic acid), pH 10.5, 200 mM lithium sulfate, 1.2 M sodium phosphate and 0.8 M potassium phosphate. The crystals were prepared for flash-cooling in liquid nitrogen by the serial addition of a mixture of 2.5 µl 40% PEG400:40% glycerol (v/v) with 7.5 µl of the reservoir solution to the drop.

Data were collected at the Advanced Photon Source at beamline 17-ID using a Pilatus 6M detector. Data were processed with the autoPROC package [Vonrhein, C., Flensburg, C, Keller, P., Sharff, A., Smart, O., Paciorek, W., Womack, T. & Bricogne, G. (2011). Data processing and analysis with the autoPROC toolbox. *Acta Crystallogr. Sect. D* 67, 293-302], including the underlying software XDS for processing, XSCALE for scaling and STARANISO for anisotropic extent of the data [W. Kabsch (2010). XDS. *Acta Crystallogr. Sect. D* 66, 125-132 and W. Kabsch (2010). Integration, scaling, space-group assignment and post-refinement. *Acta Crystallogr. Sect. D* 66, 133-144; STARANISO (Tickle, I. J., Flensburg, C., Keller, P., Paciorek, W., Sharff, A., Vonrhein, C., Bricogne, G. (2018). STARANISO (available on the world-wide web at staraniso-.globalphasing.org/cgi-bin/staraniso.cgi) Cambridge, United Kingdom: Global Phasing Ltd).

Figure 16:
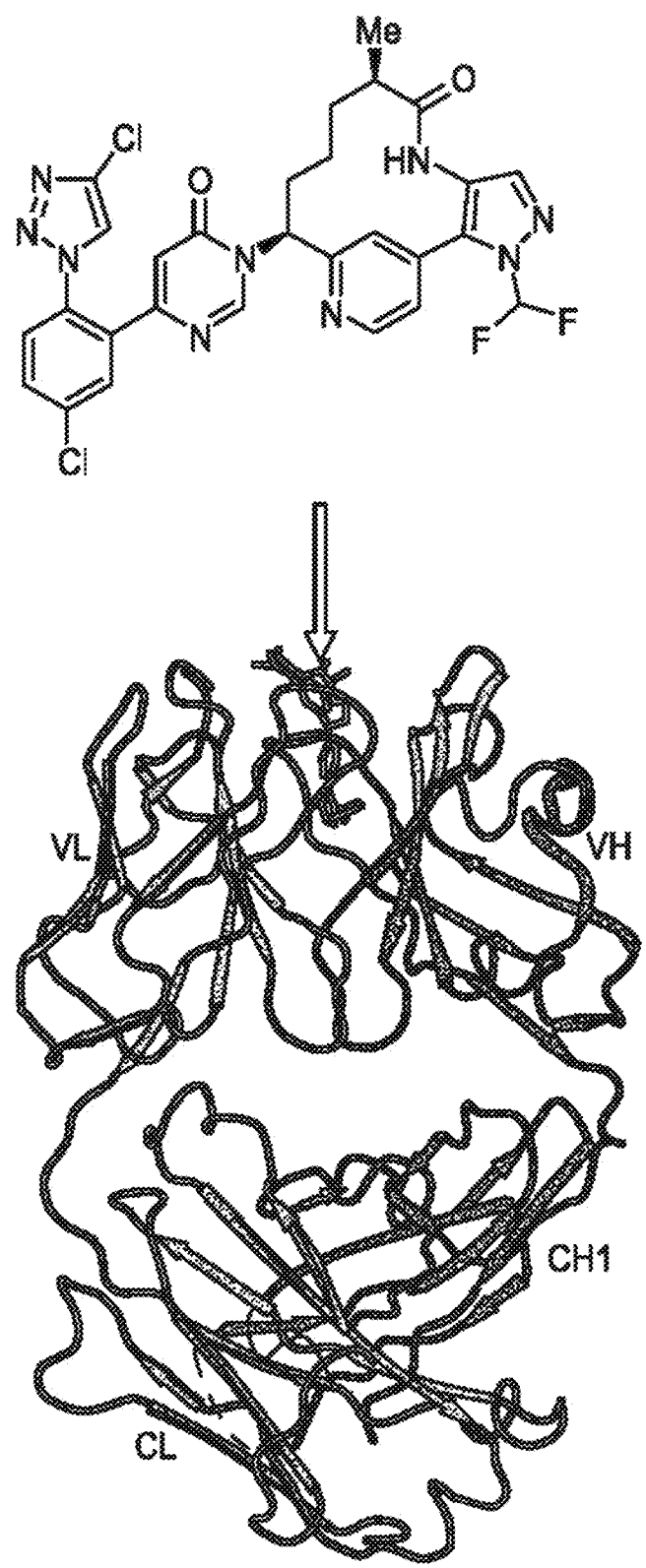
FIG. 16 depicts the structure as determined by crystallography of the antibody Fab fragment 26D5-GVR-Q-FT Fab bound to Compound A.

26D5-GVR-Q-FT-Fab-SHORT/Compound A crystals had symmetry consistent with space group $P2_12_12_1$ with unit cell edges of a=57.71; b=75.1 Å; and c=84.7 Å with one complex per asymmetric unit. Data extended to 1.471 when processed isotropically, but an ellipsoidal cutoff that extended to 1.38 Å in a*, 1.44 Å in b*, and 1.32 Å in c* was used to retain data. The structure was determined by molecular replacement using PHASER (McCoy, A. J., Grosse-Kunstleve, R. W., Adams, P. D., Winn, M. D., Storoni, L. C. & Read, R. J. (2007). Phaser Crystallographic Software. *J. Appl. Crystallogr.* 40, 658-674.) with models for CL:CH1 derived from PDB 2O5X (Verdino, P., Aldag, C., Hilvert, D., Wilson, I. A. (2008) Closely Related Antibody Receptors Exploit Fundamentally Different Strategies for Steroid Recognition. *Proc. Natl. Acad. Sci., USA* 105, 11725-11730), VL derived from PDB 4PY7 (Wyrzucki, A., Dreyfus, C., Kohler, I., Steck, M., Wilson, I. A., Hangartner, L. (2014). Alternative Recognition of the Conserved Stem Epitope In Influenza A Virus Hemagglutinin By A VH3-30-Encoded Heterosubtypic Antibody. *J. Virol.* 88, 7083-7092.), and VH derived from PDB 4TSA (Wensley, B. Structure of a Lysozyme Fab Complex, unpublished.). All CDRs (Complementarity Determining Regions) were removed from the VH and VL models. The initial electron density map showed unambiguous electron density for Compound A. Geometric restraints for the ligand were created using GRADE (Smart, O. S., Womack, T. O., Sharff, A., Flensburg, C., Keller, P., Paciorek, W., Vonrhein, C. and Bricogne, G., Global Phasing, Ltd., Cambridge, United Kingdom) and initially placed with RHOFIT (Womack, T. O., Smart, O. S., Sharff, A., Flensburg, C., Keller, P., Paciorek, W, Vonrhein, C. and Bricogne, G., Global Phasing, Ltd., Cambridge, United Kingdom). The structure was improved through alternating rounds of model building with Coot (Emsley, P., Lokhamp, B., Scott, W. G. & Cowtan, K. (2010). Features and Development of Coot. *Acta Crystallogr Sect. D* 66, 486-501) and refinement with autoBUSTER. (Bricogne, G., Blanc, E., Brandi, M., Flensburg, C, Keller, P., Paciorek, W., Roversi, P, Sharff, A., Smart, O., Vonrhein, C, Womack, T. BUSTER version 2.11.7. Global Phasing, Ltd., Cambridge, United Kingdom). The image in FIG. 16 shows the refined structure for the complex of 26D5-GVR-Q-FT-Fab-SHORT/Compound A.

Figure 17:
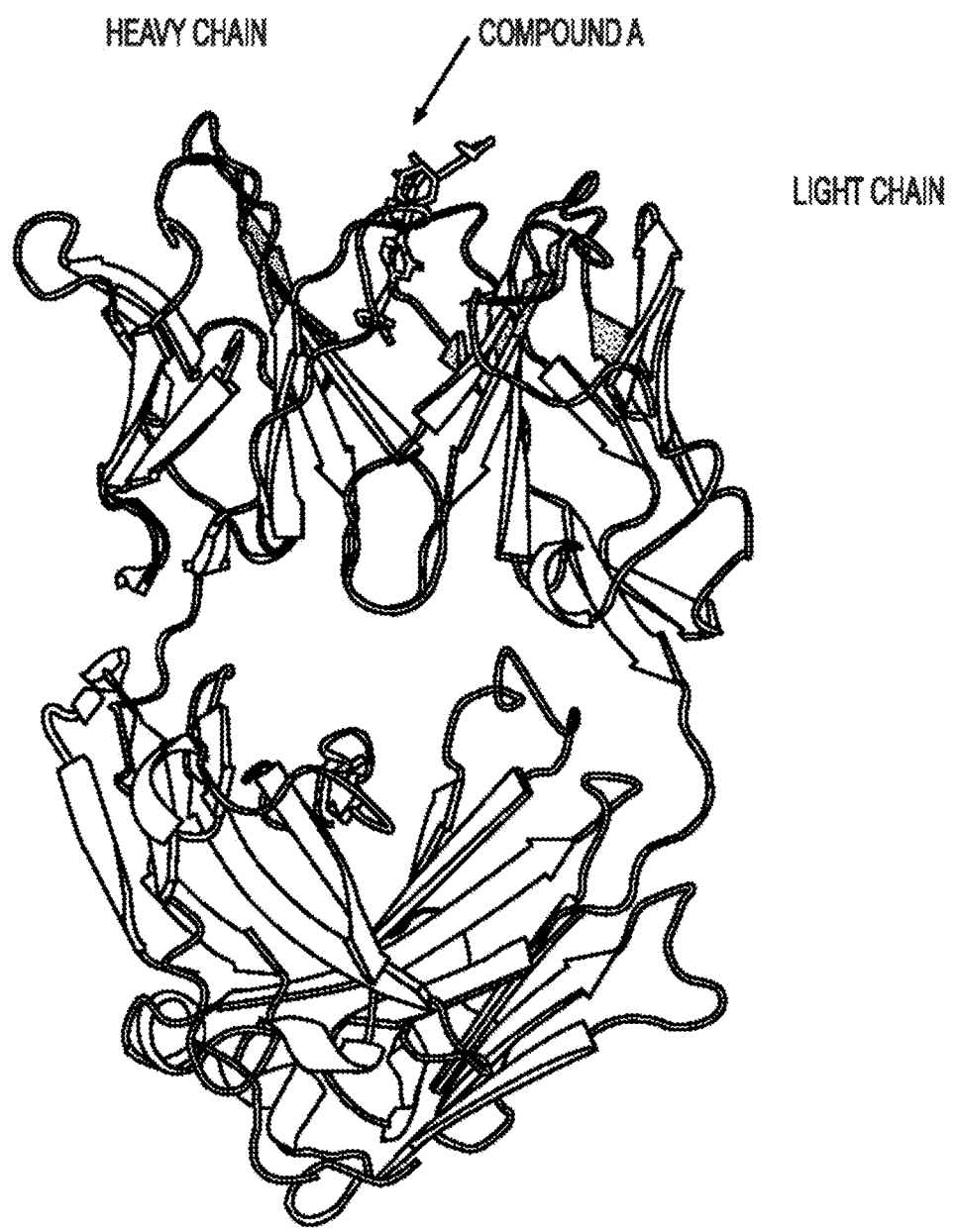
FIG. 17 depicts the structure as determined by crystallography of the antibody Fab fragment 26D5-75616-348-F10-Fab-SHORT bound to Compound A.

26D5-75616-348-F10-Fab-SHORT/Compound A crystals had symmetry consistent with space group P1 with unit cell edges of a=64.8 Å; b=84.9 Å; c=100.9 Å; α=83.4°; β=88.4°; γ=67.9° with four complexes per asymmetric unit. Data extended to 2.7 Å when processed isotropically, but an ellipsoidal cutoff that extended to 1.91 Å in 0.880a*+ 0.436b*−0.189c*, 2.20 Å in 0.063a*+0.898b*−0.436c*, and 2.98 Å in 0.093a*+0.382b*+0.920c* was used to retain data. The structure was determined by molecular replacement using PHASER (McCoy, A. J., Grosse-Kunstleve, R. W., Adams, P. D., Winn, M. D., Storoni, L. C. & Read, R. J. (2007). Phaser Crystallographic Software. *J. Appl. Crystallogr.* 40, 658-674.) with models for CL:CH1, VL and VH derived from that of antibody Fab fragment 26D5-GVR-Q-FT-Fab-SHORT with CDR-H3 removed from the VH model. The initial electron density map showed electron density for Compound A. The structure was improved through alternating rounds of model building with Coot (Emsley, P., Lokhamp, B., Scott, W. G. & Cowtan, K. (2010). Features and Development of Coot. *Acta Crystallogr Sect. D* 66, 486-501) and refinement with autoBUSTER using automated NCS restraints. (Bricogne, G., Blanc, E., Brandi, M., Flensburg, C., Keller, P., Paciorek, W., Roversi, P, Sharff, A., Smart, O., Vonrhein, C. & Womack, T. BUSTER version 2.11.7. Global Phasing, Ltd., Cambridge, United Kingdom and Smart, O. S. Womack, T. O., Flensburg, C., Keller, P., Paciorek, W., Sharff, A., Vonrhein, C. & Bricogne, G. (2012). Exploiting structure similarity in refinement: automated NCS and target-structure restraints in BUSTER. *Acta Crystallogr Sect. D* 68, 368-380). The image in FIG. 17 shows the refined structure for the complex of 26D5-75616-348-F10-Fab-SHORT/Compound A.

Two Fabs, 26D5-75229-343-A10-Fab-SHORT and 26D5-75616-348-F10-Fab-SHORT, were identified as the top two Fabs by DSC thermal stability and KinExA analysis. X-ray crystallography of antibody Fab fragment 26D5-75616-348-F10-Fab-SHORT demonstrated the 1:1 stoichiometry of binding of the antibody Fab fragment with Compound A and the mechanism of binding in the cleft between the heavy and light chains of the antibody Fab fragment.

Example 12: Plasma Binding Studies of Antibody Fab Fragments

Studies were conducted to evaluate the ability of 26D5-75616-348-F10-Fab-SHORT to reverse the anticoagulant effects of milvexian in plasma.

In Vitro Studies

The ability of antibody Fab fragment 26D5-75616-348-F10-Fab-SHORT to neutralize the in vitro anticoagulant activity of Factor XIa inhibitor Compound A was determined by combining the Fab fragment with plasma which contained a known amount of Compound A. The plasma concentration of Compound A was selected to provide a significant increase in the aPTT, where a significant increase may be defined as a coagulation time (for example aPTT) at least 20% greater than the coagulation time in the absence of the Factor XIa inhibitor. An antibody or antibody Fab fragment capable of binding to the Factor XIa inhibitor within the plasma reduces the ability of the Factor XIa inhibitor to bind to Factor XIa, resulting in a reduction in the coagulation time (for example aPTT) relative to the coagulation time in the absence of the antibody or antibody Fab fragment.

Compound A was added to pooled normal human plasma at concentrations of 8000, 4000, 2000, 1000, 500, 250, 125, 62.5, 31.3 and 15.6 nM. Antibody Fab fragment 26D5-75616-348-F10-Fab-SHORT was added to pooled normal human plasma at the same concentrations of 8000, 4000, 2000, 1000, 500, 250, 125, 62.5, 31.3 and 15.6 nM. Compound A-containing plasma, antibody Fab fragment 26D5-75616-348-F10-Fab-SHORT-containing plasma and normal plasma were combined to produce varying concentrations of each in Compound A:26D5-75616-348-F10-Fab-SHORT molar ratios of 5:5, 5:4, 5:3 and 5:2, including Compound A in the absence of antibody Fab fragment 26D5-75616-348-F10-Fab-SHORT.

The activated partial thromboplastin time (aPTT) (i.e., the human plasma clotting time) was determined for each sample by using ACTIN® FS (Siemens/Dade-Behring) following the directions in the package insert. For a description of the aPTT assay see, Goodnight, S. H. et al., "Screening Tests of Hemostasis", Disorders of Thrombosis and Hemostasis: A Clinical Guide, 2nd Edition, pp. 41-51, McGraw-Hill, New York (2001). Plasma (0.05 mL) was warmed to 37° C. for 1 minute. ACTIN® FS (0.05 mL) was added to the plasma and incubated for an additional 3 minutes. Calcium chloride (25 mM, 0.05 mL) was added to the reaction to initiate coagulation. The clotting time was the time in seconds from the moment calcium chloride was added until a clot was detected.

Figure 18:
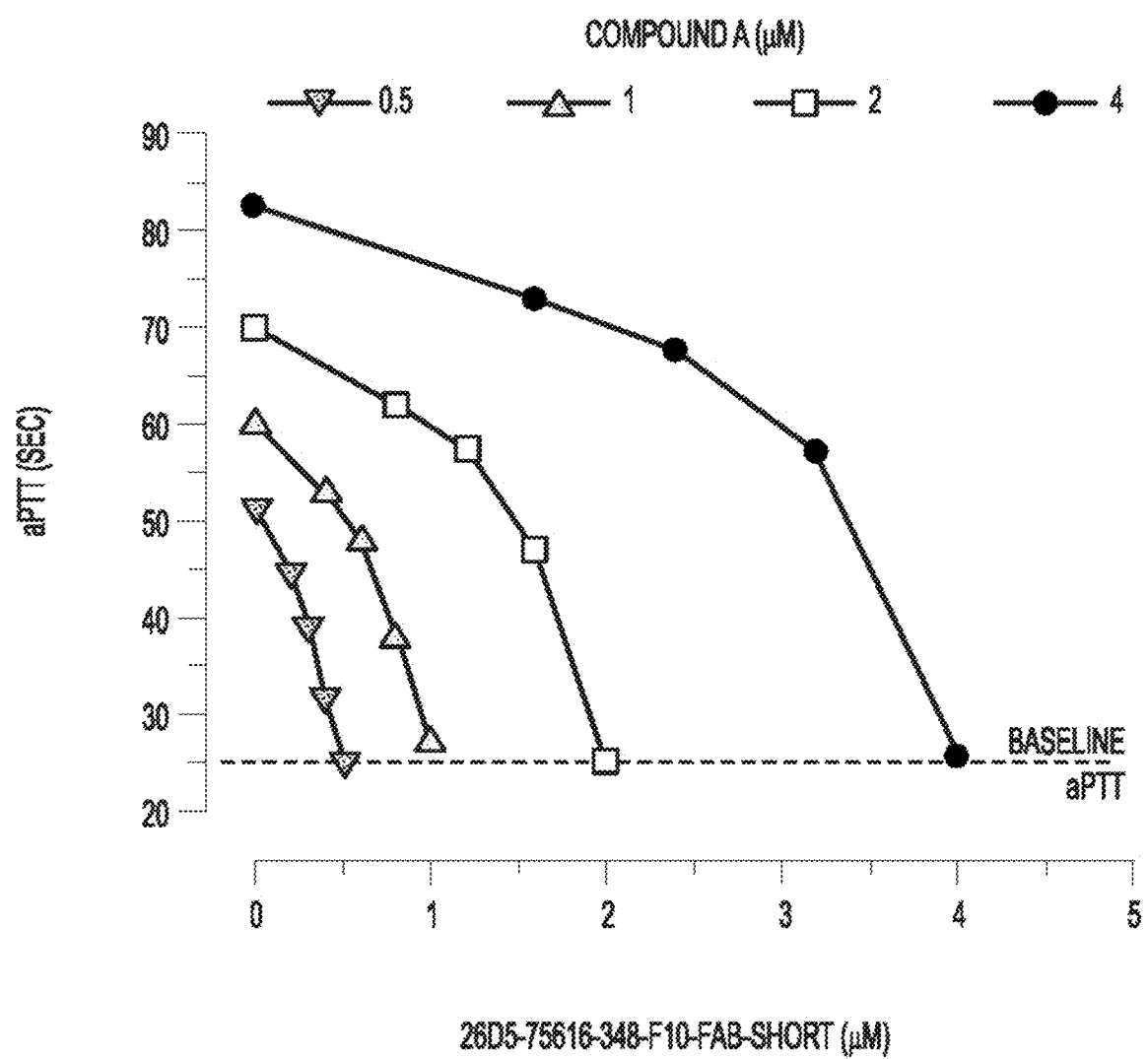
FIG. 18 depicts the reversal of the anticoagulant effects of Compound A by the neutralizing antibody Fab fragment 26D5-75616-348-F10-Fab-SHORT. The human plasma clotting time (aPTT) was plotted as a function of the plasma concentrations of Compound A and of neutralizing antibody Fab fragment 26D5-75616-348-F10-Fab-SHORT.
Figure 19:
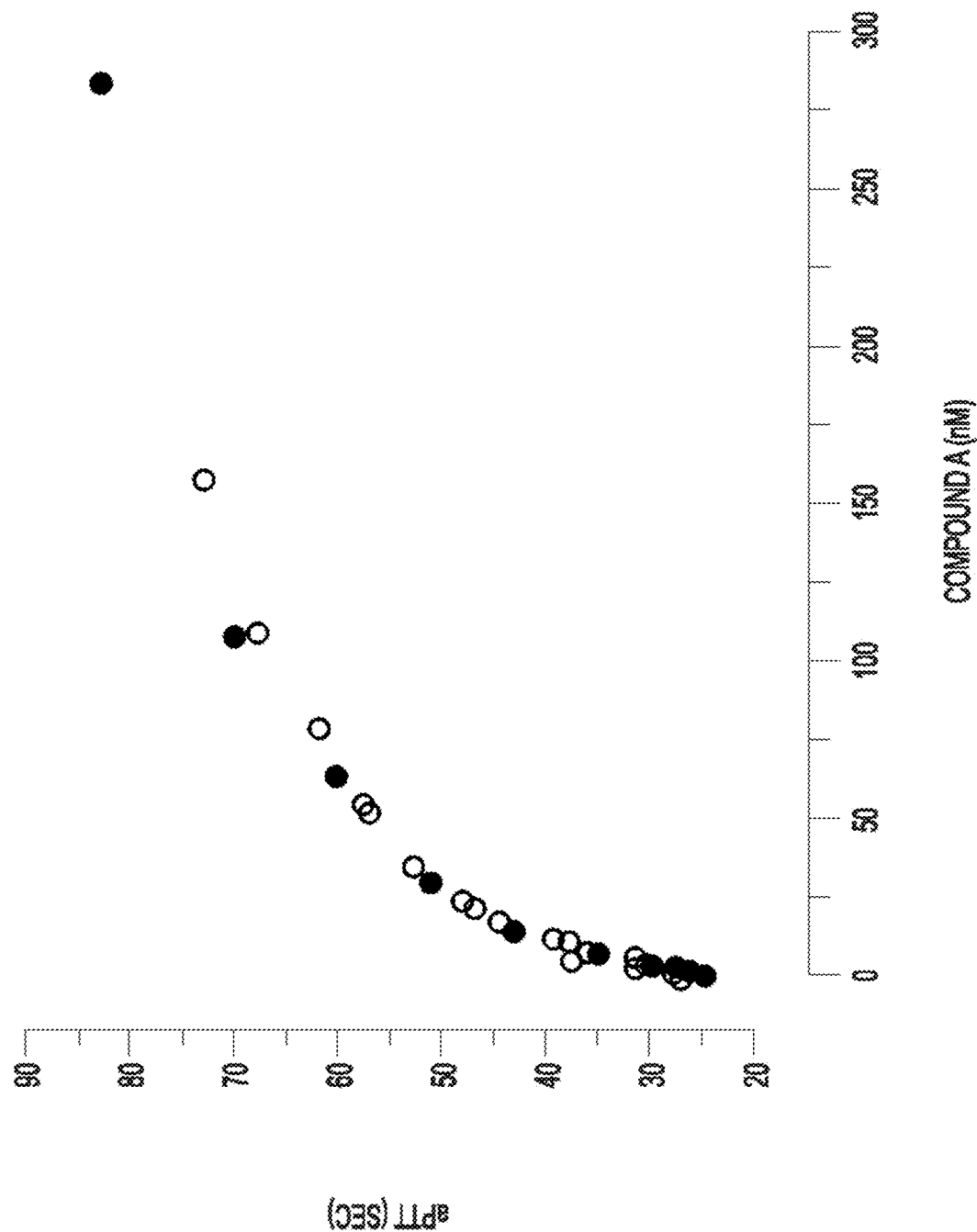
FIG. 19 depicts that human plasma clotting time (aPTT) is a function of the plasma concentration of unbound Compound A, regardless whether antibody Fab fragment 26D5-75616-348-F10-Fab-SHORT is present or absent. The human plasma clotting time (aPTT) was plotted as a function of the plasma concentration of Compound A in the absence (filled symbols) and presence (open symbols) of the neutralizing antibody Fab fragment 26D5-75616-348-F10-Fab-SHORT.

FIG. 18 shows plasma clotting time (aPTT) as a function of Factor XIa inhibitor, i.e., Compound A, concentration and neutralizing antibody Fab fragment 26D5-75616-348-F10-Fab-SHORT concentration. FIG. 19 shows plasma clotting time (aPTT) as a function of the concentration of free Factor XIa inhibitor Compound A in the absence (filled symbols) and presence (open symbols) of the neutralizing antibody Fab fragment 26D5-75616-348-F10-Fab-SHORT. The plot shows that the clotting time (aPTT) is a function of the unbound Compound A plasma concentration in the absence and the presence of antibody Fab fragment 26D5-75616-348-F10-Fab-SHORT.

The human plasma samples containing various concentrations and molar ratios of Compound A and antibody Fab fragment 26D5-75616-348-F10-Fab-SHORT were processed and the concentrations of Compound A and antibody Fab fragment 26D5-75616-348-F10-Fab-SHORT—unbound and bound—in each sample were determined as described in more detail below.

The total concentration of Compound A in plasma refers to unbound Compound A, Compound A bound to plasma proteins and Compound A bound to antibody Fab fragment 26D5-75616-348-F10-Fab-SHORT. Free or unbound Compound A refers to Compound A not bound to plasma protein or antibody Fab fragment 26D5-75616-348-F10-Fab-SHORT.

Unbound Compound A in plasma was obtained via an ultrafiltration method (Centrifree®, MilliporeSigma)(30 kDa molecular weight cut-off). Plasma (0.5 mL) was placed in the upper chamber of the ultrafiltration device (Centrifree®, Ultracel PL membrane, REF #4104; MilliporeSigma). The device was placed in a fixed angle centrifuge rotor (SORVALL SLA-3000; Thermo Scientific) and ultrafiltrate was collected after centrifugation at 2,000×g for 20 minutes (SORVALL RC 6 Plus; Thermo Scientific).

Aliquots of plasma and plasma ultrafiltrate were frozen at −80° C. in polypropylene tubes. The total concentration of Compound A in plasma and concentration of unbound Compound A in plasma ultrafiltrate was measured using liquid chromatography tandem mass spectrometry (LC/MS) analysis. The samples for the LC/MS analysis were prepared using a protein precipitation procedure described below.

An aliquot (20 µL) of biological sample was transferred into a 96-deep well plate (1.2 mL, round bottom polypropylene). A methanol solution (20 µL) containing 50% water and 0.5% formic acid was added. The plate was capped and mixed in a shaker at 95° C. for 20 minutes. The protein precipitation process was performed by adding acetonitrile (80 µL) containing an internal standard [10 nM, stable isotope-labeled (13C, 15N) Compound A] and 1% formic acid to the resulting solution of the previous step. The plate was further vortex mixed for 15 min at room temperature and then centrifuged at 3,600 rpm for 5 min. An aliquot (100 µL) of supernatant was transferred into an injection plate (96 well, 0.3 mL). The supernatant (5 µL) was injected to an Ultra Performance LC System (Waters® Acquity UPLC) interfaced with a QTRAP MS/MS (AB Sciex 6500) tandem mass spectrometer. The analytes were separated on a C18 column (Waters HSS T3, 2×50 mm, 1.8 µm) at 60° C., with a gradient flow rate of 0.7 ml/min, consisting of two buffer solutions (A: Water, 0.1% formic acid; B: acetonitrile, 0.1% formic acid). The detection was made by using multiple reaction monitoring (MRM) in the positive electrospray ionization mode, representing the precursor (M+H)$^+$ species. The MRM transitions monitored were 626→319 for Compound A, 630→323 for the isotope-labeled Compound A. The lowest limit of quantitation was 0.5 nM.

The concentration of antibody Fab fragment 26D5-75616-348-F10-Fab-SHORT in plasma was determined as follows. The plasma concentration of both total antibody Fab fragment 26D5-75616-348-F10-Fab-SHORT and antibody Fab fragment 26D5-75616-348-F10-Fab-SHORT not bound to Compound A in plasma was measured by ligand binding assays on a Gyrolab® automated microfluidics platform (Gyros Protein Technologies AB). Biotinylated mouse anti-human kappa (SouthernBiotech, AL) was used as a capture molecule for total antibody Fab fragment 26D5-75616-348-F10-Fab-SHORT. Samples, standards, and QC were brought up to a final matrix concentration of 10% plasma in 1×PTB (1% BSA/0.05% Tween20/PBS), and loaded into the Gyrolab® automated microfluidics platform. The 3-step-2-Wash Wizard method with Gyrolab® Bioaffy 200 CD was used (Gyros Protein Technologies AB). After final wash steps, the captured total antibody Fab fragment 26D5-75616-348-F10-Fab-SHORT was detected using Alexa Fluor® 647 labeled mouse anti-human Ig kappa light chain mAb clone G20-361 (BD Catalog No. 555861, Lot No. 8333691). The concentrations of total antibody Fab fragment 26D5-75616-348-F10-Fab-SHORT in plasma samples were calculated from fluorescence intensity as measured by the Gyrolab® technology using a 4-parameter logistic (4-PL) calibration curve generated from antibody Fab fragment 26D5-75616-348-F10-Fab-SHORT calibrators. The range of the total antibody Fab fragment 26D5-75616-348-F10-Fab-SHORT calibration curve was from 250 to 25000 ng/mL in plasma. The upper and lower limits of quantification were 25000 and 250 ng/mL. Quality control samples were prepared at 20000, 7500, 750 ng/mL in plasma. Calibrators and QC were analyzed in each experiment to ensure acceptable assay performance. Assay performance was within the acceptable range: % CV of the standards and QC was below 20%, and QC recovery was within ±20% of the nominal values.

COMPOUND 5 was used as a capture molecule for antibody Fab fragment 26D5-75616-348-F10-Fab-SHORT not bound to Compound A. Samples, standards, and QC were brought up to a final matrix concentration of 10% plasma in 1×PTB (1% BSA/0.05% Tween20/PBS), and loaded into a Gyrolab® automated microfluidics platform. The 3-step-2-Wash Wizard method with Gyrolab® Bioaffy 200 CD was used. After final wash steps, the captured "active/free" antibody Fab fragment 26D5-75616-348-F10-Fab-SHORT was detected using Alexa Fluor® 647 labeled mouse anti-human Ig kappa light chain mAb clone G20-361 (BD Catalog No. 555861, Lot No. 8333691). The concentrations of "active/free" Fab (26D5-75616-348-F10-Fab-SHORT) in plasma samples were calculated from fluorescence intensity as measured by Gyrolab® using a 4-parameter logistic (4-PL) calibration curve generated from antibody Fab fragment 26D5-75616-348-F10-Fab-SHORT calibrators. The range of the "active/free" antibody Fab fragment 26D5-75616-348-F10-Fab-SHORT calibration curve was from 250 to 25000 ng/mL in plasma. The upper and lower limits of quantification were 25000 and 250 ng/mL. Quality control samples were prepared at 20000, 7500, 750 ng/mL in plasma. Calibrators and QC were analyzed in each experiment to ensure acceptable assay performance. Assay performance was within the acceptable range: % CV of the standards and QC was below 20%, and QC recovery was within ±20% of the nominal values.

In Vivo Studies

In vivo experiments were conducted in accordance with the regulations of the Animal Care and Use Committee of the Bristol-Myers Squibb Company. Rabbits (male New Zealand White, 2 to 4 kg) were instrumented with indwelling catheters in the central ear artery for blood sampling and marginal ear vein for substance administration. Compound A was administered as a constant intravenous infusion at a dose of 1.0 mg/kg over 10 minutes. Beginning 20 minutes after the Compound A infusion was complete, the antibody Fab fragment 26D5-75616-348-F10-Fab-SHORT was administered as a constant intravenous infusion at a dose of 160 mg/kg over 10 minutes. The administered dose of the antibody Fab fragment 26D5-75616-348-F10-Fab-SHORT represented a nominal 2-fold molar excess to the administered dose of Compound A. Blood samples of 1.5 mL were taken prior to the administration of Compound A, at the end of the infusion of compound A, immediately prior to the administration of the antibody Fab fragment, at the end of the administration of the antibody Fab fragment and at varying intervals after the administration of the antibody Fab fragment for up to 24 hours from the start of Compound A dosing. Blood samples were added to 0.167 mL of 3.8% sodium citrate in a polypropylene tube, inverted at least two times to thoroughly mix and placed on ice. Within one hour of blood sampling, plasma was isolated by centrifuging whole blood at least 1,500× gravity for at least 10 minutes. Unbound Compound A was obtained by the above-described ultrafiltration method.

The anticoagulant effects of Compound A were measured in activated partial thromboplastin time (aPTT). The aPTT was determined using ACTIN® FS (Siemens/Dade-Behring) following the directions in the package insert. Plasma (0.05 mL) was warmed to 37° C. for 1 minute. ACTIN® FS (0.05 mL) was added to the plasma and incubated for an additional 3 minutes. Calcium chloride (25 mM, 0.05 mL) was added to the reaction to initiate coagulation. The clotting time was the time in seconds from the moment calcium chloride was added until a clot was detected.

Figure 20:
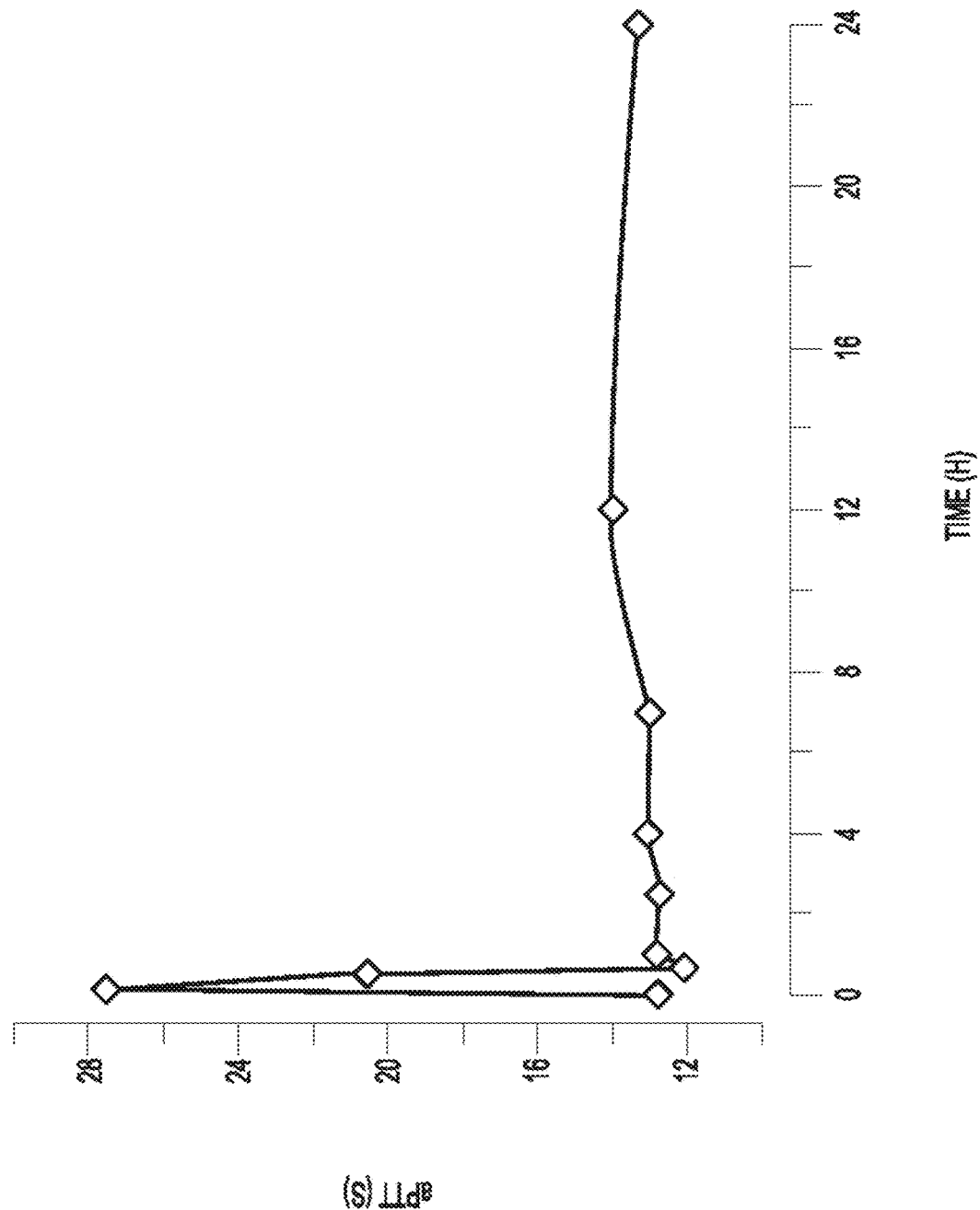
FIG. 20 depicts the reversal of the anticoagulant effects of Compound A by the neutralizing antibody Fab fragment 26D5-75616-348-F10-Fab-SHORT. An IV dose of Compound A (1 mg/kg), followed 20 minutes later by an IV dose of antibody Fab fragment 26D5-75616-348-F10-Fab-SHORT (160 mg/kg) was administered to rabbits. Plasma clotting time (aPTT) was measured at baseline, shortly before the administration of Compound A and for about 24 house afterwards.

After in vivo administration of Compound A, rabbit plasma aPTT increased approximately 2-fold relative to baseline. Following administration of antibody Fab fragment 26D5-75616-348-F10-Fab-SHORT 20 minutes later, the rabbit plasma aPTT returned to baseline and remained at that level for over 12 hours. FIG. 20 shows rabbit plasma clotting time (aPTT) after an IV dose of Compound A (1 mg/kg) followed 20 minutes later by an IV dose of antibody Fab fragment 26D5-75616-348-F10-Fab-SHORT (160 mg/kg). Results are the mean from 3 animals.

Plasma concentrations of Compound A (total and unbound) and antibody Fab fragment 26D5-75616-348-F10-Fab-SHORT were determined as described above. PK parameters were obtained by non-compartmental analysis of plasma concentration versus time data (Phoenix WinNonlin software, Version 6.4, Pharsight Corporation, Mountain View, CA). Values below the lower limit of quantification were not used in calculations. Area under the plasma concentration vs. time curve (AUC [0-T]) was calculated using a combination of linear and log trapezoidal summations. The total plasma clearance (CL), steady-state volume of distribution (Vss), terminal half-life (T-HALF), and mean residence time (MRT) were estimated after IV administration. Estimations of T-HALF were made using a minimum of 3 time points with quantifiable concentrations.

Figure 21:
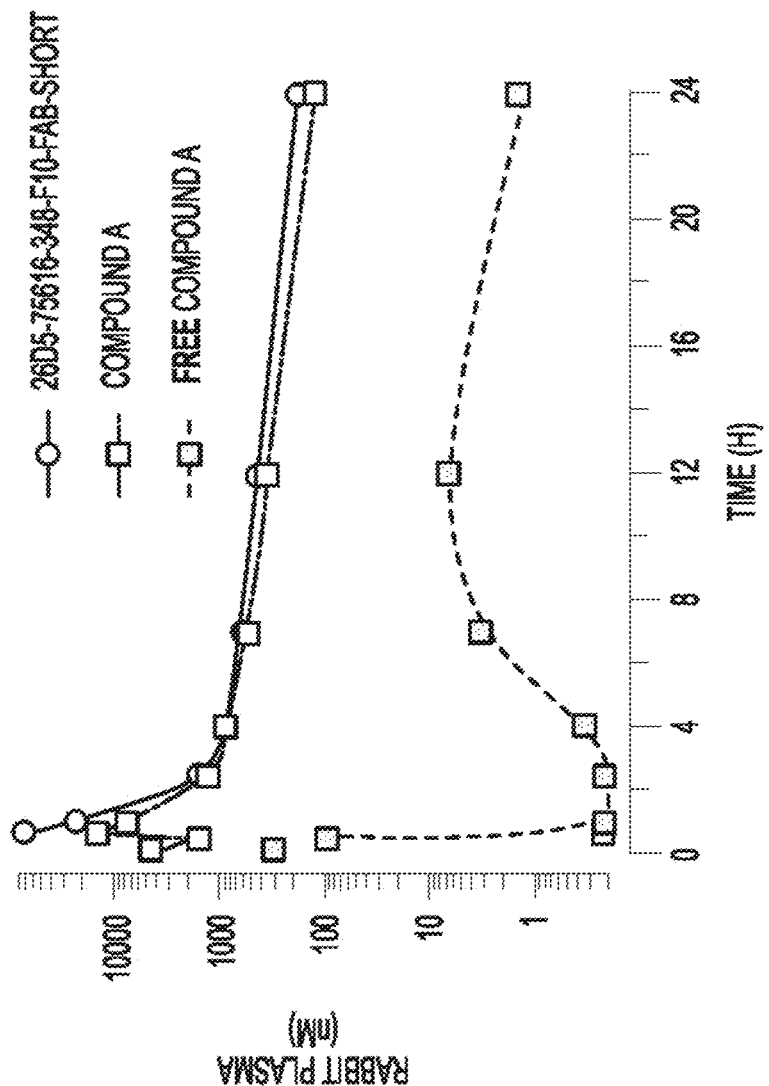
FIG. 21 depicts the pharmacokinetics (rabbit plasma concentrations) of antibody Fab fragment 26D5-75616-348-F10-Fab-SHORT, Compound A and free Compound A resulting from an IV dose of Compound A (1 mg/kg) followed 20 minutes later by an IV dose of antibody Fab fragment 26D5-75616-348-F10-Fab-SHORT (160 mg/kg).

After administration of Compound A to rabbits (1 mg/kg), the plasma concentration of Compound A was 4.3 µM and the plasma concentration of unbound Compound A was 290 nM. Following administration of antibody Fab fragment 26D5-75616-348-F10-Fab-SHORT (160 mg/kg), the plasma concentration of Compound A was 14 and the plasma concentration of unbound Compound A was less than 0.2 nM. The decrease in the plasma concentration of unbound Compound A was due to its high binding affinity to antibody Fab fragment 26D5-75616-348-F10-Fab-SHORT. The increase in plasma concentration of Compound A was due to the distribution of antibody Fab fragment 26D5-75616-348-F10-Fab-SHORT primarily in the vascular compartment and the redistribution of Compound A from extravascular to vascular space according to the law of mass action. The rabbit plasma concentration of unbound Compound A remained below 10 nM for more than 12 hours. FIG. 21 shows rabbit plasma concentration of antibody Fab fragment 26D5-75616-348-F10-Fab-SHORT, Compound A and unbound Compound A after an IV dose of Compound A (1 mg/kg) followed 20 minutes later by an IV dose of antibody Fab fragment 26D5-75616-348-F10-Fab-SHORT (160 mg/kg). Results are the mean from 3 animals.

Example 13: Pharmacokinetics of Antibody Tandem Fab Fragments

26D5-75616-348-F10-TanFab (Tandem Fab Heavy Chain SEQ ID NO: 180, Tandem Fab Light Chain SEQ ID NO: 164) was generated and purified according to standard procedures known in the art, similar to the methods described in Example 5 above.

Pharmacokinetics in Rat

In vivo experiments were conducted in accordance with the regulations of the Animal Care and Use Committee of the Bristol-Myers Squibb Company. Rats (male Sprague-Dawley, 0.2 to 0.4 kg) were instrumented with indwelling catheters in the jugular vein for blood sampling and for substance administration. The antibody Fab fragment 26D5-75616-348-F10-Fab-SHORT and antibody tandem Fab fragment 26D5-75616-348-F10-TanFab were each administered as a constant intravenous infusion at a dose of 10 mg/kg over 10 minutes. Blood samples of 0.2 mL were taken at the end of the infusion and at varying intervals for up to 48 hours from the start of dosing. Blood samples were added to EDTA in a polypropylene tube, inverted at least two times to thoroughly mix and placed on ice. Within one hour of blood sampling, plasma was isolated by centrifuging whole blood at least 1,500× gravity for at least 10 minutes. The concentrations of antibody Fab fragment 26D5-75616-348-F10-Fab-SHORT and antibody tandem Fab fragment 26D5-75616-348-F10-TanFab in plasma were determined as follows.

The concentration of 26D5-75616-348-F10-Fab-SHORT and 26D5-75616-348-F10-TanFab in plasma were determined as follows. The plasma concentrations of both total 26D5-75616-348-F10-Fab-SHORT and 26D5-75616-348-F10-TanFab, and 26D5-75616-348-F10-Fab-SHORT and 26D5-75616-348-F10-TanFab not bound to Compound A in plasma were measured by ligand binding assays on a Gyrolab® automated microfluidics platform (Gyros Protein Technologies AB). Biotinylated mouse anti-human kappa (SouthernBiotech Cat No 9230-08, Lot No K5613-X088) was used as a capture molecule for total 26D5-75616-348-F10-Fab-SHORT and 26D5-75616-348-F10-TanFab. Samples, standards, and QC were brought up to a final matrix concentration of 10% plasma in 1×PTB (1% BSA/0.05% Tween20/PBS), and loaded into the Gyrolab® automated microfluidics platform. The 3-step-2-Wash Wizard method with Gyrolab® Bioaffy 200 CD was used (Gyros Protein Technologies AB). After final wash steps, the captured total 26D5-75616-348-F10-Fab-SHORT and 26D5-75616-348-F10-TanFab were detected using Alexa Fluor® 647 labeled mouse anti-human Ig kappa light chain mAb clone G20-361 (Becton Dickinson Cat No 555861, Lot No 833694). The concentrations of total 26D5-75616-348-F10-Fab-SHORT and 26D5-75616-348-F10-TanFab in plasma samples were calculated from fluorescence intensity as measured by the Gyrolab® technology using a 4-parameter logistic (4-PL) calibration curve generated from 26D5-75616-348-F10-Fab-SHORT and 26D5-75616-348-F10-TanFab calibrators. The range of the total 26D5-75616-348-F10-Fab-SHORT and 26D5-75616-348-F10-TanFab calibration curves were from 10 to 25000 ng/mL in plasma. The upper and lower limits of quantification were 25000 and 10 ng/mL. Quality control samples were prepared at 20000, 7500, 750, 75 and 30 ng/mL in plasma. Calibrators and QC were analyzed in each experiment to ensure acceptable assay performance. Assay performance was within the acceptable range: % CV of the standards and QC was below 20%, and QC recovery was within ±20% of the nominal values.

COMPOUND 5 was used as a capture molecule for 26D5-75616-348-F10-Fab-SHORT and 26D5-75616-348-F10-TanFab not bound to Compound A. Samples, standards, and QC were brought up to a final matrix concentration of 10% plasma in 1×PTB (1% BSA/0.05% Tween20/PBS), and loaded into a Gyrolab® automated microfluidics platform. The 3-step-2-Wash Wizard method with Gyrolab® Bioaffy 200 CD was used. After final wash steps, the captured "active/free" 26D5-75616-348-F10-Fab-SHORT and 26D5-75616-348-F10-TanFab were detected using Alexa Fluor® 647 labeled mouse anti-human Ig kappa light chain mAb clone G20-361 (Becton Dickinson Cat No 555861, Lot No 8333694). The concentrations of "active/free" 26D5-75616-348-F10-Fab-SHORT and 26D5-75616-348-F10-TanFab in plasma samples were calculated from fluorescence intensity as measured by Gyrolab® using a 4-parameter logistic (4-PL) calibration curve generated from 26D5-75616-348-F10-Fab-SHORT and 26D5-75616-348-F10-TanFab calibrators. The range of the "active/free" 26D5-75616-348-F10-Fab-SHORT and 26D5-75616-348-F10-TanFab calibration curves were from 10 to 25000 ng/mL in plasma. The upper and lower limits of quantification were 25000 and 10 ng/mL. Quality control samples were prepared at 20000, 7500, 750, 75 and 30 ng/mL in plasma. Calibrators and QC were analyzed in each experiment to ensure acceptable assay performance. Assay performance was within the acceptable range: % CV of the standards and QC was below 20%, and QC recovery was within ±20% of the nominal values.

Figure 22:
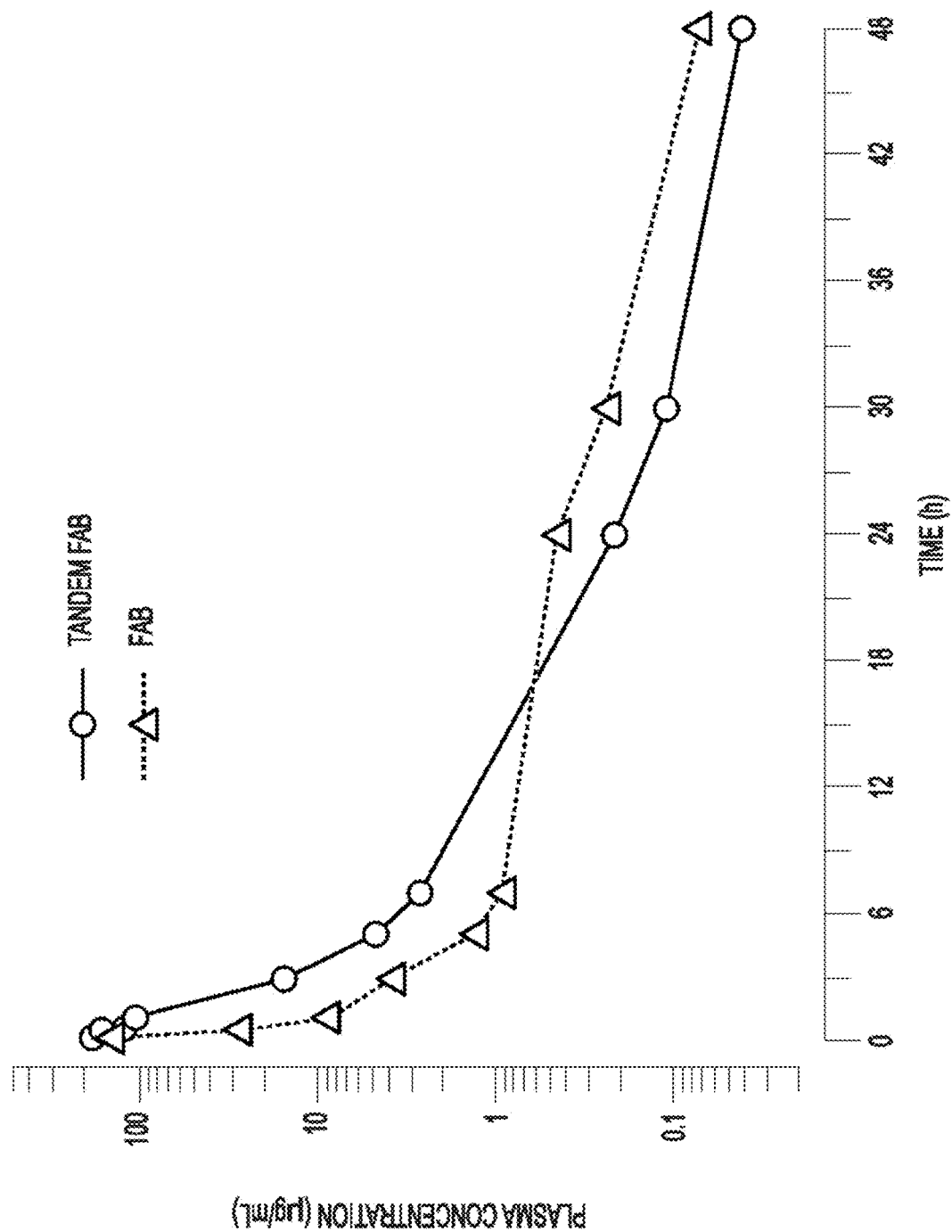
FIG. 22 depicts the pharmacokinetics (rat plasma concentrations) of antibody Fab fragment 26D5-75616-348-F10-Fab-SHORT and antibody tandem Fab fragment 26D5-75616-348-F10-TanFab resulting from IV doses each of 10 mg/kg administered by infusion over 10 minutes. Open circles/Tandem Fab indicate antibody tandem Fab fragment 26D5-75616-348-F10-TanFab data points. Open triangles/Fab indicate antibody Fab fragment 26D5-75616-348-F10-Fab-SHORT data points.

FIG. 22 shows the resulting pharmacokinetics data.

Pharmacokinetics in Rabbit

In vivo experiments were conducted in accordance with the regulations of the Animal Care and Use Committee of Bristol-Myers Squibb Company. Rabbits (male New Zealand White, 2 to 4 kg) were instrumented with indwelling catheters in the femoral artery and vein for blood sampling and marginal ear vein for substance administration. Compound A was administered as a constant intravenous infusion at a dose of 0.4 mg/kg (0.64 micromoles/kg) over 10 minutes. Beginning 20 minutes after the Compound A infusion was complete, the antibody tandem Fab fragment 26D5-75616-348-F10-TanFab was administered as a constant intravenous infusion at a dose of 40 mg/kg (0.43 micromoles/kg) over 10 minutes. The administered dose of the antibody tandem Fab fragment 26D5-75616-348-F10-TanFab represented a nominal 1.34-fold molar excess, accounting for 2:1 binding capacity, to the administered dose of Compound A (2*0.43/0.64). Blood samples of 1.5 mL were taken prior to the administration of Compound A, at the end of the infusion of compound A, immediately prior to the administration of the antibody tandem Fab fragment 26D5-75616-348-F10-TanFab, at the end of the administration of the antibody tandem Fab fragment 26D5-75616-348-F10-TanFab and at varying intervals after the administration of the antibody tandem Fab fragment 26D5-75616-348-F10-TanFab for up to 24 hours from the start of Compound A dosing.

Blood samples were added to 0.167 mL of 3.8% sodium citrate in a polypropylene tube, inverted at least two times to thoroughly mix and placed on ice. Within one hour of blood sampling, plasma was isolated by centrifuging whole blood at least 1,500× gravity for at least 10 minutes. Unbound Compound A was obtained by the above-described ultrafiltration method. Aliquots of plasma and plasma ultrafiltrate were frozen at −80° C. in polypropylene tubes. The total concentration of Compound A in plasma and concentration of unbound Compound A in plasma ultrafiltrate were measured using liquid chromatography tandem mass spectrometry (LC/MS) analysis. The samples for the LC/MS analysis were prepared using a protein precipitation procedure described below.

An aliquot (20 µL) of biological sample was transferred into a 96-deep well plate (1.2 mL, round bottom poly propylene). A methanol solution (20 µL) containing 50% water and 0.5% formic acid was added. The plate was capped and mixed in a shaker at 95° C. for 20 minutes. The protein precipitation process was performed by adding acetonitrile (80 µL) containing an internal standard [1 µM] and 1% formic acid to the resulting solution of the previous step. The plate was further vortex mixed for 15 min at room temperature and then centrifuged at 3,700 rpm for 8 min. An aliquot (100 µL) of supernatant was transferred into an injection plate (96 well, 0.3 mL). The supernatant (3 µL) was injected to an Ultra Performance LC System (Waters® Acquity iClass uPLC) interfaced with a Quadrapole MS/MS (Thermo Quantiva) tandem mass spectrometer. The analytes were separated on a C18 column (Waters HSS T3, 2×50 mm, 1.8 µm) at 40° C., with a gradient flow rate of 0.6 ml/min, consisting of two buffer solutions (A: Water, 5 mM Ammonium Formate, 0.1% formic acid; B: acetonitrile, 0.1% formic acid). The detection was made by using multiple reaction monitoring (MRM) in the positive electrospray ionization mode, representing the precursor (M+H)+ species. The MRM transitions monitored were 626.3→319.1 for Compound A, 474.3→269 for the Internal Standard. The lowest limit of quantitation was 0.5 nM.

The concentration of antibody tandem Fab fragment 26D5-75616-348-F10-TanFab in plasma was determined as described above in this Example.

Figure 23:
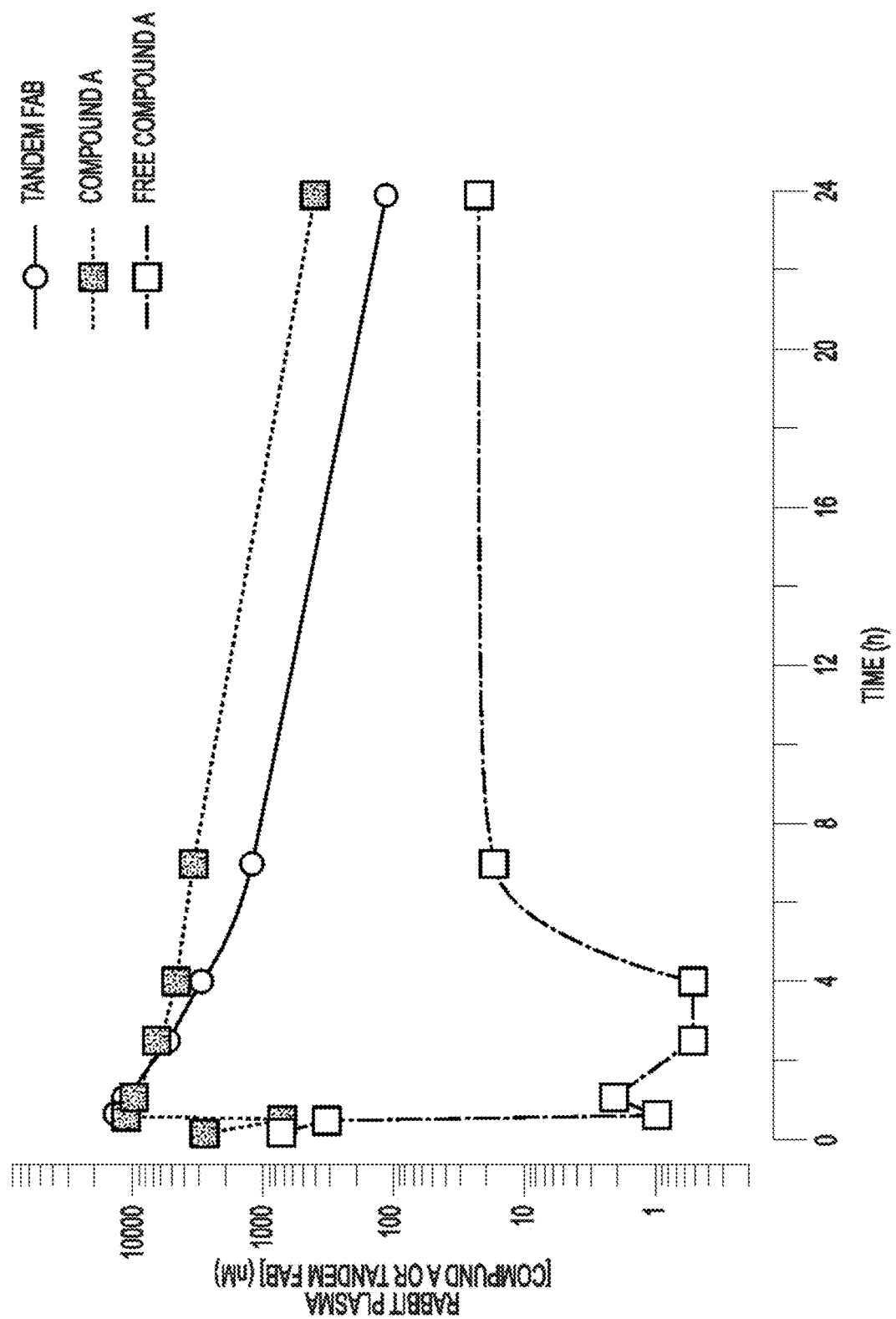
FIG. 23 depicts the pharmacokinetics (rabbit plasma concentrations) of antibody tandem Fab fragment 26D5-75616-348-F10-TanFab, Compound A and free Compound A resulting from an IV dose of Compound A of 0.4 mg/kg administered by infusion over 10 minutes, followed 20 minutes later by an IV dose of antibody tandem Fab fragment 26D5-75616-348-F10-TanFab of 40 mg/kg administered by infusion over 10 minutes. Closed circles/tandem Fab indicate antibody tandem Fab fragment 26D5-75616-348-F10-TanFab data points.

FIG. 23 shows the resulting pharmacokinetics data.

In Vitro Studies

Figure 24:
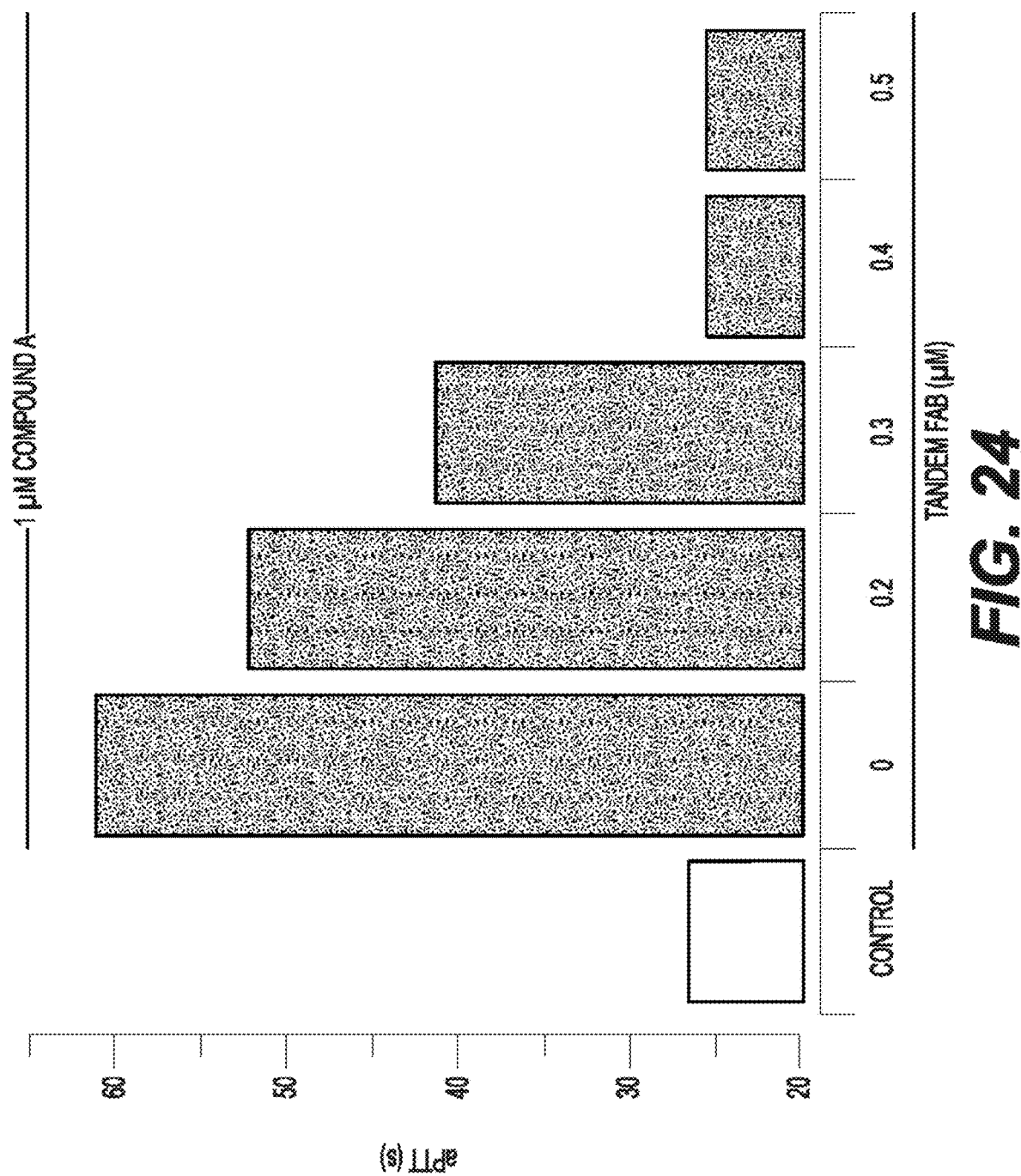
FIG. 24 depicts the reversal of the anticoagulant effects of Compound A by the neutralizing antibody tandem Fab fragment 26D5-75616-348-F10-TanFab. The human plasma clotting time (aPTT) was plotted as a function of the plasma concentrations of Compound A and of neutralizing antibody tandem Fab fragment 26D5-75616-348-F10-TanFab. "tandem Fab" refers to antibody tandem Fab fragment 26D5-75616-348-F10-TanFab.

Compound A was added to pooled normal human plasma at a concentration of 2000 nM. Antibody tandem Fab fragment 26D5-75616-348-F10-TanFab was added to pooled normal human plasma at a concentrations of 1000 nM. Compound A-containing plasma, 26D5-75616-348-F10-TanFab-containing plasma and normal plasma were combined to produce varying concentrations of each in Compound A: 26D5-75616-348-F10-TanFab molar ratios of 2:1, 2:0.8, 2:0.6 and 2:0.4, including Compound A in the absence of 26D5-75616-348-F10-TanFab. The activated partial thromboplastin time (aPTT) (i.e., the human plasma clotting time) was determined for each sample as described above in Example 12. FIG. 24 shows the resulting plasma clotting data.

We claim:

1. An isolated antigen binding peptide comprising a heavy chain variable region (VH) and a light chain variable region (VL), wherein the VH comprises three complementarity determining regions (CDRs): VH-CDR1, VH-CDR2, and VH-CDR3 and the VL comprises three CDRs: VL-CDR1, VL-CDR2, and VL-CDR3, wherein the amino acid sequences of the VH-CDR1, VH-CDR2, VH-CDR3, VL-CDR1, VL-CDR2, and VL-CDR3, respectively comprise the sequences selected from the group consisting of:

(a) SEQ ID NOs: 1, 13, 23, 29, 38, and 44, respectively;
(b) SEQ ID NOs: 1, 14, 23, 29, 38, and 45, respectively;
(c) SEQ ID NOs: 1, 13, 24, 30, 38, and 45, respectively;
(d) SEQ ID NOs: 1, 13, 24, 29, 39, and 45, respectively;
(e) SEQ ID NOs: 1, 14, 25, 29, 38, and 46, respectively;
(f) SEQ ID NOs: 2, 13, 26, 31, 40, and 47, respectively;
(g) SEQ ID NOs: 3, 15, 24, 32, 40, and 47, respectively;
(h) SEQ ID NOs: 4, 16, 24, 29, 38, and 46, respectively;
(i) SEQ ID NOs: 5, 15, 24, 29, 38, and 46, respectively;
(j) SEQ ID NOs: 1, 14, 24, 29, 38, and 46, respectively;
(k) SEQ ID NOs: 6, 13, 24, 31, 40, and 47, respectively;
(l) SEQ ID NOs: 3, 15, 24, 32, 41, and 48, respectively;
(m) SEQ ID NOs: 1, 14, 24, 33, 38, and 49, respectively;
(n) SEQ ID NOs: 1, 14, 26, 29, 38, and 46, respectively;
(o) SEQ ID NOs: 7, 17, 26, 29, 38, and 46, respectively;
(p) SEQ ID NOs: 8, 17, 24, 34, 38, and 46, respectively;
(q) SEQ ID NOs: 1, 17, 26, 29, 38, and 46, respectively;
(r) SEQ ID NOs: 1, 17, 26, 35, 38, and 46, respectively;
(s) SEQ ID NOs: 1, 17, 24, 33, 38, and 49, respectively;
(t) SEQ ID NOs: 9, 14, 26, 29, 38, and 46, respectively;
(u) SEQ ID NOs: 9, 14, 26, 35, 38, and 46, respectively;
(v) SEQ ID NOs: 9, 17, 24, 29, 38, and 46, respectively;
(w) SEQ ID NOs: 9, 17, 24, 35, 38, and 46, respectively;
(x) SEQ ID NOs: 9, 17, 24, 34, 38, and 46, respectively;
(y) SEQ ID NOs: 9, 14, 24, 29, 38, and 46, respectively;
(z) SEQ ID NOs: 9, 18, 26, 35, 38, and 46, respectively;
(aa) SEQ ID NOs: 8, 14, 24, 29, 38, and 46, respectively;
(bb) SEQ ID NOs: 8, 17, 26, 29, 38, and 46, respectively;
(cc) SEQ ID NOs: 9, 19, 26, 29, 38, and 46, respectively;
(dd) SEQ ID NOs: 9, 17, 26, 34, 38, and 46, respectively;
(ee) SEQ ID NOs: 10, 20, 27, 36, 42, and 50, respectively;
(ff) SEQ ID NOs: 11, 21, 28, 37, 43, and 51, respectively;
(gg) SEQ ID NOs: 12, 22, 26, 33, 38, and 46, respectively;
(hh) SEQ ID NOs: 12, 17, 26, 33, 38, and 46, respectively; and
(ii) SEQ ID NOs: 9, 17, 26, 33, 38, and 46, respectively.

2. The isolated antigen binding peptide of claim 1, wherein the VH region and the VL region, respectively, comprise amino acid sequences selected from the group consisting of:

(a) SEQ ID NO: 52 and SEQ ID NO: 84, respectively;
(b) SEQ ID NO: 53 and SEQ ID NO: 85, respectively;
(c) SEQ ID NO: 54 and SEQ ID NO: 86, respectively;
(d) SEQ ID NO: 54 and SEQ ID NO: 87, respectively;
(e) SEQ ID NO: 55 and SEQ ID NO: 88, respectively;
(f) SEQ ID NO: 56 and SEQ ID NO: 89, respectively;
(g) SEQ ID NO: 57 and SEQ ID NO: 90, respectively;
(h) SEQ ID NO: 58 and SEQ ID NO: 88, respectively;
(i) SEQ ID NO: 59 and SEQ ID NO: 88, respectively;
(j) SEQ ID NO: 60 and SEQ ID NO: 91, respectively;
(k) SEQ ID NO: 61 and SEQ ID NO: 89, respectively;
(l) SEQ ID NO: 57 and SEQ ID NO: 92, respectively;
(m) SEQ ID NO: 60 and SEQ ID NO: 93, respectively;
(n) SEQ ID NO: 60 and SEQ ID NO: 88, respectively;
(o) SEQ ID NO: 62 and SEQ ID NO: 88, respectively;
(p) SEQ ID NO: 63 and SEQ ID NO: 88, respectively;
(q) SEQ ID NO: 64 and SEQ ID NO: 88, respectively;
(r) SEQ ID NO: 65 and SEQ ID NO: 94, respectively;
(s) SEQ ID NO: 66 and SEQ ID NO: 88, respectively;
(t) SEQ ID NO: 66 and SEQ ID NO: 95, respectively;
(u) SEQ ID NO: 67 and SEQ ID NO: 88, respectively;
(v) SEQ ID NO: 68 and SEQ ID NO: 93, respectively;
(w) SEQ ID NO: 69 and SEQ ID NO: 88, respectively;
(x) SEQ ID NO: 69 and SEQ ID NO: 95, respectively;
(y) SEQ ID NO: 70 and SEQ ID NO: 88, respectively;
(z) SEQ ID NO: 70 and SEQ ID NO: 95, respectively;
(aa) SEQ ID NO: 71 and SEQ ID NO: 88, respectively;
(bb) SEQ ID NO: 71 and SEQ ID NO: 94, respectively;
(cc) SEQ ID NO: 72 and SEQ ID NO: 88, respectively;
(dd) SEQ ID NO: 73 and SEQ ID NO: 95, respectively;
(ee) SEQ ID NO: 74 and SEQ ID NO: 88, respectively;
(ff) SEQ ID NO: 75 and SEQ ID NO: 88, respectively;
(gg) SEQ ID NO: 76 and SEQ ID NO: 88, respectively;
(hh) SEQ ID NO: 77 and SEQ ID NO: 94, respectively;
(ii) SEQ ID NO: 78 and SEQ ID NO: 96, respectively;
(jj) SEQ ID NO: 79 and SEQ ID NO: 97 respectively;

(kk) SEQ ID NO: 80 and SEQ ID NO: 98, respectively;
(ll) SEQ ID NO: 81 and SEQ ID NO: 99, respectively;
(mm) SEQ ID NO: 81 and SEQ ID NO: 98, respectively;
(nn) SEQ ID NO: 82 and SEQ ID NO: 99, respectively; and
(oo) SEQ ID NO: 83 and SEQ ID NO: 98, respectively.

3. The isolated antigen binding peptide of claim 1, wherein the isolated antigen binding peptide specifically binds to the compound set forth in Formula (I):

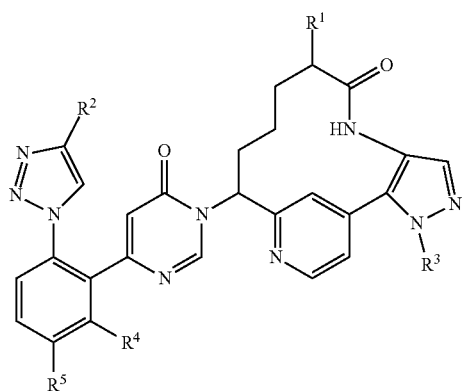

(I)

or a stereoisomer or a tautomer thereof, wherein:
$R^1$ is $C_{1-4}$ alkyl;
$R^2$ is independently selected from F, Cl, $CF_3$, $CHF_2$, $CH_2F$, $CH_3$;
$R^3$ is independently selected from $CF_3$, $CHF_2$, $CH_2F$, and $CH_3$;
$R^4$ is H; and
$R^5$ is independently selected from F and Cl.

4. The isolated antigen binding peptide of claim 3, wherein the compound has Formula (II):

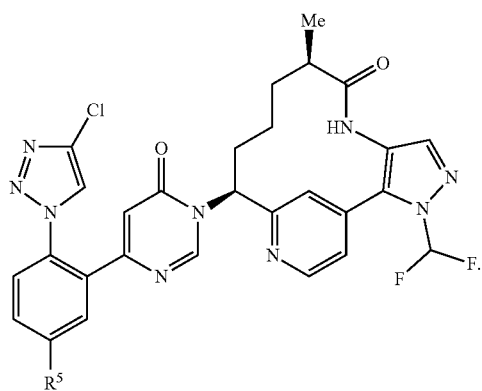

(II)

5. The isolated antigen binding peptide of claim 1, wherein said isolated antigen binding peptide is an antibody, a Fab, Fab', F(ab')2, Fd, single chain Fv or scFv, disulfide linked Fv, V-NAR domain, IgNar, intrabody, IgGACH2, minibody, F(ab')$_3$, tetrabody, triabody, diabody, single-domain antibody, DVD-Ig, Fcab, mAb$^2$, (scFv)$_2$, scFv-Fc, or a tandem Fab.

6. The isolated antigen binding peptide of claim 1, wherein the N-terminal portion of the heavy chain and full length light chain compriseing sequences selected from the group consisting of:

(a) SEQ ID NO: 100 and SEQ ID NO: 160, respectively;
(b) SEQ ID NO: 101 and SEQ ID NO: 160, respectively;
(c) SEQ ID NO: 102 and SEQ ID NO: 161, respectively;
(d) SEQ ID NO: 103 and SEQ ID NO: 161, respectively;
(e) SEQ ID NO: 104 and SEQ ID NO: 162, respectively;
(f) SEQ ID NO: 105 and SEQ ID NO: 162, respectively;
(g) SEQ ID NO: 104 and SEQ ID NO: 163, respectively;
(h) SEQ ID NO: 105 and SEQ ID NO: 163, respectively;
(i) SEQ ID NO: 106 and SEQ ID NO: 164, respectively;
(j) SEQ ID NO: 107 and SEQ ID NO: 164, respectively;
(k) SEQ ID NO: 108 and SEQ ID NO: 165, respectively;
(l) SEQ ID NO: 109 and SEQ ID NO: 165, respectively;
(m) SEQ ID NO: 110 and SEQ ID NO: 166, respectively;
(n) SEQ ID NO: 111 and SEQ ID NO: 166, respectively;
(o) SEQ ID NO: 112 and SEQ ID NO: 164, respectively;
(p) SEQ ID NO: 113 and SEQ ID NO: 164, respectively;
(q) SEQ ID NO: 114 and SEQ ID NO: 164, respectively;
(r) SEQ ID NO: 115 and SEQ ID NO: 164, respectively;
(s) SEQ ID NO: 116 and SEQ ID NO: 167, respectively;
(t) SEQ ID NO: 117 and SEQ ID NO: 167, respectively;
(u) SEQ ID NO: 118 and SEQ ID NO: 165, respectively;
(v) SEQ ID NO: 119 and SEQ ID NO: 165, respectively;
(w) SEQ ID NO: 110 and SEQ ID NO: 168, respectively;
(x) SEQ ID NO: 111 and SEQ ID NO: 168, respectively;
(y) SEQ ID NO: 116 and SEQ ID NO: 169, respectively;
(z) SEQ ID NO: 117 and SEQ ID NO: 169, respectively;
(aa) SEQ ID NO: 116 and SEQ ID NO: 164, respectively;
(bb) SEQ ID NO: 117 and SEQ ID NO: 164, respectively;
(cc) SEQ ID NO: 120 and SEQ ID NO: 164, respectively;
(dd) SEQ ID NO: 121 and SEQ ID NO: 164, respectively;
(ee) SEQ ID NO: 122 and SEQ ID NO: 164, respectively;
(ff) SEQ ID NO: 123 and SEQ ID NO: 164, respectively;
(gg) SEQ ID NO: 124 and SEQ ID NO: 164, respectively;
(hh) SEQ ID NO: 125 and SEQ ID NO: 164, respectively;
(ii) SEQ ID NO: 126 and SEQ ID NO: 170, respectively;
(jj) SEQ ID NO: 127 and SEQ ID NO: 170, respectively;
(kk) SEQ ID NO: 128 and SEQ ID NO: 164, respectively;
(ll) SEQ ID NO: 129 and SEQ ID NO: 164, respectively;
(mm) SEQ ID NO: 128 and SEQ ID NO: 171, respectively;
(nn) SEQ ID NO: 129 and SEQ ID NO: 171, respectively;
(oo) SEQ ID NO: 130 and SEQ ID NO: 164, respectively;
(pp) SEQ ID NO: 131 and SEQ ID NO: 164, respectively;
(qq) SEQ ID NO: 132 and SEQ ID NO: 169, respectively;
(rr) SEQ ID NO: 133 and SEQ ID NO: 169, respectively;
(ss) SEQ ID NO: 134 and SEQ ID NO: 164, respectively;
(tt) SEQ ID NO: 135 and SEQ ID NO: 164, respectively;
(uu) SEQ ID NO: 134 and SEQ ID NO: 171, respectively;
(vv) SEQ ID NO: 135 and SEQ ID NO: 171, respectively;
(ww) SEQ ID NO: 136 and SEQ ID NO: 164, respectively;
(xx) SEQ ID NO: 137 and SEQ ID NO: 164, respectively;
(yy) SEQ ID NO: 136 and SEQ ID NO: 171, respectively;
(zz) SEQ ID NO: 137 and SEQ ID NO: 171, respectively;
(aaa) SEQ ID NO: 138 and SEQ ID NO: 164, respectively;
(bbb) SEQ ID NO: 139 and SEQ ID NO: 164, respectively;
(ccc) SEQ ID NO: 138 and SEQ ID NO: 170, respectively;
(ddd) SEQ ID NO: 139 and SEQ ID NO: 170, respectively;
(eee) SEQ ID NO: 140 and SEQ ID NO: 164, respectively;
(fff) SEQ ID NO: 141 and SEQ ID NO: 164, respectively;
(ggg) SEQ ID NO: 142 and SEQ ID NO: 171, respectively;

(hhh) SEQ ID NO: 143 and SEQ ID NO: 171, respectively;
(iii) SEQ ID NO: 144 and SEQ ID NO: 164, respectively;
(jjj) SEQ ID NO: 145 and SEQ ID NO: 164, respectively;
(kkk) SEQ ID NO: 146 and SEQ ID NO: 164, respectively;
(lll) SEQ ID NO: 147 and SEQ ID NO: 164, respectively;
(mmm) SEQ ID NO: 148 and SEQ ID NO: 164, respectively;
(nnn) SEQ ID NO: 149 and SEQ ID NO: 164, respectively;
(ooo) SEQ ID NO: 150 and SEQ ID NO: 170, respectively;
(ppp) SEQ ID NO: 151 and SEQ ID NO: 170, respectively;
(qqq) SEQ ID NO: 152 and SEQ ID NO: 172, respectively;
(rrr) SEQ ID NO: 153 and SEQ ID NO: 172, respectively;
(sss) SEQ ID NO: 154 and SEQ ID NO: 173, respectively;
(ttt) SEQ ID NO: 155 and SEQ ID NO: 173, respectively;
(uuu) SEQ ID NO: 156 and SEQ ID NO: 174, respectively;
(vvV) SEQ ID NO: 157 and SEQ ID NO: 174, respectively;
(www) SEQ ID NO: 158 and SEQ ID NO: 175, respectively;
(xxx) SEQ ID NO: 159 and SEQ ID NO: 175, respectively;
(yyy) SEQ ID NO: 158 and SEQ ID NO: 174, respectively;
(zzz) SEQ ID NO: 159 and SEQ ID NO: 174, respectively;
(aaaa) SEQ ID NO: 176 and SEQ ID NO: 160, respectively;
(bbbb) SEQ ID NO: 177 and SEQ ID NO: 160, respectively;
(cccc) SEQ ID NO: 178 and SEQ ID NO: 160, respectively;
(dddd) SEQ ID NO: 179 and SEQ ID NO: 160, respectively;
(eeee) SEQ ID NO: 180 and SEQ ID NO: 164, respectively;
(ffff) SEQ ID NO: 181 and SEQ ID NO: 164, respectively;
(gggg) SEQ ID NO: 182 and SEQ ID NO: 164, respectively;
(hhhh) SEQ ID NO: 183 and SEQ ID NO: 164, respectively;
(iiii) SEQ ID NO: 184 and SEQ ID NO: 163, respectively;
(jjjj) SEQ ID NO: 185 and SEQ ID NO: 163, respectively;
(kkkk) SEQ ID NO: 186 and SEQ ID NO: 163, respectively;
(llll) SEQ ID NO: 187 and SEQ ID NO: 163, respectively;
(mmmm) SEQ ID NO: 184 and SEQ ID NO: 162, respectively;
(nnnn) SEQ ID NO: 185 and SEQ ID NO: 162, respectively;
(oooo) SEQ ID NO: 186 and SEQ ID NO: 162, respectively;
(pppp) SEQ ID NO: 187 and SEQ ID NO: 162, respectively;
(qqqq) SEQ ID NO: 188 and SEQ ID NO: 165, respectively;
(rrrr) SEQ ID NO: 189 and SEQ ID NO: 165, respectively;
(ssss) SEQ ID NO: 190 and SEQ ID NO: 165, respectively;
(tttt) SEQ ID NO: 191 and SEQ ID NO: 165, respectively;
(uuuu) SEQ ID NO: 192 and SEQ ID NO: 161, respectively;
(vvvv) SEQ ID NO: 193 and SEQ ID NO: 161, respectively;
(wwww) SEQ ID NO: 194 and SEQ ID NO: 161, respectively; and
(xxxx) SEQ ID NO: 195 and SEQ ID NO: 161, respectively;

wherein said isolated antigen binding peptide specifically binds to the compound of Formula (II):

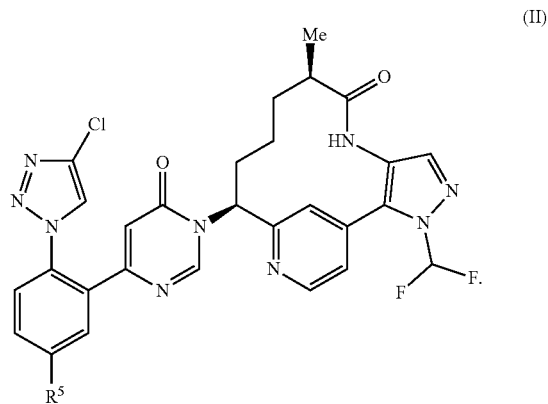

7. The isolated antigen binding peptide of claim 6, comprising sequences SEQ ID NO: 106 and SEQ ID NO: 164, respectively.

8. The isolated antigen binding peptide of claim 7, wherein the isolated antigen binding peptide is an antibody Fab fragment.

9. The isolated antigen binding peptide of claim 6, comprising sequences SEQ ID NO: 180 and SEQ ID NO: 164, respectively.

10. The isolated antigen binding peptide of claim 9, wherein the antigen binding peptide is an antibody tandem Fab fragment.

11. An isolated polynucleotide comprising a nucleic acid sequence encoding the antigen binding peptide of claim 1.

12. A vector comprising the isolated polynucleotide of claim 11.

13. A host cell comprising the vector of claim 12.

14. A method of making an antigen binding peptide comprising (a) culturing the host cell of claim 13 under culture conditions that promote protein production such that the host cell produces the antigen binding peptide, and (b) isolating said antigen binding peptide from said culture.

15. A detection reagent comprising the isolated antigen binding peptide of claim 1 and a detectable label.

16. A method of reducing the antithrombotic effect of the compound of Formula (I) or a stereoisomer or a tautomer thereof, in a subject in need thereof, comprising administering to the subject a pharmaceutically effective dose of the isolated antigen binding peptide of claim 1, wherein the isolated antigen binding peptide specifically binds to the compound set forth in Formula (I):

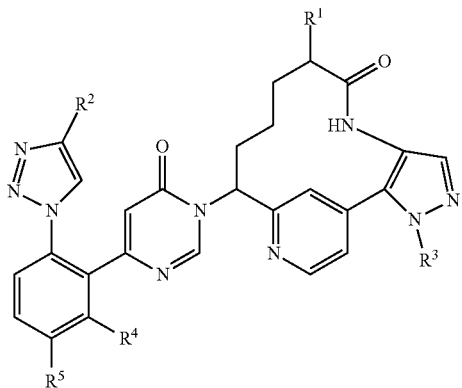

(I)

R[1] is $C_{1-4}$ alkyl;
R[2] is independently selected from F, Cl, $CF_3$, $CHF_2$, $CH_2F$, $CH_3$;
R[3] is independently selected from $CF_3$, $CHF_2$, $CH_2F$, and $CH_3$;
R[4] is H; and
R[5] is independently selected from F and Cl.

17. A method of detecting the level of a compound of Formula (I) or a stereoisomer, a tautomer, or a pharmaceutically acceptable salt thereof, in a biological sample, wherein:

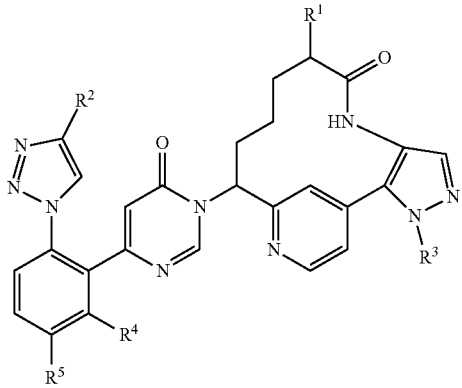

(I)

R[1] is $C_{1-4}$ alkyl;
R[2] is independently selected from F, Cl, $CF_3$, $CHF_2$, $CH_2F$, $CH_3$;
R[3] is independently selected from $CF_3$, $CHF_2$, $CH_2F$, and $CH_3$;
R[4] is H; and
R[5] is independently selected from F and Cl; the method comprising:
(a) contacting the biological sample with the isolated antigen binding peptide of claim 1, and
(b) detecting the level of a bound complex of the compound and the isolated antigen binding peptide.

18. A method of binding a compound of Formula (I) or a stereoisomer or a tautomer thereof, in a subject who is taking therapeutically effective amount of the compound of Formula (I) or a stereoisomer or a tautomer thereof, comprising administering to the subject a pharmaceutically effective dose of the isolated antigen binding peptide of claim 1, wherein

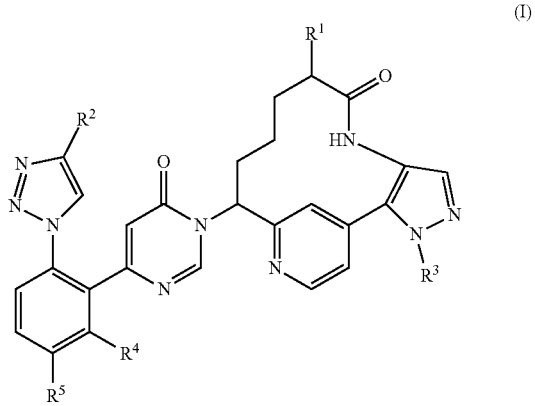

(I)

R[1] is $C_{1-4}$ alkyl;
R[2] is independently selected from F, Cl, $CF_3$, $CHF_2$, $CH_2F$, $CH_3$;
R[3] is independently selected from $CF_3$, $CHF_2$, $CH_2F$, and $CH_3$;
R[4] is H; and
R[5] is independently selected from F and Cl.

* * * * *

UNITED STATES PATENT AND TRADEMARK OFFICE
CERTIFICATE OF CORRECTION

Page 1 of 2

PATENT NO. : 12,065,505 B2
APPLICATION NO. : 17/570649
DATED : August 20, 2024
INVENTOR(S) : Joseph M. Luettgen et al.

It is certified that error appears in the above-identified patent and that said Letters Patent is hereby corrected as shown below:

In the Claims

In Column 337, at Lines 40-55, in Claim 4, delete " 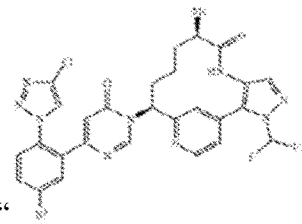 " and insert

 --.

In Column 337, at Line 66, in Claim 6, delete "compriseing" and insert -- comprise --.

In Column 340, at Lines 13-29, in Claim 6, delete " 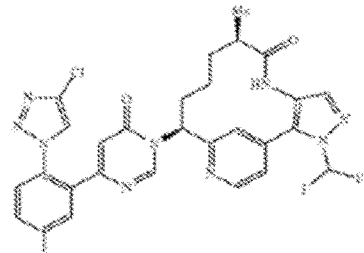 " and insert

Signed and Sealed this
Fourth Day of March, 2025

Coke Morgan Stewart
*Acting Director of the United States Patent and Trademark Office*

CERTIFICATE OF CORRECTION (continued)
U.S. Pat. No. 12,065,505 B2

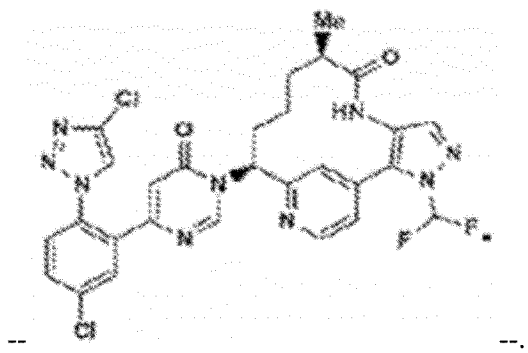

-- --.

SEQUENCE LISTING

```
<160> NUMBER OF SEQ ID NOS: 222

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Asn Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Asn Ala Val Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Asn Ala Phe Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Asn Gln Phe Ser
```

```
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Asn Asp Met Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Asn Ala Ile Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Asn Ala Met Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Asn Tyr Met Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Asn Tyr Met Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 10

Ser Gly Tyr Tyr Trp Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly His Tyr Trp Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Asn Tyr Met Ser
1               5

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ile Tyr Pro Gly Gly Arg Thr Tyr Tyr Ala Asp Ser Val Lys Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Ile Tyr Pro Gly Gly Arg Thr Tyr Tyr Ala Asp Ser Val Lys Gly
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ile Tyr Ser Gly Gly Arg Thr Tyr Tyr Ala Asp Ser Val Lys Gly
1               5                   10                  15

<210> SEQ ID NO 16

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Phe Tyr Pro Gly Gly Arg Thr Tyr Tyr Ala Asp Ser Val Lys Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Ile Tyr Ser Gly Gly Arg Thr Tyr Tyr Ala Asp Ser Val Lys Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Ile Tyr Pro Gly Gly Glu Thr Tyr Tyr Ala Asp Ser Val Lys Gly
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Ile Tyr Ser Gly Gly Glu Thr Phe Tyr Ala Asp Ser Val Lys Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Ile Tyr His Ser Gly Asn Thr Tyr Tyr Ser Pro Ser Leu Gln Ser
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

```
Gly Ile Tyr His Ser Gly Thr Thr Tyr Tyr Asn Pro Ser Leu Lys Ser
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Ile Tyr Ser Gly Gly Ser Thr Tyr Tyr Ala Asp Ser Val Lys Gly
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Gly Phe Gly Gly Pro Asp Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Gly Phe Gly Gly Gly Asp Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Glu Phe Gly Leu Glu Asp Ile
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Phe Gly Gly Gly Asp Tyr
1               5

<210> SEQ ID NO 27
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 27

Gly Gly Asp Phe Asp Ile Leu Thr Gly Tyr Tyr Lys Gly Trp Phe Glu
1               5                   10                  15
Pro

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Gly Tyr Tyr Asp Ile Leu Thr Gly Tyr Tyr Asn Gln Tyr Phe Gln
1               5                   10                  15
His

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Gly Ile Ser Ser Asn Leu Ala
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Gln Gly Ile Tyr Ser Asn Leu Ala
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ala Ser Gln Gly Ile Ser Ser Asn Asn Gln
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Arg Ala Ser Gln Gly Ile Ser Ser Gln Val Ala
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Gly Ile Ser Ser Trp Leu Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ala Ser Gln Tyr Ile Ser Ser Asn Leu Ala
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Ser Gln Tyr Ile Glu Ser Asn Leu Ala
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser Gln Gly Ile Ser Ser Ala Leu Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Ser Gln Ser Val Ser Ser Ser Tyr Leu Ala
1               5                   10

<210> SEQ ID NO 38
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 38

Ala Ala Ser Ser Leu Gln Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Ser Thr Leu Gln Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Ala Ser Ser Leu Gln Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Ala Ser Asn Leu Trp Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ala Ser Ser Leu Glu Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ala Ser Ser Arg Ala Thr
1               5
```

```
<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Ala Asn Gln Phe Pro Leu Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Ala Asn Glu Phe Pro Leu Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Ala Asn Ser Phe Pro Leu Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Gly Asn Glu Phe Pro Leu Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Ala Asn Asn Phe Pro Leu Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

Gln Gln His Asn Ser Phe Pro Leu Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Phe Asn Ser Tyr Pro Gln Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Gly Ser Ser Pro Phe Thr
1               5

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Ile Gln Pro Gly Gly

```
                1               5                   10                  15
        Ser Leu Arg Leu Ser Cys Ala Ala Ser Gly Phe Thr Val Ser Ser Asn
                        20                  25                  30

Ala Met Ser Trp Val Arg Gln Ala Pro Gly Lys Gly Leu Glu Trp Val
                        35                  40                  45

Ser Phe Ile Tyr Pro Gly Gly Arg Thr Tyr Tyr Ala Asp Ser Val Lys
                        50                  55                  60

Gly Arg Phe Thr Ile Ser Arg Asp Asn Ser Lys Asn Thr Leu Tyr Leu
         65                  70                  75                  80

Gln Met Asn Ser Leu Arg Ala Glu Asp Thr Ala Val Tyr Tyr Cys Ala
                        85                  90                  95

Arg Ala Gly Phe Gly Gly Pro Asp Tyr Trp Gly Gln Gly Thr Leu Val
                        100                 105                 110

Thr Val Ser Ser
                115

<210> SEQ ID NO 54
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Gly Leu Ile Gln Pro Gly Gly
         1               5                   10                  15

Ser Leu Arg Leu Ser Cys Ala Ala Ser Gly Phe Thr Val Ser Ser Asn
                        20                  25                  30

Ala Met Ser Trp Val Arg Gln Ala Pro Gly Lys Gly Leu Glu Trp Val
                        35                  40                  45

Ser Tyr Ile Tyr Pro Gly Gly Arg Thr Tyr Tyr Ala Asp Ser Val Lys
                        50                  55                  60

Gly Arg Phe Thr Ile Ser Arg Asp Asn Ser Lys Asn Thr Leu Tyr Leu
         65                  70                  75                  80

Gln Met Asn Ser Leu Arg Ala Glu Asp Thr Ala Val Tyr Tyr Cys Ala
                        85                  90                  95

Arg Ala Gly Phe Gly Gly Gly Asp Tyr Trp Gly Gln Gly Thr Leu Val
                        100                 105                 110

Thr Val Ser Ser
                115

<210> SEQ ID NO 55
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Ile Gln Pro Gly Gly
         1               5                   10                  15

Ser Leu Arg Leu Ser Cys Ala Ala Ser Gly Phe Thr Val Ser Ser Asn
                        20                  25                  30

Ala Met Ser Trp Val Arg Gln Ala Pro Gly Lys Gly Leu Glu Trp Val
                        35                  40                  45

Ser Phe Ile Tyr Pro Gly Gly Arg Thr Tyr Tyr Ala Asp Ser Val Lys
```

```
                  50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Glu Phe Gly Leu Glu Asp Ile Trp Gly Gln Gly Thr Leu Val
            100                 105                 110

Thr Val Ser Ser
        115

<210> SEQ ID NO 56
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
            20                  25                  30

Ala Val Ser Ile Val Arg Gln Ala Pro Gly Lys Gly Leu Glu Trp Val
        35                  40                  45

Ala Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Ile Gly Gly Phe Gly Gly Gly Asp Tyr Trp Gly Gln Gly Thr Leu Val
            100                 105                 110

Thr Val Ser Ser
        115

<210> SEQ ID NO 57
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
            20                  25                  30

Ala Phe Ser Trp Val Arg Gln Ala Pro Gly Lys Gly Leu Glu Trp Val
        35                  40                  45

Ser Tyr Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Ala Gly Phe Gly Gly Gly Asp Tyr Trp Gly Gln Gly Thr Leu Val
```

-continued

```
                100                 105                 110
Thr Val Ser Ser
        115

<210> SEQ ID NO 58
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Gln Phe Ser Trp Val Arg Gln Ala Pro Gly Lys Gly Leu Glu Trp Val
        35                  40                  45

Ser Tyr Phe Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ala Gly Phe Gly Gly Gly Asp Tyr Trp Gly Gln Gly Thr Leu Val
            100                 105                 110

Thr Val Ser Ser
        115

<210> SEQ ID NO 59
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Asp Met Ser Tyr Val Arg Gln Ala Pro Gly Lys Gly Leu Glu Trp Val
        35                  40                  45

Ala Tyr Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Thr Ala Gly Phe Gly Gly Gly Asp Tyr Trp Gly Gln Gly Thr Leu Val
            100                 105                 110

Thr Val Ser Ser
        115

<210> SEQ ID NO 60
<211> LENGTH: 116
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 61
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Ile Ala Trp Val Arg Gln Ala Pro Gly Lys Gly Leu Glu Trp Val
        35                  40                  45

Ala Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Thr Ala Gly Phe Gly Gly Gly Asp Tyr Trp Gly Gln Gly Thr Leu Val
            100                 105                 110

Thr Val Ser Ser
        115

<210> SEQ ID NO 62
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Gly Leu Ile Gln Pro Gly Gly
1               5                   10                  15

```
Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 64
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
 50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 65
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 66
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 67
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 68
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 69
<211> LENGTH: 116
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 70
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 71
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Ile Gln Pro Gly Gly
1               5                   10                  15
```

```
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 72
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Glu Thr Tyr Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 74
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser
        115

<210> SEQ ID NO 75
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 76
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Glu Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 77
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Ile Gln Pro Gly Gly
1               5                   10                  15

Ser Leu Arg Leu Ser Cys Ala Ala Ser Gly Ile Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 78
<211> LENGTH: 126
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Asn Thr Tyr Tyr Ser Pro Ser Leu
    50                  55                  60

Gln Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Asp Phe Asp Ile Leu Thr Gly Tyr Tyr Lys Gly Trp
            100                 105                 110

Phe Glu Pro Trp Gly Gln Gly Thr Leu Val Thr Val Ser Ser
        115                 120                 125

<210> SEQ ID NO 79
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Ser Trp Ile Arg Gln Pro Pro Gly Lys Gly Leu Glu Trp
        35                  40                  45

Ile Gly Gly Ile Tyr His Ser Gly Thr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Tyr Tyr Asp Ile Leu Thr Gly Tyr Tyr Asn Gln Tyr
            100                 105                 110

Phe Gln His Trp Gly Gln Gly Thr Leu Val Thr Val Ser Ser
        115                 120                 125

<210> SEQ ID NO 80
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Asn

```
              20                  25                  30

Tyr Met Ser Trp Val Arg Gln Ala Pro Gly Lys Gly Leu Glu Trp Val
            35                  40                  45

Ser Phe Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 81
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
            35                  40                  45

Ser Phe Ile Tyr Ser Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser
        115

<210> SEQ ID NO 82
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Phe Ile Tyr Ser Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
```

```
                65                  70                  75                  80
Gln Met Asn Ser Leu Arg Ala Glu Asp Thr Ala Val Tyr Tyr Cys Ala
                    85                  90                  95

Arg Gly Gly Phe Gly Gly Gly Asp Tyr Trp Gly Gln Gly Thr Leu Val
                100                 105                 110

Thr Val Ser Ser
        115

<210> SEQ ID NO 83
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Ala Leu Ile Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Phe Ile Tyr Ser Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                    85                  90                  95

Arg Gly Gly Phe Gly Gly Gly Asp Tyr Trp Gly Gln Gly Thr Leu Val
                100                 105                 110

Thr Val Ser Ser
        115

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gln Phe Pro Leu
                    85                  90                  95

Thr Phe Gly Gly Gly Thr Lys Val Glu Ile Lys
                100                 105
```

```
<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Glu Phe Pro Leu
                85                  90                  95

Thr Phe Gly Gly Gly Thr Lys Val Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Glu Phe Pro Leu
                85                  90                  95

Thr Phe Gly Gly Gly Thr Lys Val Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30
```

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Glu Phe Pro Leu
                85                  90                  95

Thr Phe Gly Gly Gly Thr Lys Val Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Asn Gln Trp Tyr Gln Gln Lys Pro Gly Lys Ala Pro Lys Leu Leu Ile
            35                  40                  45

Tyr Tyr Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Glu Phe Pro Leu
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Gln
            20                  25                  30

Val Ala Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Glu Phe Pro Leu
                85                  90                  95

Thr Phe Gly Gly Gly Thr Lys Val Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Leu Ala Trp Trp Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Gln
            20                  25                  30

Val Ala Trp Tyr Gln Gln Lys Pro Gly Lys Ala Pro Lys Leu Leu Ile
        35                  40                  45

Tyr Pro Ala Ser Asn Leu Trp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Val Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Ser Phe Pro Leu
                85                  90                  95

Thr Phe Gly Gly Gly Thr Lys Val Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Tyr Ile Ser Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

```
Thr Phe Gly Gly Gly Thr Lys Val Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Tyr Ile Glu Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Gln
                85                  90                  95

Thr Phe Gly Gln Gly Thr Lys Val Glu Ile Lys
            100                 105

<210> SEQ ID NO 97
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Ile Val Leu Thr Gln Ser Pro Gly Thr Leu Ser Leu Ser Pro Gly
```

```
            1               5                  10                 15
Glu Arg Ala Thr Leu Ser Cys Arg Ala Ser Gln Ser Val Ser Ser
                20                  25                 30

Tyr Leu Ala Trp Tyr Gln Gln Lys Pro Gly Gln Ala Pro Arg Leu Leu
                35                  40                 45

Ile Tyr Gly Ala Ser Ser Arg Ala Thr Gly Ile Pro Asp Arg Phe Ser
        50                  55                 60

Gly Ser Gly Ser Gly Thr Asp Phe Thr Leu Thr Ile Ser Arg Leu Glu
65                  70                  75                 80

Pro Glu Asp Phe Ala Val Tyr Tyr Cys Gln Gln Tyr Gly Ser Ser Pro
                85                  90                 95

Phe Thr Phe Gly Pro Gly Thr Lys Val Asp Ile Lys
                100                 105

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Val Ser Ala Ser Val Gly
1               5                   10                 15

Asp Arg Val Thr Ile Thr Cys Arg Ala Ser Gln Gly Ile Ser Ser Trp
                20                  25                 30

Leu Ala Trp Tyr Gln His Lys Pro Gly Lys Ala Pro Lys Leu Leu Ile
                35                  40                 45

Tyr Ala Ala Ser Ser Leu Gln Ser Gly Val Pro Ser Arg Phe Ser Gly
        50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Ala Asn Ser Phe Pro Leu
                85                  90                 95

Thr Phe Gly Gly Gly Thr Lys Val Glu Ile Lys
                100                 105

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Val Ser Ala Ser Val Gly
1               5                   10                 15

Asp Arg Val Thr Ile Thr Cys Arg Ala Ser Gln Gly Ile Ser Ser Trp
                20                  25                 30

Leu Ala Trp Tyr Gln Gln Lys Pro Gly Lys Ala Pro Lys Leu Leu Ile
                35                  40                 45

Tyr Ala Ala Ser Ser Leu Gln Ser Gly Val Pro Ser Arg Phe Ser Gly
        50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Ala Asn Ser Phe Pro Leu
```

Thr Phe Gly Gly Gly Thr Lys Val Glu Ile Lys
                100                 105

<210> SEQ ID NO 100
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 101
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys

```
            50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Gly Phe Gly Gly Pro Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His
    210                 215                 220

<210> SEQ ID NO 102
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                20                  25                  30

Ala Met Ser Trp Val Arg Gln Ala Pro Gly Lys Gly Leu Glu Trp Val
            35                  40                  45

Ser Phe Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Gly Phe Gly Gly Pro Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190
```

Gly Thr Gln Thr Tyr Ile Cys Asn Val Asn His Lys Pro Ser Asn Thr
            195                 200                 205

Lys Val Asp Lys Arg Val Glu Pro Lys Ser Cys
    210                 215

<210> SEQ ID NO 103
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His
    210                 215                 220

<210> SEQ ID NO 104
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

```
Ser Tyr Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
210                 215

<210> SEQ ID NO 105
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                 20                  25                  30

Ala Met Ser Trp Val Arg Gln Ala Pro Gly Lys Gly Leu Glu Trp Val
             35                  40                  45

Ser Tyr Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His
    210                 215                 220
```

<210> SEQ ID NO 106
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Glu Phe Gly Leu Glu Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215
```

<210> SEQ ID NO 107
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45
```

Ser Phe Ile Tyr Pro Gly Gly Arg Thr Tyr Tyr Ala Asp Ser Val Lys
            50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Glu Phe Gly Leu Glu Asp Ile Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His
    210                 215                 220

<210> SEQ ID NO 108
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                 20                  25                  30

Ala Val Ser Ile Val Arg Gln Ala Pro Gly Lys Gly Leu Glu Trp Val
                 35                  40                  45

Ala Tyr Ile Tyr Pro Gly Gly Arg Thr Tyr Tyr Ala Asp Ser Val Lys
            50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Ile Gly Gly Phe Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu

```
                180                 185                 190
Gly Thr Gln Thr Tyr Ile Cys Asn Val Asn His Lys Pro Ser Asn Thr
            195                 200                 205
Lys Val Asp Lys Arg Val Glu Pro Lys Ser Cys
        210                 215
```

<210> SEQ ID NO 109
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Thr Val Ser Ser Asn
            20                  25                  30
Ala Val Ser Ile Val Arg Gln Ala Pro Gly Lys Gly Leu Glu Trp Val
        35                  40                  45
Ala Tyr Ile Tyr Pro Gly Gly Arg Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Thr
                85                  90                  95
Ile Gly Gly Phe Gly Gly Gly Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His
    210                 215                 220
```

<210> SEQ ID NO 110
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Thr Val Ser Ser Asn
            20                  25                  30
Ala Phe Ser Trp Val Arg Gln Ala Pro Gly Lys Gly Leu Glu Trp Val
```

```
                   35                  40                  45
Ser Tyr Ile Tyr Ser Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Ala Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys
    210                 215

<210> SEQ ID NO 111
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Ser Ser Asn
                 20                  25                  30

Ala Phe Ser Trp Val Arg Gln Ala Pro Gly Lys Gly Leu Glu Trp Val
                 35                  40                  45

Ser Tyr Ile Tyr Ser Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Ala Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220
```

<210> SEQ ID NO 112
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Gln Phe Ser Trp Val Arg Gln Ala Pro Gly Lys Gly Leu Glu Trp Val
        35                  40                  45

Ser Tyr Phe Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ala Gly Phe Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215
```

<210> SEQ ID NO 113
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30
```

```
Gln Phe Ser Trp Val Arg Gln Ala Pro Gly Lys Gly Leu Glu Trp Val
             35                  40                  45
Ser Tyr Phe Tyr Pro Gly Gly Arg Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Lys Ala Gly Phe Gly Gly Gly Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Arg Val Glu Pro Lys Ser Cys Asp Lys Thr His
                210                 215                 220

<210> SEQ ID NO 114
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Ile Gln Pro Gly Gly
  1               5                  10                  15
Ser Leu Arg Leu Ser Cys Ala Ala Ser Gly Phe Thr Val Ser Ser Asn
                 20                  25                  30
Asp Met Ser Tyr Val Arg Gln Ala Pro Gly Lys Gly Leu Glu Trp Val
                 35                  40                  45
Ala Tyr Ile Tyr Ser Gly Gly Arg Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Val
                 85                  90                  95
Thr Ala Gly Phe Gly Gly Gly Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
        210                 215

<210> SEQ ID NO 115
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Asp Met Ser Tyr Val Arg Gln Ala Pro Gly Lys Gly Leu Glu Trp Val
        35                  40                  45

Ala Tyr Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Thr Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 116
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30
```

```
Ala Met Ser Trp Val Arg Gln Ala Pro Gly Lys Gly Leu Glu Trp Val
            35                  40                  45

Ser Phe Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
            210                 215

<210> SEQ ID NO 117
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
            35                  40                  45

Ser Phe Ile Tyr Pro Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                    165                 170                 175
Gly Leu Tyr Ser Leu Ser Ser Val Val Thr Val Pro Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His
        210                 215                 220

<210> SEQ ID NO 118
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Ile Ala Trp Val Arg Gln Ala Pro Gly Lys Gly Leu Glu Trp Val
        35                  40                  45

Ala Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Thr Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 119
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
```

-continued

```
                    20                  25                  30
Ala Ile Ala Trp Val Arg Gln Ala Pro Gly Lys Gly Leu Glu Trp Val
            35                  40                  45

Ala Tyr Ile Tyr Pro Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Val
                85                  90                  95

Thr Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220
```

<210> SEQ ID NO 120
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 121
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 122
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Glu Ser Gly Gly Gly Leu Ile Gln Pro Gly Gly
1               5                   10                  15
```

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 123
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His
    210                 215                 220

<210> SEQ ID NO 124
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
    210                 215

<210> SEQ ID NO 125
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Leu Ile Gln Pro Gly Gly
1               5                   10                  15
```

```
Ser Leu Arg Leu Ser Cys Ala Ala Ser Gly Phe Thr Val Ser Glu Asn
             20                  25                  30

Ala Met Ser Trp Val Arg Gln Ala Pro Gly Lys Gly Leu Glu Trp Val
         35                  40                  45

Ser Phe Ile Tyr Ser Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Gly Gly Phe Gly Gly Gly Asp Tyr Trp Gly Gln Gly Thr Leu Val
             100                 105                 110

Thr Val Ser Ser Ala Ser Thr Lys Gly Pro Ser Val Phe Pro Leu Ala
             115                 120                 125

Pro Ser Ser Lys Ser Thr Ser Gly Gly Thr Ala Ala Leu Gly Cys Leu
 130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
             165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
             195                 200                 205

Lys Val Asp Lys Arg Val Glu Pro Lys Ser Cys Asp Lys Thr His
     210                 215                 220

<210> SEQ ID NO 126
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
             20                  25                  30

Tyr Met Ser Trp Val Arg Gln Ala Pro Gly Lys Gly Leu Glu Trp Val
         35                  40                  45

Ser Phe Ile Tyr Ser Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Ala Gly Phe Gly Gly Gly Asp Tyr Trp Gly Gln Gly Thr Leu Val
             100                 105                 110

Thr Val Ser Ser Ala Ser Thr Lys Gly Pro Ser Val Phe Pro Leu Ala
             115                 120                 125

Pro Ser Ser Lys Ser Thr Ser Gly Gly Thr Ala Ala Leu Gly Cys Leu
 130                 135                 140

Val Lys Asp Tyr Phe Pro Glu Pro Val Thr Val Ser Trp Asn Ser Gly
```

```
                145                 150                 155                 160
Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
                    180                 185                 190

Gly Thr Gln Thr Tyr Ile Cys Asn Val Asn His Lys Pro Ser Asn Thr
                    195                 200                 205

Lys Val Asp Lys Arg Val Glu Pro Lys Ser Cys
                    210                 215
```

<210> SEQ ID NO 127
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
                20                  25                  30

Tyr Met Ser Trp Val Arg Gln Ala Pro Gly Lys Gly Leu Glu Trp Val
            35                  40                  45

Ser Phe Ile Tyr Ser Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His
            210                 215                 220
```

<210> SEQ ID NO 128
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Glu Val Gln Leu Val Glu Ser Gly Gly Gly Leu Ile Gln Pro Gly Gly
```

```
            1               5                  10                 15
Ser Leu Arg Leu Ser Cys Ala Ala Ser Gly Phe Gln Val Ser Ser Asn
                20                  25                 30

Ala Met Ser Trp Val Arg Gln Ala Pro Gly Lys Gly Leu Glu Trp Val
            35                  40                 45

Ser Phe Ile Tyr Ser Gly Gly Arg Thr Tyr Tyr Ala Asp Ser Val Lys
         50                  55                 60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Phe Gly Gly Gly Asp Tyr Trp Gly Gln Gly Thr Leu Val
             100                 105                110

Thr Val Ser Ser Ala Ser Thr Lys Gly Pro Ser Val Phe Pro Leu Ala
             115                 120                125

Pro Ser Ser Lys Ser Thr Ser Gly Gly Thr Ala Ala Leu Gly Cys Leu
         130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
         195                 200                 205

Lys Val Asp Lys Arg Val Glu Pro Lys Ser Cys
     210                 215
```

<210> SEQ ID NO 129
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Glu Val Gln Leu Val Glu Ser Gly Gly Gly Leu Ile Gln Pro Gly Gly
 1               5                  10                 15

Ser Leu Arg Leu Ser Cys Ala Ala Ser Gly Phe Gln Val Ser Ser Asn
                20                  25                 30

Ala Met Ser Trp Val Arg Gln Ala Pro Gly Lys Gly Leu Glu Trp Val
            35                  40                 45

Ser Phe Ile Tyr Ser Gly Gly Arg Thr Tyr Tyr Ala Asp Ser Val Lys
         50                  55                 60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Phe Gly Gly Gly Asp Tyr Trp Gly Gln Gly Thr Leu Val
             100                 105                110

Thr Val Ser Ser Ala Ser Thr Lys Gly Pro Ser Val Phe Pro Leu Ala
             115                 120                125

Pro Ser Ser Lys Ser Thr Ser Gly Gly Thr Ala Ala Leu Gly Cys Leu
         130                 135                 140
```

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His
    210                 215                 220

<210> SEQ ID NO 130
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
    210                 215

<210> SEQ ID NO 131
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Phe Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
210                 215                 220

<210> SEQ ID NO 132
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215
```

<210> SEQ ID NO 133
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220
```

<210> SEQ ID NO 134
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Phe Gly Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys
    210                 215

<210> SEQ ID NO 135
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Phe Gly Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
```

```
                130                 135                 140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His
                210                 215                 220

<210> SEQ ID NO 136
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
                20                  25                  30

Tyr Met Ser Trp Val Arg Gln Ala Pro Gly Lys Gly Leu Glu Trp Val
                35                  40                  45

Ser Phe Ile Tyr Ser Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys
                210                 215

<210> SEQ ID NO 137
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 137

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 138
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215
```

<210> SEQ ID NO 139
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220
```

<210> SEQ ID NO 140
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys
    210                 215

<210> SEQ ID NO 141
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

```
Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
210                 215                 220
```

<210> SEQ ID NO 142
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Glu Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
210                 215
```

<210> SEQ ID NO 143
<211> LENGTH: 223
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 143

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Glu Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 144
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala

```
                115                 120                 125
Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
210                 215

<210> SEQ ID NO 145
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
210                 215                 220

<210> SEQ ID NO 146
<211> LENGTH: 219
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 146

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 147
<211> LENGTH: 223
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 147

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Gln Val Ser Glu Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
210                 215                 220
```

<210> SEQ ID NO 148
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Glu Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
210                 215
```

<210> SEQ ID NO 149
<211> LENGTH: 223
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 149

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Glu Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 150
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Gln Leu Val Glu Ser Gly Gly Gly Leu Ile Gln Pro Gly Gly
1               5                   10                  15

Ser Leu Arg Leu Ser Cys Ala Ala Ser Gly Ile Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Gly Gly Asp Tyr Trp Gly Gln Gly Thr Leu Val
            100                 105                 110
```

```
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 151
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Val Glu Ser Gly Gly Gly Leu Ile Gln Pro Gly Gly
1               5                   10                  15

Ser Leu Arg Leu Ser Cys Ala Ala Ser Gly Ile Thr Val Ser Ser Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Phe Gly Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 152
<211> LENGTH: 229
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Asn Thr Tyr Tyr Ser Pro Ser Leu
    50                  55                  60

Gln Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Asp Phe Asp Ile Leu Thr Gly Tyr Tyr Lys Gly Trp
            100                 105                 110

Phe Glu Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys
225

<210> SEQ ID NO 153
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Asn Thr Tyr Tyr Ser Pro Ser Leu
    50                  55                  60

Gln Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys

```
                    85                  90                  95
Ala Arg Gly Gly Asp Phe Asp Ile Leu Thr Gly Tyr Tyr Lys Gly Trp
            100                 105                 110

Phe Glu Pro Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Arg Val
    210                 215                 220

Glu Pro Lys Ser Cys Asp Lys Thr His
225                 230

<210> SEQ ID NO 154
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Ser Trp Ile Arg Gln Pro Pro Gly Lys Gly Leu Glu Trp
        35                  40                  45

Ile Gly Gly Ile Tyr His Ser Gly Thr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Tyr Tyr Asp Ile Leu Thr Gly Tyr Tyr Asn Gln Tyr
            100                 105                 110

Phe Gln His Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205
```

```
Cys Asn Val Asn His Lys Pro Ser Asn Thr Lys Val Asp Lys Arg Val
        210                 215                 220

Glu Pro Lys Ser Cys
225
```

<210> SEQ ID NO 155
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Ser Trp Ile Arg Gln Pro Pro Gly Lys Gly Leu Glu Trp
        35                  40                  45

Ile Gly Gly Ile Tyr His Ser Gly Thr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Tyr Tyr Asp Ile Leu Thr Gly Tyr Tyr Asn Gln Tyr
            100                 105                 110

Phe Gln His Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His
225                 230
```

<210> SEQ ID NO 156
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Asn
            20                  25                  30
```

```
Tyr Met Ser Trp Val Arg Gln Ala Pro Gly Lys Gly Leu Glu Trp Val
            35                  40                  45

Ser Phe Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 157
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Arg Asn
                20                  25                  30

Tyr Met Ser Trp Val Arg Gln Ala Pro Gly Lys Gly Leu Glu Trp Val
            35                  40                  45

Ser Phe Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
    210                 215                 220

<210> SEQ ID NO 158
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Phe Gly Gly Gly Asp Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys
    210                 215

<210> SEQ ID NO 159
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
        35                  40                  45

Ser Phe Ile Tyr Ser Gly Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His
        210                 215                 220

<210> SEQ ID NO 160
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Gln Phe Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser 165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 161
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Glu Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Asn

```
                20                  25                  30
Leu Ala Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Glu Phe Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 163
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Asn
            20                  25                  30
Leu Ala Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Glu Phe Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 164
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 165
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Gly Ile Ser Ser Asn
            20                  25                  30

Asn Gln Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Glu Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Gln
            20                  25                  30

Val Ala Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Glu Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 167
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Asn
            20                  25                  30

Leu Ala Trp Trp Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 168
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Gly Ile Ser Ser Gln
             20                  25                  30

Val Ala Trp Tyr Gln Gln Lys Pro Gly Lys Ala Pro Lys Leu Leu Ile
         35                  40                  45

Tyr Pro Ala Ser Asn Leu Trp Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Asn Phe Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 169
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Asn Ser Phe Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
```

145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 170
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Tyr Ile Ser Ser Asn
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 171
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Ile Gln Met Thr Gln Ser Pro Ser Ser Val Ser Ala Ser Val Gly

```
                1               5                   10                  15
        Asp Arg Val Thr Ile Thr Cys Arg Ala Ser Gln Tyr Ile Glu Ser Asn
                        20                  25                  30

Leu Ala Trp Tyr Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                        50                  55                  60

Ser Gly Ser Gly Thr Asp Phe Thr Leu Thr Ile Ser Ser Leu Gln Pro
        65                      70                  75                  80

Glu Asp Phe Ala Thr Tyr Tyr Cys Gln Gln Ala Asn Ser Phe Pro Leu
                        85                  90                  95

Thr Phe Gly Gly Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Lys Val Asp Asn Ala Leu Gln Ser Gly Asn Ser Gln
        145                     150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                        210

<210> SEQ ID NO 172
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Ala Ile Gln Leu Thr Gln Ser Pro Ser Ser Leu Ser Ala Ser Val Gly
        1               5                   10                  15

Asp Arg Val Thr Ile Thr Cys Arg Ala Ser Gln Gly Ile Ser Ser Ala
                        20                  25                  30

Leu Ala Trp Tyr Gln Gln Lys Pro Gly Lys Ala Pro Lys Leu Leu Ile
                        35                  40                  45

Tyr Asp Ala Ser Ser Leu Glu Ser Gly Val Pro Ser Arg Phe Ser Gly
                        50                  55                  60

Ser Gly Ser Gly Thr Asp Phe Thr Leu Thr Ile Ser Ser Leu Gln Pro
        65                      70                  75                  80

Glu Asp Phe Ala Thr Tyr Tyr Cys Gln Gln Phe Asn Ser Tyr Pro Gln
                        85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 173
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215
```

<210> SEQ ID NO 174
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 175
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 176
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220

Pro Glu Val Gln Leu Val Glu Ser Gly Gly Gly Leu Ile Gln Pro Gly
225                 230                 235                 240

Gly Ser Leu Arg Leu Ser Cys Ala Ala Ser Gly Phe Thr Val Ser Ser
                245                 250                 255

Asn Ala Met Ser Trp Val Arg Gln Ala Pro Gly Lys Gly Leu Glu Trp
            260                 265                 270

Val Ser Tyr Ile Tyr Pro Gly Gly Arg Thr Tyr Tyr Ala Asp Ser Val
```

```
                275                 280                 285
Lys Gly Arg Phe Thr Ile Ser Arg Asp Asn Ser Lys Asn Thr Leu Tyr
    290                 295                 300

Leu Gln Met Asn Ser Leu Arg Ala Glu Asp Thr Ala Val Tyr Tyr Cys
305                 310                 315                 320

Ala Arg Ala Gly Phe Gly Gly Pro Asp Tyr Trp Gly Gln Gly Thr Leu
                325                 330                 335

Val Thr Val Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Arg Val Glu Pro Lys Ser Cys
        435                 440

<210> SEQ ID NO 177
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Arg Val Glu Pro Lys Ser Cys Ala Ser Thr Lys Gly
210                 215                 220

Pro Ser Val Phe Pro Leu Ala Pro Glu Val Gln Leu Val Glu Ser Gly
225                 230                 235                 240

Gly Gly Leu Ile Gln Pro Gly Gly Ser Leu Arg Leu Ser Cys Ala Ala
            245                 250                 255

Ser Gly Phe Thr Val Ser Ser Asn Ala Met Ser Trp Val Arg Gln Ala
            260                 265                 270

Pro Gly Lys Gly Leu Glu Trp Val Ser Tyr Ile Tyr Pro Gly Gly Arg
            275                 280                 285

Thr Tyr Tyr Ala Asp Ser Val Lys Gly Arg Phe Thr Ile Ser Arg Asp
            290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Ala Arg Ala Gly Phe Gly Gly Pro Asp
            325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
            370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
            405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Arg Val Glu Pro
            435                 440                 445

Lys Ser Cys
450

<210> SEQ ID NO 178
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
            35                  40                  45

Ser Tyr Ile Tyr Pro Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Glu Leu Gln Leu Glu
    210                 215                 220

Glu Ser Ala Ala Glu Ala Gln Glu Gly Glu Leu Glu Val Gln Leu
225                 230                 235                 240

Val Glu Ser Gly Gly Gly Leu Ile Gln Pro Gly Gly Ser Leu Arg Leu
            245                 250                 255

Ser Cys Ala Ala Ser Gly Phe Thr Val Ser Ser Asn Ala Met Ser Trp
        260                 265                 270

Val Arg Gln Ala Pro Gly Lys Gly Leu Glu Trp Val Ser Tyr Ile Tyr
    275                 280                 285

Pro Gly Gly Arg Thr Tyr Tyr Ala Asp Ser Val Lys Gly Arg Phe Thr
290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Ala Gly Phe
                325                 330                 335

Gly Gly Pro Asp Tyr Trp Gly Gln Gly Thr Leu Val Thr Val Ser Ser
            340                 345                 350

Ala Ser Thr Lys Gly Pro Ser Val Phe Pro Leu Ala Pro Ser Ser Lys
        355                 360                 365

Ser Thr Ser Gly Gly Thr Ala Ala Leu Gly Cys Leu Val Lys Asp Tyr
    370                 375                 380

Phe Pro Glu Pro Val Thr Val Ser Trp Asn Ser Gly Ala Leu Thr Ser
385                 390                 395                 400

Gly Val His Thr Phe Pro Ala Val Leu Gln Ser Ser Gly Leu Tyr Ser
                405                 410                 415

Leu Ser Ser Val Val Thr Val Pro Ser Ser Ser Leu Gly Thr Gln Thr
            420                 425                 430

Tyr Ile Cys Asn Val Asn His Lys Pro Ser Asn Thr Lys Val Asp Lys
        435                 440                 445

Arg Val Glu Pro Lys Ser Cys
    450                 455

<210> SEQ ID NO 179
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Gly Gly Gly Gly Ser
    210                 215                 220

Gly Gly Gly Gly Ser Gly Gly Gly Ser Glu Val Gln Leu Val Glu
225                 230                 235                 240

Ser Gly Gly Gly Leu Ile Gln Pro Gly Gly Ser Leu Arg Leu Ser Cys
                245                 250                 255

Ala Ala Ser Gly Phe Thr Val Ser Ser Asn Ala Met Ser Trp Val Arg
            260                 265                 270

Gln Ala Pro Gly Lys Gly Leu Glu Trp Val Ser Tyr Ile Tyr Pro Gly
        275                 280                 285

Gly Arg Thr Tyr Tyr Ala Asp Ser Val Lys Gly Arg Phe Thr Ile Ser
    290                 295                 300

Arg Asp Asn Ser Lys Asn Thr Leu Tyr Leu Gln Met Asn Ser Leu Arg
305                 310                 315                 320

Ala Glu Asp Thr Ala Val Tyr Tyr Cys Ala Arg Ala Gly Phe Gly Gly
                325                 330                 335

Pro Asp Tyr Trp Gly Gln Gly Thr Leu Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

```
Ser Val Val Thr Val Pro Ser Ser Leu Gly Thr Gln Thr Tyr Ile
            420                 425                 430

Cys Asn Val Asn His Lys Pro Ser Asn Thr Lys Val Asp Lys Arg Val
            435                 440                 445

Glu Pro Lys Ser Cys
    450

<210> SEQ ID NO 180
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Glu Phe Gly Leu Glu Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220

Pro Glu Val Gln Leu Val Glu Ser Gly Gly Gly Leu Ile Gln Pro Gly
225                 230                 235                 240

Gly Ser Leu Arg Leu Ser Cys Ala Ala Ser Gly Phe Thr Val Ser Ser
                245                 250                 255

Asn Ala Met Ser Trp Val Arg Gln Ala Pro Gly Lys Gly Leu Glu Trp
            260                 265                 270

Val Ser Phe Ile Tyr Pro Gly Gly Arg Thr Tyr Tyr Ala Asp Ser Val
        275                 280                 285

Lys Gly Arg Phe Thr Ile Ser Arg Asp Asn Ser Lys Asn Thr Leu Tyr
    290                 295                 300

Leu Gln Met Asn Ser Leu Arg Ala Glu Asp Thr Ala Val Tyr Tyr Cys
```

```
                305                 310                 315                 320
Ala Arg Ala Glu Phe Gly Leu Glu Asp Ile Trp Gly Gln Gly Thr Leu
                    325                 330                 335

Val Thr Val Ser Ser Ala Ser Thr Lys Gly Pro Ser Val Phe Pro Leu
                    340                 345                 350

Ala Pro Ser Ser Lys Ser Thr Ser Gly Gly Thr Ala Ala Leu Gly Cys
                    355                 360                 365

Leu Val Lys Asp Tyr Phe Pro Glu Pro Val Thr Val Ser Trp Asn Ser
            370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                    405                 410                 415

Leu Gly Thr Gln Thr Tyr Ile Cys Asn Val Asn His Lys Pro Ser Asn
                    420                 425                 430

Thr Lys Val Asp Lys Arg Val Glu Pro Lys Ser Cys
            435                 440
```

<210> SEQ ID NO 181
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Glu Phe Gly Leu Glu Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220
```

```
Pro Ser Val Phe Pro Leu Ala Pro Glu Val Gln Leu Val Glu Ser Gly
225                 230                 235                 240

Gly Gly Leu Ile Gln Pro Gly Gly Ser Leu Arg Leu Ser Cys Ala Ala
            245                 250                 255

Ser Gly Phe Thr Val Ser Ser Asn Ala Met Ser Trp Val Arg Gln Ala
            260                 265                 270

Pro Gly Lys Gly Leu Glu Trp Val Ser Phe Ile Tyr Pro Gly Gly Arg
            275                 280                 285

Thr Tyr Tyr Ala Asp Ser Val Lys Gly Arg Phe Thr Ile Ser Arg Asp
            290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Ala Arg Ala Glu Phe Gly Leu Glu Asp
                325                 330                 335

Ile Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Leu Gly Thr Gln Thr Tyr Ile Cys Asn
                420                 425                 430

Val Asn His Lys Pro Ser Asn Thr Lys Val Asp Lys Arg Val Glu Pro
            435                 440                 445

Lys Ser Cys
    450

<210> SEQ ID NO 182
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Glu Phe Gly Leu Glu Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125
```

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Glu Leu Gln Leu Glu
210                 215                 220

Glu Ser Ala Ala Glu Ala Gln Glu Gly Glu Leu Glu Glu Val Gln Leu
225                 230                 235                 240

Val Glu Ser Gly Gly Gly Leu Ile Gln Pro Gly Gly Ser Leu Arg Leu
                245                 250                 255

Ser Cys Ala Ala Ser Gly Phe Thr Val Ser Ser Asn Ala Met Ser Trp
            260                 265                 270

Val Arg Gln Ala Pro Gly Lys Gly Leu Glu Trp Val Ser Phe Ile Tyr
        275                 280                 285

Pro Gly Gly Arg Thr Tyr Tyr Ala Asp Ser Val Lys Gly Arg Phe Thr
290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Ala Glu Phe
                325                 330                 335

Gly Leu Glu Asp Ile Trp Gly Gln Gly Thr Leu Val Thr Val Ser Ser
            340                 345                 350

Ala Ser Thr Lys Gly Pro Ser Val Phe Pro Leu Ala Pro Ser Ser Lys
        355                 360                 365

Ser Thr Ser Gly Gly Thr Ala Ala Leu Gly Cys Leu Val Lys Asp Tyr
370                 375                 380

Phe Pro Glu Pro Val Thr Val Ser Trp Asn Ser Gly Ala Leu Thr Ser
385                 390                 395                 400

Gly Val His Thr Phe Pro Ala Val Leu Gln Ser Ser Gly Leu Tyr Ser
                405                 410                 415

Leu Ser Ser Val Val Thr Val Pro Ser Ser Ser Leu Gly Thr Gln Thr
            420                 425                 430

Tyr Ile Cys Asn Val Asn His Lys Pro Ser Asn Thr Lys Val Asp Lys
        435                 440                 445

Arg Val Glu Pro Lys Ser Cys
450                 455

<210> SEQ ID NO 183
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn

-continued

```
                 20                  25                  30
Ala Met Ser Trp Val Arg Gln Ala Pro Gly Lys Gly Leu Glu Trp Val
                 35                  40                  45
Ser Phe Ile Tyr Pro Gly Gly Arg Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Ala Glu Phe Gly Leu Glu Asp Ile Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
                130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Arg Val Glu Pro Lys Ser Cys Gly Gly Gly Gly Ser
210                 215                 220
Gly Gly Gly Gly Ser Gly Gly Gly Ser Glu Val Gln Leu Val Glu
225                 230                 235                 240
Ser Gly Gly Gly Leu Ile Gln Pro Gly Gly Ser Leu Arg Leu Ser Cys
                245                 250                 255
Ala Ala Ser Gly Phe Thr Val Ser Ser Asn Ala Met Ser Trp Val Arg
                260                 265                 270
Gln Ala Pro Gly Lys Gly Leu Glu Trp Val Ser Phe Ile Tyr Pro Gly
                275                 280                 285
Gly Arg Thr Tyr Tyr Ala Asp Ser Val Lys Gly Arg Phe Thr Ile Ser
                290                 295                 300
Arg Asp Asn Ser Lys Asn Thr Leu Tyr Leu Gln Met Asn Ser Leu Arg
305                 310                 315                 320
Ala Glu Asp Thr Ala Val Tyr Tyr Cys Ala Arg Ala Glu Phe Gly Leu
                325                 330                 335
Glu Asp Ile Trp Gly Gln Gly Thr Leu Val Thr Val Ser Ser Ala Ser
                340                 345                 350
Thr Lys Gly Pro Ser Val Phe Pro Leu Ala Pro Ser Ser Lys Ser Thr
                355                 360                 365
Ser Gly Gly Thr Ala Ala Leu Gly Cys Leu Val Lys Asp Tyr Phe Pro
                370                 375                 380
Glu Pro Val Thr Val Ser Trp Asn Ser Gly Ala Leu Thr Ser Gly Val
385                 390                 395                 400
His Thr Phe Pro Ala Val Leu Gln Ser Ser Gly Leu Tyr Ser Leu Ser
                405                 410                 415
Ser Val Val Thr Val Pro Ser Ser Ser Leu Gly Thr Gln Thr Tyr Ile
                420                 425                 430
Cys Asn Val Asn His Lys Pro Ser Asn Thr Lys Val Asp Lys Arg Val
                435                 440                 445
```

Glu Pro Lys Ser Cys
    450

<210> SEQ ID NO 184
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220

Pro Glu Val Gln Leu Val Glu Ser Gly Gly Gly Leu Ile Gln Pro Gly
225                 230                 235                 240

Gly Ser Leu Arg Leu Ser Cys Ala Ala Ser Gly Phe Thr Val Ser Ser
                245                 250                 255

Asn Ala Met Ser Trp Val Arg Gln Ala Pro Gly Lys Gly Leu Glu Trp
            260                 265                 270

Val Ser Tyr Ile Tyr Pro Gly Gly Arg Thr Tyr Tyr Ala Asp Ser Val
        275                 280                 285

Lys Gly Arg Phe Thr Ile Ser Arg Asp Asn Ser Lys Asn Thr Leu Tyr
    290                 295                 300

Leu Gln Met Asn Ser Leu Arg Ala Glu Asp Thr Ala Val Tyr Tyr Cys
305                 310                 315                 320

Ala Arg Ala Gly Phe Gly Gly Asp Tyr Trp Gly Gln Gly Thr Leu
                325                 330                 335

Val Thr Val Ser Ser Ala Ser Thr Lys Gly Pro Ser Val Phe Pro Leu

```
                340                 345                 350
Ala Pro Ser Ser Lys Ser Thr Ser Gly Gly Thr Ala Ala Leu Gly Cys
            355                 360                 365

Leu Val Lys Asp Tyr Phe Pro Glu Pro Val Thr Val Ser Trp Asn Ser
        370                 375                 380

Gly Ala Leu Thr Ser Gly Val His Thr Phe Pro Ala Val Leu Gln Ser
385                 390                 395                 400

Ser Gly Leu Tyr Ser Leu Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Arg Val Glu Pro Lys Ser Cys
        435                 440

<210> SEQ ID NO 185
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220

Pro Ser Val Phe Pro Leu Ala Pro Glu Val Gln Leu Val Glu Ser Gly
225                 230                 235                 240

Gly Gly Leu Ile Gln Pro Gly Gly Ser Leu Arg Leu Ser Cys Ala Ala
                245                 250                 255
```

```
Ser Gly Phe Thr Val Ser Ser Asn Ala Met Ser Trp Val Arg Gln Ala
            260                 265                 270

Pro Gly Lys Gly Leu Glu Trp Val Ser Tyr Ile Tyr Pro Gly Gly Arg
        275                 280                 285

Thr Tyr Tyr Ala Asp Ser Val Lys Gly Arg Phe Thr Ile Ser Arg Asp
    290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Ala Arg Ala Gly Phe Gly Gly Gly Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Arg Val Glu Pro
        435                 440                 445

Lys Ser Cys
    450

<210> SEQ ID NO 186
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Val Glu Ser Gly Gly Gly Leu Ile Gln Pro Gly Gly
1               5                   10                  15

Ser Leu Arg Leu Ser Cys Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Glu Leu Gln Leu Glu
    210                 215                 220

Glu Ser Ala Ala Glu Ala Gln Glu Gly Glu Leu Glu Glu Val Gln Leu
225                 230                 235                 240

Val Glu Ser Gly Gly Gly Leu Ile Gln Pro Gly Gly Ser Leu Arg Leu
                245                 250                 255

Ser Cys Ala Ala Ser Gly Phe Thr Val Ser Ser Asn Ala Met Ser Trp
                260                 265                 270

Val Arg Gln Ala Pro Gly Lys Gly Leu Glu Trp Val Ser Tyr Ile Tyr
            275                 280                 285

Pro Gly Gly Arg Thr Tyr Tyr Ala Asp Ser Val Lys Gly Arg Phe Thr
        290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Ala Gly Phe
                325                 330                 335

Gly Gly Gly Asp Tyr Trp Gly Gln Gly Thr Leu Val Thr Val Ser Ser
                340                 345                 350

Ala Ser Thr Lys Gly Pro Ser Val Phe Pro Leu Ala Pro Ser Ser Lys
            355                 360                 365

Ser Thr Ser Gly Gly Thr Ala Ala Leu Gly Cys Leu Val Lys Asp Tyr
        370                 375                 380

Phe Pro Glu Pro Val Thr Val Ser Trp Asn Ser Gly Ala Leu Thr Ser
385                 390                 395                 400

Gly Val His Thr Phe Pro Ala Val Leu Gln Ser Ser Gly Leu Tyr Ser
                405                 410                 415

Leu Ser Ser Val Val Thr Val Pro Ser Ser Ser Leu Gly Thr Gln Thr
            420                 425                 430

Tyr Ile Cys Asn Val Asn His Lys Pro Ser Asn Thr Lys Val Asp Lys
        435                 440                 445

Arg Val Glu Pro Lys Ser Cys
    450                 455

<210> SEQ ID NO 187
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Tyr Ile Tyr Pro Gly Gly Arg Thr Tyr Tyr Ala Asp Ser Val Lys
```

```
                50              55              60
Gly Arg Phe Thr Ile Ser Arg Asp Asn Ser Lys Asn Thr Leu Tyr Leu
 65                      70                  75                  80

Gln Met Asn Ser Leu Arg Ala Glu Asp Thr Ala Val Tyr Tyr Cys Ala
                     85                  90                  95

Arg Ala Gly Phe Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Gly Gly Gly Ser
210                 215                 220

Gly Gly Gly Gly Ser Gly Gly Gly Ser Glu Val Gln Leu Val Glu
225                 230                 235                 240

Ser Gly Gly Gly Leu Ile Gln Pro Gly Gly Ser Leu Arg Leu Ser Cys
                245                 250                 255

Ala Ala Ser Gly Phe Thr Val Ser Ser Asn Ala Met Ser Trp Val Arg
                260                 265                 270

Gln Ala Pro Gly Lys Gly Leu Glu Trp Val Ser Tyr Ile Tyr Pro Gly
            275                 280                 285

Gly Arg Thr Tyr Tyr Ala Asp Ser Val Lys Gly Arg Phe Thr Ile Ser
            290                 295                 300

Arg Asp Asn Ser Lys Asn Thr Leu Tyr Leu Gln Met Asn Ser Leu Arg
305                 310                 315                 320

Ala Glu Asp Thr Ala Val Tyr Tyr Cys Ala Arg Ala Gly Phe Gly Gly
                325                 330                 335

Gly Asp Tyr Trp Gly Gln Gly Thr Leu Val Thr Val Ser Ser Ala Ser
                340                 345                 350

Thr Lys Gly Pro Ser Val Phe Pro Leu Ala Pro Ser Ser Lys Ser Thr
            355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
                420                 425                 430

Cys Asn Val Asn His Lys Pro Ser Asn Thr Lys Val Asp Lys Arg Val
            435                 440                 445

Glu Pro Lys Ser Cys
    450

<210> SEQ ID NO 188
```

```
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Val Ser Ile Val Arg Gln Ala Pro Gly Lys Gly Leu Glu Trp Val
        35                  40                  45

Ala Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ile Gly Gly Phe Gly Gly Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220

Pro Glu Val Gln Leu Val Glu Ser Gly Gly Gly Leu Ile Gln Pro Gly
225                 230                 235                 240

Gly Ser Leu Arg Leu Ser Cys Ala Ala Ser Gly Phe Thr Val Ser Ser
                245                 250                 255

Asn Ala Val Ser Ile Val Arg Gln Ala Pro Gly Lys Gly Leu Glu Trp
            260                 265                 270

Val Ala Tyr Ile Tyr Pro Gly Gly Arg Thr Tyr Tyr Ala Asp Ser Val
        275                 280                 285

Lys Gly Arg Phe Thr Ile Ser Arg Asp Asn Ser Lys Asn Thr Leu Tyr
    290                 295                 300

Leu Gln Met Asn Ser Leu Arg Ala Glu Asp Thr Ala Val Tyr Tyr Cys
305                 310                 315                 320

Thr Ile Gly Gly Phe Gly Gly Gly Asp Tyr Trp Gly Gln Gly Thr Leu
                325                 330                 335

Val Thr Val Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
```

-continued

```
                370                 375                 380
Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
                420                 425                 430

Thr Lys Val Asp Lys Arg Val Glu Pro Lys Ser Cys
                435                 440

<210> SEQ ID NO 189
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
                20                  25                  30

Ala Val Ser Ile Val Arg Gln Ala Pro Gly Lys Gly Leu Glu Trp Val
                35                  40                  45

Ala Tyr Ile Tyr Pro Gly Gly Arg Thr Tyr Tyr Ala Asp Ser Val Lys
                50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ile Gly Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Ala Ser Thr Lys Gly
                210                 215                 220

Pro Ser Val Phe Pro Leu Ala Pro Glu Val Gln Leu Val Glu Ser Gly
225                 230                 235                 240

Gly Gly Leu Ile Gln Pro Gly Gly Ser Leu Arg Leu Ser Cys Ala Ala
                245                 250                 255

Ser Gly Phe Thr Val Ser Ser Asn Ala Val Ser Ile Val Arg Gln Ala
                260                 265                 270

Pro Gly Lys Gly Leu Glu Trp Val Ala Tyr Ile Tyr Pro Gly Gly Arg
                275                 280                 285
```

```
Thr Tyr Tyr Ala Asp Ser Val Lys Gly Arg Phe Thr Ile Ser Arg Asp
    290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Thr Ile Gly Gly Phe Gly Gly Gly Asp
                325                 330                 335

Tyr Trp Gly Gln Gly Thr Leu Val Thr Val Ser Ser Ala Ser Thr Lys
                340                 345                 350

Gly Pro Ser Val Phe Pro Leu Ala Pro Ser Ser Lys Ser Thr Ser Gly
                355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
                420                 425                 430

Val Asn His Lys Pro Ser Asn Thr Lys Val Asp Lys Arg Val Glu Pro
            435                 440                 445

Lys Ser Cys
    450

<210> SEQ ID NO 190
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
                20                  25                  30

Ala Val Ser Ile Val Arg Gln Ala Pro Gly Lys Gly Leu Glu Trp Val
            35                  40                  45

Ala Tyr Ile Tyr Pro Gly Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ile Gly Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190
```

```
Gly Thr Gln Thr Tyr Ile Cys Asn Val Asn His Lys Pro Ser Asn Thr
            195                 200                 205

Lys Val Asp Lys Arg Val Glu Pro Lys Ser Cys Glu Leu Gln Leu Glu
    210                 215                 220

Glu Ser Ala Ala Glu Ala Gln Glu Gly Glu Leu Glu Glu Val Gln Leu
225                 230                 235                 240

Val Glu Ser Gly Gly Gly Leu Ile Gln Pro Gly Gly Ser Leu Arg Leu
                245                 250                 255

Ser Cys Ala Ala Ser Gly Phe Thr Val Ser Ser Asn Ala Val Ser Ile
            260                 265                 270

Val Arg Gln Ala Pro Gly Lys Gly Leu Glu Trp Val Ala Tyr Ile Tyr
        275                 280                 285

Pro Gly Gly Arg Thr Tyr Tyr Ala Asp Ser Val Lys Gly Arg Phe Thr
    290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Thr Ile Gly Gly Phe
                325                 330                 335

Gly Gly Gly Asp Tyr Trp Gly Gln Gly Thr Leu Val Thr Val Ser Ser
            340                 345                 350

Ala Ser Thr Lys Gly Pro Ser Val Phe Pro Leu Ala Pro Ser Ser Lys
        355                 360                 365

Ser Thr Ser Gly Gly Thr Ala Ala Leu Gly Cys Leu Val Lys Asp Tyr
    370                 375                 380

Phe Pro Glu Pro Val Thr Val Ser Trp Asn Ser Gly Ala Leu Thr Ser
385                 390                 395                 400

Gly Val His Thr Phe Pro Ala Val Leu Gln Ser Ser Gly Leu Tyr Ser
                405                 410                 415

Leu Ser Ser Val Val Thr Val Pro Ser Ser Ser Leu Gly Thr Gln Thr
            420                 425                 430

Tyr Ile Cys Asn Val Asn His Lys Pro Ser Asn Thr Lys Val Asp Lys
        435                 440                 445

Arg Val Glu Pro Lys Ser Cys
    450                 455

<210> SEQ ID NO 191
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Val Ser Ile Val Arg Gln Ala Pro Gly Lys Gly Leu Glu Trp Val
        35                  40                  45

Ala Tyr Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
```

```
                 85                  90                  95
Ile Gly Gly Phe Gly Gly Gly Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Gly Gly Gly Gly Ser
            210                 215                 220

Gly Gly Gly Gly Ser Gly Gly Gly Ser Glu Val Gln Leu Val Glu
225                 230                 235                 240

Ser Gly Gly Gly Leu Ile Gln Pro Gly Gly Ser Leu Arg Leu Ser Cys
                245                 250                 255

Ala Ala Ser Gly Phe Thr Val Ser Ser Asn Ala Val Ser Ile Val Arg
                260                 265                 270

Gln Ala Pro Gly Lys Gly Leu Glu Trp Val Ala Tyr Ile Tyr Pro Gly
            275                 280                 285

Gly Arg Thr Tyr Tyr Ala Asp Ser Val Lys Gly Arg Phe Thr Ile Ser
            290                 295                 300

Arg Asp Asn Ser Lys Asn Thr Leu Tyr Leu Gln Met Asn Ser Leu Arg
305                 310                 315                 320

Ala Glu Asp Thr Ala Val Tyr Tyr Cys Thr Ile Gly Gly Phe Gly Gly
                325                 330                 335

Gly Asp Tyr Trp Gly Gln Gly Thr Leu Val Thr Val Ser Ser Ala Ser
            340                 345                 350

Thr Lys Gly Pro Ser Val Phe Pro Leu Ala Pro Ser Ser Lys Ser Thr
            355                 360                 365

Ser Gly Gly Thr Ala Ala Leu Gly Cys Leu Val Lys Asp Tyr Phe Pro
        370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Arg Val
            435                 440                 445

Glu Pro Lys Ser Cys
    450
```

<210> SEQ ID NO 192
<211> LENGTH: 444
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 192

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
210                 215                 220

Pro Glu Val Gln Leu Val Glu Ser Gly Gly Gly Leu Ile Gln Pro Gly
225                 230                 235                 240

Gly Ser Leu Arg Leu Ser Cys Ala Ala Ser Gly Phe Thr Val Ser Ser
                245                 250                 255

Asn Ala Met Ser Trp Val Arg Gln Ala Pro Gly Lys Gly Leu Glu Trp
            260                 265                 270

Val Ser Phe Ile Tyr Pro Gly Gly Arg Thr Tyr Tyr Ala Asp Ser Val
        275                 280                 285

Lys Gly Arg Phe Thr Ile Ser Arg Asp Asn Ser Lys Asn Thr Leu Tyr
290                 295                 300

Leu Gln Met Asn Ser Leu Arg Ala Glu Asp Thr Ala Val Tyr Tyr Cys
305                 310                 315                 320

Ala Arg Ala Gly Phe Gly Gly Pro Asp Tyr Trp Gly Gln Gly Thr Leu
                325                 330                 335

Val Thr Val Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
```

-continued

```
                405                 410                 415

Leu Gly Thr Gln Thr Tyr Ile Cys Asn Val Asn His Lys Pro Ser Asn
            420                 425                 430

Thr Lys Val Asp Lys Arg Val Glu Pro Lys Ser Cys
        435                 440

<210> SEQ ID NO 193
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ser Thr Lys Gly
    210                 215                 220

Pro Ser Val Phe Pro Leu Ala Pro Glu Val Gln Leu Val Glu Ser Gly
225                 230                 235                 240

Gly Gly Leu Ile Gln Pro Gly Gly Ser Leu Arg Leu Ser Cys Ala Ala
                245                 250                 255

Ser Gly Phe Thr Val Ser Ser Asn Ala Met Ser Trp Val Arg Gln Ala
            260                 265                 270

Pro Gly Lys Gly Leu Glu Trp Val Ser Phe Ile Tyr Pro Gly Gly Arg
        275                 280                 285

Thr Tyr Tyr Ala Asp Ser Val Lys Gly Arg Phe Thr Ile Ser Arg Asp
    290                 295                 300

Asn Ser Lys Asn Thr Leu Tyr Leu Gln Met Asn Ser Leu Arg Ala Glu
305                 310                 315                 320
```

Asp Thr Ala Val Tyr Tyr Cys Ala Arg Ala Gly Phe Gly Gly Pro Asp
            325                 330                 335

Tyr Trp Gly Gln Gly Thr Leu Val Thr Val Ser Ser Ala Ser Thr Lys
        340                 345                 350

Gly Pro Ser Val Phe Pro Leu Ala Pro Ser Ser Lys Ser Thr Ser Gly
    355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Arg Val Glu Pro
        435                 440                 445

Lys Ser Cys
    450

<210> SEQ ID NO 194
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Glu Leu Gln Leu Glu
    210                 215                 220

-continued

Glu Ser Ala Ala Glu Ala Gln Glu Gly Glu Leu Gly Glu Val Gln Leu
225                 230                 235                 240

Val Glu Ser Gly Gly Gly Leu Ile Gln Pro Gly Gly Ser Leu Arg Leu
            245                 250                 255

Ser Cys Ala Ala Ser Gly Phe Thr Val Ser Ser Asn Ala Met Ser Trp
        260                 265                 270

Val Arg Gln Ala Pro Gly Lys Gly Leu Glu Trp Val Ser Phe Ile Tyr
    275                 280                 285

Pro Gly Gly Arg Thr Tyr Tyr Ala Asp Ser Val Lys Gly Arg Phe Thr
290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Ala Gly Phe
            325                 330                 335

Gly Gly Pro Asp Tyr Trp Gly Gln Gly Thr Leu Val Thr Val Ser Ser
        340                 345                 350

Ala Ser Thr Lys Gly Pro Ser Val Phe Pro Leu Ala Pro Ser Ser Lys
    355                 360                 365

Ser Thr Ser Gly Gly Thr Ala Ala Leu Gly Cys Leu Val Lys Asp Tyr
370                 375                 380

Phe Pro Glu Pro Val Thr Val Ser Trp Asn Ser Gly Ala Leu Thr Ser
385                 390                 395                 400

Gly Val His Thr Phe Pro Ala Val Leu Gln Ser Ser Gly Leu Tyr Ser
            405                 410                 415

Leu Ser Ser Val Val Thr Val Pro Ser Ser Ser Leu Gly Thr Gln Thr
        420                 425                 430

Tyr Ile Cys Asn Val Asn His Lys Pro Ser Asn Thr Lys Val Asp Lys
    435                 440                 445

Arg Val Glu Pro Lys Ser Cys
450                 455

<210> SEQ ID NO 195
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Gly Gly Pro Asp Tyr Trp Gly Gln Gly Thr Leu Val
            100                 105                 110

Thr Val Ser Ser Ala Ser Thr Lys Gly Pro Ser Val Phe Pro Leu Ala

```
            115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Gly Gly Gly Gly Ser
210                 215                 220

Gly Gly Gly Gly Ser Gly Gly Gly Ser Glu Val Gln Leu Val Glu
225                 230                 235                 240

Ser Gly Gly Gly Leu Ile Gln Pro Gly Gly Ser Leu Arg Leu Ser Cys
                245                 250                 255

Ala Ala Ser Gly Phe Thr Val Ser Ser Asn Ala Met Ser Trp Val Arg
            260                 265                 270

Gln Ala Pro Gly Lys Gly Leu Glu Trp Val Ser Phe Ile Tyr Pro Gly
        275                 280                 285

Gly Arg Thr Tyr Tyr Ala Asp Ser Val Lys Gly Arg Phe Thr Ile Ser
    290                 295                 300

Arg Asp Asn Ser Lys Asn Thr Leu Tyr Leu Gln Met Asn Ser Leu Arg
305                 310                 315                 320

Ala Glu Asp Thr Ala Val Tyr Tyr Cys Ala Arg Ala Gly Phe Gly Gly
                325                 330                 335

Pro Asp Tyr Trp Gly Gln Gly Thr Leu Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Arg Val
        435                 440                 445

Glu Pro Lys Ser Cys
    450

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Ser Thr Lys Gly Pro
1               5
```

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Ser Thr Lys Gly Pro Ser Val Phe Pro Leu Ala Pro
1               5                   10

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Glu Leu Gln Leu Glu Glu Ser Ala Ala Glu Ala Gln Glu Gly Glu Leu
1               5                   10                  15

Glu

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Gly Gly Gly Ser Gly Gly Gly Ser Gly Gly Gly Ser
1               5                   10                  15

<210> SEQ ID NO 200
<211> LENGTH: 329
<212> TYPE: PRT
<213> ORGANISM: Homo sapiens

<400> SEQUENCE: 200

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 201
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Ala Met Ser Trp Val Arg Gln Ala Pro Gly Lys Gly Leu Glu Trp Val
        35                  40                  45

Ser Phe Ile Tyr Pro Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Glu Phe Gly Leu Glu Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175
```

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 202
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

Arg Val Glu Pro Lys Ser Cys
            100

<210> SEQ ID NO 203
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His
            100                 105

<210> SEQ ID NO 204
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 205
<211> LENGTH: 97
<212> TYPE: PRT
<213> ORGANISM: Homo sapiens

<400> SEQUENCE: 205

Glu Val Gln Leu Val Glu Ser Gly Gly Gly Leu Ile Gln Pro Gly Gly
1               5                   10                  15

```
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg

<210> SEQ ID NO 206
<211> LENGTH: 94
<212> TYPE: PRT
<213> ORGANISM: Homo sapiens

<400> SEQUENCE: 206

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe
                85                  90

<210> SEQ ID NO 207
<211> LENGTH: 12
<212> TYPE: PRT
<213> ORGANISM: Homo sapiens

<400> SEQUENCE: 207

Leu Thr Phe Gly Gly Gly Thr Lys Val Glu Ile Lys
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Phe Thr Val Ser Ser Asn Tyr Met Ser
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209
```

```
Phe Ile Tyr Ser Gly Gly Arg Thr Tyr Tyr
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Ala Ser Gln Gly Ile Ser Ser Asn Leu Ala Trp Tyr
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Leu Ile Tyr Ala Ala Ser Ser Leu Gln Ser
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Gln Ala Asn Ser Phe Pro Leu Thr Phe
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Phe Thr Val Ser Ser Asn Ala Met Ser Trp Val
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Trp Val Ser Phe Ile Tyr Pro Gly Gly Arg Thr Tyr Tyr
1               5                   10

<210> SEQ ID NO 215
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 215

Ala Arg Ala Gly Phe Gly Gly Gly Asp Tyr Trp
1               5                   10

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asn Leu Ala Trp Tyr
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Met Ser Trp Val
1               5

<210> SEQ ID NO 218
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Val Ser Phe Ile
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Arg Ala Gly Phe
1               5

<210> SEQ ID NO 220
<211> LENGTH: 13
<212> TYPE: PRT
<213> ORGANISM: Homo sapiens

<400> SEQUENCE: 220

Asp Tyr Trp Gly Gln Gly Thr Leu Val Thr Val Ser Ser
1               5                   10

<210> SEQ ID NO 221
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 221

His His His His His His
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly His His His His His His His
1               5
```